US008715980B2

(12) United States Patent  
Clarke

(10) Patent No.: US 8,715,980 B2  
(45) Date of Patent: May 6, 2014

(54) SYSTEM FOR CULTIVATION AND PROCESSING OF MICROORGANISMS, PROCESSING OF PRODUCTS THEREFROM, AND PROCESSING IN DRILLHOLE REACTORS

(75) Inventor: William Severn Clarke, Mt Macedon (AU)

(73) Assignee: Winwick Business Solutions Pty Ltd, Mt Macedon, Victoria (AU)

( * ) Notice: Subject to any disclaimer, the term of this patent is extended or adjusted under 35 U.S.C. 154(b) by 315 days.

(21) Appl. No.: 12/928,405

(22) Filed: Dec. 10, 2010

(65) Prior Publication Data

US 2011/0092726 A1 Apr. 21, 2011

Related U.S. Application Data

(63) Continuation-in-part of application No. PCT/AU2009/000750, filed on Jun. 12, 2009.

(30) Foreign Application Priority Data

Jun. 12, 2008 (AU) ................................ 2008902944

(51) Int. Cl.
*C12N 13/00* (2006.01)
*C11B 7/00* (2006.01)
*C11B 13/00* (2006.01)

(52) U.S. Cl.
USPC .................... 435/173.7; 435/173.9; 554/175; 554/174; 554/124; 554/169

(58) Field of Classification Search
None
See application file for complete search history.

(56) References Cited

U.S. PATENT DOCUMENTS

2004/0033557 A1* 2/2004 Scott et al. ...................... 435/42
2007/0071660 A1* 3/2007 McGrew ........................ 422/196
2007/0295505 A1* 12/2007 Pfeiffer et al. ................. 166/263

FOREIGN PATENT DOCUMENTS

DE         102006045872      *  4/2008  ............ C12M 1/107

OTHER PUBLICATIONS

DE102006045872: Schulz, H. et al., Biogas plant, 2008, English translation, (7 pages).*

* cited by examiner

*Primary Examiner* — Yate K Cutliff
(74) *Attorney, Agent, or Firm* — Henry I. Schanzer, Esq.

(57) ABSTRACT

Described are methods of cultivating autotrophic microorganisms, particularly microalgae or diatoms, in a bioreactor by entraining a culture of the microorganisms in a tenuous, gelated, thixotrophic carrier medium having nutrients therefor and moving the medium along a passage at a sufficiently slow speed to enable laminar flow which in cross section is closed and which has transparent walls through which the culture is irradiated to enable photosynthesis. The method includes effecting convective turnover of the culture and medium as they flow along the passage by differentially heating the medium laterally relative to the flow direction so as to produce a generally helical flow of the culture and medium. Also described are processing methods, both physical and chemical, performed underground e.g. in drillholes, to utilize decavitation energy under ambient elevated pressures, including processes to implement lysis of the micro-organisms, producing methanol, syngas synthesis, Haber ammonia synthesis, Fischer-Tropsch reactions, supercritical reactions, dimethyl ether synthesis, and nitric acid synthesis.

21 Claims, 9 Drawing Sheets

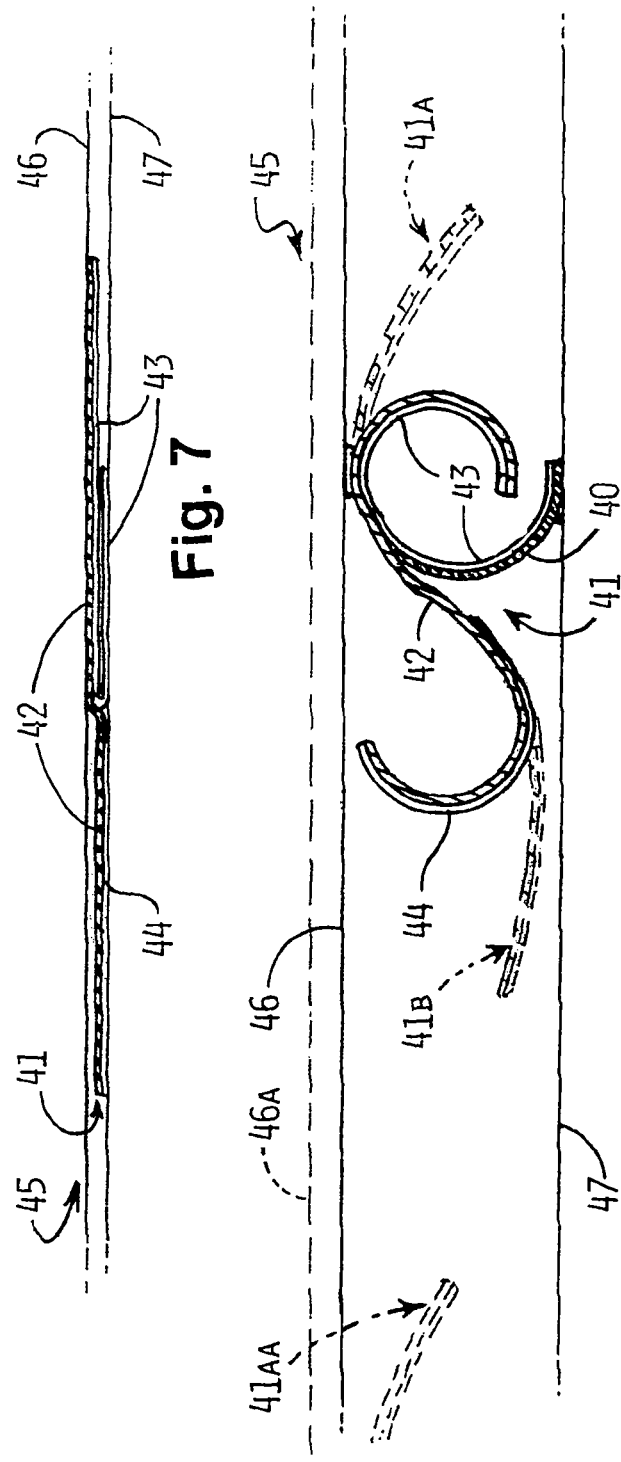

SYSTEM FOR CULTIVATION AND PROCESSING OF MICROORGANISMS, PROCESSING OF PRODUCTS THEREFROM, AND PROCESSING IN DRILLHOLE REACTORS

CROSS REFERENCE TO RELATED APPLICATION

This application is a continuation-in-part of International Patent Application No. PCT/AU2009/000750 filed 12 Jun. 2009, which in turn is based on and claims priority from Australia Patent Application No. 2008902944, filed 12 Jun. 2008, and the contents and disclosures of those two applications are incorporated herein by this cross reference.

FIELD OF THE INVENTION

This specification relates to processes and apparatus and systems for cultivating and processing microorganisms, particularly microalgae or diatoms, to processing or extracting products from such cultivation to processing other organic materials and organic wastes and organic chemicals, and to particular parts of and systems useful in the foregoing fields.

BACKGROUND

There have been proposed and sometimes implemented in the past, at least in experimental installations, systems, apparatuses and processes for cultivating microorganisms particularly microalgae to produce useful by-products such as lipids potentially useful as a source of fuels. There have been two broad approaches to such microorganism cultivation on a large scale, the first using large open ponds, raceways, vats or the like in which the microorganisms such as microalgae are grown and subsequently harvested, and the second involving closed vessels or passages in which the microorganisms are moved in a nutrient medium while being exposed to incident radiation, either solar or artificial radiation, to promote the growth and propagation of the microorganism culture. The open systems are particularly vulnerable to contamination by other organisms which can either predate the desired species or become more dominant in the population of microorganisms thus degrading the productive output and commercial viability or, at the very least, requiring continual measures to inhibit or remove the contaminating population. The closed system designs have been far too costly to be commercially viable for commercial fuel production. Both have tended to use land with high alternative use value.

In most of the above systems, the aqueous nutrient medium carrying the microorganism culture has been agitated or moved at flow velocities to nutrify the medium with $CO_2$ to maintain turbulent conditions for the purposes of preventing or minimising settling of microorganisms, coagulation or flocculating of microorganism clusters limiting optimum growth within the culture, and to continuously mix nutrients and microorganisms and to remove waste products so as to ensure that all receive adequate nutrition, space and insolation to optimise growth and reproduction. However, such turbulent flow can require substantial energy inputs to pump the nutrient and microorganism soup and maintain the required turbulence.

There have been many other limitations and drawbacks of particular large scale microorganism cultivating and processing systems which will be mentioned in this specification where relevant in the particular context of the description of parts of the present applicant's method, apparatus and system.

The above and following references, including references in the Appendix of the present specification, to and descriptions of prior proposals or products are not intended to be, and are not to be construed as, statements or admissions of common general knowledge in the art.

Throughout the specification, including the claims, the present applicant's overall system, process, and apparatus, many individual aspects of which are not in themselves essential and may be omitted or varied in particular implementations of the applicant's system, will be referred to as the "Winwick system", "Winwick process", "Winwick apparatus", etc. This is for convenient reference but it is to be understood that the particular aspect of the system, method or apparatus being described, or indeed the references to the system, method and apparatus as a whole are not to be construed as being necessarily essential to the present invention.

SUMMARY OF THE INVENTION

According to a first aspect of the invention there is provided a method of performing processing operations on a flowable feed material in a drillhole reactor, the flowable feed material being composed of a carrier liquid, reactants to be subjected to and to take part in the processing operations, and gas bubbles of predetermined sizes and/or contents that are entrained in or formed in the carrier liquid and which perform functionally in the processing operations, the method comprising the steps of:

flowing the feed material from an initial level down a confined path or drill hole which descends underground by a substantial vertical distance to a working depth so that the pressure experienced by the feed material at that working depth is substantially greater than the initial level and the gas bubbles are reduced in size by compression, said gas bubbles being of sizes chosen to decavitate at predetermined pressures which are reached or exceeded in the feed material at various working depths;

providing working conditions for the flowing feed material at the working depth to utilise the relatively high pressure in performing the processing operations on the feed material and so produce a flowable output material, the working conditions including conditions under which the pressurised gas bubbles participate in or promote the processing operations which produce reaction products which are included in the flowable output material, said working conditions comprising conditions in which the gas bubbles collapse violently or implode upon decavitation producing energetic microjets of liquid and intense but short-lived, and highly-localised heating which promote the performance of the processing operations in the immediate vicinity of each gas bubble decavitation even when the bulk temperature of the feed material would otherwise be insufficient to progress the desired reactions; and returning the flowable output material produced by the processing operations at the working depth by a return passage from the working depth at least a substantial vertical distance away from the working depth so as to conduct further processing operations on the reaction products within the flowable output material.

Preferably the composition of the flowable feed material includes at least one promoter agent operative to promote the performance of the process operations at the working depth, the promoter agent being selected from:
- gaseous materials of which the gas bubbles are composed,
- densifiers,
- additives in the carrier liquid in addition to the reactants, and
- catalysts provided in the carrier liquid.

In one embodiment the promoter agent comprises the gas bubbles that compress at increasing depth, providing adiabatic heating to the processes and cooling when the bubbles decompress The processing operations carried out on the flowable feed material preferably include at least one physical change of the flowable medium and reactants therein, the physical change being brought about by the effects of the pressurisation of and the decavitation of gas bubbles including the effects of the energetic microjets rupturing nearby cell walls.

For example, in another aspect on the invention there is provided a method of performing processing operations on a flowable feed material in a drillhole reactor, the flowable feed material being composed of a carrier liquid, reactants to be subjected to and to take part in the processing operations, and gas bubbles of predetermined sizes and/or contents that are entrained in or formed in the carrier liquid and which perform functionally in the processing operations, said reactants comprise organic cellular material from which valuable substances are to be recovered, the method comprising the steps of:

flowing the feed material which comprises a slurry of the cellular material, the flowable carrier liquid and gases including the gas bubbles from a ground surface level down a confined path or drill hole which descends underground by a substantial vertical distance to a working depth so that the pressure experienced by the feed material at that working depth is substantially greater than the ground surface level whereby the cellular material is exposed to substantially increased pressure and osmotic gas transfer from the bubbles to the carrier liquid and thence into the cells of the cellular material and into their inner vesicles but without active pressurisation providing working conditions for the flowing feed material at the working depth to utilise the relatively high pressure in performing the processing operations on the cellular material and so produce a flowable output material, the working conditions including conditions to produce rapidly changing pressures by means of depth change, choking and decompression, including decompression and the formation of pressurised gas within the cells that cannot osmose out sufficiently quickly to avoid cell and vesicle rupture as a result of rapid ascent in the fluid column, that induces lysis of the cellular material and thereby produces reaction products which are included in the flowable output material; and returning to the ground surface level an output slurry of lysed cellular material and substances released by the lysis for processing and separation of released valuable substances.

Preferably the cellular material comprises microalgae or diatoms or other microorganisms.

Preferably the step of providing conditions to induce lysis comprises flowing the slurry in a closed and profiled passage or loop, typically formed by a profiled pipe within an outer pipe, with a series of expansion and compression zones where the gas-bubble-containing slurry of microorganisms or other cellular material undergoes abrupt pressure changes thereby inducing lysis of the microorganisms via ruptures of cells and vesicles caused by explosive decompression and creation, release or expansion of gas bubbles, and by the microjets and the intense, localised heating resulting from decavitation of the gas bubbles. The passage has multiple restrictions inducing rapid pressure increases in the slurry and promoting decavitation of gas bubbles, the restrictions being arranged in series so that the slurry passes through the restrictions sequentially, each of the restrictions being followed in the flow path in the passage by an abrupt increase in cross-sectional area of the passage to thereby define the respective expansion zone of relatively lower pressure causing the explosive decompression. The downward passage or bore may descend underground by at least 100 meters to produce a relatively slow-moving material in the compression and osmosis stages and to allow subsequent rapid upward passage de-pressurisation sufficient for the lysis process.

In one preferred embodiment, the output slurry comprising the carrier liquid, gases and the lysed cellular material resulting from the reaction at the working level includes lipids released upon lysis of the cellular material, the method including the further steps of separating or at least concentrating the lipids by gravitational or centrifugal separation, and reacting the lipids in a transesterification reaction with excess methanol conducted under controlled temperature and pressure conditions at a predetermined level in a drillhole reactor where elevated pressures and decavitation are experienced sufficient to facilitate the transesterification reaction.

Preferably, the possible processing operations include chemical reactions induced to occur within the flowable feed material, the chemical reactions being initiated, caused, accelerated, or enhanced as a result of the increase in pressure and temperature to which the feed material is subjected in descending from the initial level to the working level or experienced at the working level including adiabatic compression of the gas bubbles, decavitation and the consequent promotion of the chemical reactions. Surfaces of the confined path for the feed material may provide locations of catalytic surfaces promoting the chemical reactions.

In one possible chemical process, the path comprises a passage or bore which descends underground by at least 100 meters, and preferably by some thousands of meters, so that the pressure in the fluid at that depth is of the order of 1,000 atmospheres, and wherein the feed material comprises a heated mixture of reactant fluids (typically heated via heat exchangers located on the ground surface level or by the underground introduction of superheated steam or other fluid into the feed material in the passage) which are entrained typically as said bubbles in a fast moving, catalyst bearing high boiling point carrier liquid such as residual fuel oil, and at the working depth in the passage or bore there is generated methanol from stoichiometric volumes of methane, steam, oxygen and carbon dioxide. The methane is preferably sourced from anaerobic digestion of algal cell walls from the processing of microorganisms, or from waste organic material, or from hydrocarbon deposits, and wherein the oxygen is sourced from photosynthesis by microorganisms.

Another possible chemical reaction comprises synthesis of a syngas comprising a mixture of carbon monoxide (CO) and hydrogen ($H_2$), the feed material comprising said bubbles composed of a mix of oxygen and carbon dioxide and steam in an aqueous carrier liquid forming a slurry of carbon based, organic substances and wherein the slurry at least upon reaching the working level achieves supercritical water conditions. The carbon-based substances may include one or more of: microorganisms, algae or algal cell wall material, crop and forestry wastes, lignocellulose products, sewage, plastics and rubber, wastewater, or wastes from agribusiness, pulp mills, or other carbon based products from industrial sources and waste recycling. The slurry flowed down the path from the initial level may include a proportion of said gas bubbles whereby, upon pressurisation of the slurry as it flows downwardly to the working level, the slurry experiences adiabatic heating. The carbon based reactants preferably include the cell walls of micro-organisms and other cellular materials which have undergone lysis so as to release lipids and proteins which have been recovered and removed therefrom.

Another possible chemical process comprises a Haber ammonia synthesis and the feed material includes the gas bubbles composed of mixed nitrogen and hydrogen gases in stoichiometric proportions, and suitable catalyst substances, promoters and densifiers added to the reactants or carrier liquid to promote the Haber process.

Another possible chemical process comprises a Fischer-Tropsch alkane synthesis and the feed material includes the gas bubbles composed of syngas and wherein suitable catalytic substances and promoters are either added to the reactants or to the liquid carrier or are located in a separate assembly to promote the Fischer-Tropsch process. In this process, the reactants comprise syngas derived from the method as described herein and the production of syngas is carried out at a first working depth, and the Fischer-Tropsch synthesis is carried out at a second working depth to which the products from the syngas synthesis are flowed. For the Haber and Fischer-Tropsch processes the reactants and catalysts are entrained in the carrier liquid and the small gas bubbles therein provide large surface areas exposed to the catalyst-bearing carrier liquid at, or near which, the chemical processes progress.

Preferably heat from exothermic reactions is transferred to raise the temperature of feed material flowing downwardly to undergo the chemical reaction at the working level, the feed material being heated comprising at least one of:
- the feed material in the method described flowing in the path to undergo the chemical reaction producing methanol,
- the feed material in the method described flowing in the path to undergo the syngas synthesis process,
- the feed material in the method described flowing in the path to undergo the Haber reaction,
- the feed material in the method as described flowing in the path to undergo the Fischer-Tropsch reaction.

In a preferred embodiment in which the carrier liquid is composed of at least one of the reactants and includes lipids, the chemical reaction comprises a transesterification reaction with excess methanol conducted under controlled temperature and pressure conditions at a predetermined level in a drillhole reactor where elevated pressures and decavitation are experienced sufficient to facilitate the transesterification reaction. Preferably the steps of the method are at least partially performed underground in a deep drill hole so that the elevated pressures experienced by the flowable feed material comprising carrier liquid, reactants and gas bubbles result from the ambient pressure experienced in substantial depths of liquid, the depth of the confined path or drill hole preferably being at least 100 meters and typically being in the range of from 1,000 to several thousand meters. The heat for promoting the processing operations carried out at depth preferably is in part derived from elevated temperatures of the ground in which the deep drill hole is provided or from heat derived from it in surface-mounted, geothermal heat exchangers. For example, the deep drill hole may be provided at a hot fractured rock geologic formation, most processing operations being carried out within processing apparatus lowered from ground level into the deep drill hole to the required depth for achieving the desired temperature and/or pressure conditions for the respective processing operations.

According to a second aspect of the invention there is provided a method of cultivating microorganisms, particularly microalgae or diatoms, in a bioreactor comprising the steps of:
entraining a culture of the microorganisms in a tenuous, gelated, thixotrophic carrier medium having nutrients therefor and moving the medium along a passage which in cross section is closed and which has transparent walls through which the culture is irradiated to enable photosynthesis;
providing process parameter control means associated with the passage; and
selectively varying the process parameter control means to thereby selectively control parameters or conditions of the cultivation and photosynthetic activity of the microorganisms moving within the passage.

The method of the first aspect may further include the steps of:
moving the carrier medium at a sufficiently slow speed to enable laminar flow thereof along the passage; and
effecting convective turnover of the culture and medium as they flow along the passage by differentially heating the medium laterally relative to the flow direction so as to produce a generally helical flow of the culture and medium. Preferably the carrier medium has a viscosity or tenuous structure sufficient to impede gravitational settling, surface scumming, or deposition onto solid surfaces by the microorganisms, at the same time as prolonging the residence time in the medium of the gaseous phase nutrient and impeding clumping of the microorganisms into less productive clusters.

Preferably the viscosity, structure and composition of the medium and culture are monitored and are controlled to promote an optimal concentration of active microorganisms. The viscosity and thixotrophicity may be increased by addition of a gel substance (e.g. a water swellable, or hygroscopic, organic polymer gel with high water absorptivity) to increase the impedance to gravitational settling and to the passage of gaseous phase nutrient up through the medium (except at locations of designated medium agitation, where the viscosity is deliberately reduced to enable gas liberation, algal harvesting and sparging with nutrient gas to proceed) but without preventing access by the microorganisms to nutrients in the medium nor preventing removal of excreta of the microorganisms in a gas liberation process.

In a preferred embodiment of the method of the first aspect, the convective turnover is promoted by exposing one lateral side of the passage to greater radiant, conductive or convective heat than the opposite lateral side. Preferably the radiant heat comprises angled incident solar radiation, or alternatively, the heat differential from heating or cooling is applied via a thermal element running longitudinally and next to the passage.

A heating or cooling mechanism may extend along one lateral side of the passage so that heat transfers promote convective turnover in the medium to expose otherwise shaded microorganisms to radiation. The heating (or cooling) mechanism preferably comprises a pipe in which is circulated fluid at a temperature greater or less than the culture and medium.

In the preferred embodiment of the method of the second aspect the process parameter control means includes at least one envelope located around part or all of the closed passage (or, where multiple co-extending adjacent passages are provided, the envelope(s) surround part or all of the grouped, multiple, closed passages). The closed passage is preferably enclosed within the envelope (and preferably multiple further passages also being enclosed side by side within the same envelope) and the process parameter control means includes a control space defined between the outside of the wall of the passage and the inside of the wall of the envelope, the control space being provided with an insulating material, the method including the step of selectively controlling radiation conduction and convection passing heat between envelope and passage, either way by selectively varying a property (such as the quantity, dispersion or quality) of the insulating material.

In this embodiment the insulating material preferably comprises a foam formed or maintained by selectively variably bubbling a control gas into a control liquid provided within the envelope adjacent the passage. The composition, state, pressure, volume and/or temperature of the control liquid and control gas media that provide the insulating bubbles or foam in the insulating envelope when required may be selectively varied. The foam provides a control of insolation and of insulation for the passage in which the microorganism bearing medium is moving by altering the amount of heat passing through the control space, and wherein the selective variation of the bubbling of the gas includes selectively varying at least one of the following: gas composition, gas volume, gas pressure, control liquid temperature, control liquid composition, and control liquid state.

Preferably both the microorganism bearing medium within the passage and the control space are pressurised separately at greater than atmospheric pressure. The pressure differential of gas and/or liquid between the passage and the control space may be selectively varied so as to control the cross sectional shapes of the passage and the control space, and optimise the shape and depth of the medium in the passage to suit changing external parameters or cultivation requirements. In this embodiment the control liquid within the control space provides hydraulic support to the side walls of the passage which are flexible and thereby promotes adoption by the walls of the passage of a more optimal cross-sectional shape for the microorganism bearing medium.

The envelope may be provided with condensate collection channels extending longitudinally partway along the inside of the envelope walls, the channels being arranged gently sloping to collect water condensing inside the envelope, the collected water being capable of providing sterile distilled water for use in the cultivation, harvesting and processing of the microorganisms, such as by enabling the replacement of water removed during harvesting with a safe, local equivalent.

The preferred process parameter control means (preferably the envelope) has provided externally thereof a base sheet or groundsheet sub-assembly providing an upper light reflecting surface located under and on both lateral sides of the passage and in proximity thereto so as to reflect incident photosynthetically active radiation (PAR) into the medium through the transparent walls and base of the passage, and to provide physical protective properties beneath the envelope when being located on, moved on, or removed from a supporting ground surface.

The passage is preferably defined by a flexible polymeric material composed of the material of the transparent wall and the envelope also comprises a tube composed of a flexible polymeric material of greater dimensions than the passage so as to enclose the same, the passage and envelope being initially flattened and provided in a form of a roll, being deployed by unwinding the roll, and thereafter being expanded to their operative configurations by supplying them with fluids. This preferred embodiment further includes servicing ducting or pipes through which fluids flow to support processes occurring in the bioreactor. The flexible polymeric tube constituting the envelope also encloses the servicing ducting or pipes, and the servicing ducting or pipes are composed of flexible materials and being in the roll and being deployed by unwinding the roll along with the passage, envelope, and any attachments. The passage when deployed from the roll and expanded preferably adopts a shape when the medium is moving therein of rounded cross sectional shape having a greater width than depth.

Preferably the microorganism bearing medium is moved through alternating zones of relatively higher and relatively lower insolation so that microorganisms are exposed to PAR in a pulsed manner, preferably for PAR exposure periods substantially less than one second and preferably somewhat greater recovery times of relative darkness whereby radiation can most efficiently be photosynthesised by microorganisms and reducing the likelihood or effect of photoinhibition in the microorganisms. The transparent outer envelope top surface may be provided with bands or stripes having PAR attenuating or excluding properties relative to the transparent parts of the envelope between successive bands, the bands extending generally transverse to the direction of flow of the medium, whereby the bands, their adaptive width and their relative placement define the width and separation of the alternating zones of relatively higher and relatively lower insolation within the passage.

In this preferred embodiment, the bands are composed of photovoltaic (PV) material electrically connected whereby incident solar radiation can be utilised by the PV bands to generate electricity for use in performing the method or for use in associated operations (or for sale) and, in the zones intermediate between successive bands or beyond them, the incident radiation can be used in photosynthesis by the microorganisms. The bands may be located within fluting made largely of transparent polymer film enabling airflow therethrough, so as to promote passive PV air-cooling to improve PV conversion efficiency and to help maintain the microorganisms within their most productive temperature range, the PV material comprising ribbons of transverse-curved material, attached to and/or acting as part or all of the support members within the fluting and projecting into the airflow passages of the fluting, the fluting being affixed to the top surface of the envelope of the bioreactor. The fluting, comprised of the envelope, the outer film of the fluting, and the support members of PV ribbon and other material are preferably able to be compressed in thickness, along with the bioreactor tubes, to improve transportability.

In one possible embodiment the ribbons, bands, strips or stripes are provided by bodies having shapes or configurations that are thermally responsive so as to provide relatively greater areas to intercept incident radiation upon being heated above a certain threshold. In one possible configuration, the bodies may comprise transverse-curled or rolled material having the property of progressively uncurling or unrolling upon exposure to a threshold and higher temperatures by incident radiant energy or increasing ambient temperature. The exposure of the transverse-curled ribbons, bands or stripes to a threshold temperature preferably commences uncurling by utilising differential coefficients of expansion of different materials forming part of the ribbon material, thereby reducing excessive insolation that would otherwise enter the medium and increasing the amount of electric power produced, and conversely, when lower insolation or ambient temperatures cool the strips, they curl up transversely, allowing more light to the medium and producing less power.

In this possible embodiment, the transverse-curled ribbons, bands or stripes are preferably generally S-shaped in transverse section when in the curled condition and wherein the different materials include a material with different (higher or lower) thermal coefficient of expansion to the PV or to another layer in the ribbon on one surface section of the S-shaped ribbon so as partly or wholly to uncurl that section upon being heated to or beyond the threshold temperature by incident radiation.

In an alternative possible construction, the bodies are movable from retracted positions towards extended positions in which they present greater surface area to incident radiation and hence greater interception of incident radiation upon exposure to a threshold and higher temperatures by incident radiant energy or increasing ambient temperature. The bodies may comprise wings and exposure of the bodies to the threshold temperature commences raising of the wings from retracted positions towards their extended positions by utilising differential coefficients of expansion of different materials forming mountings of the wings, thereby reducing excessive insolation that would otherwise enter the medium and increasing the amount of electric power produced, and conversely, when lower insolation or ambient temperatures cool the mountings, they lower the wings towards their retracted positions, allowing more light to the medium and producing less power. The mountings of the wings may form hinges to which the respective wings are mounted and the hinges may be each composed of different materials in laminar form with different (higher or lower) thermal coefficients of expansion so as to progressively open out and raise the wings mounted thereto upon being heated to or beyond the threshold temperature by incident radiation or ambient temperature increase. The mountings of the wings are preferably located on supports within an air space between transparent polymer films, the supports being initially in a collapsed condition for storage and, upon being installed, adopt an erected condition and ratchet arrangements prevent return to the collapsed condition.

Preferably the gaseous nutrients in the carrier medium are introduced, at least in part, to the medium by introducing gas by way of sparged microbubbles to the medium. The step of introducing gas preferably includes introducing carbon dioxide gas into the medium before the medium enters and moves in the tubular passage. The step of introducing gas to the medium may be performed at a processing station through which the microorganism bearing medium is circulated and from which medium flows into the passage and into which the medium after having passed through the passage and its return passage is returned, the step of introducing gas being performed in a treatment zone of the processing station by bubbling carbon dioxide in fine bubbles into the medium within the treatment zone. The step of bubbling carbon dioxide in fine bubbles into the medium within the treatment zone may be performed by a sparging member having raised-edge perforations through which carbon dioxide gas bubbles are introduced into the medium, the sparging member or plate being vibrated (e.g. by a piezoelectric or magnetostrictive transducer mechanism associated with the sparger) at a frequency, preferably a sonic frequency, to promote the ready release of carbon dioxide bubbles from the perforations enabling smaller or microbubbles to be generated.

The method may further include the step of releasing waste gas from the medium performed at a waste release zone of the processing station, and the waste release zone may be downstream of the point where the medium and microorganisms therein return from the passage and enter the processing station and may be upstream of both the treatment zone where carbon dioxide gas is introduced into the medium and of the zone where harvesting of the microorganisms occurs. At the waste release zone preferably there is performed a fluidising step in which the medium and microorganisms therein are agitated by an agitator which reduces viscosity or dethixotropises the medium and thereby to promote the release of gaseous waste (oxygen) from the medium into the gas body above it.

Preferably, the step of moving the medium along the passage comprises impelling the medium by an impeller at the processing station which propels the medium into which nutrient gas has been introduced at the processing station in a manner to promote laminar flow of the medium along the passage, and preferably the impeller and the agitator are coupled together so as to operate synchronously. The agitator has a vigorous action upon the medium and the impeller has a gentler impelling action.

In the preferred embodiment a gas phase exists within the closed passage above the level of the carrier medium, the gas phase within the passage accepting oxygen from the photosynthetic process in the medium below which oxygen is progressively collected in the treatment zone along with microorganisms for recovery and processing.

Preferably the processing station includes a harvesting zone in which microorganism bearing medium is sparged with a flow of harvesting gas which promotes froth flotation and concentration in the froth of microorganisms, the sparging gas being taken renewably from that immediately above the medium in the processing station and typically comprising an oxygen and carbon dioxide mixture of around a 90:10 ratio, together with lesser component gases such as water vapour and nitrogen. Preferably, the harvest sparger is vibrated at a suitable power level and/or frequency by a transducer for short time periods, preferably less than 60 seconds per day in total, so as to limit adverse effects on the microorganisms so that the vibration serves to clean the harvest sparging member and immersed surfaces within the processing station.

According to a third aspect of the invention there is provided a method of cultivating microorganisms, particularly microalgae or diatoms, in a bioreactor comprising the steps of:

entraining a culture of the microorganisms in a carrier medium having nutrients therefor and moving the medium along a closed passage at a sufficiently slow speed to enable laminar flow thereof along the passage, the passage having transparent walls through which the culture is irradiated to enable photosynthesis;

effecting convective turnover of the culture and medium as they flow along the passage by differentially heating the medium laterally relative to the flow direction so as to produce a generally helical flow of the culture and medium;

providing process parameter control means associated with the passage; and selectively varying the process parameter control means to thereby selectively control parameters or conditions of the cultivation and photosynthetic activity of the microorganisms moving within the passage and the processing centre.

According to a fourth aspect of the invention there is provided a method of cultivating microorganisms, particularly microalgae or diatoms, in a bioreactor comprising the steps of:

entraining a culture of the microorganisms in a carrier medium having nutrients therefor and moving the medium along a closed passage having transparent walls through which the culture is irradiated to enable photosynthesis, the transparent walls having externally thereof multiple bands or strips or ribbons of material having PAR attenuating properties relative to the transparent walls between successive bands, the bands, strips or ribbons extending generally transverse to the direction of flow of the medium, whereby the bands, strips or ribbons, their effective width and their relative placement define the width and separation of the alternating zones of relatively higher and relatively lower insolation within the passage;

providing process parameter control means associated with the passage; and selectively varying the process parameter control means to thereby selectively control parameters or conditions of the cultivation and photosynthetic activity of the microorganisms moving within the passage.

In this fourth aspect, the microorganism bearing medium is preferably moved through the alternating zones of relatively higher and relatively lower insolation so that microorganisms are exposed to PAR in a pulsed manner, preferably with the duration of each complete cycle of higher and lower PAR exposure being less than one second and preferably with somewhat greater recovery time of relative darkness than the PAR exposure time of each cycle whereby radiation can most efficiently be photosynthesised by microorganisms and reducing the likelihood or effect of photoinhibition.

The bands, strips or ribbons are preferably composed mainly of photovoltaic (PV) material electrically connected whereby incident solar radiation can be utilised by the PV material to generate electricity for use in performing the method or for use in associated operations (or for sale) and, in the zones intermediate between successive bands, strips or ribbons, the incident radiation can be used in photosynthesis by the microorganisms.

According to a fifth aspect of the invention there is provided a method of cultivating microorganisms, particularly microalgae or diatoms, in a bioreactor comprising the steps of:

entraining a culture of the microorganisms in a carrier medium having nutrients therefor and moving the medium along a closed passage having transparent walls through which the culture is irradiated to enable photosynthesis, the transparent top surfaces having externally thereof multiple bands or strips or ribbons having PAR shielding properties relative to the transparent areas between successive bands or ribbons, the bands or ribbons extending generally transverse to the direction of flow of the medium, whereby the bands or ribbons, their effective width and their relative placement define the width and separation of the alternating zones of relatively higher and relatively lower insolation within the passage, and wherein the bands or strips or ribbons are provided by bodies having shapes or configurations that are thermally responsive so as to provide relatively greater area to intercept incident radiation upon being heated significantly.

In this fifth aspect, the bodies preferably comprise curled or rolled bands, strips or ribbons of material having the property of progressively uncurling or unrolling upon exposure to a threshold temperature and higher temperatures by incident radiant energy. The exposure of the curled or rolled bands, strips or ribbons to a threshold heating effect of insolation preferably commences uncurling by utilising differential thermal coefficients of expansion of different materials forming part of the material, thereby reducing excessive insolation that would otherwise enter the medium. Alternatively, the bodies may be movable from retracted positions towards extended positions in which they present greater horizontal surface area to incident radiation and hence greater interception of incident radiation upon exposure to a threshold and higher temperatures by incident radiant energy or increasing ambient temperature. The bodies may comprise wings and exposure of the bodies to the threshold temperature commences raising of the wings from retracted positions towards their extended positions by utilising differential coefficients of expansion of different materials forming mountings of the wings, thereby reducing excessive insolation and heat that would otherwise enter the medium, and conversely, when lower insolation or ambient temperatures cool the mountings, they lower the wings towards their retracted positions, allowing more light and heat to the medium.

According to a sixth aspect of the invention there is provided a method of performing processing operations on a flowable feed material in a drillhole reactor, the flowable feed material being at least partially composed of a carrier fluid, and bio-mass material to be subjected to and to take part in the processing operations, the method comprising the steps of:

pumping the bio-mass material down the drillhole reactor by a substantial vertical distance to a working depth with the bio-mass material being mixed with the carrier fluid, the working depth being sufficient so that the feed material experiences sub- or super-critical pressure and temperature conditions whereby product organic chemicals are formed in, and/or dissolved from the bio-mass material in, the carrier fluid thereby forming a product bearing fluid;

directing the product bearing fluid to an upflow passage having a conformation which causes helical upward flow of the product bearing fluid so as to centrifugally induce stratification of different density components of the product bearing fluid;

separating a first component product from the upflow at least one takeoff location where the stratified first component product is cut from the flow.

Preferably the method of the sixth aspect also includes continuing the upflow of the product bearing fluid beyond the takeoff location(s) for the first component product whereby the consequent reducing pressure causes separation of a different dissolved component product from the product bearing fluid at a different and lesser depth in the drillhole reactor (and preferably causes serial separation to multiple different dissolved products at reducing depths); and separating the different component product from the upflow at least one different and higher level takeoff location where the stratified different component product is cut from the flow.

Further description and detail of aspects of the processing method according to this sixth aspect of the invention are described in the accompanying Appendix under the heading "Winwick Supercritical Extraction".

According to a seventh aspect of the invention, there is provided a method of performing processing operations on a flowable feed material in a drillhole reactor so as to produce dimethyl ether, the method comprising mixing bubbles of syngas in a carrier fluid and flowing the feed material thus formed to a working depth where exposure to a suitable catalyst results in the desired chemical reaction. Further detail of the various aspects of the method according to this seventh aspect, and further preferred or optional features, can be seen in more detail by referring to the accompanying Appendix under the heading "Winwick DMA Synthesis".

According to an eighth aspect of the invention, there is provided a method of performing processing operations on a flowable feed material in a drillhole reactor so as to synthesize ammonia from nitrogen and hydrogen mixed in and flowed downwardly in a carrier fluid, preferably to reach super-critical conditions at a working depth where, in the presence of an appropriate catalyst, the required chemical operation progresses. Further features of the method according to this eighth aspect, and further preferred and optional features, can be understood by referring to the Appendix under the heading "Winwick Ammonia Synthesis".

According to a ninth aspect of the invention, there is provided a method of performing processing operations on a flowable feed material in a drillhole reactor so as to produce nitric acid, the flowable feed material comprising ammonia and oxygen entrained in bubbles in a carrier fluid and flowed down the drillhole reactor to a working depth, preferably where decavitation of bubbles occurs and the required chemical reaction to produce NO (nitric oxide) and water progresses, the NO being used as precursor or feed reactant to produce nitric acid. Further features of the method according to this ninth aspect, and further preferred and optional features of the method, can be seen from the accompanying Appendix under the heading "Winwick Nitric Acid Synthesis".

BRIEF INTRODUCTION TO THE DRAWINGS

Possible and preferred features of the present invention will now be described with particular reference to the accompanying drawings. However it is to be understood that the features illustrated in and described with reference to the drawings are not to be construed as limiting on the scope of the invention. In the drawings:

FIG. 6 is a sectional view through one version of a fluting passage overlying the phytotubes;

FIG. 7 is a sectional view through the fluting of FIG. 6 when compressed;

DESCRIPTION OF POSSIBLE EMBODIMENTS OF THE INVENTION

Bioreactor Design

Figure 1:
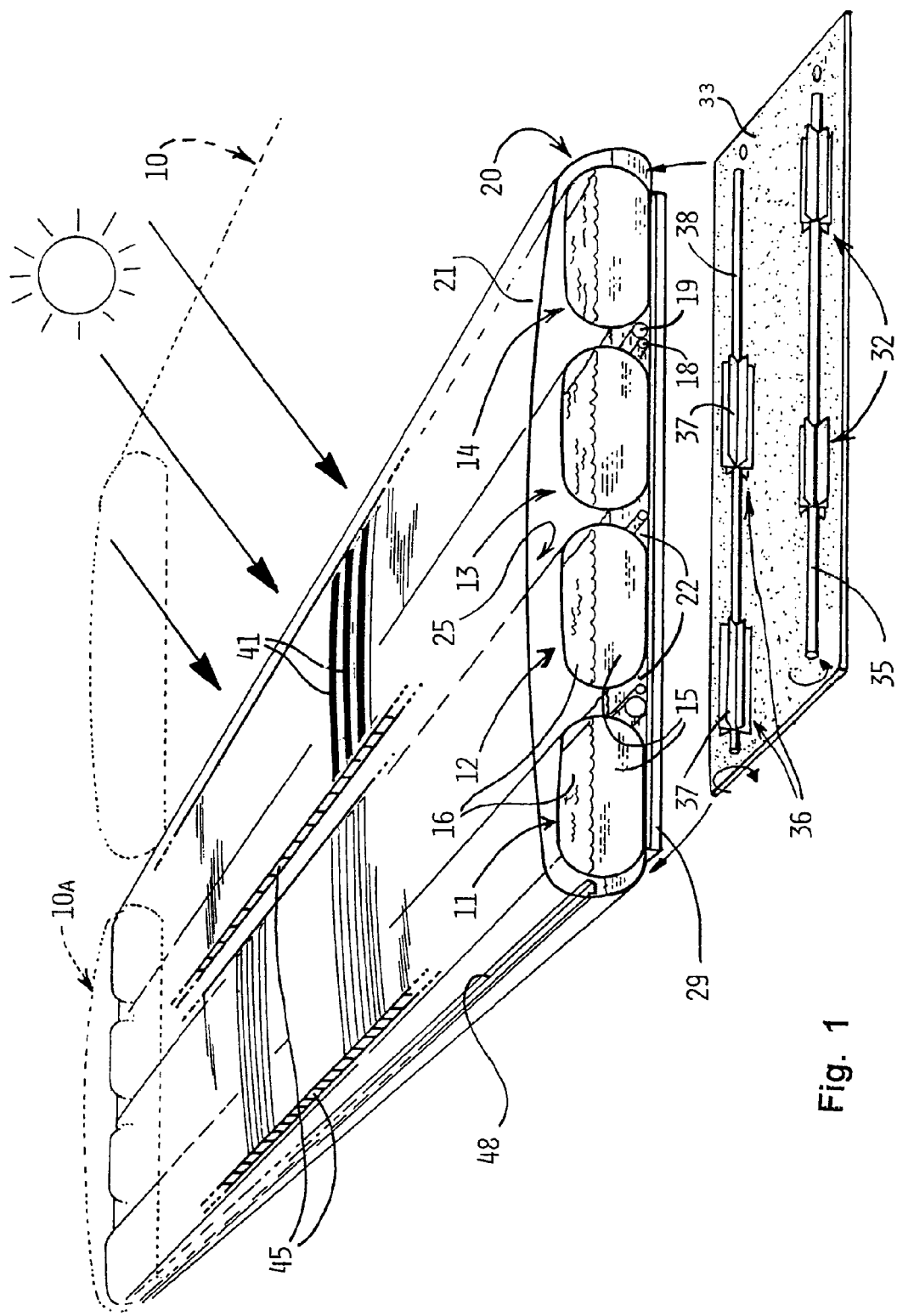
FIG. 1 is a schematic perspective view of a bioreactor embodying aspects of the present invention.

Winwick bioreactors and their associated impeller/harvester units, are designed to be mass produced as complete assemblies in a factory environment. The bioreactors are designed to be transported in flattened form on reels, together with their enclosed piping. Reels are unwound or rewound on-site using high, wheel-base tractors with reel management attachments. A bioreactor body 10 (see FIG. 1) comprises four, suitably separated, clear plastic film phytotubes 11-14 (the tubular containers for growing the microalgae, diatoms or other or phytoplankton in aqueous, growth media with room 16 for exhaust gas above), within a protective and insulating, outer envelope 21 and solar-adaptive fluting 45. All the tubes are produced by standard blow-moulding or extrusion techniques. The envelope 21 is temporarily sliced open lengthwise to facilitate the placement and fixing of the tubular contents, the fluting 45, the photovoltaic (PV) 41, the supporting members, and the protective/reflective groundsheet 29, prior to re-sealing.

The PV 41 is formed into complex, centrally-vented (to permit the exit of cooling air), transverse bands or strips of PV running inside fluting 45, crosswise along the bioreactor 10. In one version, two PV strips are attached edgewise to a third, non-PV supporting strip. These together form a combination strip that holds apart the external film or face of the fluting that is thus produced with the envelope forming or located at its lower part. When cold, the strips 41 in FIG. 6 are transversely curled to expose more of the algal medium to insolation. When warmed by progressively hotter sunlight, they uncurl to shade more of the medium. The uncurling is mediated by differential thermal expansion of the two sides of each strip, one side being composed of metal foil and/or dense, polymer foam or other material with different expansion coefficients to the other PV layer. In the alternative embodiment of FIG. 8, the PV strips or bodies 41 comprise wings and exposure of the bodies to the threshold temperature commences raising of the wings from retracted positions towards their extended positions by utilising differential coefficients of expansion of different materials forming mountings of the wings. The wings 41 are mounted on support walls or struts 150.

The shading caused by the strips means that each alga in the algal soup, moving along the bioreactor, under the motivational force of the rotating impeller blades, experiences rapid changes of dark and light. When these changes occur at sub-second frequency, i.e. the total dark-light cycle duration, the algae use the incident light most efficiently in photosynthesis and are less subject to photoinhibition caused by excessive light. The flashing effect appears to increase light-usage efficiency by nearly double, so less light is required for photosynthesis and more can be diverted to daytime power generation.

The striping solution is also one that is adaptable to different conditions and algal strains. Given flexibility in PV dimensions, both the PV strips and the spacings between them can easily be set differently at envelope assembly, whilst the frequency of light variation to each algal strain can be varied for a given spacing simply by changing the variable impeller speed.

The recently discovered antenna-reduction effect helps make the unusually large cross-section of the Winwick phytotubes efficient at biomass production, without requiring high turbulence, even for moderately high algal concentrations.

The elevated pressure in the phytotubes also serves to increase the concentration of nutrient gas in the soup, leading to increased productivity for most algal species.

The phytotubes contain the growing microalgae, nutrient media and gases. They are encased by a clear, outer plastic film tube, the envelope, that lies on, and is affixed to, the groundsheet. The gas in the envelope is chosen from $CO_2$, $O_2/CO_2$ or other filtered gas, whichever represents the best site choice when the factors of: heat retention, fire risk, maintenance workers, pests, lichen/mould growth and bubblemix contamination are considered together. The envelope encloses, and is fixed to, the phytotubes and to the internal piping, to keep them in place. Following deployment, it also encloses the bubblemix, gases, algae and algal growth media.

The separation distance between the inflated phytotubes 11-14, within the inflated envelope 21, is important for two reasons. First, it allows sunlight to penetrate the algal media 15 from several directions, thereby permitting the algal soup to be either denser in algae or the soup deeper. Second, as it allows sunlight (or the bed heating mechanism in cooler times) to warm one or other side of each phytotube 11-14, this results in slow, convective, circumferential flow or turnover in the soup as it passes along the phytotube passages. Combined with the low-energy, laminar flow lengthwise in the phytotubes 11-14 that is provided by the energy-efficient, rotating impeller blades 32, the resulting slow, helical flow along the bioreactor passages results in all the algae being periodically exposed to suitable amounts of photosynthetically active radiation (PAR). The periodicity, when combined with the striping effect of PV and possibly antennae-reduction, is designed to be sufficient for most algae in the soup to survive, grow and reproduce optimally, without the need for rapid, energy-intensive agitation, turbulent flow, costly artificial illumination, or the high, pipe resistance involved in small-bore, enclosed tubular bioreactors.

Selected, thixotrophic (i.e. having the property of becoming less viscous upon agitation) gelators added to the soup 15 mean that the algae are grown in a thin, tenuous thixotrophic gel. This or these additions have several major benefits. First, suspension in even a weak gel means that a far wider range of algal strains can be used—not just the few that remain well-dispersed and suspended in aqueous media. Therefore, algal strains with superior growth and lipid-producing abilities can be used, without the need for the turbulent flow and costly agitation required by prior proposed methods. Second, even a weak gel will tend to prevent dead or flocculating algae from either scumming at the surface or precipitating, under which latter action they become less available for harvesting. Third, it means that individual algae are less likely to be occluded from nutrients or sunlight and the effective exchange of gases that is necessary for their optimal growth. Fourth, use of a gel means that the energy used for agitation and propulsion can be very significantly reduced, principally because agitation for the purpose of aeration, mixing and dispersion is much less necessary. Fifth, vigorous or violent agitation is no longer required to ensure that algae do not plate, or scum out, on interfaces, thereby involving costly material losses, downtime and/or cleaning operations. And sixth, because using a gel and allowing additional, sunset-time oxidation of the soup, by means of reducing carbonation and/or aeration means that the high energy cost of impulsion, agitation and sparging at night-time, required by prior proposed methods, may be omitted entirely, or else very significantly reduced. This only-daytime power requirement also fits in nicely with the timing of solar electric power delivery from the local PVs.

Figure 2:
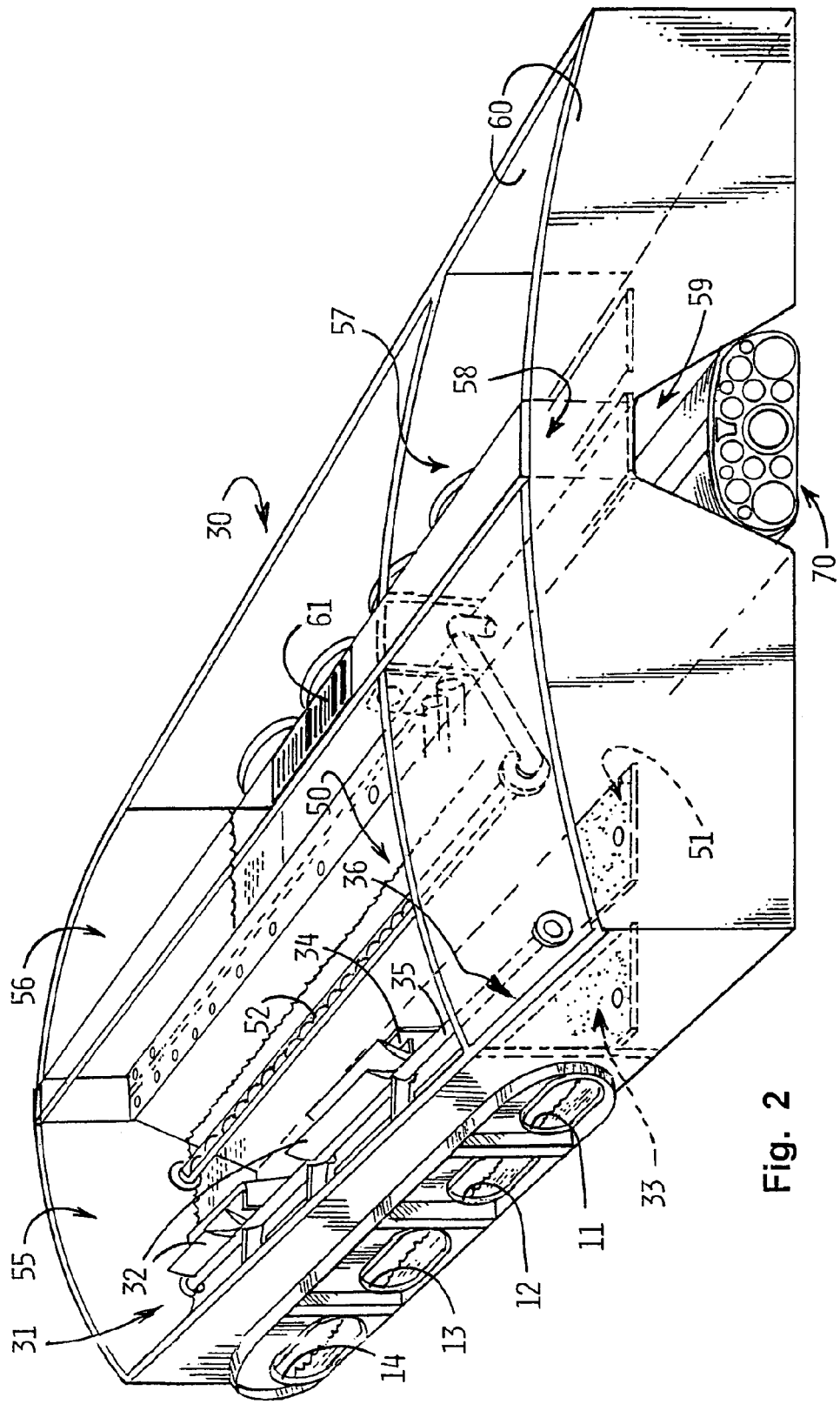
FIG. 2 is a simplified perspective view of a processing station embodying some aspects of the present invention.

Although sparging (generating bubbles of gas to travel up through the algal soup) happens at two places, at different rates, and for two different purposes in the impeller/harvester unit 30 (FIGS. 2 and 3), they both affect the productivity and dispersion of the algae, nutrients and waste products travelling in the soup in the phytotubes 11-14 and impeller/harvester unit 30. Small-bubble introduction is done by sparging means 33 in a treatment zone 31 to provide the algal stock with a sufficient amount of carbon dioxide nutrient to feed it during its passage through the length of one of two outgoing phytotubes 12, 14 and return phytotubes 11, 13 (until another active sparge plate is reached). The sparging in zone 31 also helps to remove the photosynthetic waste product of oxygen, which can otherwise retard algal growth. A gel that slows upward bubble movement to almost any desired extent, also helps to ensure that there is high utilisation of the (initially nearly pure) carbon dioxide content of the sparged bubbles by the algae, before the gas is largely lost to that above the soup, which is pumped off (typically, as a 90:10 oxygen:carbon dioxide mixture). Slow, small-bubble movement upwards in the weak gel also helps to ensure that, in the absence of turbulence, there are continuous micro-exchanges of small, transient groups of algae and of materials amongst different levels in the soup, thereby contributing to productivity. The helical motion of the soup in the phytotube also helps to prolong bubble residence time and hence gas interchange in the soup.

The bubbling of carbon dioxide in fine bubbles into the medium within the treatment zone 31 is performed by a sparging member 33 having raised-edge perforations through which carbon dioxide gas bubbles are introduced into the medium. The sparging member or plate 33 is vibrated (e.g. by piezoelectric or magnetostrictive transducer mechanism—not shown but incorporated in the small-bubble sparge plate) at a sonic frequency to promote the ready release of carbon dioxide bubbles from the perforations enabling smaller or microbubbles to be generated than would otherwise emerge naturally from perforations of such diameter in such a medium. Piezoelectric or magnetostrictive transducer produced vibration at higher power settings and/or frequencies or with the use of different transducers integrated with a harvest sparge plate 51 also serve to clean nearby surfaces and components of the impeller/harvester unit 30. The processing station includes a harvesting zone 50 in which microorganism bearing medium is sparged with a flow of harvesting gas through a harvest sparger 51, the flow of harvesting gas promoting froth flotation and concentration in the froth of microorganisms, the sparging gas being taken renewably from that immediately above the medium in the processing station 30 and typically comprising an oxygen and carbon dioxide mixture of around a 90:10 ratio, together with lesser component gases such as water vapour and nitrogen. The harvest sparger 51 is vibrated at a suitable power level and/or frequency for short time periods so as to limit adverse effects on the microorganisms so that the vibration serves to clean the harvest sparging member and immersed surfaces within the processing station. The processing station 30 also has a waste release zone 36 where waste gas is released from the medium. The waste release zone 36 is immediately downstream of the points where the medium 15 and microorganisms therein returns from the return passages 11, 13 and enters the processing station 30 and is upstream of both the treatment zone 31 where carbon dioxide gas is introduced into the medium and of the harvesting zone 50 where harvesting of the microorganisms occurs.

Figure 3:
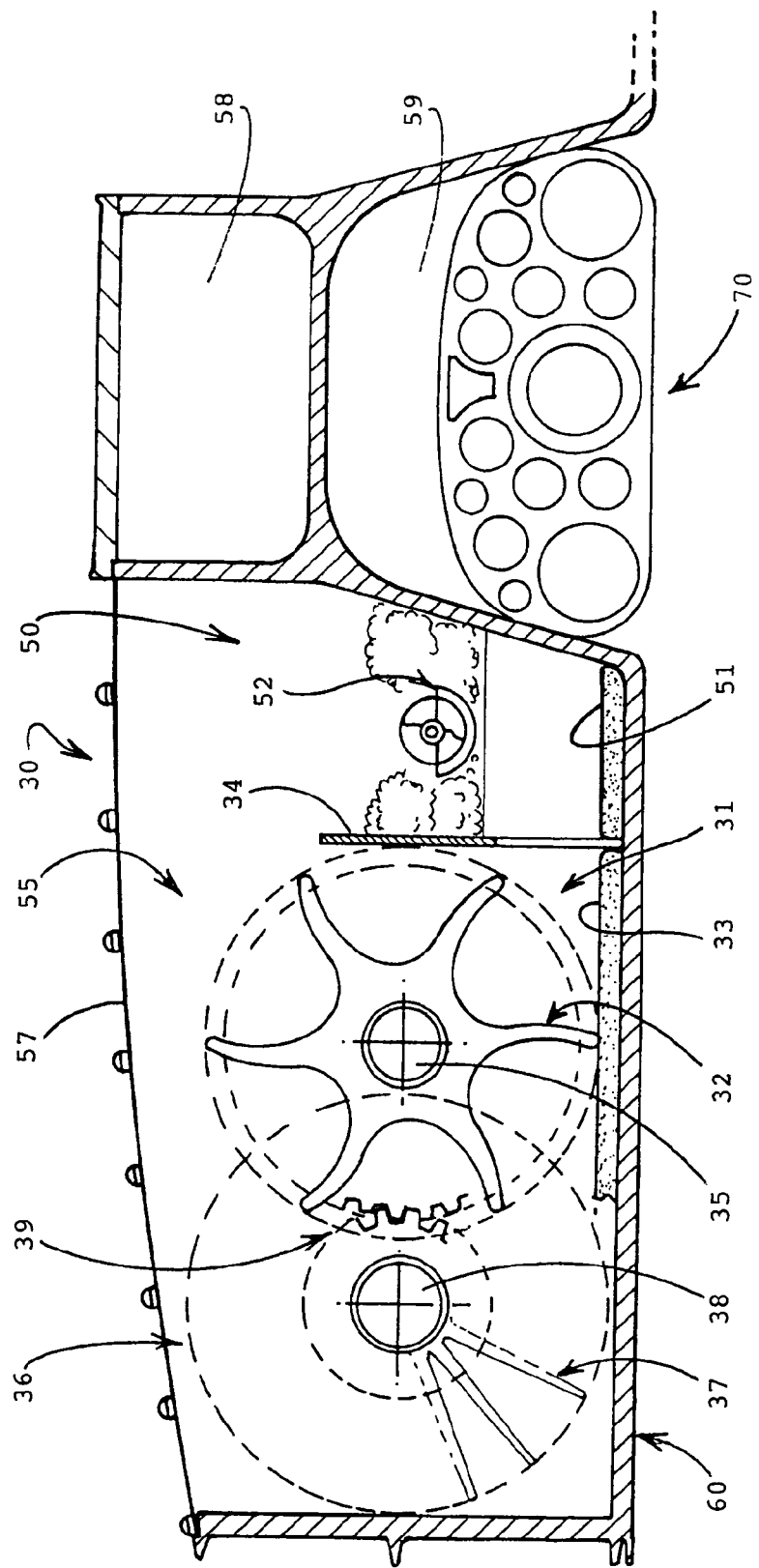
FIG. 3 is a cross-section through a portion of the processing station showing arrangement and action of the impeller and agitator.

At the waste release zone 36 there is performed a fluidising step in which the medium and microorganisms therein are agitated by agitators 37 which both impel the medium and agitate it to reduce viscosity or dethixothropise the medium and thereby to promote the release of gaseous waste (oxygen) from the medium into the gas body above it. The agitators 37 are on shaft 38 which is slave coupled to the shaft 35 by gears 39 so as to counter-rotate. In FIGS. 1 and 3 the agitators 37 are shown as having elongated blades but they may have multiple paddles or fingers to more effectively break up the gel and promote release of the gaseous oxygen.

Large-bubble sparging at a harvesting zone 50 may only occur at intervals when algal harvesting is desired, though continuous harvesting is also possible. Whilst small bubble sparging in treatment zone 31 uses $CO_2$, large-bubble sparging will recycle the $O_2/CO_2$ mix above the algal soup for its gas supply. This serves four purposes: it conserves CO2; it ensures an adequate gas supply for harvesting for all bioreactors, even when many are harvesting at once; it maintains the relative purity of the gases; and it means that correct pressures are easier to maintain in the system. Large-bubble sparging only has a minor effect upon the dissolved or small bubbles of gas remaining after agitation in the soup. Most of these remain in the soup after passing the harvester 50. $CO_2$ thereby continues to nutrify the algae until the microbubbles dissolve, rise to the surface and burst, or are conveyed away with the harvested algal slurry. Typically, by the time the microbubbles reach the surface, the algae and aqueous soup solution will have extracted most of their $CO_2$ content, replacing it with oxygen.

Large-bubble production by sparging means 51 is more vigorous or violent than small-bubble sparging. This is so because it is designed to maintain the agitators' break down of the somewhat crystalline or ordered, thixotrophic soup structure. A thin harvesting fluid is desirable to allow large bubbles to move easily and algae to be exposed to frequent gas-liquid bubble interfaces, to which they may loosely adhere and thus be carried upwards with the bubble to form a froth or algae-rich slurry that can readily be harvested. Another beneficial effect of this froth-flotation process is that the algal content of the froth, after the larger bubbles have preferentially burst, is many times greater than that in the original algal soup. Large-bubble sparging also has the effect of breaking up undesirable agglomerations of algae and of lipid, of providing additional macro-scale mixing, and even of partially cleaning the equipment. In metallurgical froth-flotation, surfactants are usually needed to ensure that the valuable mineral particles are selectively captured by the bubble surfaces, leaving behind the dross. As algae tend to have a natural attraction to bubble surfaces, the addition of surfactant may not be required. However, if its use does deliver a net benefit for harvesting a given algal strain, then the surfactant(s) chosen may be able to be one that has a secondary use as algal macronutrient or catalyst.

Similar, sparge plates 33, 51 in stainless steel are used to produce both small and large bubble sparging. The main differences being: the internal diameter and number of the sparge holes; the pressure and composition of the gas; the presence in 33 of piezoelectric transducers to vibrate the plate at sonic frequencies and promote release of microbubbles; the sparge plate locations; and transducers of the harvest sparger 51 that are vibrated at a higher power level and/or frequency for short time periods so as to limit adverse effects on the microorganisms.

To a reasonable maximum extent possible, the plant and other constructed elements are designed to be made from a single, cheap, available, adaptable, easily-formed, long-lasting and non-reactive thermoplastic. This maximises opportunities for economical re-use, recycling and transportation— and minimises material separation difficulty and other environmental issues and costs. Most plastic elements forming the bioreactor farm are currently designed to be made of endlessly-recyclable and cheap polythene. However, another polymer or polymers may end up replacing this, without adversely affecting the concept.

In FIGS. 6 and 7, attached to the top of the envelope 21 are bands or (broken) strips 41 of semi-flexible photovoltaic film, mounted in the airspace of two lengthwise sheets 46, 47 of fluted, transparent polymer 45. The slightly inclined, transverse fluting serves passively to air-cool the curved top of the envelope and the PV, thereby increasing its solar conversion efficiency. The PV strips are fixed to the supporting member to project into the air between the fluting film or coating 46 above and the envelope 21, or lower sheet 47 below to keep the strips relatively cool and thereby reasonably efficient. The air cooled fluting also serves to reduce unwanted heating to the bioreactor phytotubes 11-14 and the algal medium 15. When cold, the strips 41 are curled up to a fraction of their fully deployed width. However, as their surfaces are laminated with a different coefficient of expansion materials (e.g. a dense, foam polymer, glass ceramic or metal foil), when the composite strip is warmed by the sun, it uncurls proportionately in response to the heating, thereby increasing the depth of the fluting 45 (raising the upper surface to the level 46A) to allow more air to circulate and increasing the extension of the PV thereby to shade more of the algal media 15 from excessive insolation and heat, and producing more PV electric power.

Referring particularly to FIGS. 6 and 7, the fluting 45 includes in the air space between the upper sheet 46 and the lower sheet 47, ribbons or bands or strips of curled S-shaped PV and supporting materials. The PV material 42 on one part of the S has a lower thermal coefficient of expansion to 43 of the bi-layered support material 40, 43 and a higher one than 44 on the other part of the S. Material 43 has a higher coefficient of expansion than does 40 on the same supporting member. These differences mean that the ribbons uncurl and the fluting expands at the same time under increasing temperature, and vice versa. In this heated condition, the uncurled strip 41 intercepts a greater proportion of the incident radiation thus shielding the medium moving beneath the lower sheet 47. The space between the end 41B of the strip 41 and the next adjacent end 41AA of an adjacent strip remains as a window for incident PAR to irradiate the medium and microorganisms moving past that space. Conversely, when there is less incident radiation and consequently less solar heating, the ends 41A, 41B of the strip 41 progressively curl up towards the S-shaped configuration shown in FIG. 6, thus allowing greater insolation of the medium moving beneath sheet 47. The width and positioning of adjacent strips and the extent by which they uncurl are the factors that principally determine the proportion of the insolation transmitted to the algae and that is used to produce power.

In FIG. 7, the fluting 45 is shown compressed (which would be effected when the strips 41 are heated and in their uncurled condition) so as to enable the fluting to be formed into a roll, desirably with the sheet 47 already attached as the upper surface of the envelope 21.

Figure 8:
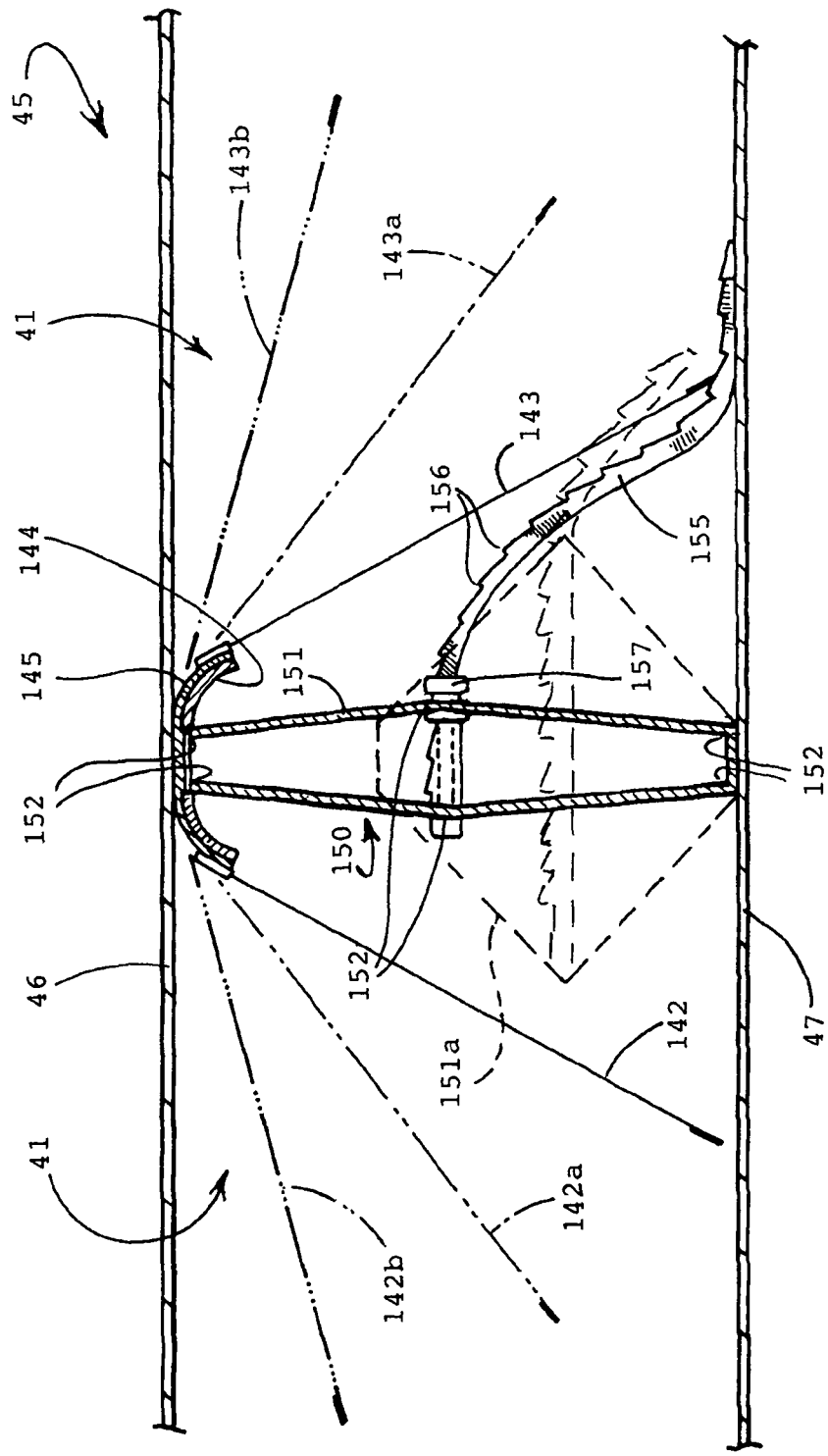
FIG. 8 is a sectional view through an alternative system for shading medium in the bioreactor responsive to radiation intensity or ambient temperature.

In FIG. 8, the PV strips or bodies 41 comprise wings 142, 143 shown in solid line in retracted positions. Exposure of the bodies to a threshold temperature commences raising of the wings 142, 143 from their retracted positions towards their extended positions 142a, 142b and 143a, 143b by utilising differential coefficients of expansion of different materials 144, 145 forming mountings of the wings. The raised positions 142a and b, 143a and b of the wings shown in broken lines intercept incident radiation that would otherwise enter the medium and also increase the amount of electric power produced. Conversely, when lower insolation or ambient temperatures cool the mountings 144, 145, they lower the wings 142, 143 towards their retracted positions, allowing more light to the medium and producing less power. The mountings 144, 145 of the wings form hinges to which the respective wings are mounted. The hinges are each composed of different materials in laminar form with different (higher or lower) thermal coefficients of expansion so as to progressively open out and raise the wings mounted thereto upon being heated to or beyond the threshold temperature by incident radiation or ambient temperature increase.

The fluting 45 in FIG. 8 can be initially flat for transport or storage The central support 150 shown erected is composed of a hexagonal section 151 of plastics material with flexible hinged corners 152 and strap 155 with a ratchet bearing face 156. When initially collapsed, the section 151 has a low height and walls 46, 47 are close together. When the fluting 45 is first deployed e.g. from a rolled up condition, an airfoil effect over the top face 47 lifts the face 47, the hexagonal section 151 erects and passes through a partially erected condition shown in broken line at 151a in FIG. 8 to its fully deployed position shown in solid line at 151. During erection the strap 155 passes through an aperture 157 in the centre of the section 151, and the ratchet teeth 156 prevent the central support 150 from collapsing again, thus making the fluting 45 effectively self-erecting.

Commercial, anti-condensation coatings are provided to appropriate surfaces of the envelope 21, phytotubes 11-14 and even fluting 45, with the coatings being selected from ones having little effect on PAR transmission and (for the internal surface of the phytotubes) do not encourage algal adhesion. A Teflon™ or FEP coating may be used to reduce such adhesion where a given algal strain in use or prospect has that tendency.

Should potential conditions make it advisable, the open ends of the flutes 45 may be covered with strips of transparent, thermoplastic flywire mesh the better to secure the fluting to the adjacent fluting and to the envelope at the other open end and to hinder the ingress of detritus and insects.

The PV fluting system serves a fourfold purpose: shielding the algae and plastic tubes from excessive or damaging heat and insolation (sunlight); producing solar electric power to run the machinery and to generate excess power for sale; strengthening the envelope around its area of prime, near-horizontal exposure to radiation and weathering; and providing the alternation of light and dark to the moving algal soup that is necessary to gain optimal radiation usage, without photo-inhibition. The width of the strips 41 and the intervals between them is so calculated as to provide the required, sub-second light and longer dark-recovery intervals between light exposures that result from the modest velocity of the soup 15 along the bioreactor 11-14 that is, in turn, provided by the relatively slow-spinning impeller blades 32.

Any of several existing commercial or near-commercial brands of flexible, preferably thermoplastic polymer, PVs may be employed. The width and spacing of PV strips 41 along the envelope 21 would be selected at assembly time in order to suit the climatic conditions of the site and the algal strains for which the bioreactor 10 was being built.

Inside, attached to one (or to each) side of the envelope 21 and sloping down towards the impeller/harvester unit 30 are narrow plastic channels 48 to collect and conduct water that condenses on the internal, upper surface of the envelope 21 to valves (not shown) which, when open, remove the water so distilled from the protective, salty bubblemix 22 lying in the bottom of the envelope tube. When the valves are shut, the distillate simply overflows back into the bubblemix 22. Water for the original bubblemix mixture will usually be sourced from local, possibly brackish bore water. This, like the water for the algal media 15 itself, if desirable, be sterilised by one of the heat sources, such as heat from a nearby solar pond, or geothermal or hot fractured rock power generating facilities (known as HFR), to ensure that no unwanted, living organisms or spores remain viable. The bubblemix 22 develops its wildlife-repellent, briny nature from the distillation process that concentrates the brine. Its long-lasting, bubble-forming properties are given it by the addition of bubblemix concentrate, which may be a form of detergent and/or gel. A biocide will normally be another component of the bubblemix, to keep it transparent and free of organisms.

Distilled water from the distillate channels 48 that is not recycled to the bubblemix 22 is directed to the impeller box 55, 56 or can be pumped into the fresh/distilled water main. Water from this main pipe can be used to increase or replace phytotube liquid volume removed by harvesting and/or to reduce the salinity of the algal media 15, or the bubblemix 22.

The distillate channels 48 and valves therefore act as essentially passive, solar-powered salinity controllers and as economic producers of distilled water for the algal soup or other purposes. The condensation process also serves as a mechanism to transfer excess heat from the bioreactor contents to the envelope, from whence it moves readily to the atmosphere.

Distilled water for a variety of uses may also be stored locally by the system, typically within a double hull of the impeller/harvester casing, should that be desirable. A sensor and pump may be activated to remove such an accumulation of distilled water to a central, sealed reservoir. Alternatively, the double hull can be used to hold brine or concentrated nutrient solution to deter wildlife seeking fresh water. Such a water ballast would also serve to stabilise the impeller/harvester unit 30 when otherwise empty. It could be useful when new bioreactors were being set up, as water ballast might avoid undesirable movement of the impeller/harvester unit when a bioreactor 10 was being unrolled from it.

Changing the salinity, sodicity, pH, temperature, level, pressure, algal strain or nutrient concentration of the algal media 15 or bubblemix 22 may be done by pumping the relevant material from or to a mains pipe—an action that is usually mediated by the local microcomputer and implemented by equipment in the impeller/harvester unit 30. Initiation for this is directed by locally-stored program or is done remotely from the facility control centre, either by pre-set computer program or over-riding human intervention, possibly requested on location by the installation or maintenance staff.

Four types of tube reside within the envelope 21: the phytotubes 11-14, distillation channels 48, bubblers 18 and warming tubes 19. The three, porous bubbler tubes 18 are used to produce masses of bubbles from the briny bubblemix 22 in order to create a semi-stable foam that fills the control space 25 of the envelope 21, thereby insulating the algal soup from excessive heat, cold or insolation. The warming tubes 19 bring (typically waste) warm water from either: industry; hot fractured rock (HFR) geothermal sources (typically, after its steamy, higher temperatures have already been used for other purposes); ordinary geothermoclines; warm bores; or solar ponds. When the warm (or else cold, if bioreactor cooling is required) water pumps and/or valves are actuated, warm water flows in two pipes 19, through the bubblemix 22, in the envelope 21, between each of the two pairs 11, 12 and 13, 14 of phytotubes. This both warms (or cools) the bed of the bioreactor and maintains algal, temperature-dependent activation levels. At the same time, it sets up circumferential convection currents in the algal soup 15, thereby replicating the beneficial effect of warm-season, angled sunlight during cold or overcast times. The two warming tubes 19 are joined at their far ends, to form a U-shaped loop. Local, microcomputer controls can reverse the flow periodically in these to ensure that the different pairs 11-12 and 13-14 and sections of phytotube are warmed approximately equally. Afterwards, the now-cooled water is pumped by return pipe to the original heating or cooling facility for re-use.

The far end 10a of the bioreactor 10 is made of hollow, rotomoulded polythene. Its form is roughly that of a flaccid ellipse, freestanding on its long, flatter edge and supported on stability supports projecting from its lower, long edge. Its cross-section resembles a thin "witches hat" with five extra protrusions on one side, by which to attach the envelope 21 and the four, phytotube 11-14 elliptical ends. Subsequent to the rotomoulding operation, the centres of the phytotube formers on the rotomoulded item are cut out to allow lengthwise and transverse passage of the algal soup. The barcode of the impeller/harvester unit, plus an endpiece code, are heat embossed in large characters on the exposed side of the bioreactor endpiece for identification and navigation purposes. The central database associates each barcode with the farm, access road, rectangle, layout, kytail, sequence, impeller/harvester, bioreactor, GPS location, age, contents and status of the unit. This information is remotely available to maintenance workers, as are their team members' GPS positions, schedules, timing, tech information, guidance and communications.

The bioreactors 10 in one production-scale embodiment envisaged can be initially designed as being 100 m long, 2.5 m wide and 0.55 m high at the slightly curved apex. The bubblemix 22 is normally only around 0.13 m deep, but this can be increased to as much as 0.30 m in order to cope with less-level terrain, or to help resist overheating or damaging bioreactor movement by way of floodwater or cyclone The depth of the bubblemix 22 is what allows the phytotubes 11-14 to be filled as deep as they are with soup, and to become as round in cross-section as they are, without the enclosing membrane of which the tubes 11-14 are composed coming under unnecessarily high stress. It also means that the phytotube membrane only has to withstand a pressure of water from 0.27 less 0.13 equals 0.14 m depth, rather than the full 0.27 m depth of the soup 15 in the phytotube 11-14. Each phytotube 11-14 has a similar, though rounder, cross-sectional shape to the envelope and has dimensions 100×0.5×0.4 m. When inflated, phytotubes have spacing between them of around 0.12 m. This allows sunlight to penetrate between them and perhaps sideways into the phytotubes. Some rays are reflected from the underlying, aluminised groundsheet 29 and penetrate into the lower, outer levels of the algal soup 15 on both sides. Normal operating depth for the algal soup in the phytotubes is 0.27 m. However, they can still operate from between depths ranging from 0.15-0.37 m. The normal operating depth has sufficient leeway as to be able to accommodate minor land surface irregularities that occur along the contour of the flat, natural (or possibly levelled) surface on which the bioreactor is laid, whilst still providing an adequate channel depth for soup transport. The extended range of depth allows accommodation to somewhat greater landform variations. At normal operating depth, there is a space 16 of around 0.13 m above the algal soup 15 in the phytotube 11-14 for gas accumulation and transport. The gas in space 25 of the envelope 21 and phytotubes is lightly pressurised to create the desired shape by means of the gas pumps (not shown) in the impeller/harvester unit 30 or that of the pressure in the inlet and outlet pipes. The pressure in the phytotubes 11-14 is maintained slightly higher than that of the envelope 21, in order to maintain the desired cross-sectional shape. This also serves slightly to increase the CO2 concentration in the soup, and thereby to increase algal productivity.

The volume of gas in each type of tube 11-14 and 21 can be altered temporarily, to allow easier, or less potentially damaging, access for repairs, maintenance and replacement. On partly deflating the bioreactor envelope 21 and/or phytotubes 11-14, weighted, padded bars placed across them is usually sufficient temporarily to isolate the bulk of their contents, with little chance of rupture or wrinkle formation. When replacing a bioreactor 10, the tubes 11-14, 21, 18, 19 may be rolled up from the far end 10a, pumping off the contents, until they can be tied and cut like umbilical cords. The replacement tubes can then be attached over the nubs of the previous ones, or replacing them. Whereupon the nubs can mainly be cut away and removed via the inside the impeller/harvester unit 30.

Impeller/Harvester Design

Each impeller/harvester unit 30 (see FIGS. 2 and 3) has a bioreactor 10 attached to both ends. There are four, distinct, internal chambers in an impeller/harvester unit, two of which 55, 56 each share the algal soup and gases with its own bioreactor, a third 57 for the drive box containing shared machinery, and a fourth 58 as the shared internal conduit located over the external pipe bundle 70 that transports external fluids and which conduit is sealed by a plastic board embossed with the unit's barcode 61 for easy aerial and ground-level identification. The unit also has a trapezium-shaped tunnel 59 running under its middle. This straddles the pipe bundle 70. Pipe-bundle offtakes typically lead through holes in the roof of the tunnel 59 to the relevant chamber and item of equipment. The tunnel 59 is also used to connect services to a surveillance pole and part-buried computer post (neither shown).

The housing or body 60 of the impeller/harvester 30 is made of rotomoulded, hollow polythene or similar, thermoplastic polymer, which may be of recycled bioreactor or impeller/harvester material. It is tank-like and has a rectangular base and a curved, openable top 57 which is covered by the barcode plank 61 and twin, separately removable, clear plastic covers, sealed at their edges by strapping, fasteners and seals. The impeller/harvester body's outer dimensions are approximately 2.5×2.2×0.9 m.

Each chamber 55, 56 that connects to a bioreactor 10 has two injection-moulded polythene, drive shafts 35 and 38, one say 35 being slave-driven from the other 38 by gear cogs 39. The shaft 35 mounts a spaced pair of multi-bladed, polythene impellers in the form of paddlewheels 32, having paddles or blades shaped rather like some curved turbine blades. The shaft 38 mounts a spaced pair of multi-bladed, polythene agitators 37 in the form of drums with knife-like radial protrusions shaped to create agitation in the medium without splashing. Each paddlewheel impeller 32 and agitator 37 is located non-adjacently at the mouth of a respective one of the four phytotubes 11-14. Underneath almost the entire length of the impellers 32 and agitators 37 is a flat, small-bubble, sparge plate 33 made of stainless steel (see FIGS. 2 and 3) and incorporating piezoelectric transducers. This sparge plate 33 provides tiny, carbonating bubbles to the algal soup.

At a waste release zone there is performed a fluidising step in which the medium and Microorganisms therein are agitated by the agitator 37 which reduces viscosity of the medium or dethixotropises it and thereby promotes the release of gaseous waste (oxygen) from the medium into the gas body above it. The movement of the medium along the phytotubes 12, 14 is caused by the two impellers 32 which propel the medium into which nutrient gas has been introduced by sparger 33 in a manner to promote laminar flow of the medium along the passage. The impellers 32 and the agitators 37 are coupled together so as to operate synchronously, with the agitators 37 having a vigorous action upon the medium and the impellers 32 having a gentler impelling action.

Baffles 34 permit only soup from the lower half of the soup body in chamber 55, 56 to reach the two expelling impellers 32. This ensures that little of the froth produced by the large-bubble harvesting sparger 51, set further back, is destroyed before it can bubble over into the open Archimedes screw channel 52 above, which does the harvesting. Two drive belts (not shown), powered by either or both of twin electric motors (not shown) in the common drive box in the machinery chamber 57 power all drive shafts in the unit. Solenoids controlled by the unit's microcomputer, and over-ridable by central control, engage individual valves, pumps, drives and devices.

The sparge plates 33, 51 type have dimensions approximately 2.3×0.018 m with widths of 0.6 and 0.3 respectively. They are constructed of two sheets of approximately 0.5 mm thick stainless steel sheet, welded together at the down-tapered edges and spot welded at points where the lower sheet is dimpled upwards to maintain a separation of 15-20 mm between the plates. In the small-bubble sparge plates 33, piezoelectric transducers are sealed into some of the dimples. Transducer height may require some protrusion of the upper plate surface. One or more reinforced plugholes admit a removable nozzle that is joined to an offtake pipe containing pressurised carbon dioxide gas. Prior to welding, the upper sheet of the sparge plate has many holes of controlled diameter and pattern made in its surface, with raised and smoothed edges round the holes. This is done so as to minimise the chance of algae and grit clogging the holes. In the small-bubble sparge plates 33, the holes are preferably smaller than the smallest algal strain used. The large-bubble sparge plates 51 tend to be self-cleaning. Electrically-driven ultrasonic piezoelectric transducers in the large-bubble sparge plate 51, vibrating at about 42 kHz, perform regular, computer-controlled cleaning of plates, nearby equipment and impeller box. The small-bubble sparge mounts a low power, low frequency sonic transducer that facilitates the formation and detachment of microbubbles from sparger 33.

In the machinery chamber 57 drive box are located motors, pumps, and valves. If feasible using commercially-available equipment, all gas is to be directed through a universal gas valve and pumped, if pumping is necessary to increase the pressure, by a single gas pump. Similarly, all liquids, except the algal slurry, are to be directed through a universal liquid valve and pumped, if necessary, through a single liquid pump. The flushing of pumps and valves to keep them clean and the materials they convey uncontaminated, is controlled by the microcomputer.

Pipe Bundle

Figure 4:
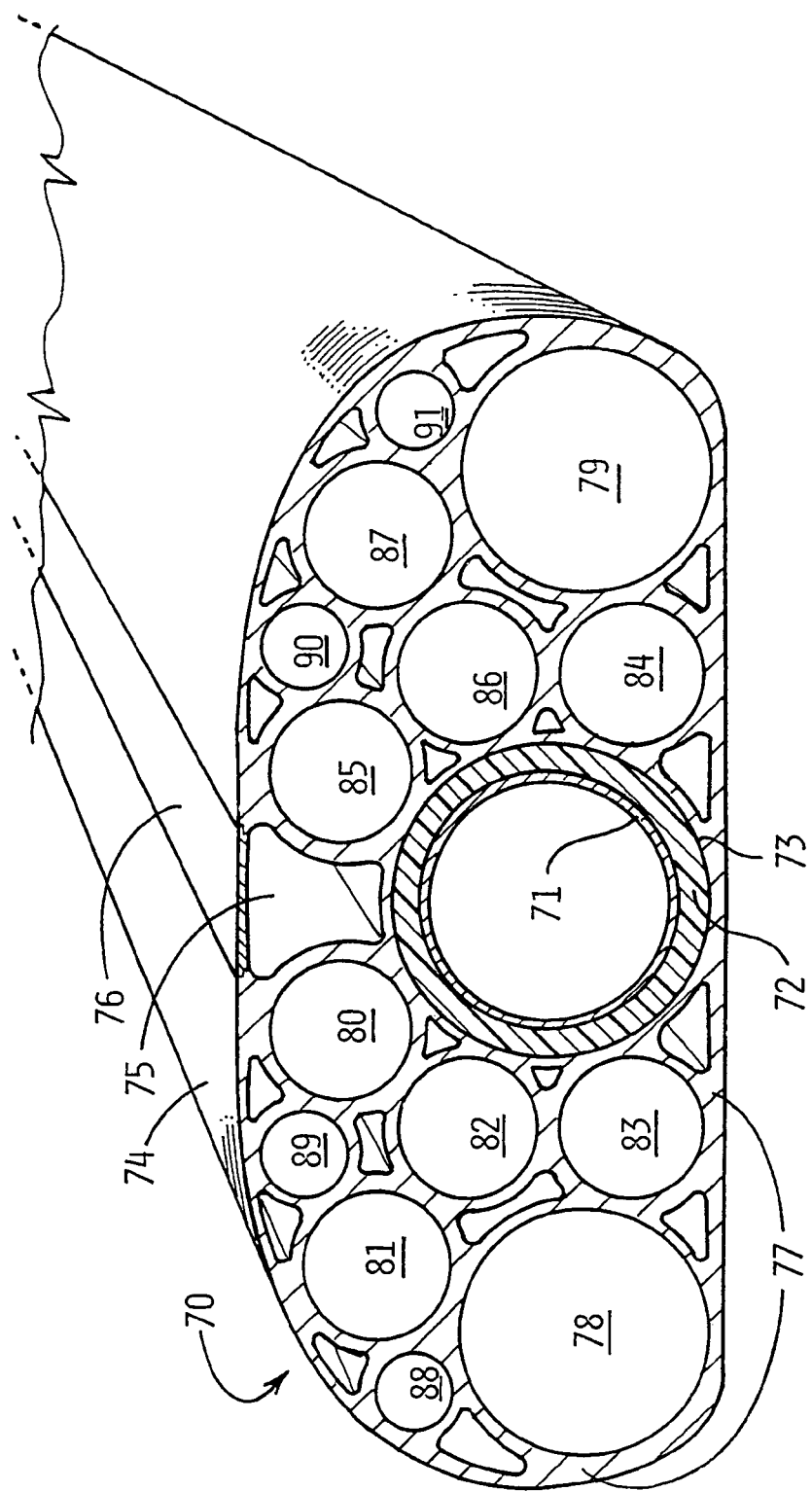
FIG. 4 is a cross-section through a pipe bundle for supply of working fluids and off takes in a system embodying some aspects of the present invention.
Figure 5:
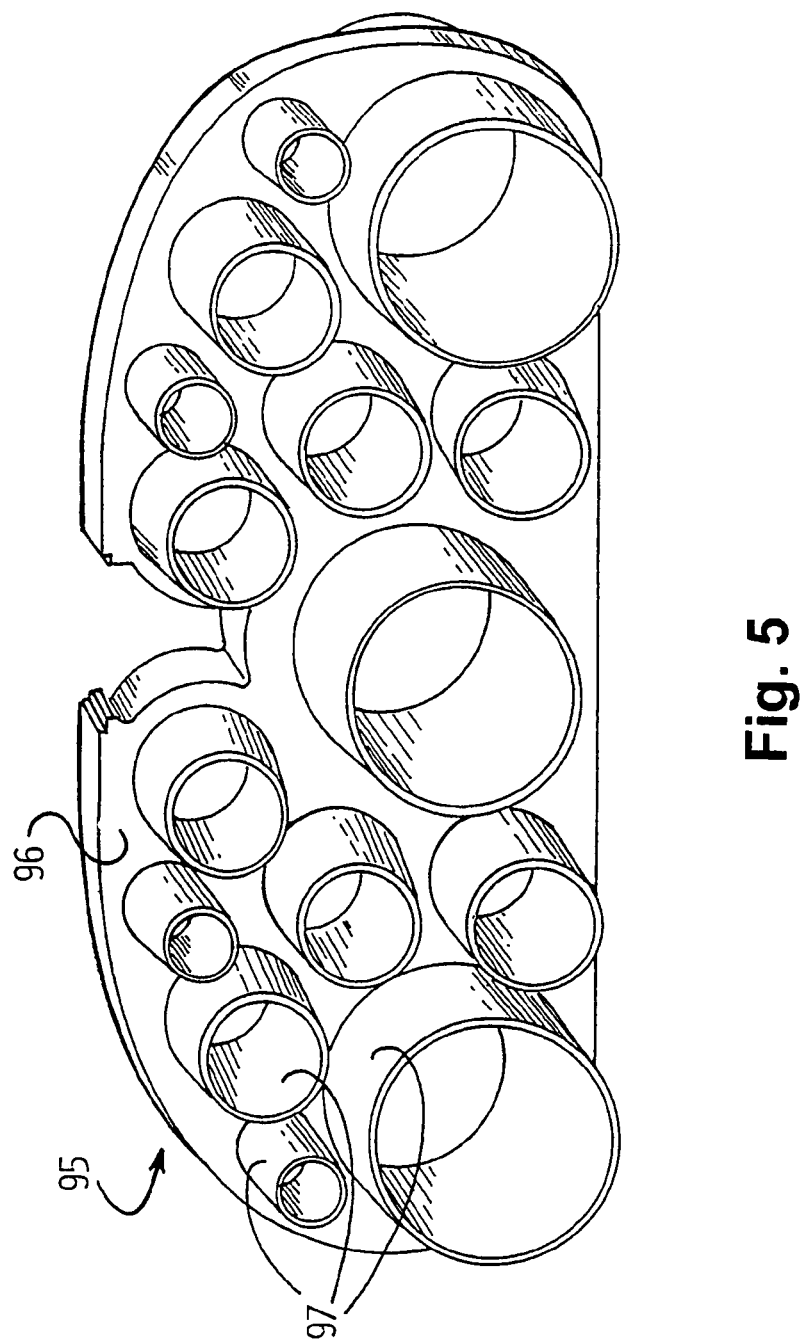
FIG. 5 is a perspective view of a pipe bundle joiner for use with the pipe bundle of FIG. 4.

For purposes of easier management, neatness, standardisation, mutual protection, cost and insulation, the different pipes, fibres and wires required to service the bioreactors 10 are combined in their own cluster or pipe bundle 70—see FIGS. 3 and 4. The general-purpose bundle connector plate 95 in FIG. 5 is used to connect both standard pipe bundle 70 lengths together, as well as offtake bundles to standard pipe bundles. The connector 95 takes the form of a connection plate 96 having some fifteen, joined, hollow, male, pipe connectors 97 on both sides. It is formed by injection moulding high-density polythene (HDPE). The ordinary pipe bundles 70 are simply pushed against their matching plate 96 and over the male connectors 97.

The contents of the fifteen pipes in the pipe bundle 70 are as follows. The three largest diameters contain: hot water in 71 within covering 72, cooled return water in 78, and algal slurry in 79. The eight middle-sized pipes contain: algal soup in 80; nitrogenous algal soup in 81; sterilised, typically-brackish bore water in 82; carbon dioxide ($CO_2$) gas in 83; 90:10 oxygen O2/$CO_2$ gas mix in 84; distilled or sterilised fresh water in 85; nutrient water from the anaerobic digester (possibly plus some replacement gel mix) that has subsequently been sterilised in 86; and brine or bubblemix brine in 87. The four smallest diameter pipes 88-91 contain: nutrient mixes #1, 2, 3 or 4; or inoculants of seasonal or replacement algal strains that temporarily replace the contents of one or more of the nutrient mixes. Any replacement may if required be preceded by a flushing process with distilled water. The nutrient mixes themselves are so specified that they can be combined in various ways to make many different, algal media, nutrient mixes. Each can also be temporarily replaced to address a particular situation. The contents of the conduit 75 include any insulated wire, fibreoptic or other cable that is necessary to conduct power or communications.

Processing Plant

Processing plant includes various, relatively standard, chemical engineering units, such as liquid, slurry and gas pipes, heat exchangers, filtration plant, centrifuges, pumps, valves, sensors, actuators, fractional distillation towers, an anaerobic digestor, and storage reservoirs or tanks. The presence of gelators will tend to improve slurry piping mechanics.

Novel plant comes about from newly perceived opportunities (described in connection with FIGS. 9 and 10):

to implement chemical and physical processing methods underground in a deep drill hole so that the elevated pressures experienced by a flowable feed material comprising flowable carrier medium, reactants, catalysts and promoters result from the ambient pressure experienced at substantial depths below ground surface level, the use of heat for promoting the processing operations carried out at depth being in part derived from geothermal heat derived typically from hot fractured rock (HFR) geologic formation utilising other deep drill holes created to access the hot rock formations deep below ground surface level. The processing operations are carried out within processing apparatus lowered from ground level into processing drill holes to the required depth for achieving the desired temperature and/or pressure conditions for the respective processing operations;

use of HFR, hydrocarbon extraction and solar resources and infrastructure for chemical process engineering and algacultural purposes;

use of the cultivation of algae to produce a 90:10 $O_2$:$CO_2$ gas mix that can be combined with local methane to produce methanol most economically for on-site transesterification of algal lipids or sale. Any excess oxygen may also be separately saleable for piped industrial use particularly where exchanges for carbon dioxide are both feasible and desirable;

use of fast moving high boiling point liquid such as residual fuel oil as carrier for reactant bubbles and catalysts, and to use the high pressures at working depth in the drill hole to generate methanol from stoichiometric volumes of methane, steam, oxygen and carbon dioxide;

use of an aqueous slurry of reactants including algal cell or biomass and other carbon based substances and oxygen, so that when the slurry reaches the working level in the drill hole reactor, supercritical conditions enable synthesis of syngas comprising a mixture of carbon monoxide (CO) and hydrogen ($H_2$);

use of the pressure experienced deep underground to carry out Haber ammonia synthesis in a drill hole reactor using a feed material of suitable catalytic substances added to the reactants comprising suitable mixed gas in bubbles in an oil carrier to achieve a variant of the Haber synthesis of ammonia from hydrogen and nitrogen;

use of the pressure experienced deep underground in a twin pipe to carry out Fischer-Tropsch syntheses using a feed material of suitable catalytic substances added to the gas bubble reagents to promote any of several Fischer-Tropsch processes includes ones for alkane production from syngas.

Process Engineering Using HFR

Extracting heat from HFR typically requires making deep, and consequently high-pressure drill holes into hot, fractured rock formations. The same heat and/or pressure, when combined with input reactants, suitable catalysts and processing steps, can be utilised to produce desirable physical and chemical changes in materials, such as lysis of algal cell walls and the consequent release of lipids or the production of methanol or other compounds requiring the application of heat and/or pressure for their synthesis. Processing steps using HFR are likely to be far more economical and friendly to the environment than are traditional methods that rely on fossil fuel and high-pressure pumps to achieve elevated temperatures and/or pressures.

Processing microalgal cells to produce biofuels and co-products involves overcoming several physical and economic problems. These include the high costs involved in: rupturing the tough algal cell walls; heating; dewatering; chemically transforming the viscous, algal lipids into suitable transport fuels and the non-lipid fractions into other useful materials; producing the methanol to make lipid transesterification possible; and separating the output components into valuable products and recyclable material. Brute force methods have traditionally been used to address these problems. However, these are increasingly costly, unsustainable and typically involve serious greenhouse emissions. The novel method proposed, bypasses the step of removing water from the algae by processing the algae in aqueous phase, thereby facilitating oil/water phase separation. It also rationalises the number of separate processing steps, making use of carbon-neutral and economical HFR resources.

A developed HFR resource has two useful components: accessible pressure and carbon-neutral heat. These components can separately be replicated away from an HFR resource, but at typically much greater financial and environmental cost. In the present process, pressure and heat are used successively to produce the desired transformations in the algal slurry, and later to separate the individual fractions. They can also be used to produce methanol, syngas from biomass, alkanes from syngas and ammonia from hydrogen and nitrogen.

Figure 9:
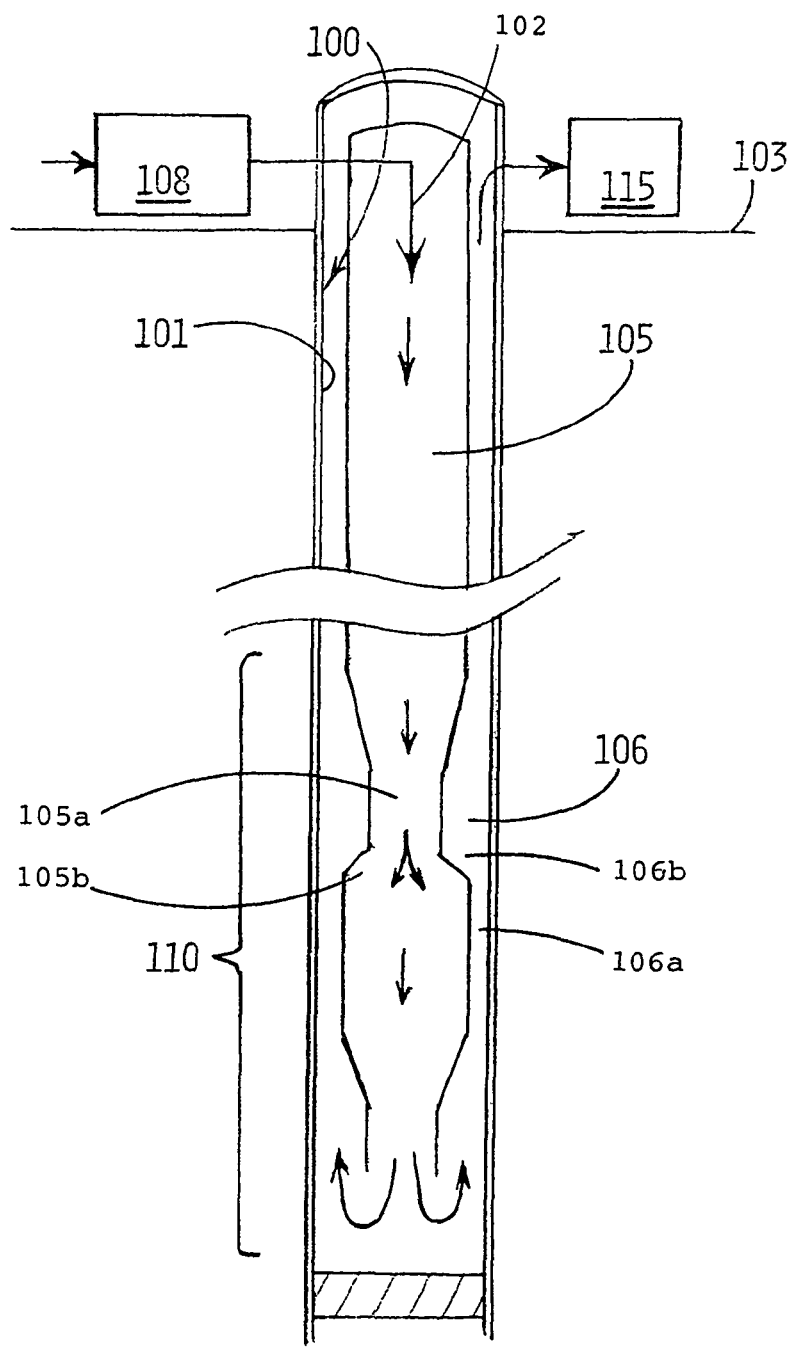
FIG. 9 is a schematic vertical sectional view through a system for processing microorganisms embodying aspects of the present invention.

Referring to FIG. 9 a flowable feed material 102 is caused to undergo at least one physical change brought about by the effects of the pressurisation of the feed material descending from the initial level to the working depth 110 as well as the working conditions provided at the working depth which include conditions to effect depressurisation. In particular, a gas-rich aqueous slurry of microalgae or diatoms such as from the impeller/harvester units 30 is flowed e.g. by pumping deep down a closed-ended drill-hole 100 to a working depth 110, via a profiled pipe 105, set inside the casing 101 of the drill-hole. The closed and profiled passage, typically formed by the profiled pipe 105 within an outer pipe in this case being casing 101, has a series of expansion and compression zones where the partly gas-bubble-filled microorganism slurry undergoes abrupt pressure changes thereby inducing lysis of the microorganisms. HFR resources are usually located a few kilometers below the surface 103, however a much lesser depth, for example of the order of about 100 meters, (and hence lesser pressure) may still be adequate. The increasing pressure progressively dissolves most of the gas bubbles into the algal media water and, by osmosis, into the algal cells and their inner vesicles.

The microorganisms are caused by explosive decompression along down and up their flow paths to lyse. A second beneficial effect is caused by de-cavitation. As the bubbles of gas implode as their last vestiges dissolve, tiny and highly-localised, but highly energetic, shock waves and penetrating microjets occur and very high, very localised, instantaneous temperatures result. The energy of these jets and shockwaves is often sufficient to rupture nearby algal cell walls and to progress chemical reactions.

The profiling of the inner pipe 105 is such that at points within it, and on the upward return slurry journey in the surrounding zone 106 outside it, there are created regions 105a, 106a of relative compression and regions 105b, 106b of decompression, as well as different velocities and degrees of turbulent mixing. When gases are involved, compression and decompression also result in significant adiabatic local heating and cooling. At decompression regions 105b, 106b, gas tends to come out of solution. When it comes out of solution suddenly within a vesicle or alga, the sudden increase in gas pressure inside tends to rupture the container (the vesicle or algal cell wall), releasing its contents into the main, aqueous solution with minimal damage to its contents. Thus, the algal lipids and other cell contents are freed, unharmed to take part in further transformational processes.

As lipids are hydrophobic, they tend naturally to aggregate and to separate from the aqueous phase with only minimal subsequent de-watering effort being necessary.

At this stage, desirable co-products, such as some nutraceuticals and proteins, that would be deleteriously affected by the higher temperatures occurring later, may, if desired, be extracted. However, as the algal lipids are somewhat viscous at ambient temperature, the mixture may first be passed through a heat exchanger akin to the one at 108, using waste HFR heat or other sourced heat, to bring its temperature up to a modest 60° C. This is sufficient to reduce the viscosity of the lipids significantly, making physical separation easier, less costly, and more complete, whilst not usually being high enough to damage fragile co-products.

The four main phases: the solid components (chiefly the ruptured cell walls comprised of glycoproteins and polysaccharides); the aqueous phase; the immiscible, oily lipid phase; and the gaseous phase are then coarsely separated by means of centrifuging at 115, using an inline, vortex centrifuge and near ambient pressure. It should be noted that it is far easier to separate ruptured cell walls from water than it is to separate complete algae from water—particularly when the cell walls can remain wet. After removal of lipids and the more valuable proteins and sugars, the wet slurry of remaining solids is piped to a biomass to syngas drill hole reactor or to an anaerobic digester, where the action of anaerobic bacteria converts it mainly to methane, $CO_2$ and free macronutrients. These are all recycled. Alternatively, if economical sources of macronutrients can be made available (e.g. treated sewage, agribusiness or industrial waste), the cell walls can readily be turned into high-protein, human food or stockfeed. Note also, that for algae and diatoms having cell walls of silicic acid, the digester's action will produce less methane and may require special treatment to free the silicic acid for recycling. The methane can be used to synthesise methanol as described later in relation to FIG. 10.

Following the algal lysis process, the aqueous phase, that contains the bulk of the macronutrients, may be treated to extract its more valuable components by electrophoresis, adsorption or other methods. Its residues may then be piped to either a biomass to syngas drill hole reactor or the digester both of which release nutrients and water for recycling back to the bioreactors, or some residues may be sent directly back to the bioreactors to make up most of the material that had been removed during harvesting.

As the presence of water deleteriously affects transesterification (it can cause undesirable saponification), the lipid-rich liquid from the rupture process is heated and any residual water is allowed to boil off as steam at atmospheric pressure when the lipid-rich mixture is heated to over 100° C. The resulting steam itself is condensed and returned to the system. After the steam has been removed from the lipids, they are pumped through a heat exchanger to bring them to 107° C. and thence pumped into a sealed reaction vessel or HFR drill hole where there is 5 atm pressure. Where HFR heat is not available, this heat may be produced by any other economical means. In warm to hot climates, this may best be done using solar ponds. Otherwise, ordinary geothermal heat may be used or waste heat from industry. Because the triglycerides that make up the algal lipids have boiling points well above these temperatures, they are not lost earlier on.

The viscous lipids in the lipid-rich liquid are then transesterified in the reaction vessel. This is done by mixing one or more of the many recognised catalysts, together with six moles of methanol for every mole of triglyceride in the lipids to be transesterified and adding the mixture to the lipids. Although only three moles of methanol are required to react stoichiometrically, the excess methanol is added so as to drive the equilibrium reaction to transform methanol and triglyceride into methyl esters and glycerine. Due to the pressure applied, the methanol at this temperature remains liquid so that it reacts in close contact with the lipids to produce fatty acid methyl esters (FAMES, which together may be used to produce several different types of biofuel) and glycerine. With the possible use of ultrasonics to hasten the reaction, and the right selection of vessels, pumping and catalysts, the whole process can be made a continuous one, rather than a batch one. Alternatively, and probably more cost-effectively for this purpose, the mixing, cavitation and decavitation produced when the reactants are pumped hot through a (this time modestly) deep, pressurised, profiled pipe 105 may be used to replace the function and cost of ultrasonic irradiation in transesterification, or else the reaction can just be left to take its time.

When the transesterification reaction has occurred, the heavier glycerine may be drawn off from the bottom of the containing vessel or centrifuged. The lighter fractions may then be fractionally distilled (fractionation) using additional HFR heat to produce the various fuel products: methanol (the excess), petrol, jet turbine fuel, biodiesel and residual fuel oil (RFO). Now, HFR temperatures of 250° C. are not unknown. However, as only the C8:0 and C10:0 long FAMES have lower boiling points than this at atmospheric pressure, the C12, 14 and 16 FAMES will require either partial-vacuum distillation, or else the application of higher temperatures from a different, hotter heat source.

The partial vacuum distillation route is probably the most economical here. Particularly, as the bulk of the FAMES can be separated using atmospheric pressure distillation at less than maximum HFR temperatures. Furthermore, as most of the remaining FAMES can be separated using vacuum distillation at these temperatures, no extra high temperature heat source should be required. The smallest, least valuable, fraction is RFO which is left behind undistilled with possibly some of the catalysts and other impurities. Unless catalytic recovery is economical, this may be sold as fuel oil or cracked, possibly with the use of HFR or solar resources to form more valuable hydrocarbons, together with possibly carbon char and free catalysts.

Should high temperature distillation be required to produce any product, the availability of gas/oil well methane and oxygen, or the development of local solar concentrators for this and other purposes at some facilities, makes these obvious and reasonably economical sources of such incremental heat energy.

Any heat recovered from these processes might be: fully utilised in the lower temperature processes of the process; used to generate power; used in nearby agribusiness, factories and towns; or returned to the cooled, HFR fluid. Waste heat from the higher temperature processes is re-used in the lower temperature ones in cascade. The heat waste from the lowest temperature process may be employed to warm the bioreactors during cold or dark periods or for growing thermophilic strains of algae.

Due to the availability of economical heat sources at the facility, the crude glycerine will usually be: distilled to pharmaceutical grade; used as raw material to produce more fuel; or used elsewhere in the biorefinery or in associated agribusinesses.

At cool times, the waste heat resulting from the cascading of heat reuse and production in these processing steps, and/or other HFR heat, is used to improve algal insolation (exposure to sunlight) by convection and to warm the algae sufficiently to keep them at high activation and productivity. Cool times may also be a signal to introduce cool-climate algal inoculant into the bioreactors, and vice versa in warm or hot times.

The catalysts from the transesterification process may be recovered from the residue after fractionation. These may or may not be reusable or recyclable, depending on their nature and whether or not they have been neutralised or otherwise affected. The methanol is recycled.

The methane from the anaerobic digestion processes described in relation to FIG. 9 is used, possibly with impure methane from other sources (typically from gas/oil wells and coal mines), and combined with the $O_2/CO_2$ mix from the bioreactors and steam as bubbles in an entraining liquid to form methanol via catalysis in the drill-hole 100 and may be used later in the transesterification of the algal lipids as previously described. Any catalysts used would either be included with the entraining, high boiling point liquid and/or be coated onto the wall of the pipes, thereby providing them with close contact to the turbulent reactant gases.

Figure 10:
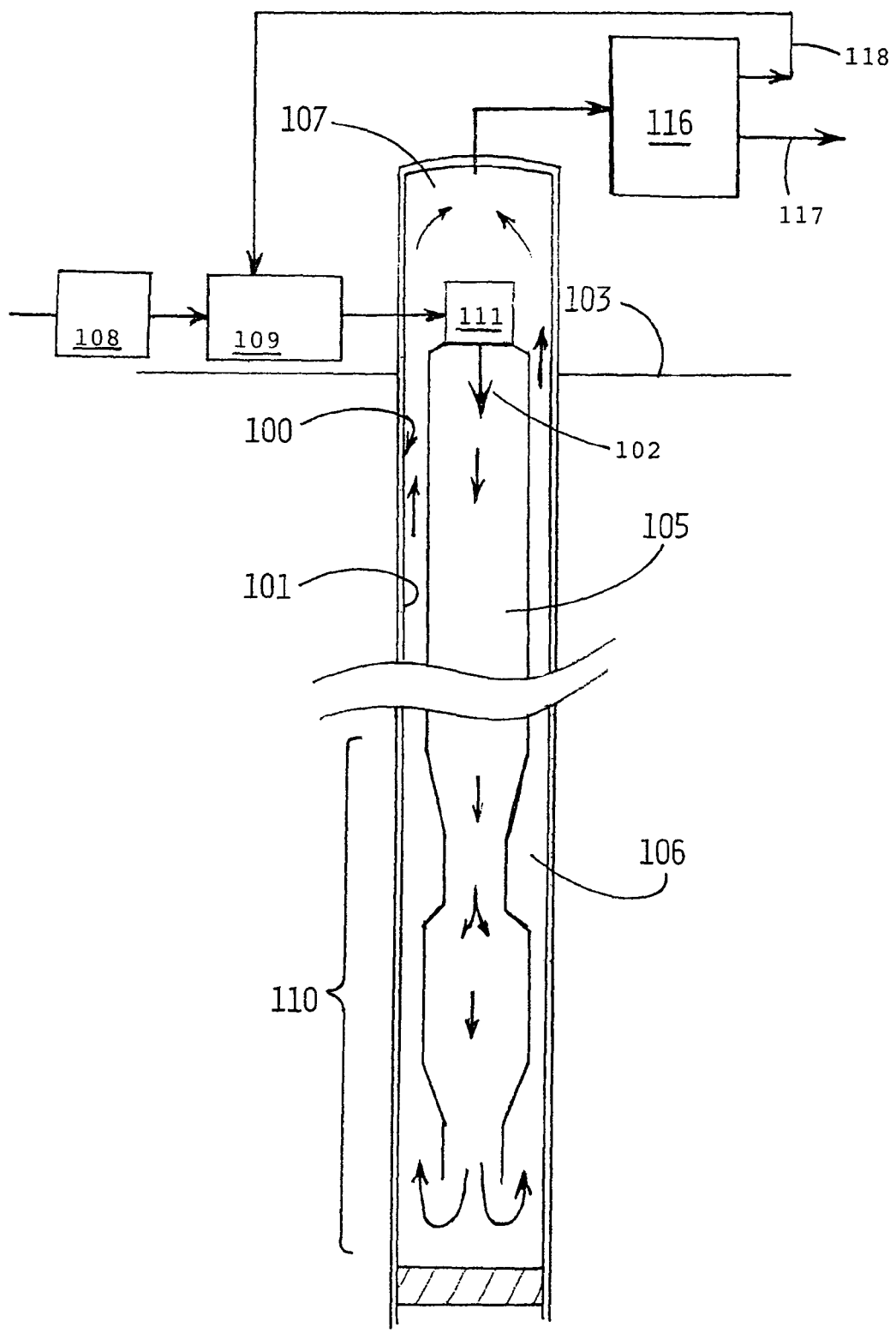
FIG. 10 is a schematic vertical sectional view through a system for producing methanol or other fuels and chemicals embodying aspects of the present invention.

The apparatus schematically illustrated in FIG. 10 can be used to implement chemical reactions induced to occur within the flowable feed material 102, the chemical reactions being initiated, caused, accelerated, or enhanced as a result of the increase in pressure to which the feed material is subjected in descending from the initial level to the working level 110 or experienced at the working level 110. The apparatus in FIG. 10 can be used in the methanol production process. This can be done by forming and if desired preheating the mixture of methane, $O_2/CO_2$ mix, steam and catalysts in heat exchanger 108, prior to liquid carrier entrainment of gas mixture bubbles in mixer 109, and pumping by pump 111 to descend by at least 300 meters and preferably by a few thousand meters to create further compression heating to reaction promoting temperatures and pressures. Heavy finely divided catalysts can help increase the density of the carrier fluid which can be important in drill hole reactors and processes. The reaction products returning upwardly in the annular return passage 106 reach the head space 107 from which the gaseous products are output to the condenser or other separation stage 116 where methanol in particular can be separated through line 117 and from whence unreacted materials can be recycled through line 118 to mixer 109. As methanol is typically produced by employing pressures of up to 1,000 atm and modest to high temperatures (80-800° C.), depending on the intermediates and catalysts used, it may also be produced, with very substantial economies, using HFR or other drill holes, where the pressures can exceed 1000 atm and the unimproved temperatures can exceed 250° C. at 4,200 meters depth. Even higher temperatures may be achieved as entrained gases heat up under high gravitational compression in drill-holes or by pre-heating.

Other chemical engineering processes may similarly be facilitated with this drill hole technology. Although FIG. 10 schematically depicts only a single down flow path 105 and single inflow path 106, the drill hole can accommodate multiple down flow paths or pipes for conveying reactants and carrier substances to various working depths and respective return paths or pipes, or even using multiple down flow paths or pipes and a shared or common upflow path for reaction products. Many of the possible processes utilise heating and instead of, or in addition to, heat exchangers on the surface or adiabatic heating effect of gas bubbles in the fluid being compressed, control of fluid temperature may be achieved by the use of superheated steam or chilled water introduced to the fluid by means of a long, hollow metal pipe or lance, typically running centrally down the drill hole pipe, e.g. 30-300 m. Alternatively, steam may be introduced by means of one or more hollow, split collars around the drillhole casing at selected depths. A separate drill hole located adjacent to the reactor hole may be used for the steam pipe for insulation purposes. These constructions are described in more detail in the Appendix in the section DRILLHOLE REACTOR CONSTRUCTION.

In one further use, the chemical reaction comprises synthesis of a syngas comprising a mixture of carbon monoxide (CO) and hydrogen ($H_2$). The feed material 102 comprises an aqueous slurry of reactants including oxygen in sufficient quantity to ensure partial oxidation of the organic material substances which may comprise biomass such as organic matter from the processing of microorganisms as described herein (i.e. the carbon based reactants include micro-organisms or diatoms which have undergone lysis so as to release lipids which have been recovered and removed therefrom), agri-wastes (e.g. lignocellulose products, crop wastes or by-products), sewage or pulp mill waste or other waste water processing products, and may comprise carbon based products from industrial processes or waste recycling collections, e.g. plastics materials, rubber wastes, etc. The slurry at least upon reaching the working level 110 achieves supercritical water conditions. Under supercritical conditions of temperature and pressure, the reactants can produce syngas by chemical reactions which are known in the chemical industry. The slurry being flowed down the path 105 from the initial level may include a proportion of gaseous material so that pressurisation of the slurry as it flows downwardly to the working level 110 is compressed and the slurry thereby experiences adiabatic heating.

In another further use, the chemical reaction comprises a Haber ammonia synthesis. For this chemical reaction, the feed material 102 includes suitable catalyst substances added to the reactants (hydrogen and nitrogen gas) to promote the Haber synthesis of ammonia.

In another further use, the chemical reaction comprises a Fischer-Tropsch alkane synthesis. The feed material 102 includes suitable catalyst substances added to the reactants to promote the Fischer-Tropsch process. In this process, the reactants in the feed material 102 may comprise syngas derived from the chemical processing method described above with the production of syngas being carried out at a first working depth, and the Fischer-Tropsch synthesis is carried out at a second working depth 110 to which the products from the syngas synthesis are transferred to achieve the required working pressure in the flowable medium suitable for the Fischer-Tropsch process. The syngas is produced in a process using an aqueous carrier so the syngas is separated before being fed to and mixed with the oil carrier for the Fischer-Tropsch process. The Fischer-Tropsch and the syngas production processes may be performed in separate but proximate drill holes because of their different process parameter requirements.

In the Haber and in the Fischer-Tropsch processes, the reactants and catalysts are entrained in an oil carrier medium and small bubbles therein provide surface conditions for the chemical processes to progress.

In performing any of these processes, heat can be available from the exothermic reactions and this can be transferred to raise the temperature of any one or more of the feed materials flowing downwardly to undergo the any of the chemical reactions in the underground processes. For example, the feed material being heated from one of the exothermic processes may comprise at least one of:
  the feed material to undergo lysis of the micro-organisms,
  the feed material flowing down in the path to undergo the chemical reaction producing methanol,
  the feed material flowing down the path to undergo the syngas synthesis process,
  the feed material flowing down in the path to undergo the Haber reaction,
  and indeed the feed material flowing down in the path to undergo the Fischer-Tropsch reaction itself.

Also it will be understood that a useful cooling action can occur when employing regenerative heat utilisation in some processes. For example heat transfer from exothermic chemical reactions, e.g. to heat the reactants in the syngas production, can be useful to maintain desired temperature and avoid excessive temperature rises.

Low-Nitrogen Oxygen from Algae for Industry

Many industries use oxygen in their processes. Typically, the majority content of nitrogen in air reduces the efficiency, and increases the cost, of these noticeably. Those that extract oxygen from air, typically by membrane techniques, pay a cost for the process. However, if algae are provided with nearly pure carbon dioxide, such as is available as a waste product from several industries, including hydrocarbon extraction ones, algae can produce very low-cost, carbon-negative oxygen.

The Appendix at the end of the present description provides further background information, including sources of technical data, and provides descriptions and examples of the processes according to various aspects of the Winwick systems and inventions. The disclosures of that Appendix therefore constitute part of the disclosure of the present patent specification.

It can be seen from the foregoing description and from the Appendix that the Winwick systems, methods and apparatus can provide an integrated process by which microalgae can be grown on low-cost land, then harvested, transported and processed economically to produce carbon-neutral biofuels and co-products. Co-products include solar electricity, where the bioreactors form an economical, low, highly-accessible and standardised platform for photovoltaic films covering potentially thousands of square kilometers of otherwise unproductive land.

Although novel concepts are proposed for several individual processes, there are also novel combinations of several, hitherto unrelated, resources and methods.

The technology is somewhat dependent upon the availability of concentrated sources of $CO_2$ (though less concentrated sources can also be used). However, these are less expensive to deliver to areas where flat, non-arable land is available than are most other materials. This is so for several reasons: $CO_2$ is often available as a waste product from other industries and widespread deposits; as a gas, $CO_2$ is less costly to pump over mountains, up elevations, or over long distances than are other forms of matter; several industries, including power generation and metal refining, can benefit doubly by exchanging their $CO_2$ emissions for algal-produced oxygen using pipelines sharing the same trench; and liquid $CO_2$ may readily and economically be back-loaded in cryotankers or pipelines from LPG and LNG transporting operations. Furthermore, $CO_2$ may even be extracted from industry sources or the atmosphere itself using zeolitic imidazolate frameworks (ZIFs) or quicklime (CaO) to absorb it, provided there is an economical source of high temperature, such as solar concentrators located on non-arable land, to regenerate the quicklime from limestone, $CaCO_3$.

Whilst the initial application is to produce biofuels, the same technology is equally applicable to the production of algal biomass for other purposes. The main difference is that more nutrients need to be added for non-biofuels, as biomass takes all its macronutrients with it, whereas biofuel production allows most of them to be recycled endlessly. In turn, the biomass can be used to produce many different products, including: human food, stockfeed for a wide variety of organisms, nutraceuticals, pharmaceuticals, chemicals, fertilisers, plastics, raw materials and many other items.

As the Winwick process is land intensive, it is best located on land with little in the way of alternative, productive use and value. Whilst the production of biofuels from algae by the Winwick process may be most economic when located beside or on top of a geothermal resource, the production of biomass from algae using the process is best located sufficiently near (or at least not much higher in elevation than) sources of cheap macronutrients, such as sewage plants, agribusiness, or coal-fired power plants, so that the waste macronutrients from them (including $CO_2$) can be piped (as the most efficient transport means) to the bioreactors at modest or negative, net triple-bottom-line cost.

The great variety of organisms that are supportable from food chains that start with very large volumes of cheap, pumpable, microalgal slurry, at biofarm locations on otherwise unproductive land, when combined with the co-production of cheap, solar electric power, leads to opportunities for integration with large-scale agribusinesses and chemical engineering plants. Moreover, being collocated, these can benefit from vertical and cross-industry flows of recyclable waste, energy and by-products.

It is to be understood that alterations, modifications and/or additions may be made to the features of the embodiment(s) of the invention as herein described without departing from the scope of the invention.

APPENDIX

Winwick System for Cultivation and Processing of Microorganisms and Products
Inventor: Clarke, William Severn

ABSTRACT OF THE APPENDIX

This paper describes the technology for a new and integrated, renewable energy industry. It discloses processes, methods and designs to grow and harvest algal biomass and those to process it into biofuels, as well as generating solar electricity and chemicals as co-products. Central to the concept is the use of organic waste and purpose-grown biomass, including that from the cultivation of microalgae in sealed, water-conserving photobioreactors of low capital and operating cost. However, of equal importance is the validation and refinement of the sustainable processing technologies, together with the development of associated support systems & logistics, of funding, and of community acceptance.

What Winwick promises is to replace our unsustainable use of oil and coal with renewable algal oils and co-produced photovoltaic power, biofuels, food, feedstock, nutriceuticals and chemicals. These are to be generated mainly in the flat, temperate deserts or wastelands of the world, preferably on land having no better use. The production operation requires no fossil-fueled power, no commercial fertilizer, and negligible water—which can itself be salty or polluted. It takes carbon dioxide from any large, stationary producer by utility pipeline and turns it into biomass (vegetable matter, including oils, proteins and carbohydrates) and oxygen for industry. Virtually all wastes, including old plant and equipment, are recycled, usually indefinitely.

The drillhole reactors which process the algal biomass can also process most other organic waste, such as that from weed species, crop and forestry wastes. Thus, the processing technology is also suited to non-desert regions. By deriving biochar from these diverse, major, biomass sources and spreading it through topsoil, bval0404means we can improve its fertility, increase its water-holding ability, and remove greenhouse gases from the atmosphere and sea. Performed very extensively, this could help prevent the world from overheating, as well as improving agricultural productivity and turning marginal land productive.

What differentiates Winwick's algaculture technology from others, is that Winwick theoretically solves all twenty or so of the problems of algal biofuel production, including that of scale production and profitability, that have stopped other groups from making transport biofuels commercially (except ethanol which cannot readily be used in planes, trucks and ships—and only a proportion in automobiles). Winwick should also be able to produce its products with unparalleled economy, once any teething problems have been overcome by applied R&D.

Most current algaculture technologies suffer from more than one of the following disadvantages: high cost land; substantial site preparation costs; high capital equipment cost per square meter of growing space; low algal productivity; high net energy cost; costly commercial chemical inputs; batch operation; non-scalability; contamination by algal predators and wild strains; excessive downtime; regulatory hurdles; infrastructure incompatibility; dependence on large volumes of low-cost water; blowdown issues; inflexible biomass inputs; seasonal dependence, including non-optimal growing temperatures in large parts of the year; very poor light usage; algal inhibition; uneconomic harvesting and processing operations; a lack of valuable co-products; and slow rollout due to lack of automation and/or portability to remote sites.

The economics of algal cultivation are improved by means of several novel steps, including the use of: adaptive-aperture photovoltaic strips to control insolation; light/dark flashing; thixotrophic gel media; low agitation; passive convective turnover; differential sparging; nutrient recycling; heat, light and salinity control; and active, fine control of algal growing conditions, growth media and strain change. In addition, innovative methods are described for: processing virtually any biomass economically and ecologically into biofuels and chemicals; for mechanical handling; for bioreactor access, construction, security and surveillance; for logistics; and for the automated and/or remote control of operations.

The algal cultivation process involves the use of sunlight and water, together with waste carbon dioxide sourced from oil/gas wells, industry and/or carbon dioxide captured from the atmosphere by other means. Other nutrients and energy values incorporated by the algae are typically recovered and recycled, with some being produced on-site using Winwick's drillhole, or gravity pressure vessel, reactor technology. Algal processing is made economical by: the avoidance of traditional de-watering steps; the creative use of geothermal heat and geopressures; and an innovative combination of processing technologies.

The Winwick concept incorporates that of an integrated biorefinery, where not only the waste products from individual processes are re-used, but also the heat from processing operations and the materials from which the plant and associated structures are built. The biorefinery is designed to accept most other forms of biomass besides algae, for processing into biofuels. These include biomass from: crop and forestry waste; harvested, regenerative species such as eucalypts, saltbush, poplar and perennial native grasses; lignite and coal; pulp and sugar mill wastes (bagasse); other agribusiness wastes, such as food processing wastes or manure; garden wastes; weed species for destruction; sewage; waste fats, oils, paints, solvents and organic chemicals; waste paper and polymers; or almost any other organic waste. These can all be processed in the same facility, which has a small footprint. Such processing can even be performed in locations or climates where algal bioreactors themselves may not be economical to run all year round, such as in snowy climates. Thus, the biorefinery operation is not seasonally-bound and can run continuously using a wide variety of feedstock.

Biomass processing utilising a supercritical water partial oxidation (SCWPO) process completely destroys otherwise dangerous or intractable pollutants such as dioxins, viruses, hazardous organic chemicals and all plastics. At the end of the SCWPO process, syngas is obtained and most of the remaining biomass nutrients can be recycled and valuable metals and inorganics can be recovered. Water from sewage, pulpmill and industrial wastes is upgraded by the process to a quality that is typically suitable for irrigation and/or many industrial uses. Depending on the salinity of the feedstock, it may even produce potable water at less cost than many other forms of treatment. Only low concentrations of nutrients and soluble salts will typically remain (mainly sodium chloride and plant-nutritive ammonium salts) in the sanitised water. If not used directly as dilute, liquid fertiliser for agriculture or to nutrify algal bioreactors, this water can become an input to desalination plants that is both more cost-effective and resource-efficient than is seawater. The concentrated, nutrient-laden brine from the desal plant, after the extraction of any valuable heavy metals, may then be piped to a bioreactor farm for productive use, instead of causing possible ecological problems by being piped to the sea or otherwise wasted.

Thus, it may be economical to locate Winwick SCWPO treatment plants or biorefineries to treat waste biomass wherever the resource availability reaches a certain minimum, yearly volume. Such plants may use various Winwick drillhole reactor processes described later on, these being clean, efficient and of low physical and ecological footprint. The economics of such plants can be improved wherever there is access to additional sources of biomass. The outputs of such plants are typically syngas, transport biofuels, industrial chemicals, possibly food, nutraceuticals and stockfeed, and organics-free, lightly nutrified water.

Existing power stations that depend on coal, especially moist brown coal (lignite), or new ones that use more recently fixed biomass (perhaps woodchips, sawdust pellets, crop or forestry wastes), can improve their profitability, asset life, water use, product range and emissions by forming Winwick drillhole reactors on-site to produce valuable syngas/town gas, biofuels, chemicals and coolant water, as well as reducing their greenhouse gas (GHG) emissions, and improving their electricity generation efficiency.

Extracting geothermal heat from hot fractured rock (HFR) typically requires making deep, and consequently high-pressure drillholes into rock formations. The same pressure, even when present only in drillholes that have been sealed off from the HFR or other extractable mineral resource, and when combined with heat from HFR heat exchangers, input reactants, suitable catalysts and processing steps, can be utilised to produce desirable physical and chemical changes in feedstock materials, such as algae, sewage, coal, cellulose and lipids.

Methods are divulged how piggy-backing on the existing infrastructure and under-utilised resources of associated industries can be used to improve markedly the economics and reduce the developmental risks of establishing operations at bioreactor and biorefinery sites.

The construction and operation of each algal bioreactor farm is designed such that its deployment and extension (scale-up) is relatively easy and carries low cost and risk. This is so because the actual bioreactor units are simply replicated as many times as are required, on a dendritic layout, that is akin to that of leaves on a tree or, more accurately, on a ground-hugging vine. Only the size of the vine stem and processing plant require scaling.

Farm construction and operation have been designed to have minimal impact on the environment. Whilst the bioreactor design has been crafted to suit flat, temperate desert locations, it is also designed to be adaptable to many other environments, including flat: mid-latitude, arid tropical, high plain, rangeland, salt or clay pan, barren, degraded or highly polluted ones. Production may even be possible using Winwick bioreactors floating on calm water, with fish, shrimp, molluscs or other forms of aquaculture occurring beneath or beside them. Indeed, the algae from the bioreactors can be used as a secure and plentiful source of premium-quality food for the other creatures, particularly their juvenile forms, thereby possibly avoiding the algal concentration and processing costs.

Provided the temperature is within their growing range, most microalgae require only modest amounts of insolation—typically 10-25% of the incident insolation (sunlight or solar radiation) in mid latitudes in summer. Moreover, many microalgal strains use angled and sub-second flashing light more efficiently than they use near-vertical, strong and continuous light. The Winwick photobioreactor design makes use of both these effects to increase the efficiency and to extend the latitudes and altitudes suitable for the commercial production of algae using its cheap, closed bioreactors in the field.

Using the Winwick system, some of what have until now been regarded as unsuitable climatic and insolation conditions for growing algae no longer pose insuperable constraints. With suitable adaptations to the standard Winwick system, microalgae may now be grown commercially at higher altitudes and in cooler and hotter climates than ever before. Cooler temperatures are addressed using bed heating, chiefly from parasitic (virtually free) sources, larger units, and/or additional, insulating envelopes. At the other extreme, excessive insolation and temperature are addressed: by increasing the proportion of the bioreactor covered by photovoltaics to provide increased solar screening and energy conversion; by providing passive, air-cooled transparent, fluting on the upper surface of the bioreactor envelope; by using photo-antenna-reduced algae to increase the light path into the algal soup; by controlling the amount of insulation provided by a temporary foam 'blanket'; by using algal adaptation, acclimation and algal extremophiles; by varying the cross-section of the bioreactor; and/or by using selection, breeding and/or modification of algal, cyanobacterial and diatom strains to suit different operating conditions. A similar technique may be to employ algal selection, breeding or genetic modification to increase the number of reaction centres of photosynthesis in each alga, so that the bottleneck of the rate at which the reaction centres can transform light's component photons into chemical energy at higher than low insolation is overcome. Indeed, implementing such a transformation may be the only way to overcome the dissonance between maximal solar conversion efficiency and maximal growth rate.

The novel methods of processing the algal biomass are equally important to viable Winwick operations, though they may equally well be applied to processing industrial organic wastes. Key to these is the use of deep (up to 5 km) drillholes. Such drillholes are typically drilled for exploration purposes or to extract geothermal heat or hydrocarbons. These tend to be lined with a thick, steel drill casing inside a subsequently-injected concrete matrix. When no longer useful for resource extraction, these drillholes can be sealed at the bottom and transformed into hyperbaric (high-pressure) reactors for processing industrial-scale biomass into biofuels and other useful chemicals with unparalleled economy and no emissions. Alternatively, new drillholes may be drilled specifically for Winwick purposes.

Winwick technology (WT) is an umbrella term that incorporates many different processes and methods. Some of these are novel, some are developments on, or variants of, current and even old technology. For ease of reference, each of the twelve different technologies is given a name and a Winwick acronym as follows:

Winwick Microalgal Growth (WMG) technology
Winwick Solar Power (WSP) technology
Winwick Cell Rupture (WCR) process
Winwick Lipid Esterification (WLE) process
Winwick Oil Fractionation (WOF) process
Winwick Syngas Synthesis (WSS)
Winwick Methanol Synthesis (WMS)
Winwick DME Synthesis (WDS)
Winwick Ammonia Synthesis (WAS)
Winwick Nitric Acid Synthesis (WNAS)
Winwick Fischer-Tropsch Alkane Synthesis (WFTAS)
Winwick Supercritical Extraction (WSX)
Description of the Invented Industry When linked, these inventions provide an integrated process by which microalgae can be grown on low-cost land, then be harvested, transported and processed economically to produce carbon-neutral biofuels and co-products. Co-products include nutraceuticals, glycerine, methanol, ammonia, nitric acid, oxygen, chemical & pharmaceutical feedstock, food, fodder and solar electricity, for which the bioreactors form an economical, low, highly-accessible and standardised platform for thin-film, photovoltaic (PV) strips covering potentially thousands of square kilometers of otherwise unproductive land.

Although novel concepts are proposed for several processes and structures, the single most inventive step lies in the novel combination of several, hitherto unrelated, resources and methods.

Excepting perhaps the thin-film PV, nano-texturisation, and possible genetic modification to algal strains, none of the technology involves more advanced technology than is used in standard engineering practice. The above advanced technologies proposed for use are now in commercial production and under further rapid development in a number of organizations.

Thus, the level of technical risk in Winwick technology development is not that high, though the integration risk lies between moderate and high. Nor is there substantial social or environmental risk. Indeed, insofar as the technology, if deployed successfully, reduces the risk of oil and soil depletion, global warming and biodiversity loss, it should reduce the overall risk to life on Earth.

As far as global equity is concerned, excepting developed nations possessing flat, temperate deserts, most of the countries to benefit most from deploying all Winwick technologies are those belonging to the less-developed world, including many of the poorest nations. The level of financial risk is thought to be low for many site locations and markets; and anyway is manageable using standard business techniques. Sovereign risk is another matter, but one that may best be addressed via franchising, on-going shared development, logistic support and marketing arrangements, rather than by entire reliance upon facility ownership, proprietary knowledge, diplomacy, dollars, negotiation, force, patent law and licensing.

Whilst the initial aim of Winwick technology is to produce biofuels, power and chemicals, it can equally well be applied to the production of algal biomass for other purposes. The main difference is that more nutrients need to be added for non-biofuel production, as biomass produced for food takes its nutrients with it, whereas biofuel production allows most of them to be recycled endlessly. Biomass can be used to produce many different products and services, including: human food, stockfeed for a wide variety of organisms, nutraceuticals, vitamins, pharmaceuticals, chemicals, fertilisers, plastics, water/waste water sanitization, industrial decarbonisation, biochar and other organic raw materials. Some of these materials, such as biochar, can biosequester carbon in the soil for thousands of years without risk, with additional beneficial results upon soil fertility, ecology, nutrient capture and moisture retention.

Winwick technology may also be employed to reduce emissions of methane, $CO_2$ and other acidic gases (chiefly $NO_x$ and $SO_x$), and thereby to mitigate climate change. Weeds, crop waste, forest litter and forestry wastes are typically degraded by fungi, microfauna and microbes, using a combination of aerobic and anaerobic processes, into the emitted end products of methane, $CO_2$ and water. However, by feeding material from these sources into Winwick drillhole reactors and bioreactors, they may be converted into foods, feedstocks, transport biofuels, biochar and valuable chemicals, without there being any greenhouse gas emissions. Considering that methane has a global warming potential 21 times greater than $CO_2$ when averaged over 100 years, processing these wastes through Winwick processes might reduce the materials' natural contribution to global warming by a factor of perhaps fivefold. Thus, for every dry tonne of organic waste processed by Winwick facilities, the global warming effect of perhaps three tonnes of $CO_2e$ (carbon dioxide equivalent) might be avoided.

As Winwick technology is both land extensive and intensive, it is best located on land with little in the way of alternative, productive use and hence value. Whilst the production of biofuels from algae by the Winwick process is likely to be most economic when located beside, or on top of, a geothermal resource, the production of food biomass from algae using the Winwick process may best be located sufficiently near (or at least not much higher in elevation than) sources of cheap macronutrients, such as sewage plants, agribusiness, harvestable vegetable biomass, or power plants generating chemical emissions. Macronutrients and biomass for conversion into biofuel may also be sourced from any waste biomass, such as macroalgae (seaweed), weed species, nearby regenerative vegetation, or crop and forestry wastes. Such proximity means that the waste macronutrients can be slurry-piped (as the most efficient transport means) to the bioreactors at modest or negative, net triple-bottom-line cost.

Provision of the macronutrient $CO_2$ is a somewhat different case, as gases can be piped economically over very long distances, and even over mountainous terrain or underwater, without incurring high cost, due to frictional losses and the gravity effects of differences in elevation being much less important. Thus, Winwick facilities producing biofuels may still be highly profitable even when remote from cheap sources of $CO_2$; whereas those facilities which produce products that incorporate the other macronutrients are more favourably sited where cheap sources of these can be piped to them economically as liquids, slurries, or in pipeline-borne containers. Macronutrient transportation by ship or rail may be economical enough to some facilities, but long-distance trucking is likely to be prohibitively expensive, even when good road links exist. Distance, elevation variations over the pipeline route, topography, climate and political boundaries can all affect the economics of transporting most macronutrients adversely. Of course, some remote sites may have local access to cheap sources of macronutrients, either in the form of mineral deposits (even quite low-grade ones may often be usable), mineralised bore water, wastes from local (typically mining, forestry or farming) industry, or macronutrients derivable from nearby vegetation via the WSS process (in this case the facility would typically produce both biofuels and food or fodder). Pipelines are also likely to be important for the transportation of facility products to market, possibly extending to ones for: a slurry of algal cellwall biomass, algal carbohydrate (made up of previously-unseparated storage polysaccharides (starches, glycogen, chrysolaminarin and glucose polymers)), loose proteins, minerals, and metabolites—provided these could be transported without incurring undue product degradation); syngas; methanol/ethanol; other biofuels; oxygen; chemicals; and aqueous slurries of biomass for processing at the biorefinery that are piped in from other, typically rural, regions or industry. Note, it will usually be more economical for raw, city sewage and industrial organic waste to be processed using the WSS process at possibly limited-scope biorefineries, located near the point of the biomass' origin, rather than at distant, but possibly more comprehensive, biofarm biorefineries. In such cases, the sterilised, nutriated and slightly salty product water would tend to find use in nearby irrigation or for other industrial and domestic purposes (via recycled and non-potable, purple water piping), rather than for algaculture. The syngas product would either be used by the organisation itself or distributed and sold via the syngas pipeline system.

$CO_2$ for biosequestration might also be sourced from back-loaded, LNG cryotanker ships delivering to the coastal end of connecting pipelines or grids. By this means, even countries without suitable areas or climates for Winwick bioreactor farms would also benefit from Winwick's low-cost, carbon biosequestration capability. This is particularly so, as Winwick technology is likely to be commercially-ready and widely deployed long before geosequestration using carbon capture and storage (CCS) from burning coal is sufficiently well-proven and substantially deployed—if it ever is. Moreover, the Winwick solution is also likely to be available at considerably lower cost and environmental risk than is CCS.

Many countries already have pipeline networks carrying methane or natural gas, often piped from distant sources, sometimes passing through several countries and going undersea or across mountain ranges. Sometimes the gases are transported by cryotanker (where gases are cooled and compressed to a compact, easily-pumped liquid form). Recently, geosequestration protagonists in several countries have suggested that there be developed national networks of pipelines carrying $CO_2$ for sequestration. This concept is hereby extended and complemented to include separate pipeline networks, possibly one each for syngas, oxygen, flue gas, together with trunklines, loops or grids for biofuel (methanol, ethanol, petrol, DME, diesel and/or jet fuel), biomass slurry, hydrogen, liquid fertilisers and ammonia gas.

The pipeline networks would typically be laid in a common trench or else a common, underground tunnel or conduit for locations where it is desirable to minimise surface disturbance or to avoid irregular surface features. Such arrangements tend to minimise cost and facilitate access. However, for safety reasons it may sometimes be prudent to separate the fuel lines from the rest. Pipelines for other materials, such as treated sewage, industrial waste, water, polymer slurries, powerlines and fibre-optic communications might also be laid advantageously in the same trench.

Due to the likely flow rate of flue gas and $CO_2$ to be stored and treated, pipe diameters of up to a few metersmeters could well be necessary. The lesser-diameter pipes of the other materials to be transported might well use a larger pipeline as the backbone of their support structures. A single, 100 km stretch of flue gas pipeline of 3.5 m internal diameter contains nearly a million cubic meters which, when pressurised and vented (see below), could store, transport and process the overnight flue gas emissions of more than one power plant.

Depending on the type of fuel and combustion-emitting plant, raw flue gas volume composition tends roughly to approximate: $N_2$ 77%, $O_2$ 9%, $CO_2/CO$ (~90:10) 9%, $H_2O$ 5%, with the residual of less than 0.2% comprised of acidic gases ($NO_x$, $SO_x$, etc.) and argon, plus the principally non-gaseous components of fly ash and unburned or partly-burned fuel (soot). Condensing, the water can be made to extract the acids and solids for use, perhaps as fertiliser feedstock when combined with limestone, from which reaction more $CO_2$ might be extracted for algal use. After extraction by ZIFs (see later) or other means, the $CO_2$ component of the flue gas would then be released and transferred to the adjacent $CO_2$ pipeline, leaving behind a large volume of gas that would be some 89% $N_2$ with a little $O_2$, CO and argon. These could be vented, thereby saving long-distance piping and pumping costs. The venting might be done via sintered catalytic converters that converted residual CO into less harmful $CO_2$, possibly extracting useful power in the process. Oxygen from the adjacent oxygen pipeline might be used to increase the extracted power. Controlling the rate of the venting could also serve to moderate the flue gas pipeline pressure to maintain it within the desirable range.

There exist already international gas, oil, communications and electric power networks spanning continents. Soon, large quantities of oxygen may be produced as a by-product of hydrogen fuel production from the direct splitting of water by solar and other means. Even larger quantities may be produced of the roughly 90:10 $O_2:CO_2$ mixture generated by microalgae in bioreactors using mined and industrial $CO_2$ waste. Now, to limit climate change, carbon emissions, carbon taxes and costs, the worldwide community, governments and industry are going to wish to collect and sequester whatever $CO_2$ emissions are easiest and cheapest to collect in bulk. As well, industry will want to improve the burning efficiency of fossil fuels by burning them in oxygen (if it can be provided cheaply enough), rather than in air. Plus, there is an increasing need for large amounts of oxygen for use in underground coal gasification (UCG) to produce relatively clean syngas (with a low nitrogen content). Both of the aforementioned uses are unlikely to be troubled by the presence of a 10% $CO_2$ component in Winwick-generated oxygen. However, such uses will not in the future be able to accept the inefficiency of using air that has 78% of its content as deadweight nitrogen ($N_2$). The more we can keep nitrogen apart from burning operations, the more efficient they will be, and the less greenhouse gases (GHG) and pollutants ($NO_x$) will they emit per unit of beneficial output. A complementary network of pipes for a mixture of predominantly oxygen and a little $CO_2$, possibly laid in the same trench and complementing the existing supply of hydrocarbon gas, would address this concern. Thus, a firm would draw on its fuel source and the oxygen pipe for burning, and send the resulting, relatively pure, $CO_2$ output to the other pipeline for sequestration (of either bio or geo type). At the biofarm end of the pipeline, filters and intense UV irradiation would ensure that no viable microorganisms entered the bioreactors with the $CO_2$ to contaminate their contents.

Fuel sources would be drawn upon for heating, for ore reduction and refining. The oxygen source would be drawn on for steel-making and other forms of oxidation. Some types of mining, fertiliser, fermentation, waste processing and refinery plants, and processes using oxygen rather than air for combustion can produce gaseous emissions with a relatively high proportion of $CO_2$ These emissions might be pumped directly into the $CO_2$ pipeline network. Plants using air for combustion, such as most current, fossil fuel power plants and cement works, would need to use the flue gas network, so that the principal other components of nitrogen, oxygen, CO and acidulated water could be separated out, prior to the $CO_2$ being pumped into the $CO_2$ network.

By these means, stationary $CO_2$ emitters could share in the carbon sequestration and/or combustion benefits of the system, or at least to reduce their escalating carbon emission costs. Algal bioreactor farms would do the reverse, producing oxygen from the $CO_2$ whilst biosequestering the carbon—thus completing the cycle. Each pipeline network would double as a pressurised, gas storage system. Time- or demand-set price change management (smart metering) for each resource, pumps, and exchanges with non-pipeline storage systems would be used to keep each gas pressure within the preferred range.

A simplistic analysis might indicate that saving the cost of heating the 78% deadweight nitrogen component of air in a burning operation would save 78% of the cost. In fact, many other factors come into the equation. Amongst these are included: the cost of the oxygen; the amortisation and operating costs of the pipelines; some carbon costs; taxes; metering & inspection costs; gas analysis, gas impurity premiums; exhaust gas handling and cooling costs; pressurisation costs; contaminant allowances & penalties; process efficiency benefits; and pollution reduction credits (particularly of the GHG oxides of nitrogen, which would be virtually eliminated). The actual savings to industry might still be a useful 20-40% of fuel costs.

Regarding gas cooling costs in transporting gas, considerable economies may be achieved at one or both ends of cryotanker voyages when there is backloading of $CO_2$. These can be achieved by using the low temperature of one liquefied gas in the cycle to help chill an ambient or warm temperature gas via a heat exchanger, and vice versa. Thus, methane/natural gas coming from an oil/gas well or extracted from a coal seam could be chilled by the cold, liquid $CO_2$ being off-loaded from a ship coming from the other direction and before, or as, the methane enters the cryotanker as LNG (liquefied natural gas or ~methane). At the other end, the cold LNG might be used to chill outbound $CO_2$, depending on whether the LNG and $CO_2$ were to be piped overland as gases, rather than to be transported as cryogenic liquids. As the various gases liquefy at different temperatures and are of different density and mass, sometimes additional energy would be required to complete the liquefaction. Nevertheless, considerable dollar and emissions savings would be made. However, care would need to be taken regarding the loading capacity of the ships, as the liquid $CO_2$ is more than twice as dense as is LPG.

Many industries use oxygen in their processes. Typically, the majority content of nitrogen in air reduces the efficiency, creates polluting nitrogen oxides, and increases the cost of these processes markedly. Using air-burned, moist brown coal to generate power is a notorious example of such inefficiency. Those processes that are sought to improve their efficiency by first extracting oxygen from air, typically by membrane separation techniques, pay a substantial cost penalty. However, if algae are provided with nearly pure carbon dioxide, such as is available as a waste product from several industries, including hydrocarbon extraction ones, algae can produce very low-cost, carbon-negative oxygen. The Winwick process may be the first to be registered as a process designed to do this on an industrial scale.

The great variety of organisms that are supportable from food chains that start with very large volumes of cheap, pumpable, microalgal slurry at bioreactor farm locations on otherwise unproductive land, when combined with the co-production of cheap, clean, solar electric power and Winwick drillhole reactor technology, leads to opportunities for integration with large-scale agribusinesses, refineries and chemical engineering plants. Moreover, when collocated, these could benefit from vertical and cross-industry flows of recyclable waste, heat, water, chemicals, energy and by-products.

Bioreactor Design

Winwick bioreactors and their associated impeller/harvestor units are designed to be mass-produced cheaply as complete assemblies in a factory environment. A material flow design for bioreactor construction has been drafted. The bioreactor bodies (separate from their boxlike end pieces) are designed to be transported in flattened form on large reels, together with their enclosed, but collapsed tubing, piping, PV fluting, wiring and groundsheet assemblies. Reels are unwound or rewound in the field using high-wheel-base tractors with reel management attachments.

To a reasonable maximum extent possible, the bioreactor plant and other constructed elements are designed to be made from one or two cheap, available, adaptable, easily-formed, long-lasting and non-reactive thermoplastics. This maximises opportunities for economical re-use, recycling and transportation—and minimises material separation, environmental problems and costs. Most plastic elements forming the bioreactor farm are currently designed to be made of nearly-endlessly-recyclable and cheap polythene and/or PET (polyethylene terephthalate). However, other polymers may end up replacing these, without adversely affecting the concept.

A bioreactor body comprises four, suitably separated, clear plastic film phytotubes (the tubular containers for growing the microalgae, diatoms, cyanobacteria or other phytoplankton in aqueous, growth media with room for exhaust gas above), within a protective and insulating, outer tube called the envelope. All the tubes and pipes are produced by standard blow-moulding or extrusion techniques. Subsequent calendering, nanoimprint lithography and/or vapour deposition produces the coatings, groundsheets, reflectors and Fresnel lens sheets. Many tubes are coated with anti-condensation coatings, the phytotubes being coated both inside and out. The blown envelope tube is temporarily sliced open lengthwise to facilitate the placement and fixing of the tubular contents, together with possibly the fluting, the photovoltaic (PV) strips and the protective/reflective groundsheets, prior to re-sealing.

In between bioreactors are curved reflective surfaces (aluminised, plastic sheet, mirror reflectors) that direct additional sunlight into the algal soup contained by the outer phytotubes. The reflectors are of two shapes, depending on whether they are to reflect concavely on one or both sides.

Reflectors sited in the narrow space between two bioreactors in the same quad are designed to reflect both ways. These are shaped somewhat like a railway rail, but with a narrow top and a widely-flaring, flat base, each curve of which directs sunlight into the lowest third of the nearest phytotube on its side. The reflectors also incorporate bands of reflective, Fresnel lenses that focus light into the phytotubes in wedges or bands, adding to the banding produced by the transparent Fresnel lenses on the phytotube uppers. These curve-sided, roughly triangular reflectors have approximate dimensions of: height 310 mm and base width 900 mm. Reflector sections are 3 m long and butt up against each other, possibly having connectors something like centreline hooks and rings (possibly by the heat/vacuum formation of pegs with matching indentations in the thin sheeting), or those of railway carriages, to maintain the correct distance between them. Their flatter parts may be walked on in specially-designed, soft footwear, perhaps surf slippers or kadaitchas, with little damage.

The type of reflector located on the outside of each quad of bioreactors has a cross-sectional outline shape akin to that of a medieval shoe, the kind which has hugely elongated, pointed toes. In this case, the curved, reflective area runs from the top front of the shoe down to the top of the flattened toe. As in the other type of reflector, this surface directs sunlight into the lowest third of the nearest phytotube. This kind of reflector has approximate dimensions: height 310 mm, width at the flared base of 600 mm, and length 3 m, with similar connectors as above. The toe tucks under the inwards curve of the envelope at its base. Spaced holes (each supported by spaced, stumpy feet around the bottom of each hole and formed from the same sheet) along the toe edge of reflector sections allow for dirt to be flushed away.

Each reflector unit is a sealed tube that can be filled through a plug with brine or bubblemix so that it is stable in storms and under minor flooding. Plugs at the base at either end of each section allow for emptying or to retrieve the contents by pumping out. The tube material consists of ~0.5 mm transparent PET film. The upper surface of reflecting sheet is embossed with nanodomes by calendering or nanoimprint lithography (NIL) in order to shed water. Little able to adhere to the nanodome surface, water droplets roll down, taking with them dust and grime that would otherwise reduce the reflectivity of each silvered reflector. The under side of the reflecting area is heat-embossed (possibly in the same pass as the one forming the nanodomes) with reflective, Fresnel lens bands. After coating with aluminium vapour, then a protective polymer coating, to turn them into mirrors, these bands are able to focus sunlight in tranverse bands or wedges in the algal soup. These bands are separated by interlacing, darkened wedges. The total effect is designed to add to the banding effect of the nearly-horizontal, transparent Fresnel lenses on top of each phytotube. Both types of reflector are made concave on one or more of their sides in order to reflect light into the lower half of the phytotube nearest them.

The initially-flat, thin reflector material is heat-formed and heat-sealed into its two types of tubular shape. Before the tube ends of each section are sealed onto polymer end-forms, in order to allow the protrusions nearest to the envelope to be walked on with least damage, warm-melt polymer is made to fill the thinner parts, inner edges and corners. Care is taken that no lens is formed such that its focussed rays will deleteriously affect people, plant, algae, plants or aircraft. However, it may be beneficial if birds and insects can be discouraged by some of the light reflections.

The bioreactors and reflectors will concentrate dew and rainfall runoff to strips alongside each bioreactor. The degree of concentration could be as high as sixfold and, due to their being covered by water-filled polymer containers, would include a marked degree of protection from evaporative loss. Particularly in arid climes, but also more generally, this would have the effect of providing strips of concentrated, soil moisture sufficient to grow (designedly) low-growing, valuable plants, such as root, leaf, stem or seed vegetables, flowers, nuts and fruits, or native species, that otherwise could not grow there. A constraint might well be that only hand cultivation and harvesting could be allowable. Indeed, gardens might flourish between the rows of bioreactors. These could be fertilised with local fertilisers deriving from the facility's pipelines, biorefinery and drillhole reactors via soaker hoses located under the plants. The gardening soil might also be improved with biochar that is similarly derived. The biochar would be mixed with the soil around and under the reflectors (before their placement), so that it formed a wick to draw the stored soil moisture to the plants from where it accumulated at the intersection of the reflector and the bioreactor envelope.

Organic waste from the gardens could be transformed into biofuel, fodder or nutriceuticals by the biorefinery. Moreover, the return, external pipelines from the facility, if containerised (made to transport sealed containers, or slugs), might be used to deliver the resulting produce to ports and cities at low cost and high reliability. Such a variety of sustainable industries, based on the biofarms and biorefineries, could well form a solid, diverse and long-term economic basis for townships and regional development.

Should alternative crops between bioreactors require biological control to prevent them from deleteriously affecting algaculture, it may be convenient as well as profitable to introduce plant grazers to control them periodically. Controls might take the form of introducing benign animal or insect life to eat the plants. Whilst the sharp hooves of sheep and goats, and the sharp claws and beaks of some bird species, might be too damaging, despite their otherwise high economic benefit; and the teeth, claws and/or burrowing habits of rats and rabbits likewise; it may not be impossible to find species, possibly amongst them some threatened native ones, that could do the job. Of species with economic potential, vicunas, quail, reptiles, worms and guinea pigs come to mind. These might flourish, as they would be in an environment protected from most of their natural and introduced enemies. Some might also be used to control pest infestations.

The bioreactors are initially designed as being 100 m long, 2.5 m wide and 0.55 m high at the slightly curved apex and sit on the land's gentle contours. Their parts are thus easily accessible. The briney bubblemix liquid in the envelope is normally only around 0.13 m deep, but this can be increased to as much as 0.35 m in order to cope with less-level terrain, or to help resist overheating or damaging bioreactor movement by way of floodwater or cyclone. The depth of the bubblemix is what allows the phytotubes to be filled as deep as they are with algal soup, and to become as round in cross-section as they are, without the enclosing membrane coming under unnecessarily high stress. It also means that the phytotube membrane only has to withstand a pressure of water from 0.27 less 0.13 equals 0.14 m depth, rather than the full 0.27 m depth of the algal soup in the phytotube. Each phytotube has a similar, though rounder, cross-sectional shape to the envelope and has dimensions approximately 100×0.5×0.4 m. When filled with media and inflated with gas, phytotubes have spacing between them of around 0.12 m, less to the envelope at the outside edges. These spaces allow sunlight to penetrate between the phytotubes and sideways into them. Some rays are reflected from the underlying, aluminised groundsheet and penetrate into the lower, outer levels of the algal soup on both sides and internally. Normal operating depth for the algal soup in the phytotubes is 0.27 m. However, they can still operate from between depths ranging from 0.15-0.35 m. The normal operating depth has sufficient leeway as to be able to accommodate minor land surface irregularities that occur along the contour of the relatively flat, natural (or possibly levelled) contour surface on which the bioreactor is laid, whilst still providing an adequate channel depth for soup and gas transport. The extended range of depth allows accommodation to somewhat greater landform variations. At normal operating depth, there is a space of around 0.13 m above the algal soup in the phytotube for gas accumulation and transport. The gas in both envelope and phytotubes is lightly pressurised to create the desired shape by means of the gas pumps in the impeller/harvestor unit or that of the pressure in the main $CO_2$ inlet pipe, mediated by the solenoid-operated entry valve. Outlet valves, pipes and pumps relieve excess pressure. The pressure in the phytotubes is maintained slightly higher than that of the envelope, in order to maintain the desired, rounder cross-sectional shape. This also serves slightly to increase the $CO_2$ concentration in the soup, and thereby possibly to increase algal productivity.

The volume of gas in each type of tube can be altered temporarily to allow easier, or less potentially damaging, access for repairs, maintenance and replacement. On partly deflating the envelope and/or phytotubes, weighted bars placed across them are usually sufficient to isolate the bulk of their contents, with little chance of rupture or wrinkle formation. When replacing a bioreactor body, the tubes may be rolled up from the far end, pumping off the contents to the paired bioreactor or mains piping, until they can be tied and cut like umbilical cords. The replacement tubes can then be attached by long cable ties over the nubs of the previous ones, or replacing them, whereupon the nubs can mainly be cut away and removed from inside the impeller/harvestor unit. Temporary, elasticised bands around the tubes can aid this operation.

Four types of tube reside within the envelope: the phytotubes, distillation tube channels, bubblers and warming tubes. The three, porous bubbler tubes are used to produce masses of bubbles from the briny bubblemix in order to create a semi-stable foam that fills the envelope, thereby insulating the algal soup from excessive heat, cold or insolation. The warming tubes bring (typically waste) warm water from either: industry; from recirculating water that has been indirectly heated by hot fractured rock (HFR) geothermal sources (typically, after its steamy, higher temperatures have already been used for other purposes); from ordinary geothermoclines; process heat; warm bores; solar ponds; or ordinary dam water. When the warm (or else cold, if bioreactor cooling is required) water pumps and/or valves are actuated, water flows in two pipes lying in the bubblemix in the envelope, one between each of the two pairs of phytotubes. This warms (or cools) part of the bed of the bioreactor to maintain algal, temperature-dependent activation levels. At the same time, it sets up slow, circumferential convection currents in the algal soup, thereby replicating the beneficial effect of warm-season, angled sunlight during cold or overcast times.

If profitable, at each end of a phytotube, the helical flow may be assisted by the insertion of a polymer annulus just inside and pressing against the phytotube wall. The annulus bears short, helically-directing vanes, baffles, curving strips or projecting rifling, that project a few to several centimeters-meters into the flowing algal soup. The slant of the vanes in each phytotube may be adjustable via software, so that their slant adds to the circumferential flow of the algal soup contributed by other means, such as the changing angle of the sunlight or pipe heating, rather than opposing it.

The helical flow serves to keep both microbubbles and algae dispersed, in suspension, and moving between different depth levels. The two warming tubes are joined at their far ends, to form a U-shaped bend. Local, microcomputer controls can reverse the flow periodically to ensure that the different pairs and sections of phytotube are warmed approximately equally. Afterwards, the now-cooled water is pumped by return pipe to the original heating facility for re-use. Such artificial warming may be used in the early mornings, or in overcast or cold times, when there is insufficient warming by sunlight alone to generate helical flow.

The phytotubes contain the growing microalgae, nutrient media and gases. They are encased by a clear, outer plastic film tube, the envelope, that lies on, and is affixed to, the reflective groundsheet. Bonding of polymer films is achieved typically by the application of heat and pressure (thermal bonding), ultrasonic welding, plasma activation or hotmelt glue. The outer surfaces of both envelope and phytotubes are also formed into nanodomes that reduce light reflection from them and induce self-cleaning via water droplets rolling off them gathering up loose, solid deposits or encrustation. Should the inner surfaces of the various, transparent tubes and fluting through which light passes before it reaches the algae tend to reflect undesirably large amounts of light, they may be similarly treated. However, the cross-sectional shape of underside of these anti-reflection nanodomes may need to differ somewhat from the top surfaces, due to the refraction being opposite in effect and the light-pipe and end-effects different.

Winwick phytotubes are of substantial cross-section relative to most other closed bioreactors. Therefore they incur less wall friction losses. This, together with laminar flow of the contents and no aeration/turbulence requirement (except at one end), contributes to Winwick's extremely low power usage. The recently discovered algal antenna-reduction effect helps make the unusually large cross-section of the Winwick phytotubes efficient at biomass production, without requiring high turbulence or high power input.

The materials of the bioreactor body are mainly transparent, thermoplastic polymers. The fluting that encloses the PVs is typically made of PET, as are the phytotubes. These are UV-stabilized with standard additives, such as benzophenones. The envelope is typically made from PET or from low-density polythene (LDPE), both of which are typically UV-stabilized with hindered amine light stabilizers (HALS, especially HALS-3) and UV absorbers (UVA-5). The piping and channels are of polyethylene or polythene (PE) and the groundsheet is of aluminised PE or PE/PET mix that can be recycled polymer from the more transparent uses.

The gas in the envelope is chosen from $CO_2$, $O_2/CO_2$, nitrogen, argon or other gas or mix of gases, whichever represents the best site choice when the factors of: heat retention, fire risk, maintenance workers' safety, pests, vermin, lichen/mould growth and bubblemix contamination are considered together. The envelope encloses, and is fixed to, the phytotubes and to the internal piping, to keep them, as well as the transducers and wiring in place. Following field deployment, the envelope also encloses the bubblemix, other tubes, gases, algae and algal growth media.

The separation distance between the inflated phytotubes, within the inflated envelope, is important for two reasons. First, it allows sunlight to penetrate the algal media from several directions, thereby permitting the algal soup to be either denser in algae or the soup deeper. Second, as it allows sunlight (or the bed heating mechanism in cooler times) to warm one or other side of each phytotube, this results in slow, convective, circumferential flow in the soup. Combined with the low-energy, laminar flow lengthwise in the phytotubes that is provided by the energy-efficient, rotating impeller blades, the resulting slow, helical flow along the bioreactor results in all the algae being periodically exposed to suitable amounts of photosynthetically active radiation (PAR). The periodicity, when combined with the striping and other flashing light effects and possibly antennae-reduction, is designed to be sufficient for most algae in the soup to survive, grow and reproduce optimally, without the need for rapid, energy-intensive agitation, turbulent flow, costly artificial illumination, or the high, pipewall resistance involved in small-bore tubular or thin-film bioreactors.

Commercial, anti-condensation (AC) coatings are provided to appropriate surfaces of the envelope, phytotubes and fluting to reduce solar reflection by water droplets, the coatings being selected from ones having little affect on PAR transmission and (for the internal surface of the phytotubes) do not encourage algal adhesion. A Teflon™-PFA or FEP coating may be used to reduce such adhesion where a given algal strain in use or prospect has that tendency. If such a coating reduces insolation transmission markedly, then it could just be applied to the film that would be in contact with the soup.

The far end of the bioreactor is made of hollow, rotomoulded polythene, PET or recycled PE/PET mix, possibly with an admixture of carbon black, stabiliser and/or colorant to improve its shelf life under prolonged UV insolation. Its form is roughly that of a sagging ellipsoid, freestanding on its long, flatter edge and supported on stability supports projecting from its lower, long edge. Its cross-section resembles a thin "witches hat" with five extra, roughly elliptical protrusions on one side, by which to attach the envelope and the four, phytotube ends. Subsequent to the rotomoulding operation, the centres of the phytotube formers on the rotomoulded item are cut out to allow lengthwise and transverse passage of the algal soup. The barcode of the impeller/harvestor unit, plus an endpiece code, are heat embossed with large, paint or metal foil characters on the exposed side of the bioreactor endpiece for identification and navigation purposes. The central database associates each barcode with the farm, access road, rectangle, layout, kytail (see Farm Layout section), sequence number, impeller/harvestor, bioreactor, GPS location, age, contents, history and status of the unit. This information is remotely available to maintenance workers, as are their team members' GPS positions, schedules, timing, tech information, guidance and communications.

Inside, attached to each side of the envelope and sloping down towards the bottom of the impeller/harvestor unit are narrow, open plastic channels to collect and conduct water that condenses on the internal, upper surface of the envelope to (as one alternative) the storage area in the double hull of the I/H unit. This surface may also be formed into nanodomes to discourage water drop adhesion, though it may well be less effective than on an external, raindrop-prone surface and could interfere with the effectiveness of the anti-condensation coating. Some sterilised water ballast in the I/H unit would serve to stabilise it when otherwise empty. It might also be useful when new bioreactors were being set up, as water ballast might avoid undesirable movement of the impeller/harvestor unit when a bioreactor was being unrolled from it. When the I/H unit double hull is partway full, excess distilled water simply flows back into the bubble mix or algal soup. Depending upon the distillation capacity required, the channels may need only to go partway along the envelope, perhaps only 10 m from the I/H unit on each side. Alternatively to filling the double hull, the distilled water may be pumped directly to the main—particularly if algal growth is likely in the double hull. Distilled water may be pumped into the algal soup or bubblemix at any time, or be tapped by maintenance workers for other purposes. The double hull may better be filled with brine or bubblemix.

Water from the fresh/distilled mains pipe can be used to increase or replace phytotube liquid volume removed by harvesting and/or to reduce the salinity of the algal media or the bubblemix. The envelope, condensate channels and pumping control system therefore act as essentially passive, solar-powered salinity controllers and as economic producers of sterilised, distilled water for the algal soup and other purposes. The system can also be used for internal evaporative cooling, as the warm, condensing water vapour, once it has given up part of its heat to the air-cooled envelope, can be removed and replaced with cooler dam or bore water.

Water for the original bubblemix mixture will usually be sourced from local, brackish bore water, seasonal stream flows or dams. This, like the water for the algal media itself, can, if desirable, be initially and thoroughly sterilised by one of the heat sources, such as geothermal or solar pond, to ensure that no unwanted, living organisms or spores remain viable. The bubblemix develops its wildlife-repellant, briny nature from the distillation process that concentrates the brine. Its long-lasting, bubble-forming properties are given it by the addition of bubblemix concentrate, which may be a form of detergent and/or gel. A biocide will normally be another component of the bubblemix, to keep it transparent and free of living organisms.

Any excess bubblemix brine from the distillation operation may be used in transparent-film, covered solar ponds to generate either process heat, algal-bed warming fluid and/or electricity. Such a source has the advantage of being available at night and at over-clouded times. The electricity might be generated efficiently using Stirling engines. The large amounts of heat that could be stored in an extensive system of solar ponds might thus act as a backup process heat reserve, or, as already noted, as a ready energy resource for all-hours power generation, or to meet customers' power demand surges.

Salts from the harvested algal slurry may also end up in the solar ponds by way of the WSS process. This is one of the means by which the build-up of salts in the algal media may be counteracted, or their concentration even reduced as much as is required. This salty water extraction is called blowdown. Its sterilisation prior to ponding would simply require the use of one or more of the low-cost, local, high temperature heat sources, followed by heat recovery. Being held in polymer-lined, solar ponds largely prevents the salt's release to the environment and any consequential harm. The salt may even become a mine-able resource when it is made open to the air and allowed to dry out, thereby becoming suitable for harvesting.

In order to conserve heat and to avoid the solar ponds from becoming polluted or hazardous to wildlife, each will typically be covered by two, different, transparent polymer covers, each of which may be treated with anti-reflective coatings. The first, which floats on the pond surface by its low density or contained bubbles (possibly as in bubblewrap, but with many fewer bubbles to reflect insolation), reduces heat loss to evaporation—unless it is rolled up specifically to allow evaporation, thereby to concentrate the brine and to produce distilled water, as with the bioreactor envelopes. The second is an inflated, or an inflated-rib, dome designed to keep out dust, rainfall, debris and wildlife. Typically, it would have a nanodome-textured exterior surface, to help maintain its cleanliness and transparency, and a non-fogging interior surface. Water condensing on the interior would run down the sides and be harvested and transferred to a potable water storage system. The bottom of the solar ponds would be sheeted in a black polymer designed to absorb heat. There may also be a number of transparent films horizontally through the pond, separating the layers of increasingly salty water downwards. Each film would be on a roller, so that it could be retracted and cleaned. Two sets of heat exchange pipes, probably near the bottom would harvest the heat as required, the one converting it into electricity via closed-cycle Stirling engines, the other set or sets producing hot water of selected temperature for various biomass heating or processing requirements. The solar pond heat bank would act as large and ready energy stores for cheap and rapid energy conversion into power to cover overnight power to the facility, retail demand peaks or to make up the difference when irregular energy sources, such as wind or direct solar, fail.

Fluorophores (fluorescent materials) may also be added to convert green/yellow and selected ultraviolet light into frequencies more usable by algae for photosynthesis. It is conjectured that pre-algal species, using purple photosynthetic dyes, may have absorbed green-yellow light, leaving algae to develop dyes for the other wavelengths, and by progress down this evolutionary route, making it virtually impossible for algae to evolve to capture yellow-green light when they became dominant. We may eventually be able to give some algae this capability by means of genetic modification. If so, then fluorophores could become redundant. However, it might mean that the bioreactor contents then became an unattractive, though more productive, black, when the different-wavelength-absorbing species were mixed to maximise solar uptake.

Algae tend to be able to utilise some of the longer ultraviolet wavelengths but not so much the middle or shorter ones. Some of the ultraviolet light frequencies will be absorbed and possibly transformed into usable frequencies by the UV stabilisers in the tube materials. Selective transformation of the remainder may be able to increase PAR to the algae. Used most effectively by involving the fewest step-downs in frequency, such fluorophores might tend to make the bubblemix emit a mixture of orange and violet light. It may even be possible to incorporate such fluorophores in coatings on the reflectors, so that reflected insolation is converted to frequencies best usable by algae before it impinges on the phytotubes. A fluorophore coating on the reflectors might also be used to convert IR insolation to even lower frequencies that are absorbed or reflected by the material of the envelope, thereby reducing the non-PAR insolation (in particular the infra-red rays that cannot be utilised by algae for photosynthesis) entering the envelope. Any frequency step-down involves the excess energy being transformed into heat. Thus, similar but subimposed (placed underneath the other coating), semitransparent fluorophore coatings on the reflectors and on the underside of the lower third of each phytotube might be used to convert UV light of unusable frequencies to ones usable by algae for photosynthesis—thereby also avoiding another effect that might otherwise heat the phytotubes undesirably.

Most plants and many microalgal species look green because they are unable to utilise light in green-yellow wavelengths for photosynthesis. Now, there are many minerals, such as fluorite, and some organic, fluorescing dyes that transform light of one or more bands of wavelengths into one or more longer, less energetic wavelength bands. Thus, it is possible to transform unusable ultraviolet or green-yellow light into lower wavelength light that is usable by algae. Several transformational steps (hence several dyes or minerals concatenating the overall light wavelength change) may be required as each step may be too small to accomplish, say, the green to orange-red transformation in just one step. Presently, organic, fluorescing, designer dyes are both expensive and unstable under prolonged illumination. However, it may be that ground up fluorite of a certain kind and/or the invention of more stable and economic dyes will enable utilisation of this additional source of energy by the algae in the bioreactors. The more insolation that can be transformed into PAR, the less is the possible overheating problem and the greater the potential algal productivity gain. As with the algae, a thixotrophic gel may be a useful bubblemix additive to keep the fluorite in suspension and hence near the algae. The gel and the suspended mineral might together also serve to retard leakage from any pinholes. Bubbler operation would tend to keep the fluorite in suspension and the bubblemix mixed. Of course in cold climates, at least for much of the year, any heating effect may be a boon.

The design of the Winwick bioreactors allows the typically toxic (to algae) dyes to be incorporated safely into the bubblemix, which is separate from the algae, thereby potentially providing an additional, useful light source that is adjacent to the darker, lower part of the phytotubes at the precise time that this portion of the total insolation is transformed from a potentially harmful heat source into a beneficial, additional photosynthetic energy source for the algae.

Including or modifying algae to have the newly-discovered chlorophyll f pigment may be yet another way whereby Winwick bioreactors might be empowered to utilise more of the solar spectrum to generate biomass. This could be important as over half of the light from the sun comes in at infrared wavelengths. The in-vitro absorption (706 nm) and fluorescence (722 nm) maxima of algae possessing this chlorophyll f pigment are red-shifted compared to all other chlorophylls from oxygenic phototrophs.

The groundsheet, or inflatable, reflective 'mattress', is in transverse, fluted form that is deflated in transport. It is composed of a set of parallel, joined 'sausages' made of PE film bonded to a base of protective foam PE or PET having raised edges to support the edge of the envelope. Sausages run the width of the bioreactor and are bonded together, typically by the application of an outer PET or PE casing. The area of each sausage-edge sealed by the casing, and by being squashed together, gives it its rough shape of a plank on its side. Each sausage has two small orifices near the top of the sausage's sides, one near each end of the sausage on opposite sides of it. Matching orifices are aligned and glued together, typically with hotmelt polymer that also serves to strengthen the orifice. For redundancy purposes, twin, PET or PE collapsible pipes are hotmelt-glued to each of the serried ends of the sausages to convey water to the far end of the groundsheet from the I/H unit. The orifices permit water or air to be pumped slowly into the flattened fluting so that, as the fluting fills and expands upwards, the envelope and phytotubes are raised sufficiently, starting from the far end of the bioreactor, to move their liquid contents by gravity into the I/H unit, from whence they may be pumped away. Once emptied, the groundsheet fluting may be pumped out and collapsed again.

A special pipe connects the twin bioreactors, so that soup from one may be pumped directly into the other. Typical uses for this arrangement are when one bioreactor is requiring downtime or replacement, or when one is providing the stressing conditions for the algal contents of the other. After use, the inflating fluid might be pumped to the bubblemix in the envelope to reduce the admittedly small chance of contamination by unwanted microorganisms.

Should the inflatable part of the groundsheet become damaged or dysfunctional over time, a remotely-controlled, battery-powered vehicle could be used to move just under the bioreactor endpiece and groundsheet from the far end, thereby pushing the algal soup ahead of it. It would look rather like a wide beetle, tortoise or gunless, battle tank with dimensions roughly 2.6×1.0×0.25 m high. It would have four, wide, powered belts or tracks, two of them as caterpillar treads mounted on the base, the other two powering twin, parallel, triangular cross-section, rounded-lengthwise, turret-forming belts. The separate drives of the four belts propel and are used to steer the tortoise along, between ground and groundsheet.

For operation in cooler or more variable climates, several modifications may readily be applied to the construction of a Winwick bioreactor or farm. These follow. First, more than one concentric envelope may be used with the bioreactors to insulate the phytotubes, the outer envelope of which may require an antifreeze bubblemix and/or be made from a polymer better suited to low-temperatures and possibly one with greater solar transparency than PET or polythene. The PV shading might also be made less in proportion to clear envelope. Conversely, at high altitudes where the insolation is over strong, more PV may be useful. Cross-sectionally larger dimensions for the bioreactor would help to reduce heat loss in cool climates and to even out algaculture temperatures where day to night ones vary greatly. Denser packing of bioreactors on the farm might have a similar effect. Amongst ways, this could be done by levelling the land prior to positioning the bioreactors. Algal strains active at lower temperatures or requiring greater salinity or sodicity might be selected, bred or created, as the algal soup of these would be less likely to freeze at the edges or in pipes overnight. In more extreme climates, the impeller/harvestor units, pipes and pipe bundles would require better insulation, which might be achieved with earth berming or burying and/or polymer foam coatings or blankets. In cooler climates, bed heating would be required for longer periods each year. For this to happen, the sources of waste heat for bed heating might need to be widened to include geothermal heating from tapping ordinary geothermoclines, or using heat from any biomass or industrial waste heat source that is locally available. On the credit side, less investment would be required for heat dissipation; there would be less chance of photo-inhibition (caused probably by photo-oxidative stress and damage due to the over-production of free oxygen radicals) occurring; and cooler, probably wetter climates would tend to provide better sources of organic waste nutrients for growing algae than do arid ones.

For very hot climates or seasons, adaptability takes more the form of using thermophilic algal species and using greater proportions of PV on the envelope. Insulation, or the burying of some pipes, may also be used against external heat and diurnal variation. Bed heating would probably not be required. This in turn might suggest a reduction in the cross-section of the phytotubes and envelope. Cold water from a dam, deep lake or shallow aquifer could be used both to cool the algae and to induce circumferential motion in the phytotubes. Evaporative cooling of structure or contents could be considered, but might only be economical near a large body of water, such as a lake, the sea, or a major, not fully committed aquifer.

For location on terrain that is less level or flat, and at some increase to capital and operating costs, bioreactors may be made shorter than 100 m and possibly wider to hold more phytotubes; whereas on extremely flat terrain their length might be increased. However, changes in length might tend to require offsetting changes in soup velocity and other factors.

Photovoltaic Design

Using the bioreactors as a platform for the generation of photovoltaic power, whilst using the photovoltaic strips to optimise light to the algae, provides an elegant solution to two problems.

Attached to the top of the envelope are bands or (broken) strips of typically semi-flexible photovoltaic film, mounted in the airspace between flutes (separators) inside two lengths of transparent polymer film. The slightly inclined fluting, running in centrally-broken strips across each bioreactor, serves passively to cool the PV, thereby increasing its solar conversion efficiency. What energy is not converted into biomass or electricity, the air-cooled fluting helps convect as hot air away from the PV and algae, thereby increasing the efficiency of the PV and helping to maintain the algae at their most productive temperature range.

Should potential external conditions make it advisable, the open ends of the flutes may be covered with strips of transparent, thermoplastic flywire mesh, the better to secure the fluting to the adjacent fluting and to the envelope at the other open end, and also to hinder the ingress of detritus, birds, animals and insects. Cleaning the fluting and PVs may be effected either by streams of high-pressure air or water, and/or by light rollers mounted on tubular supports that transmit backpack-powered ultrasonic cleaning. Distilled water for cleaning can be sourced from outlets on the impeller/harvestor units by maintenance personnel with backpack-mounted powerpacks and water containers.

There are several types of thin-film PVs now available. Typically, PVs reflect around 35% of light back into the sky. However, if the manufacturing technique can be adapted to produce fluting and PV surfaces comprised of nanodomes of mixed diameter of around 100 nm and set at 450 nm intervals, then the reflection loss can be reduced to 6% (per surface). An important, secondary benefit of the domes is that they encourage an inclined PV or other surface to shed water. This action takes with it dust that has fallen onto the surface, thereby cleaning it. The water-shedding effect is caused by the bumpy nanodome surface preventing droplets landing on the surface from achieving a contact angle that breaks their surface tension, so they form beads on the surface rather than wetting it. This effect has been demonstrated for silicon-based PVs. However, it is likely to be applicable to all surfaces that can be formed into nanodome-textured sheets. Thus, nanodome upper surfaces would be useful for fluting, envelope, reflector, PV and phytotube upper surfaces. If they are of too fine a structure to be made by the preferred method of calendering using heated rollers in a partial vacuum (to reduce viscosity effects), then either by one of the standard methods of nanoimprint lithography or one of four alternative methods may be tried. The first is by dusting transparent nanospheres over a surface prepared with adhesive. The second is by mixing transparent nanospheres of a different polymer, glass or ceramic with a compatible (adheres to) transparent polymer matrix, that either coats or forms the fluting, PV or phytotube material. A matrix material is chosen that dissolves in a solvent and this solvent is used to dissolve that part of the matrix material that covers the upper third of the top layer of nanospheres, thereby forming a nanodome surface. A third method is that the surface might be formed by passing the film through a 'calendering' machine that focuses streams of charged particles or electric discharges into patterns onto the film such that they erode the film surface into a honeycomb pattern of nanodomes. Letting the nanospheres fall sparsely and evenly onto a heat-softened or solvated polymer film (such as a drying glue) might be a fourth feasible method, and one that is likely to be even more economical. If the nanospheres absorb radiation at a frequency different to the polymer matrix, then nanospheres resting on a solid polymer matrix might be differentially heated by radiation of that frequency, so that they partially sink into the matrix and bond to it, thereby forming the required nanodome surface.

The performance of the PVs may also be enhanced by using transparent electrodes made of graphene to coat the upper surface of the PV.

The performance of individual PV strips can be readily monitored from the air using IR thermography and the barcodes on each bioreactor. Being relatively small, standardised and readily accessible, faulty or degraded PV strips can easily be identified and replaced.

The PV film or sheet is formed into centrally-vented (to permit the exit of cooling air), transverse bands or strips of PV running inside fluting, crosswise along the bioreactor. The strips have a lateral edge attached to springy, polymer laminate, shaped in cross-section like an S on its side, with a curving vertical support running through the upper third of the S. When cold, the strips forming the top and bottom parts of the S are curled to expose more of the algal medium to insolation. When warmed by progressively more intense sunlight or temperature, the laminate uncurls to shade more of the medium. The vertical support also uncurls, thereby increasing the thickness of the fluting and encouraging greater airflow. The uncurling is mediated by differential thermal expansion of the two sides of each PV laminate strip, one side being composed perhaps of metal foil and/or dense, polymer foam with higher expansion coefficients than that of the nanopolymer PV film.

Each PV strip is attached by one edge to the springy extrusion or strip. When cold, the PV is furled or curled up to a fraction of its width. However, in the 'S' formation, as its inside laminate surface is a material (a dense, foam polymer or metal foil) of high thermal expansion coefficient, when it is warmed by the sun, it uncurls proportionately to the heating, thereby causing the PV to shade more of the algal media from excessive insolation and heat, and to produce more PV electric power.

Alternatively and usually preferably, for economic reasons or if multiple flexing is deleterious to the selected PV material (a likelihood), two PV strips might sprout as wings from either side of the top of the long, strut walls running inside the fluting and separating its two sheets. Struts are of hexagonal cross-section in elevation view and are typically made of clear, PET polymer. Each strut or spacer (made by plastic extrusion or joined sheet) runs approximately halfway across the top of each bioreactor, before it approaches the end of its paired strut on the other side. The two narrow sides of each hollow, collapsible strut hexagon are heat-sealed or ultrasonically welded to one or other sheet, joining them by the strut body. The PV wings are attached to the top of each strut, sandwiched between film and strut, by a curved, laminated, preferably-transparent strip that uncoils on warming (is thermo-active). This action spreads the planar wings so that they intercept more sunlight the hotter it is. The spreading wings thereby narrow the aperture slot by which sunlight reaches the algal soup. As the PV strips or wings may well have lifetimes different to the transparent-film bioreactor components, and as individual PV wings that develop faults may need to be replaced during the life of the bioreactor, or be re-usable after it, each wing has one long edge thickened that slots into a 'keyhole-shaped' slot running inside both long edges of the laminate. Replacement or recovery is effected by disconnecting the wiring to the wing, pulling the wing out, and possibly replacing it with a good wing and reconnecting the wiring. Better still, the wiring may be incorporated inside each slot, so that it makes the correct connections to those on the wing, when the wing is fully inserted. Old but good PV wings from defunct bioreactors may be used as spares. The wiring, or other form of electrical connection, connecting each laminate strip to the same-sided others and thence to the outside world might be built into the fluting.

Faulty PV strips can be detected most efficaciously by thermal photography from the air—possibly by unpiloted airborne vehicle (UAV). However, to identify the faulty strip it will be helpful not only to photograph the barcode on the bioreactor, but also to record on which side is the fault and to provide an indication of its sequential number. For this purpose, every fifth broken strip of PV has printed its sequence number from the I/H unit (5, 10, 15 . . . ) on the centreline break of each strip. So that this interferes minimally with PAR transmission, the number may itself be in a visible, but PAR-transmitting, transparent dye, possibly with a black dot on either side to mark each fifth, broken or double, strip more precisely. Each strip would be one of the wings on a dual-wing, PV sub-assembly and each sub-assembly would have its twin on the other side of the bioreactor.

The ratio of light transmitted to that intercepted by the PVs can be determined at manufacture by changing either the spacing of the struts, the length of the wings, the length of laminate, or the degree of uncurling mediated by the thermal expansion coefficient differentials of materials comprising the laminate. Typical light to dark ratios might vary in a range from 2:1 to 0.1:1 to provide roughly a twentyfold light-passing variation factor (this will be reduced by the effect of the unshielded reflectors to perhaps sevenfold). Should it be economically beneficial, the width of the struts may be increased and their end-assemblies kept transparent so that they form a set of additional, fixed-width PAR apertures, thereby doubling the frequency of flashing light to the algal soup moving under the strips.

As sunlight will tend to fall more on left or right wings, depending on time of day and PV orientation, wings of each type are separately connected electrically. Typically, one type of wing on a given bioreactor will generate a higher voltage than the other at a given time of day. The orientation of one set of wings will tend to intercept more sunlight at low angles than would a near-horizontal, fixed PV receptor. And at low angles, more light will tend to enter the phytotubes from the side, thereby avoiding shading by the PVs above.

The elongated hexagon shapes of the struts are transported in flattened form on reels, usually already attached to the fluting and thence to the envelope and other tubular bioreactor sub-assemblies and groundsheet. The initial roll-up onto reel operation may be facilitated by warming the whole assembly so that the PV wings flatten out. The top of the bioreactor envelope forms the lower sheet of the PV fluting.

At deployment, the reels are unrolled and each bioreactor is attached to its impeller/harvestor unit and its opposite end-piece. The effect of warming on the PV wings will by itself tend to expand the fluting. After attachment and inflation of the envelope and phytotubes, gusting wind action over the curved bioreactor envelope expands the flattened-strut hexagons of the fluting vertically by an aerofoil effect until each resembles a wall bulging on both sides of its midline. Thus, the PV fluting is effectively self-erecting. The expansion is effected by means of cable tie look-alikes having strut-mounted heads and ratcheting, sawtooth-lined ties that run through the strut wall at intervals along its horizontal middle line. Ratcheting ceases when a tube encasing the cable tie section that is located inside the hexagon butts up against both walls. The cable tie tail is left extending between the struts.

Impeller/Harvestor (I/H) Design

Each impeller/harvestor unit, or central head, has a bioreactor body or arm attached to each side, rather like a spread-eagled, two-tentacled octopus. There are four, distinct, internal chambers in the I/H unit, two of which share the algal soup and gases with each of the separate bioreactor bodies, a third for the drive box containing shared machinery, and a fourth as the internal conduit located over the external pipe bundle that transports external fluids and which is sealed by a plastic board embossed with the unit's barcode for easy aerial and ground-level identification and automated recording. The unit also has a trapezium-shaped hollow or tunnel running under its middle. This straddles the pipe bundle. Pipe-bundle offtakes typically lead through holes in the tunnel roof then sideways to the relevant chamber and item of equipment. The tunnel is also used to connect services to the surveillance pole and computer post, that represent respectively the octopus's eyes and brain.

The impeller/harvestor body is made of rotomoulded, hollow, or double-hulled, polythene. It is tank-like and has a rectangular base and a curved, openable top which is covered by the barcode plank and twin, separately removable, clear plastic film covers, or semi-flexible sheeting, sealed at their edges by strapping, clips and seals. Each cover, or one cover covering the whole I/H unit, may alternatively (and probably better) be in the form of one or more low, transparent, vacuum-formed PET domes with semi-rigid, curled-over edges to aid in forming a reasonably airtight seal. The positive pressure in the tubes and I/H unit tend to preserve the system from contamination from the external environment. The impeller/harvestor's outer dimensions are approximately 2.5×2.2×0.9 m.

Each I/H chamber that connects directly to a bioreactor body has two injection moulded or rotomoulded polythene, drive shafts. Each of which mounts two multi-bladed axles made of polythene. The axles are of two kinds. One, the impeller, is designed to propel the newly-recarbonated, algal soup gently into two of the phytotubes. The gentle action is preferable to most traditional methods that require turbulent action that algae do not prefer, and which can damage them. The impeller has curved blades designed to cause neither splashing nor significant waves. They only cause ripples. The other axle, the agitator or thresher one, is designed to destroy the structure of the thixotrophic gel temporarily, so that for a short period it forms a non-viscous liquid that releases its contained microbubbles, allowing them to rise to the surface, combine and burst. The threshing action also helps to break up algal colonies and agglomerations, thereby improving the algal growth rate. The thresher axle has short, radially-aligned, possibly backwards-curving blades attached circumferentially to a wide-diameter shaft. The blades narrowly slice the soup along its direction of flow. They are designed less to propel the soup than to agitate it locally and so to dethixotropise or liquefy it. The blades cause moderate, local turbulence with minimal splashing and act partly to separate the microbubbles from any adhering algae. Thus, they are designed to rotate faster than the impeller type. They slice and disrupt the gelatinous bonds and the small eddies they create prolong the disruption.

One axle type is slaved to the other type by polythene cogwheels built into their shafts. Each thresher is located non-adjacently at the outlet of two of the four phytotubes. Each of the two impellers is located at the inlet of one of the adjacent phytotubes. Thus, in the I/H unit, the threshed algal soup moves slowly from one phytotube to another (some of it via the harvesting zone), releasing its oxygen-rich gas on the way. This is pumped out of the I/H unit to the mains oxygen pipe.

Underneath almost the entire length of the impeller drive shaft or axle is a flat, small-bubble, sparge plate made of stainless steel. This provides tiny, carbonating bubbles (microbubbles) to the outgoing algal soup. Baffles permit only soup from the lower half of the soup column to reach the impellers. This ensures that little of the froth produced by the (relatively) larger-bubble sparger, set further back, is destroyed before it can bubble over into the open Archimedes screw channel above, which does the harvesting. Although the harvesting sparger is stated above to produce larger bubbles than the microbubbles produced for carbonation, the relative sizes may in fact be reversed. The size of bubbles used to separate mined minerals from crushed rock are typically of diameter of the order of 7 mm. However, the analogous, froth flotation (FF) or dissolved air flotation (DAF) processes used to harvest microalgae tend more to use bubbles of diameter within an order of magnitude of 100 µm or 100 microns (where one micron=a millionth of a meter). Thus, the range of FF/DAF bubble diameters may be two or more orders of magnitude. Whilst 10 µm is typical for DAF, 0.2-2 mm is the expected bubble size range for Winwick harvesting and carbonation, and is of the order of half a centimeter in some wastewater FF treatments. It should be noted that Winwick processes do not require the high-energy input necessary to produce DAF-sized bubbles, as a quick and partial harvest is desirable, and rapid gel reformation holds the recarbonation microbubbles entrained until the next cycle.

The algal-capturing action of the sparged bubbles is improved by their large number and small size. In order to capture the tiny microalgae most effectively, bubbles much smaller than are used in typical, mineral-capturing froth flotation processes are used. The bubbles used here are of their designed sizes for several reasons: to maximise the capturing surface area; to minimise bubble detachment during ascent; to optimise the ascent time for capture to be effected; to ensure that most bubbles reach the surface before gel reformation; and to minimise shear damage.

Operational parameters for harvest sparging are chosen to produce a mix of two bubble sizes. The larger ones, around 2 mm in diameter (and produced by somewhat larger orifices, spread across the spargeplate), form around 1% of the bubble population and are designed to keep the algal soup thin and non-gelatinous at the harvesting station. The smaller microbubbles produced by the harvesting spargeplate, of diameter somewhere in the range of 0.2-1.2 mm (depending in part on the size and shape of the algae being harvested), being slow-rising and of high, combined surface area, have surfaces that are adhesive to algae do the actual harvesting.

No flocculant or special surfactant is typically required to improve the algal capture rate by the microbubbles. However, as changing the pH can improve flocculation in the absence of a flocculant, consideration may be given to adding either the ammonia nutrient, or the acidic nutrients from the flue gas mineral acids, salts and oxides extraction system (these may be combined beforehand with other nutrients to form one of the several, piped, nutrient mixes), at a position that is just upstream of the harvesting process, in order to enhance it. A deep, thick froth of small bubbles provides the conditions for the resulting slurry harvest to be concentrated to some 1-3% dry weight of algae. For this level of concentration to be achieved, a dense, thick foam is required, and one that is maintained for a sufficient time to allow excess water to percolate through the bubble mass back to the main body of algal media, prior to the foam being extracted.

When not required for inoculation purposes, the algal soup mains pipeline may be used to transfer mutated, contaminated or otherwise not required algal soup to a central processing station that concentrates the organics by froth flotation and perhaps other means, prior to sending them to the WCR process.

The wide, harvesting screw channel assembly is designed to accept froth from any of the acceptable operating depths for the soup, though one depth may be optimal. The screw channel sits in a loose, semi-flexible, polymer-film trough. The ends of the trough are fixed to the I/H wall, some way above each open end of the screw channel, but the upper edges of the trough (except at the very ends) are buoyed, so that they are always just above the variable soup-surface. To keep the central, buoyed edges of the trough from curving inwards and downwards, a thin, rigid, hollow boom is attached to each of them on either side of the screw. These provide the lips over which the algal froth cascades. They are Teflon coated to reduce algal adhesion. To reduce algal loss, the trough material is bonded to its adjacent casing material of the screw channel. This is also of thermoplastic polymer. This arrangement allows froth to cascade into the screw channel whenever it is produced, but prevents the soup itself from entering.

Two drive belts, powered by either or both of twin electric motors in the drive box power all drive shafts in the unit. Solenoids controlled by the unit's microcomputer, and overridable by central control, engage individual valves, pumps, drives and devices.

The small-bubble sparge plate type has dimensions approximately 2.3×0.6×0.018 m. The large-bubble one has dimensions approximately 2.3×0.3×0.018 m. Both types are constructed of two sheets of approximately 0.5 mm thick stainless steel sheet, welded together at the down-tapered edges and spot welded at points where the lower sheet is dimpled upwards to touch the upper sheet in order to maintain a separation of 15-20 mm between the plates. For the small-bubble sparger, one or more reinforced plugholes admit a removable nozzle that is joined to a valve and an inlet pipe containing pressurised carbon dioxide gas. The large-bubble sparger has unscrewable pipe and fittings connecting it to the gas pump and thence to the airspace above the sparger. The small-bubble sparger is connected via a solenoid valve directly to the $CO_2$ main, so that both sparging operations may be carried out at the same time. Prior to forming and welding, the upper sheet of each sparge plate has many holes of controlled diameter and pattern made in its surface, preferably with raised and smoothed edges round the holes. This is done so as to minimise the chance of algae and grit clogging the holes and to facilitate early bubble release. The small-bubble sparge plate has perforations in it of approximately 0.05-0.2 mm in diameter. The large-bubble sparge plate has perforations from 0.3-1 mm in diameter, the chosen diameter depending on several factors, including gas pressure, algal strain, the viscosity of the gel, and the optimal froth-bubble size for harvesting. Each type of sparge plate is perforated only on its upper surface and only where its bubbles are required.

Electrically-driven ultrasonic (probably piezoelectric ones vibrating at 42 kHz) generators or transducers are attached to the large-bubble sparge plates to perform brief, regular, computer-controlled cleaning of plates, turbines and impeller box. The small-bubble sparge plates have less-damaging-to-algae, ordinary sonic frequency transducers attached. This or these transducer settings serve to facilitate the egress and detachment of smaller, sparged bubbles (microbubbles), thereby helping to maximise gas exchange with the algal soup by increasing the total surface area of bubbles and by reducing their speed of ascent.

A third set of transducers is typically attached along the two warming tubes that are immersed in the bubblemix. These transducers are for the purpose of producing an optimally-high-frequency, flashing light regime to the algal soup. The frequency range chosen for maximum profitability is likely to be in the range 0.1-10 kHz, depending on the average insolation present in the lighted portion of the algal soup, the degree of antenna reduction, the increase in the number of photosynthetic reaction centres in each alga, and other factors, but with the frequency chosen to avoid damage or discomfort to the particular strains and sizes of algae being cultivated and to the staff. The local vibrations these low-power transducers produce, travel roughly transversely into the nearby soup in the phytotubes on either side. They cause the microbubbles there to vibrate and change shape, thereby successively brightening and shading the sunlight to the soup that is optically below them for a distance. Interference patterns and standing waves caused when vibrations of adjacent transducers interfere will add to the effect, as will the consequent rippling of the surface soup that results in water-lens effects and dappling. Care is taken that the vibrational energy is not sufficient to break the tenuous gel structure in the phytotubes and that the energy input returns a dividend. With a moderately dense concentration of microbubbles, and a relatively long light path, this high-frequency flashing light effect will be present in a substantial volume of the soup. It will add to the lower-frequency, flashing light regimes caused by: the helical soup motion; the soup movement under the PV strips and lenses; and the temporary shading of one alga to those near and optically beneath it.

It may be that microbubbles of the otherwise optimal size do not vibrate effectively at kilohertz frequencies. That may not matter for a combination of two reasons. First, even much lower vibrational frequencies of, and circling around, each bubble surface will send almost instantaneous beams of light out at many directions. Second, any one alga may intercept beams from any of the many neighbouring microbubbles. Thus, the frequency of an alga's light-gathering antenna being hit by a somewhat concentrated light beam may be one or two orders of magnitude greater than the frequency of the transducers' sonic vibration. Hence, it may be sufficient to have the transducers vibrating at less than 350 Hz in order to produce the desired, flashing light effect. It should also be noted that interference effects, the amplitude and the partly-selectable waveform produced by the transducers may also be used to optimise further the flashing light effect. In addition, there may be a range of viscosity of the gel, that suits the other requirements of Winwick algaculture, but within which a viscosity may be selected that improves the flashing light effect.

A cost-effective alternative to piezoelectric transducers may be the new, carbon nanotube speakers developed for underwater use. The sheets of carbon nanotube material can generate a wide range of frequencies, including those in the multikilohertz range. They are powered by passing alternating current through them, which probably means that the frequency can readily be adjusted to suit prevailing conditions and algal requirements. Being an areal, rather than a point source of vibration, would also tend to mean that even small regions of possibly damaging power intensity, such as those adjacent to the transducers, can be avoided. Moreover, if the film was effectively continuous along warming tubes and, separately, under each type of sparge plate, then there would be more even and controllable vibration energy throughout each active zone.

In the drive box of the I/H unit are located motors, pumps, and valves. If feasible using commercially-available equipment, gases excepting probably that from the $CO_2$ main, are to be directed through a universal gas valve and pumped, if pumping is necessary to increase the pressure, by a single gas pump. Similarly, all liquids, except the algal slurry, are to be directed through a universal liquid valve and pumped, preferably through a single liquid pump. The flushing of liquid pumps and valves to keep them clean and the materials they convey uncontaminated is controlled by the microcomputer. The gas pump requires no flushing.

Although sparging (generating bubbles of gas to travel up the soup column) happens at two places, at different rates, and for two different purposes in a Winwick impeller/harvestor unit, they both affect the productivity of the algae, as well as the dispersion of algae, nutrients and waste products travelling in the soup in the phytotubes and in the I/H unit.

High gas exit velocities from a sparger have been shown to cause algal cell death. The large number (hundreds or thousands) of perforations, their wide separation in large-area Winwick spargeplates, and low, overall gas requirement and velocity reduces this threat to negligible.

The use of sonics and ultrasonics to ensure microbubble detachment from the sparger, harvesting and periodic cleaning of surfaces in the impeller/harvestor unit is another matter. As high-energy ultrasonics can damage microalgal cell walls, algal gas vacuoles and photosynthetic antennae by decavitation and free radical formation, the frequency, energy level and timing of these processes are carefully selected to optimise the two, somewhat conflicting, requirements. Non-damaging sonics are used to facilitate microbubble detachment on a continuous basis and to produce a sub-second flashing light regime, whereas ultrasonics for cleaning purposes are used only for periods of less than a minute, probably about once or twice day, and only at the less damaging power levels and frequencies that are still consistent with cleansing action. These cleaning periods will normally be arranged to fall within harvesting periods, so that any damaged algae will tend to be harvested at that time. Ultrasonic barriers and sound absorbants may also be employed to reduce the algal soup volume affected deleteriously to a minimum.

Small-bubble sparging is done in the impeller box under the impeller shaft to provide the algal stock with a sufficient amount of carbon dioxide nutrient to feed it during its passage through the length of two phytotubes (until another active spargeplate is reached). The sparging (assisted by the temporary, viscosity-lowering effect of the thresher's agitation on the thixotrophic gel) also helps to remove the photosynthetic waste product of oxygen, which can otherwise retard algal growth.

A gel that slows upward bubble movement to almost any desired extent, also helps to ensure that there is high utilisation of the (initially nearly pure) carbon dioxide content of the sparged microbubbles by the algae, before the gas is largely lost to that above the soup, which is pumped off (typically, as a 90:10 oxygen:carbon dioxide mixture). Slow, microbubble movement upwards in the weak gel also helps to ensure that, in the absence of turbulence, there are continuous micro-exchanges for each alga for nutrition and waste material removal, thereby contributing to heightened productivity.

Large-bubble sparging may only occur at intervals when algal harvesting occurs, though continuous harvesting is also possible. Continuous harvesting may be indicated when algae, possibly under the influence of bubble attachment, rise to form a light-obscuring skin over the surface of the soup or to maintain the optimal population of algae. Whilst small bubble sparging uses $CO_2$, large-bubble sparging will recycle the $O_2/CO_2$ mix above the algal soup for its gas supply. This serves four purposes: it conserves $CO_2$; it ensures an adequate gas supply for harvesting for all bioreactors, even when many are harvesting at once; it maintains the relative purity of the gases; and it means that correct gas pressures are easier to maintain in the system. Large-bubble sparging only has a minor effect upon the microbubbles remaining in the soup after dethixotropisation. And as small-bubble (microbubble), carbonation sparging occurs just after the soup passes the harvesting chamber, so minimal $CO_2$ is lost due to harvesting. Thus, as a result of gel reformation immediately after carbonation and by slow and localised diffusion, the carbonating microbubbles continue to nutrify the algae throughout their passage along the phytotubes. Typically, by the time the microbubbles reach the surface and burst, the algae and aqueous soup solution will have extracted some 90% of their total $CO_2$ content, replacing it with oxygen.

Should the harvesting process eventually result in the evolution of algae that are resistant to being harvested by this means, algal communities in a given bioreactor may need to be replaced every so often. The controls on each bioreactor permit this to be effected automatically, once the new condition has been detected. A flush or spray with an excess of ammonia, of brine, and/or of biocide, possibly using the bubblemix pipe to supply this latter solution, may be required to kill the aberrant algal strain and/or other contaminant species, prior to replacement by the desired strain of algae. The need for such actions may be delayed or possibly even avoided by using algal strains, such as *Chlorella*, that lack a sexual cycle and hence are probably less capable of evolving defences against harvesting by froth flotation.

Large-bubble sparging is more violent than small-bubble sparging. This is so because, complementing the action of the thresher blades that liberate the microbubbles to ascend, it is designed to prolong the breakdown of the somewhat crystalline or ordered, thixotrophic soup structure into a thin fluid. A thin harvesting fluid is desirable to allow bubbles to move upwards easily and so that the algae are thus exposed to frequent gas-liquid bubble interfaces, to which they may loosely adhere and thus be carried upwards with the bubbles to form a froth or algae-rich slurry that can readily be harvested. Another beneficial effect of this froth-flotation process is that the algae to liquid content of the froth, after the larger bubbles have preferentially burst, is many times greater than that in the original algal soup. Large-bubble sparging also has the effects: of breaking up undesirable agglomerations of algae, of algal mucous, and of lipid; of providing macro-scale mixing; and even of partially cleaning the equipment.

In metallurgical froth-flotation, surfactants are usually needed to ensure that the valuable mineral particles are selectively captured by the bubble surfaces, leaving behind the dross. As algae tend to have a natural attraction to bubble surfaces, the addition of surfactant may not be required. However, if its use does deliver a net benefit for harvesting a given algal strain, then the surfactant(s) chosen may be able to be one that has a secondary use as an algal nutrient or catalyst. The use of one or more surfactants may be useful, should algae in the bioreactor evolve to avoid harvesting without them.

Similar spargeplate designs in stainless steel are used to produce both small and large bubble spargers. The main differences being: the internal diameter and number of the sparge holes; the location of perforation zones; the pressure and composition of the gas; the sonic capabilities of the attached transducers; plate dimensions; and spargeplate location. Ultrasonic cleaning transducers are attached only to the large bubble spargeplate. Sonic, bubble-freeing transducers are attached to the small bubble spargeplate.

The universal valve and pump system for liquids and the separate one for gases have the following design. Inlet pipes connect through one-way and solenoid-activated valves to one half of a length of pipe in the drive-box chamber of the I/H unit. A one-way valve and solenoid-activated pump are located at the centre of the pipe. The outlet pipes, each with its own one-way, solenoid-activated valve, are connected to the other half of the pipe. There is also attached a distilled water inlet valve at the end of the outlet side for flushing purposes. Pressure relief valves to the external environment, whose activation triggers an equipment fault signal concerning excessive pressure to the computer post and central command are located on each half of the pipe. Fluid flows when an instruction activates the selected valves and pumps. For the liquid system, a flushing action with fresh/distilled water occurs after each liquid transfer, first from the far end of the inlet end, then, overlapping in time, from far end of the 'outlet' end. This tends to clear active ingredients from the universal liquid valve and pump system. Gas residues can be ignored in the gas universal valve and pump system. Apertures between chambers of the I/H unit, to the envelope, and to the external environment are formed by tubular attachments in the rotomoulded partition linking the twin hulls at I/H construction time.

Changing the salinity, sodicity, pH, temperature, level, pressure, algal strain or nutrient concentration of the algal media or bubblemix may be done by normal, operational depletion or by pumping the relevant material from or to a mains pipe—an action that is usually mediated by the local microcomputer and implemented by equipment in the impeller/harvestor unit. Initiation for this is directed by locally-stored program or is done remotely from the campus control centre, either by pre-set computer program or over-riding human intervention, possibly requested on location by the installation or maintenance staff.

Winwick Microalgal Growth (WMG) Method

The shading caused by the PV strips means that each alga in the algal soup, moving along the phytotubes, under the motivational force of the slowly rotating impeller blades, experiences frequent changes of dark and light. When the frequency of flashing light occurs for sub-second periods, with possibly longer dark-recovery periods, the algae use the indent light more efficiently for photosynthesis and are less subject to photo-inhibition caused by excessive and prolonged light. The flashing effect is reported to increase light-usage efficiency by nearly double. It means that less light is required for photosynthesis, less is wasted as heat, there is little excess to cause photodamage, and more can be diverted to daytime solar power generation. The PV striping solution is novel, as the Barbosa paper only refers to obtaining flashing light by other, far less economical means.

The PV striping solution is also one that is adaptable to different conditions and algal strains. Given flexibility in PV assembly dimensions, both the PV strips or wings and the spacings between them can easily be set differently at assembly time, whilst the frequency of flashing to each alga can be varied for a given spacing simply by changing the variable impeller speed. The dark recovery period that is useful in maximising light usage efficiency may be optimal when it is a few to several times that of the subsecond lighted period. This lighted period may be as short as 40 $\mu$sec, but is probably here of the order of 0.2 sec, or 0.1 sec if the strut plus thermo-active laminate area is made sufficiently transparent to PAR. The lighted period may again be reduced by the insertion of a narrow, double-sided PV supported by a curved, thermo-active laminate sited between adjacent sets of wings. These could act in a fashion similar to venetian blinds to moderate algal insolation under intense sunlight and to increase the flashing frequency. The optimal ratio of light to dark is probably algal strain and/or light intensity dependent, but may also be constrained by the minimum effective width of the PVs and the velocity of the algal soup under laminar flow conditions. Algal acclimation may also play a part. As well, the extent of light dispersion and the average length of light path in the algal soup may affect the ratio giving maximum productivity under a given set of conditions.

An important aspect of the innovation is due to the fact that algae cannot use strong, continuous insolation efficiently. Therefore, using PVs to reduce excessive heating and to provide intermittent shade to the algae are both effects beneficial to algal productivity, whilst the diverted sunlight is used to generate substantial amounts of power as a valuable co-product. Confirmatory proof as to how shading can improve plant growth lies in the fact that many greenhouses are covered with shade-cloth. This helps the plants to grow by ensuring that they do not to suffer from heat stress or from over-strong sunlight, amongst other things.

There are other ways that Winwick technology makes more efficient use of solar energy than do other algacultural methods or is better economically. Selected, thixotrophic (becomes less viscous upon agitation) gels or gelators added to the soup mean that the algae are grown in a thin, tenuous thixotrophic gel. This or these additions have several major benefits. First, suspension in even a weak gel means that a far wider range of algal strains can be used—not just the few that remain well-dispersed and suspended in agitated aqueous media. Therefore, algal strains with superior growth and/or lipid-producing capabilities can be used, without the need for the turbulent flow and costly agitation required by most other methods. Second, even a weak gel will tend to prevent dead or flocculating algae from either scumming at the surface, flocculating (clumping together), or precipitating (sinking), under which actions they may become less available for harvesting and a nuisance. It should be noted here that the mucilage, gels and lipids excreted by some algal strains are unlikely to interact with the applied thixotrophic gel in any significantly adverse way. Moreover, most algae can be grown on agar gel plates, which is done for the purpose of isolating pure strains. Nor does a gel seem likely adversely to affect algal germination unduly. Third, it means that individual algae are less likely to be occluded (shielded) by other algae from nutrients, sunlight and the effective exchange of gases that is necessary for their optimal growth. Fourth, use of a gel means that the energy used for agitation and propulsion can be very significantly reduced, principally because agitation for the purposes of aeration, carbonation, suspension, mixing and dispersion is much less required. Fifth, because violent agitation is no longer required to ensure that algae: receive adequate light and nutrients and do not plate or scum out on interfaces, the system avoids, or at least minimises, costly expenditure on energy and material losses, downtime and/or cleaning operations. This suspensive action of the gel is even more important overnight, when agitation is minimal or non-existent in a Winwick system—unlike most others. Sixth, because the presence of even a weak gel substantially retards the diffusion of excessively acidifying $CO_2$ from the microbubbles into all parts of the solution and therefore into otherwise over-concentrated contact with the algae. Hence, most algae are enabled to metabolise the small amount of weak carbonic acid slowly diffusing into their immediate vicinity before it can reduce the pH to levels harmful to them. Thus, there is little or no need for the addition of neutralising, costly and complicating alkali to elevate the media's pH so it becomes more neutral and less harmful. Seventh, because using a gel and allowing additional, sunset-time oxidation of the soup, by means of reducing carbonation and/or aeration activity just before sunset, means that the high energy cost of impulsion, agitation and sparging at night-time, required by some other methods, may be omitted entirely, or else very significantly reduced (it also beneficially reduces overnight acidity levels). This only-daytime power requirement also fits in nicely with the timing of solar electric power delivery from the local PVs. Eighth, because the presence of the gel smoothes out the otherwise harmfully rapid changes of partial pressures of $CO_2$ and $O_2$ that would otherwise be experienced by an alga each time it passed through the I/H unit. Whilst algae can readily adapt over time, possibly by phenotypic change, to tolerate high partial pressures of either or both gases without losing productivity, rapidly changing partial pressures adversely affect their productivity. It has been found that adapted or acclimated cultures tolerated 0.6 atm $CO_2$ or 0.8 atm $O_2$ without any growth inhibition. The osmotic retardation effect of a gel would tend to reduce the 90:10 progressing to 10:90 $CO_2$:$O_2$ gas concentrations in the microbubbles to those in the benign range within the algae themselves. Furthermore, as $CO_2$ is on average thirty-six times more soluble in both cold and hot water than is $O_2$, the actual utilisation by the algae of the 90% $CO_2$ nutrient input gas mixture might be closer to 99% than would the amount suggested by the 90:10 to 10:90 transformation of which algae are normally thought capable. It would also mean that the oxygen product might well be closer to 99% pure, rather than only 90%. This would improve both its market value and the level of carbon biosequestration achieved. And Ninth, because the slow, helical motion of the algal soup offsets the tendency of the microbubbles of nutrient $CO_2$ to rise to the surface, thereby keeping them in suspension and maximising their gas exchanges with the soup and hence with the algae.

In flue gas studies it has been found that *Chlorella vulgaris* grows best at 30° C. and in a range of 6-11% $CO_2$, preferably nearer the lower level, though some algal strains can grow very rapidly at levels of more than 40%, even 60%. It is thought that the toxicity of very high levels of $CO_2$ may be caused by its effect on lowering the pH. That being the case, the addition of alkaline ammonia may be able to offset it, whilst retaining the benefits of a high level of $CO_2$.

Now, Winwick bioreactors are intended to be used with even higher bulk concentrations of $CO_2$. However, due to the laminar flow conditions in the algal soup; the presence of the gel that retards both mixing and osmosis; and localised $CO_2$ conversion by the algae, the actual concentration of $CO_2$ adjacent to each alga is likely to be much less—perhaps even being arranged to be within the optimal range of 6-11%. These effects are important for another reason—because the study also found that elevated $CO_2$ levels tended to reduce the lipid content by nearly half. However, even more importantly, they also found that incubation for periods of up to ten-plus days under such conditions: doubled the biomass and chlorophyll productivity; doubled the valuable carotenoid content; and more than doubled the quantity of protein, intracellular and extracellular carbohydrates, as against what the values found under atmospheric $CO_2$ concentration (0.036%) and the same temperature.

Studies also found that elevated levels of $CO_2$ substantially reduced the adverse effect of higher temperatures (even at 50° C.) on algal growth. As shading of the algae in Winwick bioreactors by PV strips and other measures may not be sufficient to prevent bioreactor temperatures from exceeding the optimal range, the protective effect of elevated $CO_2$ levels could be a useful, additional one in peak summertime. Moreover, it has a doubly beneficial effect as elevated CO2 levels reduce the increase in deleterious photorespiration (which causes deletion in intracellular $CO_2$ and other algal carbon reserves) as temperature becomes excessive.

Although cooling the algal soup at sunset would reduce the loss of biomass due to overnight algal respiration, it is likely that few sites could justify the expense of such artificial cooling (of course some natural cooling will occur at night). Moreover, a cooled algal soup might take that much longer in the morning to achieve optimal activation temperature, unless warmed just before dawn by HFR or other stored heat. However, it is conceivable that algal selection (such as for marine diatoms that use the C4 pathway for photosynthesis and consequently generally have both enhanced photosynthetic efficiency over the alternative C3 pathway used by other microalgae and reduced photorespiration), acclimation, breeding or genetic engineering might be able to reduce respiration without the need for cooling. Such a 'hibernation or sporulation (algal spore formation)' effect might be induced in the algae by some change in conditions that is less costly than temperature to change, both to implement and to reverse quickly. It may even be possible to shut down respirational activity almost entirely for several hours without damaging the algae overmuch. To this end, research might be done into the effects of reducing the oxygen requirement overnight as well as into the genetic switching of algal metabolism. Alternatively, mixotrophic (can feed either on light and/or organics) algal species (Note, there are very few species that can use either one or the other energy source, though more might conceivably be created via breeding, genetic or transgenic modification. Most mixotrophs require light, using the organic feed as but a useful supplement. For instance, supplementation causes *Chlorella* protothecoides to increase its growth rate and lipid production to more than 50% dry weight lipid) may be selected and provided with organic food during dark hours (as well) for overnight nutrition requirements, so the algae do not need to metabolise their own energy stores. It has been found that for some species, the addition of supplemental carbon results in increased lipid accumulation even under mixotrophic conditions where the substrate is not known to be transported into the cell. Such mixotrophic or heterotrophic feed may economically be provided from the substantial glycerine co-product of the WLE process (sometimes quite high concentrations, such as 0.25M, are required for heterotrophic growth in the dark); from harvested and locally-processed, lower-value algal components; or sourced from other, sterilised organic wastes, residues or products, thereby avoiding or minimising respirative loss. It may even be possible to use the waste material from the WCR process directly. As algae can lose up to 25% of their dry mass due to overnight respiration, the benefits of heterotrophic feeding (either overnight or all the time) to any of the few species that have the dual feeding capability may be substantial, even though some overnight addition of ammonia and/or oxygen may be necessary to maximise the beneficial effect. An additional benefit of overnight, heterotrophic feeding is that TAG energy stores are not then mobilized in the dark to supply the energy needed for cell division and metabolic maintenance. Thus, desirable, higher levels of TAGs should be achieved by this strategy, at the minor cost of the consumption of less valuable glycerine, acetate or sugars.

TAG levels may be boosted even higher. Studies have shown that heterotrophic growth can result in a sevenfold higher overall TAG content for *Chlorella zofingiensis* over photoautrotrophic growth. If, as is likely, this effect applies more generally as is suggested (even better results may possibly be obtained from *Chlorella* protothecoides), then arranging for harvesting to occur mainly around sunrise might well raise the TAG content of the harvest still further, as well as providing more, early morning light for each remaining alga.

However, the use of heterotrophic feeding any more extensively than overnight would probably require moderation and the optimisation of its use with other factors and metabolic pathways, as increased lipid content generally corresponds to a reduction in growth rate and cell division. The encyclopedic, secondary source of this and several other concepts mentioned here is: Greenwell et al, 2009 (electronic, available at: http://rsitroyalsocietypublishing.org/content/7/46/703.full-.pdf+html) and 2010, Placing microalgae on the biofuels priority list: a review of the technological challenges Royal Society Publishing.

The overnight alternative assumes that the chosen or bred algal strain is able to adjust its metabolism in timeframes adequate to match the diurnal cycle, and that such adjustment does not come at excessive cost to biomass productivity. Should the best autotrophic algal strains not include those with mixotrophic capability, then a mix of algal strains may be worthwhile countenancing, even though this would make growing condition and harvesting optimisation less achievable. The prospective net benefits of mixotrophy require validation. Furthermore, research into the effects of both sexual and parthenogenic (asexual) algal reproduction may also be pertinent. Unless the cost of local, night-time power is extremely low, using artificial (even efficient LED) light to maintain a level of algal photosynthesis at night is a most unlikely, alternative solution as one can never recover the full energy expended in generating the light.

Winwick technology only utilises macro-turbulence patterns important to the supply of nutrients to and the removal of waste products from the algal cells during the sparging, harvesting and threshing-agitation processes. For a given alga, this tends to occur each time it traverses the I/H unit (approximately every 17 minutes). At other times, (apart from algae that are loosely attached to $CO_2$-containing microbubbles) only the nutrients that are dissolved in the gel structure that is in immediate physical, or diffusibly-close, contact with each alga are available to it. Thus, to obtain the benefits of continuously replacing this nutrient microsupply and of avoiding the build-up nearby of oxygen and other waste products, it is important that the concentration, and hence the structural rigidity, of the gel be maintained at a level that allows microbubbles to ascend slowly enough through the soup column to expose algae to adequate nutrient supplies and waste removal processes, whilst not being fast enough for a significant proportion of the microbubbles to reach, scum and form a light-obscuring layer on the surface before they are returned to the agitator. As the retarding strength of the gel will typically vary with temperature, the gel concentration may need to be altered accordingly at times by adding gelator or by adding or removing water. Altering the temperature is also an option, but will usually be an uneconomic one. The size distribution of sparged microbubbles is also a key variable in controlling the scumming effect.

It should be noted that the pulsating action of sonically-bathed, bubble-rich algal soup, combined with what restricted locomotion is possible in the gel by motile (self-propelling) algae, will both also tend to bring new nutrients into contact with the algae. However, against these positive effects, the structure of the tenuous gel will tend to reduce the rate of diffusion of nutrients to nutrient-deleted zones (an effect offset by the use of higher nutrient concentrations). Similarly, will reduced diffusivity retard the rate of the removal of waste products and communal messages, such as oxygen and chemo-inhibitors (produced by some algae when in high concentration, presumably as a mechanism to avoid population collapse), from the immediate vicinity of each alga. Due to the low, algal concentrations used by Winwick bioreactors, this last effect is most unlikely to occur. The potentially harmful effect of excessive oxygen concentration adjacent to each alga is also unlikely to occur due to five factors: Winwick light rationing to each alga; gaseous diffusion; harvesting of dissolved oxygen into nearby microbubbles; minor physical exchanges of liquid media adjacent to each alga; and frequent, periodic purging of oxygen each time a portion of algal soup passes through the I/H unit.

Part of the nutrient sufficiency requirement may also be addressed simply by having an excess of nutrients in the medium. These levels may be kept higher than in non-gelated media, because the gel structure serves to limit nutrient flux to and from it to rates that can be metabolised by an alga, thereby avoiding the nutrient concentration impinging upon each alga from reaching harmful levels (too much of a good thing can be harmful). Ammonium and carbon dioxide nutrient concentrations, and their effects on pH, are those most usefully ameliorated by the presence of a gel.

As it has recently been found that over half of all algal species require an exogenous source of one or more vitamins, for instance B12, which in nature are typically provided by symbiotic associations with bacterial cells, it may be advisable to add such bacterial strains to the algal soup—in which case their performance and requirements in gel and under Winwick conditions will need to be established.

Winwick bioreactors are designed to grow algae at low and most-areally-productive, steady-state (turbidostat) concentrations. Consequently, large phytotubes, low algal concentrations, long light paths and low, light gradients are provided that allow sufficient PAR to penetrate to the bottom of the phytotubes for algae there to maintain some photosynthetic activity. This means that virtually all PAR possible entering the soup is used to produce biomass, rather than heat. Algae can waste up to 90% of PAR in light conversion to heat, rather than to biomass—though perhaps a 70% figure may better reflect the average, yearly wastage figure in most bioreactors. Winwick systems waste very little PAR. The low algal concentration in Winwick systems means that less of the light is diffused into the darkened zones and that therefore a more effective, light-dark regime can be maintained. It is Winwick's periodic shading of the moving algal soup by the PV strips, aided by shorter-lived shading of one alga by a microbubble or another alga just above it and between it and the sun, together with sonic effects that provide the flashing light regime necessary for efficient light usage and for minimal diversion of excess PAR by algal protective mechanisms into heat, a process known as non-photochemical quenching (NPQ). These effects make for the highest, areal (per unit of land area) photosynthetic activity necessary for maximum algal productivity.

Light rays encountering a microbubble in the soup are affected differently by which part of the microbubble they encounter. Striking near the centre of the bubble, they pass with little diversion of energy nearly straight through. Striking the bubble at an oblique angle causes almost complete reflection. Striking somewhat off-centre causes a mixture of refraction, external and internal reflection. The net effect is that most light is passed through or else around the bubble with but modest deviation. Some is deflected at various angles as intensified shafts of light, but there is also a slanting, hollow tube, or truncated cone of darkness, formed immediately below the bubble of approximately the diameter of the bubble. Each cone is of a size to shade very many algae below. There is also a similar cone of intensified light formed just outside and inside the dark cone. The inner, lighted cone is not hollow. Should the microbubble move, pulsate, wobble, compress or temporarily deform under the influence of a pressure wave, sound or vibration, then algae beneath it will typically be subject to a flashing light regime of the same frequency as the lighted zones come and go. Thus, the sonic (125-8000 Hz in the human-audible range) waves from small-bubble sparging operations; from the transducers set along the heating tubes; and from other forms of sound or vibration travelling in the phytotubes, provide a flashing light regime to a substantial portion of the algal soup. A frequency value of 1000 Hz would result in a 1 ms flashing light cycle, and one of 5000 Hz a cycle time of 0.2 ms.

Now, short-cycle flashing exposure is reported to be the only way that algae can efficiently utilise high intensities of solar insolation. It has been reported that microalgal photosynthetic rates increase exponentially with increasing light/dark frequencies from 0.05 to 5000 Hz. They also found that longer, dark recovery than lighted times are unnecessary. Thus, a possibly optimal sonic frequency of around 5-10 kHz might be chosen to improve the flashing light regime in the soup. However, for the biofarm workers' comfort and in case the increasing benefits to overall algal productivity exceed the 5 kHz value reported, investigation into using frequencies higher than this, and indeed higher than the 8 kHz maximum of standard human hearing range, should be conducted. Should the optimum frequency be somewhat higher than that of the human range, then discomfort to the workers may be avoided. Such a frequency might also usefully serve to repel some kinds of vermin from the bioreactor farm. There may also be other physiological effects of such sound upon diverse organisms to be taken into account. Should some frequencies be inadvisable for some reason, then having adjacent transducers set at selected, different frequencies, or having different phases or waveforms, may be a means of using interference effects to provide better deformation in the microbubbles.

It is likely that the optimal frequency of flashing light, and hence by inference the optimal sonic frequency or frequencies to be used, will also depend partly upon algal strain, the antenna size, and the size range of algae within each strain. The amplitude, or energy level at a given frequency, together with the waveform and separation used, may also be key parameters in determining the optimal waveforms to be used in Winwick bioreactors for a given crop, mix, or species range of algae. Furthermore, it is not inconceivable that the waveform chosen in a particular period could be used to control the intrusion or proliferation of undesirable species, such as algal competitors and predators, though probably not the alga's fungal and viral pathogens. Microbial predators, that are typically somewhat larger than the algae, may have components or vacuoles subject to harm from waveforms that are not harmful to the algae. This may be a useful technique for prolonging the productive time before contamination with undesirable species occurs.

The best waveform may well be the one that causes the modal size of microbubbles in the soup to oscillate laterally the most, thereby causing the maximum volume of the soup to be subject to the flashing light regime caused by the sound waves. Regarding the sonics, an additional constraint may be to select the energy level, its waveform and frequency to be such that they do not destroy the tenuous, gel structure.

A regular flashing light regime at an optimal frequency might be analogous to a strong, stable heartbeat pattern versus a fibrillating or erratic heartbeat. If the frequency can be made variable, then it might be varied with insolation intensity to make best use of the current light energy available at a given time. It should also be noted that particularly fragile algal strains may not be suited to some forms of sonic treatment. For example, one study found that, whilst increasing the frequency that culture flasks were shaken (Note, not vibrated with sound) from 65 to 90 oscillations per minute doubled the growth rate, whilst increasing it to 140 prevented growth entirely, due to adverse mechanical effects on the algal filaments. Nuclear division in some species can also be inhibited by agitation, even causing high mortality if continued.

Due to the light-dispersive presence of microbubbles and algae in the algal soup, a flashing light regime is most effective where insolation is strongest, near the upper or sunward surface of the soup—just where it is most needed to give protection from photoinhibition. Deep in the soup, conditions nearer to continuous insolation may occur. However, as the insolation is attenuated there, photoinhibition is less of a problem.

Algae are able partly to adapt to new insolation conditions by a process termed photoacclimation. This process takes between minutes and hours, though it may also be said to continue much longer via the processes of mutation, generation and natural selection. Under conditions of increased insolation, algae will adapt by reducing the size of their pigmented, photosynthetic antennae. This has the effect of making each alga more transparent, thereby increasing the light path in the soup for a given algal concentration. Giving algae near-perfect lighting by the above mechanisms will tend both to let them acclimate faster and to breed out by natural means those of them that do not reduce the size of their antennae. The same effects, but possibly faster and possibly even more effectively, can be achieved via human-mediated genetic selection, modification or strain change.

Unacclimatised algae cannot produce optimally. Therefore, productivity will tend to be improved when growing conditions are maintained fairly stable, or at least do not change rapidly. An exception to this is a flashing light regime in the frequency range of preferably microseconds to under a second, or at least not more than a few seconds. Some of the literature suggests a maximum cycle time of four seconds. Other text suggests that maximal photosynthetic efficiency is approached when the light/dark cycle time is close to the dark-reaction time of 1-15 ms. One study recommends light exposure times as short as 10 ms, representing full cycle times of perhaps 20-50 ms to maintain high photosynthetic efficiency. Experimentation will determine which is the most productive flashing-light regime for strains of algae growing in Winwick bioreactors under various insolation conditions.

Movement of a slow-moving algal soup under a series of PV strips and spaces of combined width around 215 mm cannot produce flashing cycles of the order of 10 ms that are supposedly necessary for high algal photosynthetic efficiency. Movement under the PV strips and the spaces between will only produce a flashing light regime of the order of 1 Hz. Moreover, the flashing effect is reduced in intensity deep in the soup due to absorption and diffusion.

One method of improving both parameters is to bond a sheet of transparent, patterned polymer to the top and sides of each phytotube, or to emboss the pattern on the phytotube material itself. The outer surface of the polymer is shaped to form a series of Fresnel lens bands running transverse to the soup flow. These lenses are designed to focus sunlight deep in the soup, to a depth only a few centimeters above the bottom. The resulting converging solar rays would therefore form roughly vertical walls of relative light and dark banding in the soup column, with the increasing, convergent light intensity being more or less offset by light absorption by the algae and light diffusion. The downwards-converging light bands near the surface would be wider (and the dark bands less wide) than those deeper in the column, but all algae could then experience flashing light regimes. If the lighted gaps between PV strips were 100 mm and each, touching Fresnel lens band were, say, 14 mm wide, then the frequency of flashing would be increased some sevenfold. However, as typically 8-10 photon captures are required to process one molecule of $CO_2$ and as the spacing between opening PV strips may vary from 80 to 126 mm, it would be useful to experiment with lens band widths varying from 7 to 28 mm (say 7, 11, 14, 21 & 28 mm) to find out which gave optimal, algal photosynthetic productivity for the algal concentration, algal strain and insolation regimes at typical sites. Should the chosen, serrated Fresnel lens tend to clog or become obscured with material, then a transparent polymer of lower refractive index than the lens might be used to coat it smooth, whilst still maintaining a somewhat reduced lensing effect. The profile of the Fresnel lens could be made to offset the reduction in concentrating power due to the coating.

Regarding the construction of the Fresnel lens sheets, these might be calendered from a higher melting point polymer than that of the phytotubes, so that when the two were sealed together (possibly by heat calendering), the lenses remained intact.

The re-sealing of the lengthwise-opened envelope and phytotubes, and the attachment of each phytotube (and possibly the other tubes, channels and groundsheet) to the envelope would be accomplished at the same time, in a single pass, typically by the use of rollers heated or with the use of sonics or infra-red light. Acting as ribs, the lens bands would also serve to strengthen the phytotubes where it was most needed and to help retain their desired tubular shape.

The net result is three superimposed, flashing light regimes of different character: PV strip, lens, and the sonically-driven shading of an alga temporarily by microbubble or another (possibly motile) alga. These regimes may be so arranged as to approach the ideal flashing light regime far more closely than it is in either open raceway ponds or most other types of closed bioreactor. It should be noted that wavelets and ripples in open or stirred systems probably contribute something akin to lens-induced algal productivity improvement that may not previously have been appreciated. However, the flashing there would typically be far from being at the optimally productive frequency.

Winwick bioreactors are designed to maintain reasonably even insolation conditions. Insolation variation throughout the day and over weather and seasonal change is smoothed by the adaptive actions of the PVs and their supports and the structural arrangement of bioreactor components. Insolation excess over timeframes under a second is controlled by flashing and by virtue of an alga's location in the phytotube relative to the illuminated surface. Deep in the soup, insolation is reduced to somewhat productive and non-harmful levels by light dispersion, conversion and attenuation. These external and internal effects, together with operational changes made to algal concentration and soup velocity, make it easier for algae in a given Winwick bioreactor to maintain an acclimated or acclimatised and optimally-productive state with antennae of stable size. The above factors, amongst others, cause the near maximum of insolation to be converted into biomass—which translates into near maximal light-usage efficiency.

Sonic waves, particularly those of regular frequency and in a fairly wide range of frequencies, bathing the algal soup may generate an additional effect—they cause ripples. Following the laws of light reflection and refraction when applied to a rippled surface, the presence of the ripples moderates the insolation entering the soup in such ways that they increase the solar transmission into the soup at high and middling angles of incidence. This is so, because at high incidence angles to the bulk liquid surface, ripples provide local incidence angles that do not almost wholly reflect the insolation away from the soup. At low angles of incidence, ripples provide at least some surfaces that undesirably reflect the insolation away from the soup, typically somewhat horizontally—so it may be prudent to avoid surface rippling when low angles of incidence occur. At 15°, perhaps 13% less light is transmitted to the soup. At a high incidence angle, say 75°, of the order of three times the light may be transmitted into the soup by a rippled surface as does a smooth surface. This is highly desirable. At 45°, roughly an additional 50% of light may be transmitted into the soup by rippling, though possibly only, or best, when the ripples are approximately transverse to the incoming light). The extra transmission at high and medium incidence angles means that more light is provided to the algae when they most need it, near sunrise and sunset and also in cool seasons away from the equator where the sun does not rise high in the sky. Should the wavelength of the induced ripples from the existing sonic transducers not fall in the productive band for beneficial effects to occur, then transducers of different frequency may be added, so as to produce the desired ripples either directly or via their interference effects with the transducers that vibrate the microbubbles. It may be advisable to arrange that the interference patterns form standing waves, so as to interfere least with the structure of the gel.

As previously stated, for Winwick bioreactors it is the efficient areal utilisation of PAR that is important, not the volume utilisation. Moreover, employing a low-concentration soup minimises problems associated with adequacies of insolation, nutrition and waste removal. It also minimises potential problems with congestion, clumping and chemo-suppression, where the proximity to many other algae and the chemical concentrations that they together release when so concentrated, tends to reduce algal growth generally.

To maximise the utilisation of $CO_2$ and to minimise its wastage, the rate that it is sparged into the soup is typically varied by the amount of insolation received by the bioreactor. Similarly, as excess $CO_2$ would lead to undesirable acidity, additional ammonia and other nutrients are added at the same time, both to raise the pH and to provide the additional nutrients needed for the increased algal growth resulting from the additional insolation—and vice versa.

The WAS process produces ammonia as the main nitrogenous nutrient required by the algae. It may be supplemented by those nitrogenous nutrients recycled from the WSS process (using biomass of any type) and/or from the anaerobic bacterial digestion of the ruptured algal cell walls and residual cell contents. Most algae use ammonium (ions) preferentially and can grow 10-30% faster on ammonium than on nitrate nutrient. This is probably the case as nitrate requires energy to reduce it to the —$NH_2$ form which is found in cell constituents. Ammonium is already in that reduced form and so is more readily metabolised. However, in one report, at least one algal species, (*Botryococcus braunii*), finds ammonia (strictly speaking, ammonium ion, or possibly also the accompanying hydroxide ion) toxic at anything above the 5 mM $NH_4^+$ level. Thus, for some algal species, or other fertilisation uses, this may need to be converted via the Ostwald process to nitric acid ($HNO_3$), possibly utilising algal-produced oxygen and neutralised to, say, calcium nitrate tetrahydrate ($Ca(NO_3)_2.4H_2O$) with limestone. The resulting $CO_2$ might be recycled to the bioreactors. Alternatively, and probably much better, the ammonium concentration might be kept below the toxic level for the given strain of algae, provided that using ammonium did not significantly reduce the strain's productivity. It should be noted that controlling the pH to below pH8 can also help avoid ammonium toxicity. The dilute acids from the WSS process may also be combined with the alkaline ammonia from the WAS process to produced nutrient ammonium salts of more neutral pH for the algae. However, using this method, care will need to taken that the relevant (and nutriating in itself) anion does not build up to toxic levels with repeated use.

Stressing microalgae with nutrient deficiency (typically of nitrogenous nutrients, but sometimes with phosphate, sulphate, iron, silicon or other nutrient deficiency) is known in the literature to cause them to reproduce less rapidly and to modify their metabolic pathways to favour the production of TAG lipids rather than proteins and carbohydrates—even to convert some of their carbohydrate and/or protein content into lipid. As Winwick bioreactors use software to vary growing conditions and algal strains, it is a simple matter for individual bioreactors to be programmed, or remotely re-set at will, to cause nitrogen or other nutrient deficiency or other stressful conditions favourable to lipid production. Thus, algal soup from nutrient-sufficient bioreactors may be pumped to nutrient-deficient and/or ones with stressful conditions, such as altered temperature or concentration, to produce harvestable algae of higher lipid content, after allowing the necessary extra photosynthetic time (ranging from 0.1-12 days, with most strains taking 3 to 4 days to reach maximum lipid content) for the metabolic change to occur and the oil accumulation phase to be fully effective. Thus, unlike most batch production or hybrid (open and closed bioreactor combinations) systems, Winwick bioreactors can maintain optimally-growing and reproducing algal cultures under nutrient-sufficient conditions with an algal concentration that is just sufficiently high as to use the available insolation most efficiently; or can maintain optimally lipid-producing algal concentrations under stressed conditions.

Separate, stressing regimes are easy to achieve in a Winwick system due to two factors. First, the pairing of Winwick bioreactors off a single, shared impeller/harvestor unit provides a ready, neighbouring bioreactor for algal stressing. Second, because each regime and bioreactor is separately controllable by remotely-adjustable parameters and software, reprogramming is easy.

Algae for stressing are moved from one bioreactor to its pair by means of a diversion from the Archimedes screw offtake. This is done, rather than by simply pumping the soup across, because removing such a volume of water from the paired bioreactor would be costly and difficult. For all the algae being transferred to a stressing bioreactor to have time to adjust their metabolisms, a batch process is most useful. Thus, using the concentrated algal foam for the periodic transfer is the better way. After each diversion, the diversion passageway is flushed, first by ordinary algal soup from the donating bioreactor, then by distilled water.

Research has revealed that TAG lipid production is maximised when a two-stage process is used: fast growth under nitrogen-sufficiency to produce maximum algal biomass, followed by an intermediate level of nitrogen limitation in the nutrients provided. That is to say, that the nitrogenous nutrient concentration is best allowed to tail off naturally by algal uptake of nitrogenous nutrients, not sudden replacement with nitrogenous-free nutrient media. Such beneficially-slow changes in growing, turbidostat (maintains the same cell density by harvesting the excess) conditions are readily provided by paired, Winwick bioreactors. It should be noted that only TAG lipids and the less-saturated fatty acids can readily be transformed into good-quality transport biofuels, whereas the lipids helping to form the algal cell walls, which contain the undesirable biofuel contaminants of nitrogen, phosphorus and sulphur, are difficult and costly to transform into standards-meeting transport biofuels.

In a study on the optimal growing conditions of *Chlorella vulgaris*, the best stressing option appears to be under mixotrophic conditions, combined with nitrogen limitation and phosphorus deprivation. These conditions maximise both lipid concentration (at ~39%) and that fraction of lipids which is most valuable for transport biofuels, the non-polar, phosphorus-poor ones (at ~80%). However, it takes a few (possibly several) days for the effect to be at its most dramatic.

An alternative to nutritive stressing may be to use the chemical trigger of a well-timed dose of bicarbonate at a specific point in the algae's growth cycle. It is claimed that this doubles or trebles the rate of production of TAGs and shortens the time it takes to reach high lipid yields. However, for Winwick's continuous growth system, and unlike a batch system, the algal population will probably never be all at the same growth stage at the same time. Therefore, the benefit of this technique is likely not to be so great.

One study showed that the (biomass) growth curve for mixotrophic conditions commenced immediately to be superior to those for both autotrophic and heterotrophic conditions. Thus, whilst night-time-only feeding might be a useful biomass productivity aid for some species in the non-stressing bioreactors, the more dramatic effect may be seen by providing, (possibly continuous) mixotrophic conditions to the stressing bioreactors. Both feedings might be done with glycerol, sugars and/or other organic nutrients derived from algal residues after extracting the more valuable components or from other biomass. In turn, these nutrients might be generated economically and on-site by a shortened WSX or WSS process that is interrupted just after the early depolymerisation stage. Thus, the reaction of the polymerised sugars of the starches/complex carbohydrates, hemicellulose, cellulose and lignin in the biomass might be interrupted when they have been transformed (at least partially) into simple sugars and other compounds that are digestible, mixotrophically or heterotrophically, by algae. Where cellulosic material in massive form, such as chipped forestry waste, woody weed species or crop residues, are to be the source of the sugars, then pretreatment to break up the mass may be economically justified, using the WCR method both to separate the fibres and to explode the cells. This process may be aided by the addition of ammonia to the input materials, as described in the AFEX process.

A second effect may be induced by the addition of sugars to the *Chlorella vulgaris*, algal soup, namely gigantism. This induction results in a cyclic transformation between the giant cell stage and the subsequent, palmelloid body stage that is composed of many conjoined autospores (nonmotile, asexually reproductive cells or nonmotile spores that are miniatures of the cell that produces them), without return to the normal state of small, single cells. It is not yet known whether this has positive or negative effects either upon biomass or lipid productivity. The addition of low concentrations of an auxin (a plant growth hormone) also produces enlarged cells, together with improving the rate of chlorophyll formation and algal photosynthesis, which are in turn possibly due to auxins being essential for both cell division and cellular expansion. If positive and without deleterious side effects, then it might usefully be included in the algal nutrient media, provided there is net economic benefit.

It should be noted that heterotrophic feeding might also be used to increase the algal biomass within a transportation pipeline. Pipelines could be employed as an efficient method of transporting live, relatively-dense, algal cultures to possibly far distant mariculture facilities, where the algae, or grazers on them, are used as premium fodder for molluscs (particularly their juvenile forms), crustaceans and fish. Moreover, if the time in the pipeline were not too long, ordinary autotrophic and mixotrophic algae would be able to survive the journey. Closer destinations for piped, live algae might include aquaculture facilities located on regional salt or clay pans (probably covered with mesh or fabric to protect the stock from waterbird predation) or to constructed facilities at which such commercial organisms might be grown in water of any suitable degree of salinity for the organism.

Heterotrophic feeding may also be used on-site in fermentors at the Winwick biofarm or biorefinery if the value of algal biomass produced is significantly greater than that of the glycerol and other inputs and than the added value of other glycerol-transforming processes or for glycerol used directly as a nutraceutical or to power fuel cells. However, a significant restriction to the use of alternating autotrophic with heterotrophic feeding is that very few species can at different times be either purely autotrophic or purely heterotrophic. Thus, unless one of these is used, there may be little net benefit.

Individual control by software in Winwick bioreactors also provides for backup in the event of, say, one harvesting unit becoming temporarily less-effective or inoperable or otherwise requiring shut-down, as algal soup could simply be pumped from one bioreactor to its twin, rather than being left poorly controlled or unharvested in the first one.

Optimally growing cultures are ones that involve exponential growth and maximal light utilisation under turbidostat conditions. As there are trade-offs between the value of total products produced per day under the various different conditions, economics will determine whether and when separate, algal stressing or nutrient change regimes are warranted in some bioreactors.

Whether to make the tradeoffs between the unstressed and stressed regimes previously referred to, will depend on a number of factors. Principal amongst these are: the WSS and WFTAS conversion efficiencies and the costs of converting algal cell wall material into syngas and thence into fuels; the relative value of the different fuels produced by each regime; the time taken (several days) and the efficiency of algae in stressed conditions to do the same; and the algal doublings lost by using bioreactor-days to produce TAG lipid concentration instead of more algae and algal biomass. Changing market conditions may well see one or other regime being more profitable for a period, only for it to be replaced with the alternative when market conditions change sufficiently much. Having such flexibility is a very useful Winwick attribute, particularly when it also encompasses the flexibility to produce gaseous fuels, food, stockfeed (both live algae and processed feeds) and/or a wide variety of chemical feedstocks.

Using WSS technology, the best value presently seems to lie with producing more algal biomass, rather than with ones delivering higher TAG lipid content. However, this could change. If it does not, then the search for better algal strains for use in Winwick bioreactors and biorefineries is much less critical than for other methods. Moreover, it should focus more on finding strains that are fast growing, rather than on ones with high lipid content or expression. This would simplify the research and possibly avoid some genetic modification and strain importation problems. Under both Winwick unstressed and stressed scenarios, a good strain to use may well be the common, robust, widespread and fast-growing *Chlorella vulgaris*—though with antennae reduction through either selection from wild strains (as long-cultured strains tend to lose their vitality), adaptation, breeding and/or genetic modification. *Nannochloropsis* spp. may also be useful to try, as these are some of the few strains that produce and store substantial amounts of triglycerides whilst actively growing and without stressing.

A diatom, *Cyclotella*, may also be useful to experiment with, due to its amenability to mass-culturing and its productivity—even though the protection given by its siliceous shell, and the energy investment in it, is unlikely to be required in a closed bioreactor; and the shell may make processing more difficult.

A second reason to prefer the use of fast-growing algal strains (which tend to be typically lipid-poor and carbohydrate-rich) and the WFTAS process to produce alkane-rich biofuels, is that the alkanes produced tend to be saturated ones (where there are no carbon-to-carbon double bonds) that comply better with European biodiesel standards. The lipids produced naturally by algae are partly unsaturated (possess some carbon-to-carbon double bonds). Where they have in excess of four such double bonds per molecule, they typically require the extra cost of hydrogenation to make them saturated and hence better suited for use as transport fuels. Isomerisation may also be called for, as branched chains tend to make better fuels.

In the inaugural issue of Biofuels magazine in January 2010, Tredici has a table that purports to specify the maximum photosynthetic efficiency (MPE) achievable in microalgae mass cultures. This is a useful exercise. However, due to factors the value of which that Tredici did not countenance, the table has been recast below for the Winwick system. It indicates that MPE may be substantially increased from 5.4% to 10.8% (say 9% in practice) using Winwick technology. This would represent a major breakthrough.

TABLE 1

Minimum energy losses of total incident solar radiation in microalgae, from interception to formation of carbohydrate

| Minimum energy losses | % Energy remaining - Tredici | % Energy remaining - Winwick | Winwick system added value due to: |
| --- | --- | --- | --- |
| Total incident solar radiation | 100 | 100 | Better photoacclimation, the algal soup depth, reduced antenna, optimal nutrition, and dilute algal culture in Winwick bioreactors brings the algae's light absorption and utilisation closer to the theoretical maximum |

TABLE 1-continued

Minimum energy losses of total incident solar radiation in microalgae, from interception to formation of carbohydrate

| Minimum energy losses | % Energy remaining - Tredici | % Energy remaining - Winwick | Winwick system added value due to: |
|---|---|---|---|
| Radiation outside PAR (55%) | 45 | 45 | Fluorophores and anti-UV coatings may also transform some non-PAR into PAR |
| Radiation increase from external reflectors, bioreactor height above ground and reflective groundsheet | 45 | 60 | Allow a 33% increase, that is beneficially delivered to the more-needful, lower half of the algal soup. |
| Degradation of absorbed PAR photons to excitation energy at 700 nm (21%) | 35.6 | 47 | It may be possible to have the algal photosynthetic system generate another PAR photon of lower energy from an absorbed, UV photon. |
| Conversion of excitation energy at 700 nm to the chemical energy of glucose (65%) in algae | 12.4 | 17 | May require some reduction due to the need to generate some higher-energy metabolites |
| Reflection (10%) | 11.2 | 15 | Use of nanodomes, sonic ripples & better transmitted high- and medium-angle insolation improve this value, but the multiple reflective surfaces of the bioreactor reduce it. Assume the effects cancel out. |
| Photorespiration (allow none in microalgae) | 11.2 | 15 | Moreover, high Winwick $CO_2$ annuls loss |
| Respiration (20%) | 9.0 | 12 | Possibly subject to further improvement via: supplementary, mixo/heterotrophic feeding; oxygenation control; induced sporulation; and/or genetic modification |
| Photosaturation and photoinhibition (usually cause a minimum 40% loss in photosynthetic efficiency in microalgae) | 5.4 | 10.8 | Only 10% reduction allowed due to Winwick measures producing an optimal, flashing light regime and by the moderation of excessive insolation caused by the adaptive PV strips. |
| WINWICK IMPROVEMENT |  | +100% |  |

Winwick Solar Power (WSP) Method

The WSP method provides standardised, economical and accessible platforms for the installation of baseload PV power generators. It utilises a simple system, based upon thermally-moderated, laminated strips that adjust the coverage of the PV progressively to optimise insolation between the algae and the PVs.

The PV fluting system serves a fivefold purpose: shielding the algae from excessive or damaging heat and insolation (sunlight); facilitating optimal algal acclimation by moderating insolation to the algae across day, weather and season; producing solar electric power to run the machinery and to generate substantial excess power for sale; strengthening the envelope around its area of prime, near-horizontal exposure to degradative, solar radiation and weathering; and to provide the alternation of light and dark to the moving algal soup that is necessary to gain optimal PAR usage, without photoinhibition. As far as is technically possible and is most economical for the thin-film PV material and fluting dimensions to be used, the width of the strips and the intervals between them is to be calculated so as to provide sub-second light and possibly longer dark-recovery intervals between light exposures that result from the modest velocity of the soup along the bioreactor that is, in turn, provided by the relatively slow-spinning impeller blades.

Any of several existing commercial or near-commercial brands of flexible, thin-film, PVs may be employed. PVs using CIGS material (Copper, Indium, Gallium Selenide) set in nanopolymer dots, or the newer, cheaper and less hazardous CZTS (copper zinc tin sulphide, $Cu_2ZnSnS_4$) or Cd/Te (cadmium/tellurium) or organic polymer PV technologies are possible options, providing the use of glass can be replaced by polymer for location inside Winwick's protective fluting. There is advantage with using any PV system that uses a highly reflective lower electrode (such as a thin layer of stainless steel), as this would tend to re-reflect light insolation reflected by the various layers in the bioreactor back to the algae. Acute solar angle reflection from the upper PV surface layers would also tend to be reflected into the algal soup. The width and spacing of PV strips along the envelope would be selected at assembly time in order to suit the climatic conditions of the site and the algal strains for which the bioreactor is being built.

Fertiliser for the Bioreactors

Particularly in remote locations, and possibly even before the pipelines to the outside world have been laid, it may be advantageous to process local biomass using the WSS process to produce initial biofuel and the recyclable fertiliser (nutrients) with which to charge the bioreactors. Sources of local biomass might include: chipped-up weed species or accessible and regeneratable vegetation (coppicing); crop, forestry or agribusiness waste; or raw sewage and other wastes from workers installing the biofarm and biorefinery or from nearby agribusiness, towns and mining camps. Fertiliser minerals may also be sourced from nearby mines or mineral processing operations (possibly from their waste products); from local hydrocarbon or mineral deposits (leaching technology can utilise quite low-grade minerals); from mineralised ground water; or as a last resort be transported-in, in the form of commercial, bulk fertiliser. Longer term sources of cheap fertiliser and trace elements may include locally-produced, WAS nitrogenous fertiliser, mined minerals, piped in sewage, flue gas components, and other agribusiness and industrial wastes.

Microcomputer and Post

Each impeller/harvestor unit has its own controlling microcomputer and communications system. These are located in a hollow, sealed (but openable) polythene post, standing buried, except for its insulated cap, just outside the impeller unit and located in the narrow corridor between pairs of impeller/harvestor units.

Proprietary lightning rods protect the whole system electrically. To save cost and minimise shrapnel damage to the nearby bioreactors when hit by lightning, these rods are made from aluminium-coated, hollow polymer fibres, resin-bonded over polymer pipe in the shape of a feather-topped javelin, the feathers being the unbound ends of the metallised fibres. The exposed javelin shape fits over a lower, part-buried part made of hollow, injection-moulded, aluminised polymer, anodised aluminium, other metal or metal-coated ceramic. This has a coarse screw thread ending in a point and a hexagonal top, by which rotational and downward pressure may be applied to drive the screw deep (~450 mm) into hard ground. The feathered top of the rod is comprised of conductive fibres that emit electrical charges into the air, thereby preferentially attracting lightning strike. Inside the hollow screw, which has designed-in, vertically weakened lines, is an amount of harmless, coloured powder or dye that, when dispersed by a lightning strike and/or water, shows up on aerial inspection as requiring rod replacement and inspection.

The temperature-sensitive microcomputer is buried sufficiently deeply as not to require temperature control. Being of low power, it should not require cooling beyond that provided by the soil. However, if necessary this earth-cooling can be augmented by a conductive rod, screwed or driven into the soil of the posthole and linked thermally or thermodynamically to the microcomputer.

Sensors gather data about conditions and the operation of each quad of four bioreactors, passing it to the microcomputer for action and/or forwarding via fibre-optic cable to central control. Similarly, the microcomputer stores a revolving log on itself, its two (or four if acting as backup) bioreactors, its impeller/harvestor unit(s), its production, sensor readings and external conditions, including pipeline pressures. Some of the more, regionally-specific data, such as weather, particulates and insolation, are gathered by several area microcomputers, each linked to appropriate sensors. Microcomputers recording both types of data send it progressively to the central controller using intranet technology and the fibre-optic network. In the event of communications breakdown, each microcomputer is programmed to operate as best it can, without guidance. To ensure power continuity in the event of powerlines going down, each microcomputer might be given its own PV power source, perhaps mounted on the I/H barcode plank and feeding a rechargeable battery in the microcomputer post.

Software in the central system receiving the data, analyses it online and directs the attention of the staff to interesting events or states. This activity includes displaying the data in real time and in historical and statistical context, so that immediate action can be taken, probably guided by an expert system and/or an expert who is online and may be located anywhere in the world, to take advantage of time zones, disabilities and wage rates. A colour-coded map of bioreactor states is displayed at central control, together with the program of planned activity.

Communications capabilities of and to each microcomputer and surveillance pole would include the ability of field staff near a pole to communicate directly with campus staff, via more than one sense, without the need of any personal, communications equipment. A key word, such as "Help", would be recognised instantly by the central computer, allowing it to patch a conversation through to a human operator. So, for instance, when in aural (hearing) range of a surveillance pole described below, rookie field staff could be guided by campus-based, experienced staff, remote advisors or suppliers, or an expert system in a difficult or unusual diagnostic and repair task or activity.

Farm Security System

As well as multiple, perimeter security fences, mobile regional surveillance, and the aforementioned, passive means of protecting the bioreactor farm, active local measures are also included. The centre of every cluster of four bioreactors (quad) has its own surveillance pole. This is a combined, pole-mounted, centrally-controllable, and directable: video camera (with zoom lens), motion-detector, directional microphone & loudspeaker, LED spotlight, mirror, and pressure hose with various nozzle settings and liquid content options, including ammonia. Night vision capabilities will only be included if they are economic, and possibly then only included for a minor proportion of quads. Routine operation of the surveillance pole security system will be controlled by one of a quad's two microcomputers, with failsafe backup from the other, for both bioreactor operation and security purposes. Pole units also have one or more direct current outlets for use by maintenance staff when servicing each quad of bioreactors. These can be used to charge (possibly backpack-mounted) powerpacks and electric vehicles, or to power tools directly.

Piping

For purposes of easier management, neatness, standardisation, mutual protection, cost and insulation, the different pipes, fibres and wires required to service the bioreactors are combined in their own cluster or pipe bundle. Bundles are made from thermoplastic polymer, typically polythene. They are formed thus: the hot water pipe is produced first, then its insulating foam and protective skin covering. This composite pipe is then drawn through a complex extrusion die that adds the other pipes, voids, conduit channel and possibly an outer, protective skin or insulation. A separate strip is extruded that clips into the conduit channel to seal it, accessibly. Any water that manages to pass the seal is drained off at junctions.

The cross-section of the pipe bundle is shaped akin to the phytotubes in cross-section and can fit, with spare space above, under the trapezium-shaped tunnel of the impeller/harvestor unit. The different sized pipes and conduit are so arranged within the bundle as to minimise construction material required and to optimise space usage, insulation requirement, protection and accessibility. Some of the pipes in the bundle are able to serve different purposes at different times, thereby providing for future requirements and backups. This provision may be particularly useful as algal cultivation at bioreactor farms becomes more diverse and sophisticated, and as it requires different strains and additives for different sets of bioreactors at different times.

The pipe bundle comprises: fifteen pipes; many voids to save material and improve insulation; a conduit duct and its clip-in cover; and possibly an outer, protective skin. The pipes come in three standard sizes having diameter ratios 3:5:8. Of these sizes, there are 4, 8 and 3 of each pipe, respectively. One of the largest, that for the hot (60-80° C.) HFR water (or cooling water in hot times), has insulating, polymer foam sandwiched between a thin, outer polymer skin (spirally wrapped on the foam) and the inner pipe wall. Otherwise, where two pipe walls merge in the bundle, their combined wall thickness is that of the larger pipe. This saves on material. The lower, outer sides of the pipe bundle are slightly thickened for additional protection.

The pipe bundle system has three additional components— an offtake bundle section; a multiple, male-male connector plate; and a similar plate connector incorporating remotely-controlled valves for each pipe for isolation purposes. Pressure reduction valves ensure that the high pressure in the larger mains is not fully transmitted to pipe bundle PE mains, thereby reducing the likelihood of blowout. The special offtake bundle section is needed to make the task easy of linking individual mains pipes, which are often buried inside the bundle, to their respective piping in the bioreactor. This requires a bundle that alters pipe and void shapes, and possibly sizes, at locations where an offtake is to be made. For connection purposes, each smaller offtake pipe is long enough that it will extend beyond the bundle of mains pipes to which it is attached at the other end. This, special, sinuous, complicated offtake bundle section is standardised for all bioreactors. Such a complex shape is not suited to moulding techniques, possibly not even to those formed from combinable slices. Instead, to form the offtake bundle, fifteen separate pipes, laid together, are conveyed lengthwise on conveyor belt along a production line.

At precise spacings, smaller T-junctions are inserted in each colour-coded mains pipe and short, similarly colour-coded offtake pipes are attached. These pipes typically have strategically placed and shaped, flattened bulges, at least within the part of their lengths that will end up within the offtake bundle, so as to avoid increasing pipe resistance overmuch, while at the same time as making it easier to thread them past outer pipes. The cross-sections of such bulges will typically be roughly elliptical. At both ends, offtake pipes are circular in cross-section to permit ready connection. When all smaller offtakes for a given section of offtake bundle are connected to mains offtakes, all mains pipes in that section are cut at the same point and each pipe end is fitted onto its matching male connector plate projection. After these connections have been made, the offtake pipes are threaded upwards, between any pipes above, to come out at standardised places on the top surface of the offtake bundle. The bundle is then bound together either by long cable ties and/or tough PET or carbon-filled polythene (possibly shrink-wrapped) wrapping. The shape of the resultant bundle is made as to fit inside the impeller/harvestor's trapezium-shaped tunnel running underneath its mid-section. Due to the offtakes, the offtake bundle is taller than the ordinary pipe bundle.

Holes are provided in each impeller/harvestor unit for each of the offtake pipes or connections. Typically, these holes are located at roughly equal intervals along the base of the chamber connecting the impeller halves. After the colour-coded pipes threading these holes are threaded and attached to their colour-coded mates inside the impeller/harvestor unit, the hole edges are sealed with formed polymer seals, polymer putty and/or hot melt polymer to prevent unwanted passage.

The general-purpose bundle connector plate mentioned above is used to connect both standard pipe bundle lengths together, as well as offtake bundles to standard pipe bundles. The connector takes the form of a connection plate having some fifteen, joined, hollow, male, pipe connectors on either side. It is formed by injection moulding high-density polythene (HDPE). The ordinary pipe bundles are simply pushed over their matching plate, male connectors, the whole bundle then being secured by long cable tie or ties. The projections are slightly tapered at their outer end to make it easy to fit them into the matching pipes. They are also ribbed with annular, backward-pointing ribs or barbs to make the connection stronger. As the bundles, pipes and connectors are somewhat flexible, the lower connections can be seen to be correctly begun, thereby assisting the middle and upper linkages to be accurately made.

The contents of the fifteen pipes in the pipe bundle are as follows. The three largest diameters contain either: hot water, cooled return water, or algal slurry. At suitable intervals, adequate slurry flow is maintained by additional pumps. The eight middle-sized pipes contain either: algal soup; cyanobacterial soup; sterilised, typically-brackish bore water; carbon dioxide ($CO_2$) gas; 90:10 oxygen $O_2/CO_2$ gas mix; distilled or sterilised fresh water; mixed nutrient water from the anaerobic digestor, ammonia plant, and/or the supercritical water reactor (that partly oxidises lipid-depleted algal biomass to syngas, thereby also releasing its macronutrients) that may have subsequently been sterilised; and bubblemix brine. The four smallest diameter pipes contain either: nutrient mixes #1, 2, 3 or 4; or inoculants of seasonal or replacement algal strains that temporarily replace the contents of one or more of the nutrient mixes. The nutrient mixes themselves are so specified that they can be combined in various ways to make many different, algal media, nutrient mixes. Each can also be temporarily replaced to address a particular situation. Any replacement will typically be preceded by a flushing operation. The contents of the conduit include any wire, fibre-optic or other cable that is necessary to conduct power or communications.

Due to the proximity of parallel bioreactor pairs, it will be convenient to make a single length of offtake bundle serve two impeller/harvestor units and hence four bioreactors. The wider distance between neighbouring parallel bioreactors, not in the same quad (two pairs), will use standard, pipe bundle, as will the attached end of each kytail.

When polymer-based pipe bundles reach the first road on the bioreactor farm, their component pipes are typically separated and joined to larger diameter polymer, composite or steel pipes carrying similar contents. Isolating valves, controllable remotely, occur periodically along most pipes. The type and size of pipe used depends on the physical capacities of each and the relative economics. These pipes are laid at roadsides, sometimes on sleepers, themselves laid directly upon virgin gibber or sandy surface, with little disturbance. Where these pipes cross roads, they may either be elevated or covered by gibber/gravel under hooked-together-plastic-hexagon mats that adjust to the surface contours and permit light traffic to pass over them without damage and with little erosion. Each hexagon is formed by injection-moulding polythene into a waffle-sided mould containing the central part of an assembly of six radial, anti-corrosion-treated steel wires that end in a broken ring or crook with springy opening. The hexagons can be linked to each other in an open-weave mat. The internal diameter of the rings is sufficient to permit the mat to adjust its contours to moderately uneven surfaces.

The access problem and cost is minimised if transverse access ways are divided into alternate vehicle access ways and pipe access ways, the latter not permitting side access by heavy vehicles, due to the presence of pipes lying on the ground along both sides of the access way. However, access by light vehicles such as quad bikes and hovercraft is made possible by the mat technology. Thus, an access way crossing a pipe access way would have two "speed bumps" over where the pipe sets lay, with a half height level joining the two sets, all covered by the one, flexible mat of roughly 10×4 m dimensions over gravel or sand mounds covering the pipes. The gravel may consist of gibber stones swept up, raked, or graded along, from the access ways.

The remaining problem of pipes entering the main arterial road is solved by elevating the pipes on supports, so that traffic passes under them. These larger diameter pipes are likely to be of steel and fixed in parallel on elevated, transverse supports, rather than bundled. Some may need to be insulated. Where necessary, additional pumps along the pipelines help push material through the pipes. Occasional, transverse links and remotely-controlled valves joining the matching set of pipes on each side of the main arterial road deliver an extra measure of backup for similar-content pipes in each set. All mains pipes are in the form of loops, so that a blockage, breakage or interruption at any one place need not prevent service delivery elsewhere.

Pipeline Transportation

External piping systems to ports, cities and other industries can be highly advantageous to Winwick operations. They are also typically the most efficient and reliable means of transporting bulk fluids. However, with good design they may also be employed to transport solids—either as slurries in liquids or by the use of neutrally-buoyant containers carried by the fluid within the pipeline. One of the additional benefits of containerised transport in a pipeline carrying containers immersed in a fluid, that may itself require transportation, is that the containers may contain any one of many different goods or materials, and may be in the form of assemblies, solids, liquids or even compressed gas.

Being typically located in temperate deserts, Winwick bioreactor farms are likely to be remote from transportation corridors and that those services that do reach the site will tend to be expensive, uncertain (due to weather and lengthy breakdowns that are common in harsh conditions), possibly infrequent, and that each trip (unless by air) would tend to take a long time. The facility's construction, operation, staff and communities will require much in the way of materials and the processing facilities will produce possibly a wide variety of products. Therefore, it would be most useful, were as much as is reasonably possible of these material movements be done by way of pipelines.

Pumping specially-designed containers, termed slugs or capsules, by pipeline adds challenges to the pumping technology used, but nothing that is unachievable. The key to high functionality and efficiency lies mainly in the design of the slugs. One feasible design involves a plastic, metal or composite material hollow slug or capsule in the shape of an elongated doughnut, of slightly less diameter than the enclosing pipe, with a separate container core. If in plastic or metal (an aluminium alloy perhaps), except for their caps, both containers might be moulded in the one operation. The somewhat rounded shape of the slugs might be similar in external shape to the multi-sized, blue plastic drums with openable ends, that are now used to hold and transport granular and liquid chemicals. The doughnut typically would contain the main, liquid or granular contents. The central hole or core is in fact a separate container, designed to contain material of sufficient weight as to make the slug and its contents of neutral buoyancy in the relevant carrier liquid—its function being akin to that of a fish's swim bladder. The weighting material may be goods requiring transportation in their own right or else cylinders of varying length, made out of a very dense material, such as depleted uranium, immersed in either gas or liquid, possibly water or a hydrocarbon. Such would allow the most flexibility in the choice of carrier liquid and slug contents. The weights would be secured centrally to ensure an even keel and thus minimal frictional contact between the capsule and the pipe's walls. Water or air might be used as trade-balancing materials for weights building up undesirably at one end of a pipeline.

Movement of refrigerated materials might be effected by the insertion of dry ice (frozen carbon dioxide) packs in the cores, with the excess pressure from the evolved gas being vented at a given quite-high pressure into the carrier fluid and thence to an external pipe for recycling.

As well as possible external colour-coding, the capsules, or insertions for them, would have internal, distantly readable and reprogrammable electronic tags, possibly similar to some RFID tags used in shops, vehicles and warehouses. Separate ones of these would identify barrel identity, doughnut and core contents. Some tags might be programmable as goods manifests, bills of lading or delivery dockets. The capsules would probably be returned to the facility via a different pipeline, one probably using a different carrier fluid. The network of such pipelines and their interchange nodes and transfer stations might well eventually form another common carrier delivery system, like that of the post office, shipping companies or internet.

Both types of container in a capsule would require both effective sealing and seals that could be quickly released and their contents removed by automated equipment. The surfaces of the capsules would also need to be readily and thoroughly cleansed of carrier fluid or material that might be as penetrating as light organics or of hazardous material. Different caps, seals, nozzles or apertures might be required for different types of content.

Farm Layout

Each bioreactor foursome (quad) is attached to its pipe bundle rather as decorative material is attached in a regular pattern on the tail of a kite (call it a kytail here, for future brevity). There may be many such 'dragonfly wing' or quad attachments on a given kytail.

On the bioreactor farm, kytails are laid out inside rectangles, each measuring 1×2 km (or standard variants thereof), with access ways separating them. Formed access ways are of three kinds: arterial, heavy vehicular, and pipeline/light vehicle. Only the first two are likely to be sealed. There are two levels below these of unmade access ways. The first of these types is the irregular-width paths or areas between adjacent kytails. The second type is the irregular-width access ways between bioreactors, which themselves have two variants, only the wider of which is accessible to full-width vehicles. The other is accessible typically by foot or by the wheels of one side of a special vehicle that can straddle a bioreactor and is used to lay and replace them.

The pattern, individual length, curvature and spacing of the kytails within each rectangle are controlled by the topography and access requirements. One end of each kytail is at one of the pipeline-access edges of the rectangle. The other depends on: how far the kytail and its bioreactor quad "dragonfly wings" can extend before they interfere with either: other wings; rectangle edges; with allowing vehicular accessibility to the far ends of the bioreactors; with other farm structures; or with meeting with unsuitable topography, land surface or vegetation.

Each bioreactor is laid on the contour line at which it intersects its kytail. Bioreactors will begin to be laid out approximately orthogonal (at right angles to) to the direction of their kytail at the junction point. They have some, but very limited ability, to follow gentle horizontal curves in the contour. Topography with tight contours is not suitable for Winwick bioreactors without significant modification to their structure, layout and support. However, as the preferred location for Winwick bioreactor farms is flat, gibber plain (typically wind-polished or eroded, sometimes flat, smallish stones over clay, sand or gravel), pan, desert or flat areas with similar, barren topography, relatively little space should be lost because of topography. Note, that whilst sand and gibber plain can both offer suitable terrain for Winwick bioreactors, gibber stones of a type that have a very rough, unpolished surface to them or which do not form an even layer, and sand that is in the form of dunes, particularly mobile ones, are less suitable.

Detailed aerial or satellite mapping, using global positioning systems (GPS) accurate to within a few centimetersmeters vertically and within half a meter horizontally, together with computer software and algorithms to determine the densest practical kytail pattern are used to plan and populate the layout of each rectangle's kytails and bioreactors. Triangle-overlaid worldwide topography from the following free database may be adequate for the task: http://www.gdem.aster.ersdac.or.jp/feature.jsp Pipe bundles, impeller/harvestor units and bioreactors are typically laid directly onto flat, virgin, gibber plain, bare sand, clay, limestone plain, salt pan (or equivalent) surfaces.

Access Ways

The immediate access ways to bioreactors are typically by sand plain or virgin gibber surface, typically using vehicles with soft, balloon tyres to minimise disturbance and jolting. In areas where travelling dunes occur, known methods of dune stabilisation may be required.

When necessary, any small, normally dry rivulets meandering across the plain may be spanned with one of a range of mass-produced, expanded and reinforced, metal-mesh plates, wired over similarly mass-produced inverted, triangular cross-section, skeletonised, metal bearers and possibly transverse pipes of various, selectable dimensions. The number and type of these components required for a given area may also be estimated by software, using the digitally-mapped satellite or aerially-mapped topography and plans.

The main road artery and every alternate side branch are either sealed or covered with polymer-based 'carpet'. This means that, for a bioreactor farm of 30×34 km (~1000 km$^2$), there are some 34+17×30=544 km of mainly single-lane, sealed road, laid typically directly onto virgin, gibber surface, though perhaps with a preparation of some dilute, sprayed adhesive (possibly cheap polyvinyl alcohol (PVA)) and wetting agent to bind the sand beneath, thereby strengthening the road bed economically. Where the gibbers are exceptionally large, rough and separated, it may be useful to 'steamroll' or 'thumper' them in to the ground to form a more even base for the bitumen. Additional rock base might also be raked in from either side.

Farm Infrastructure

Besides roads, pipes and fences, a bioreactor farm has located on it powerlines, electricity transformers, communications lines and concentrators, and possibly power storage mechanisms (typically batteries).

Fertiliser for the Bioreactors

Particularly in remote locations, and possibly before the pipelines to the outside world have been laid, it may be advantageous to process local biomass using the WSS process to produce initial biofuel and the recyclable fertiliser with which to charge the bioreactors. Sources of local biomass might include: chipped-up weed species or any accessible, possibly regenerant, vegetation; crop, forestry or agribusiness waste; raw sewage and other wastes from construction, biofarm and biorefinery workers; or from regional agribusiness, towns and mining camps. Fertiliser minerals may also be sourced from nearby mines or mineral processing operations (possibly from their waste products); from local hydrocarbon or mineral deposits (leaching technology can utilise quite low-grade minerals); from mineralised ground water; or as a last resort be transported-in, in the form of commercial, bulk fertiliser. Longer term sources of cheap fertiliser and trace elements may include locally-produced, WAS nitrogenous fertiliser, mined minerals, piped in sewage, flue gas, and other agribusiness and industrial wastes.

Processing Plant

Traditional processing plant at Winwick facilities includes various, relatively standard, chemical engineering units, such as liquid, slurry and gas pipes, heat exchangers, filtration plant, centrifuges, pumps, valves, sensors, actuators, fractional distillation towers, storage reservoirs, tanks, ponds, and possibly, but not necessarily, anaerobic digestors.

Novel processing plant includes: profiled drillhole reactors for WCR, WMS, WFTAS, WSX, WSS, WDS, WAS, WNAS and WLE purposes, together with possibly WOF units to separate the biofuel products. The novel WMG and WSP plant is located in the bioreactor farm areas, the others at campus processing facilities.

Process breakthroughs come from three, newly perceived opportunities:

to use the clean, heat energy and power obtainable from geothermal resources and bioreactor-mounted, thin-film PVs to power a biorefinery and to use the waste heat therefrom to warm the bioreactors in cold periods to algal activation temperatures. Waste heat from the hot water produced as a by-product of functioning oil and gas wells, or from solar ponds may also be used to keep algae activated;

to use the pressures available from pumping fluids (including entrained gases) down deep (sometimes pre-existing) drillholes to drive a wide range of physical and chemical engineering processes most economically and sustainably, including those of:

algal cell rupture lipid transesterification molecular fraction separation sub and supercritical water gasification (SCWG) of biomass supercritical water partial-oxidation (SCWPO) of hydrocarbons and organic waste (including gassy slurries of algal cell walls left over after lipid extraction, or similar organics ranging from forest and agribusiness wastes, bagasse, weed species, organic rubbish, mixed plastic waste, lignite and/or sewage) to produce syngas Fischer-Tropsch (F-T) reactions to produce fuels and chemicals from inputs such as syngas, utilising catalysts and promoters disseminated throughout heavy oil, wax or other carriers, that are liquid at the operating temperatures, and into which have been introduced bubbles of reactant gases that are adiabatically compressed or otherwise heated and cooled so that they react together, in the presence of catalysts, as they are pumped down and up the parallel, drillhole reactor pipes and annular passages Other similar, pressure/temperature-driven reactions, such as methanol, DME, ammonia, and nitric acid syntheses to use the cultivation of algae to biosequester $CO_2$ and to produce a 90:10 $O_2$:$CO_2$ gas mix that can be used locally to produce syngas from algal biomass, or methanol from methane, or be transported by pipeline and used by industry for combustion, refining, water remediation, and/or chemical synthesis operations.

The benefits of using a fast-moving, carrier liquid to conduct reactant gases, materials and catalysts down a deep drillhole to regions of high pressure and/or supercritical conditions are threefold. First, the extreme pressurisation achievable and the controllable subsequent depressurisation require almost no energy. Second, the decavitation and formation of gas bubbles (cavitation) that occurs during the two-way passage can produce many desirable physical and chemical changes. And third, the length of the drillhole can deliver exceptional heat exchange efficiencies and related opportunities.

The particular advantage of Winwick technology overall, beyond its simple economy, its relatively low capital cost, its minimal ecological footprint, its production of baseload solar electricity, its high productivity and scaleability, is that it frees algal strain selection, breeding and modification from concentrating solely on those few species that give high proportions of lipids. It is to be noted that robust algal strains, having the highest biomass productivity per time period, which are often several times that of lipid-rich strains, tend to be those with low lipid content. Prolific, fast-growing and robust species that tend to produce carbohydrate rather than lipids may now be seriously considered for oil production, as their carbohydrates may now be converted efficiently and economically into oils and other feedstock chemicals. The only minor downside of carbohydrate conversion appears to be that more of the nitrogenous content might possibly be lost than would be the case when the biomass is anaerobically digested to release the nutrients. However, any loss can easily be replaced by one of several means, such as: using a higher proportion of Winwick bioreactors to grow nitrogen-fixing blue-green algae/cyanobacteria (these do not accumulate storage lipids, but produce bounteous carbohydrate); by employing the WAS process; by bringing in commercial, nitrogenous fertiliser (not preferred); or by processing local (e.g. vegetation) or other biomass (e.g. sewage) in the WSS to release its nitrogenous nutrients for use in growing algae.

Drillhole Reactor Construction

As already discussed, the outer part of Winwick drillhole reactors (WDR) is formed typically from disused, in-situ drillhole casings—though in some instances new drillholes may be drilled at sites of existing other industries or resources, specifically for reactor purposes. Whilst most useful when drilled into a geothermal resource, they can still serve their reactor purposes drilled anywhere else. Their small footprint and zero operational emissions would allow them to be drilled in locations most suited to obtaining access to input materials or markets, such as beside factories, power plants or agribusinesses, in forests or on transportation corridors. The laser drilling and material expulsion technologies of the Archimedes Project of Geoternity Corporation are claimed to reduce deep, well construction costs by as much as 75%. If/when achieved, they could make purpose-built, Winwick drillholes economic at virtually all sites. Potter Drilling has similar, spallation technology to drill holes in rock, but uses superheated water instead.

Whilst it has been shown that current lasers have the necessary power to dig into rock rapidly (at rates of up to several cms/sec) and highly efficiently using spallation (causing chips of rock to explode off its surface), remaining problems, such as material removal, power delivery and clear beam access are being addressed. These are likely to be easier to solve for the larger-diameter drillholes required by Winwick and geothermal power requirements.

One solution might well be an oscillating (perhaps 90° rotation back and forth) assembly that can be lowered down the drillhole, mounting one or more lasers. The intermittent laser beams would be directed by mirrors successively into many different quartz waveguides. The wave and gas guides might be a combination, the somewhat retracted waveguides being of solid silica quartz that are both cooled and protected from flying object impact by angled, enclosing, hollow pipes in the metal assembly, down which the pressurised gas flows. The angles determine where each beam hits radially. The beams are angled to spall the rock face evenly as the assembly rotates. The assembly backswing would allow the necessary time for the rock face to cool, prior to new spalling. The waveguides would form passages for both the laser beam and high-pressure, recycling argon gas. The gas would tend to keep clear of debris the path of each beam to the rock face. The slurry of used gas and rock particles would be drawn into a round pipe or annulus and conveyed to a pressurised, subsurface (for safety) tank that would allow the rock particles to settle into a water bath and be drawn off as in a revolving door that exchanges contents without opening the building fully. Water would be sprayed to capture and settle the fine rock dust. The cleaned, cooled and then filtered argon gas would then be pumped down the drillhole for re-use. A series of gas pumps on the downward gas pipe would progressively increase the gas pressure, thereby reducing the need for very strong gas pipe. The high pressure in the upward gas pipe would ensure that the rock waste slurry did not settle and would be borne upwards. A heavy drilling mud would separate the gas and gas/slurry pipes from the drillhole casing to reduce the chance of drillhole casing fracture or implosion. Annular seals near the top of the laser assembly would separate the gas chamber and spalling/extraction operations from the mud. On drillhole completion or before maintenance, the pipes would be sealed off from the drilling chamber by rotating a lower part of the assembly so that the pipe holes no longer matched, and the annular seals would be released to permit passage of the laser assembly. Between drilling stages, the pipes would be sealed off and the annular seals would be released, thereby allowing the assembly to be lowered before commencing drilling the next section. Water would be introduced into the assembly prior to opening the tubes and using water followed by gas to expel the drilling mud that had entered the drilling chamber during the relocation. Water from the water and mud entering the surface rock would tend to improve the spallation effect for a time via explosive steam creation.

It is also reported that a variant of Geoternity's technology can be used to fuse the sides of the drillhole it makes. Should the fusing of the rock be significant and reasonably seamless, then it may be possible to do away with most of the drillhole casing and external concrete lining (perhaps all that except possibly that in the actual, and quite narrow, harsh reaction zone) and to use the drillhole's fused wall as the low-reactive barrier inside which Winwick processes can take place. The rock type, its fracturing and fluid contents would probably all be important factors regarding the feasibility of this variant. If proven feasible, this method would have substantial cost advantages. It might not matter much if the sides of the drillhole were eaten away slowly by supercritical reactions, particularly if the rock strata there were relatively impermeable, as the main result would be simply an enlarged reaction chamber or passage and some additional, but possibly minor and unimportant, mineralisation of the product fluids. Dissolved rock components in the products would not appear likely to cause later separation difficulty or other serious problems. Large, old reaction chambers might even find uses for storing seasonal water, resource gas, input liquid waste, or output biofuels and chemicals.

Although WDR can work using simple piping, the central WDR pipe, and sometimes one or more of the concentric outer pipes, is typically profiled. That is to say, it or they will often have one or more constrictions inserted, beyond those that secure an inner pipe to an outer one. Constrictions first compress then decompress the reactants, as well as contributing to their mixing. Constriction may be achieved by varying the pipe cross-section at locations along it by means of insertions. Care will need to be taken that the constrictions do not result in an undesirable amount of pipe hammer (knocking and vibration).

The Winwick method of joining sections of pipe and supporting them using frictional pressure against the next outermost pipe (which is eventually the drillhole casing or rockwall itself) provides a means of constricting the flow. Pipe sections may be some 15 m long, this being about the maximum rigid length that can be easily transported, is approved by regulation, and can be handled by drilling rigs. Unless made by a complex, rotary casting process, each (typically steel or titanium) pipe has welded to it special joining endpieces. The male end has a coarse, half-round, helical thread on its outside. This would begin a short distance from its end. Overall, the male end is slightly tapered, but with a uniform internal diameter. The pipe wall at the end is also tapered to help guide it in.

The receiving female end-piece is divided into three, evenly-spaced, longitudinal prongs. The prongs are threaded on the inside to match those of the male end. Each prong is thickened radially outwards enough, so that when expanded slightly by the male end as it is screwed in, it bridges the gap between its own pipe and the inside of the next outermost pipe, and so on to the concreted-in drillhole casing. Each prong is long enough and slightly arched so that its partial straightening can accommodate slight changes in pipe diameter and to ensure that the pipe ends butt together tightly. Together, the cross-sectional area of the three prongs is about 30% that of the annular space between the two concentric pipes.

In order to improve the annular passage's flow characteristics, the outer portion of each prong is lanceolate-shaped, being pointed at both ends and with an outer surface whose curve matches that of the inside of the outer pipe. When expanded, the prongs are shaped such that they are in tight, frictional contact with the inside surface of the outer pipe to make a strong yet reversible attachment. When a greater degree of passage constriction is required, the percentage of annular space taken up can be increased as much as is desired. The end of each prong is pointed, the points being made from its generally lanceolate shape and have planes at each end that slope outwards. The upper plane serves to guide the placement of the male end being lowered down onto the female end of the lower pipe segment. The attached end of each prong is thus pointed in its part that sits in the annular space. The female pipe end is flared to partly accommodate the slightly conical male one. The remainder of the accommodation is made by the bending outwards of each prong, under the screwing insertion of the male end. When screwed together, the two types of endpiece butt-seal firmly together. Powdered graphite and titania, mixed to a paste with siloxane may be a suitable thread lubricant, sealant and release agent for the attachment of pipes vertically.

A seating ring at the base of the prongs prevents further turning of the upper pipe and seals the join. As all but the topmost pipe segment is wedged to the outer pipe, any topmost pipe may be screwed or unscrewed without affecting the lower segments. It is probably advantageous to have the joins of all concentric pipe segments occurring at the same places, so that inner and outer prongs will deform the pipes least. All screw threads may also be best if they are of the same pitch. Purchase on each pipe to rotate it may be arranged by the use of expanding sleeves inside each, attached to narrower pipes powered from a drilling rig at the surface to rotate. Two of these may be inserted in parallel or concentrically at the same time, one for clockwise and one for counter-clockwise screwing.

A similar mechanism may be used to insert a moveable constriction into the central pipe. In this case, the prongs on the female part are formed from a pipe section that is divided by thin cuts running most of the way lengthwise. The male part is a hollow, threaded, short pipe section with possibly a flange at the upper end to help seal the splayed prongs from the flowing contents. To minimise the likelihood of the male part sticking in the pipe, the flange may be in the form of a separate ring that sits on or screws into the larger part. Both male and female parts have pipe ends whose walls are sloped to the external wall to minimise flow resistance through the middle passageway. The parts may be as short or long as to ensure the compression lasts for a sufficient time for the required reaction to occur. As the whole assembly is able to be disassembled, relocated and reassembled within the pipe using attachments on long, concentric, narrower pipes (or robotic tools), different portions of the drillhole, or different reactions may be enabled, as well as extending the life of the drillhole reactor. Should the parts become dysfunctional, corroded on to the walls, or are not able to be separated, they may be trisected lengthwise by a robotic cutting tool and either retrieved or let fall to the unused bottom of the drillhole reactor.

The constrictions of various types result in the pipe being profiled into zones where there is relative compression or decompression. In addition, where an inner pipe opens to an outer, annular one, there can be arranged to be decompression of large amount and an effective mixing zone created. Such can occur when an inner pipe stops short of the end of an outer pipe, sealed at that end creating a passage from one to the other.

Due to the harshness of the conditions in some zones of the pipe, pipe sections and end assemblies there will typically be constructed of, or coated with, material that is resistant to the conditions expected to pertain there in the drillhole. Where those conditions approach those of the harshness of supercritical water ones, the materials are required to be extremely resistant. Titania coated titanium, graded together, is one of the best composites in such circumstances.

In the simplest case, sections of pipe with male and female ends are lowered and secured successively at predetermined levels into a drillhole casing. When secured some distance above the bottom of the sealed drillhole, this forms a link between the internal pipe and the surrounding drillhole casing. Through the central pipe and annular passage a carrier fluid and reactants (often in the form of mixed-gas bubbles), catalysts, additives, promoters, neutralisers, gelators and/or densifiers can be pumped around the system at minimal energy cost in pumping and pressurisation. Pumping may be in either direction, but will typically use the central, inner pipe for the downward passage to provide widest passage for possibly coarse input material. The WCR process is an exception to this, in order to allow for upwards passage of an order of magnitude or more greater than the downwards passage.

Constriction in a passage causes additional compression of the fluid to occur there, whereas widening causes local decompression. Both generate turbulent mixing. Compression may also result in adiabatic heating and decavitation (bubble implosion) and their energetic concomitants. Chemical reactions will tend to take place either in gas phase, in solution, adsorbed on catalytic surfaces, or where gaseous or liquid reactants interface with homogeneous catalysts and possibly with other reactants at bubble surfaces.

Total bubble reactive surface area is larger when the introduced bubbles are small and many. However, bubble size at the land surface will typically be chosen such that decavitation and its beneficial concomitants will occur at the most suitable depth. Products may be partially shielded from further reaction, or from the equilibrium reaction going in the other direction, by phase separation or product dissolution in the carrier liquid that may be used to limit further reaction by removing valuable, intermediate products from further reaction. Reactions and physical or phase changes can occur in both downward and upward passages.

The processes resulting from Winwick's decavitating microbubbles and the nature of the bubbles themselves are different in both kind, intent and controllability to those produced by some other methods—for instance, the cavitation patents of Arisdyne (inventor Kozyuk) that relate mainly to conducting sonochemical reactions and to producing fine emulsions, mixtures or material homogenization using hydrodynamic cavitation. These patents are U.S. Pat. Nos. 5,969,207, 7,207,712, 7,178,975, 7,086,777, 6,502,979, 6,035,897, 6,012,492, 5,937,906, EP1359997, EP0983116, and CA2296692.

The processes are different in kind for several reasons. First, the Arisdyne microbubbles have very short lives, typically of the order of pico- to milliseconds. Only a tiny proportion of this type of bubble last over a second. On the other hand, Winwick microbubbles are typically designed to last from under a minute, to many minutes, thereby allowing sufficient time for the various drillhole processes to occur. Indeed, in some Winwick processes, whilst possibly changing the molecular character and/or mass of their contents, some of the bubbles may remain as bubbles throughout the entire process. Second, the Arisdyne and Winwick bubbles are produced by different processes. Arisdyne bubbles are generated typically by passing a liquid through a nozzle, constriction or chamber at high velocity, the liquid in the resulting stream, that also may be made to encounter the shock of obstacles or baffles in its path, suffers violent decompression that has the effect of causing cavitation (the formation of tiny bubbles or voids), which subsequently, and almost instantaneously, decavitate (disappear), thereby creating very large pressure impulses (that may reach 10,000 atm) or shock waves. On the other hand in Winwick processes, either gas bubbles of the correct size range are already present in the liquid or slurry, or they can be blended to the correct size, or they are sparged at relatively low pressure into the smoothly-flowing liquid or slurry in a way that requires relatively little energy. Third, the size ranges of the bubbles in the Arisdyne and Winwick systems are typically very different. Arisdyne bubbles formed by cavitation are typically much smaller than are Winwick bubbles. Fourth, Arisdyne 'bubbles' are either voids (temporary partial vacuums) or contain gas or vapours, formed from whatever volatile substances are dissolved in the original liquid and are brought to boiling point by the very short term pressure reduction. Winwick bubbles typically have their gaseous contents and mix precisely determined in advance by the requirements of the required process or reaction, or by the predetermined nature of the slurry's gases. Fifth, the effectiveness and efficiency of Winwick processes typically depend on the ability to select not only the mass of each input bubble fairly precisely, within one or more mass ranges (so that each will decavitate at predetermined depths, pressures and temperatures in the drillhole reactor), but also depends on the proportion input of gas mass to liquid mass. Sixth, where Winwick processes depend on catalyzation, the amount of catalyst or the catalytic area presented at the bubble surfaces, or on the drillhole reactor walls, or inside the bubbles, the liquid or solid/liquid slurry, and the duration of the exposure, can all be controlled tightly under Winwick processes—but not so well under those of Arisdyne's and similar processes. Seventh, Arisdyne processes are far more energy intensive than are most Winwick ones. Eighth, Winwick drillhole processes, being passively pressurised, are readily scalable over scales of around $10^8$ or by a factor of 100 million or more. For instance, using Winwick processes, one can produce outputs ranging from less than a gm/sec to many tonnes/sec of product. Whereas, being based on active pressurisation, Arisdyne's sonochemical processes cannot be nearly so scalable. They are therefore less useful at large industrial scale.

When a liquid (possibly with solid or gaseous inclusions) or supercritical fluid fills the drillhole passages, gravity ensures that the pressure increases with depth. Depending on the average density of the fluid slurry, in a 5 km deep drillhole the pressure may reach 500 atm, and pressures well in excess of 1,000 atm are not unachievable with the use of densifiers and/or greater depth. However, most drillhole reactions can be made to occur quickly and effectively at depths and pressures a fraction of these.

The density of the fluid may also need to be increased by the addition of heavy, often powdered or granular solid materials (densifiers), in order to offset part of the tremendous pressure of the surrounding rock and fluids, or so that reactions can take place in drillholes of lesser depth. This density requirement can be an advantage, as solid catalysts often take the form of transition metals, or their oxides, that both tend to be of high, specific gravity (density). In a liquid carrier, they can be highly concentrated, yet dispersed for easy access, provided that the presence of carrier fluid at active catalytic sites does not hinder reactant access or reaction overmuch. Such 'drilling mud' fluids are often made up with a component of thixotrophic or other gelator to ensure that the densifying solids do not separate. Drilling mud, made from water, bentonite clay and heavy-mineral powders is an example of the liquid's pressure-balancing and lubricating effects. However, for Winwick purposes, a combination of powdered titanium dioxide ($TiO_2$) and gel-forming aluminium hydroxide ($Al(OH)_3$) may be more preferable—at least for the WSS process, and possibly for some others as well.

The deeper, drillhole processes may also require the addition of an even heavier, powdered material to offset the very high geopressures and the typically low density of supercritical fluids. Besides using titanium dioxide (density 4.23 g/cm$^3$) as a densifier and potential catalyst, another dense, powdered material to use might be pitchblende ($U_3O_8$) of density 8.3 g/cm$^3$. This, although very toxic like other uranic ores, particularly when particles are <3 microns in diameter, is stable under oxidative conditions. Another candidate densifier, depleted uranium dioxide ($DUO_2$) of density 10.97 g/cm$^3$, has the additional, potentially useful, properties of catalysing the degradation of volatile organic compounds in gaseous phase, such as the oxidation of methane to methanol, and of having long-term, catalytic stability, unlike titanium dioxide. Magnetite ($Fe_3O_4$) of density 5.15 g/cm$^3$ is another Winwick densifier candidate having (possibly temporary) catalytic properties but which has no toxicity and is cheap. Heavy sulphides that are sometimes used as densifiers may not be good to use here, due to their own possible oxidation and the consequent release of acid gases and acidity.

When the pressure at any given deep level in both linked drillhole pipes is approximately equal, it takes very little energy to pump material through them both. Thus, hyperbaric pressures that assist chemical reactions or desirable physical changes to occur can be achieved at very little energy (and typically modest capital) cost—far less than those of surface-mounted pressure vessels.

Whereas suitable, gross reaction temperatures may be achieved: by the use of heat exchangers on the surface (typically making use of low-cost, geothermal heat); by heat exchange between products and reactants along adjacent passages; or by the adiabatic heating effect of gas bubbles in the fluid being compressed, fine control of fluid temperature may be achieved by the use of superheated steam introduced to the fluid by means of a long, hollow metal pipe or lance. Typically, this will run from the surface someway down the centre of the inner pipe, perhaps 30-300 m. The lance may be inserted to adjustable depths or have openable vents at several depths, should different reactions benefit from these capabilities. The selected depth of the lance's nozzle opening could be used: to minimise the chance of blowout; to ensure that reactant bubbles in the fluid had been suitably compressed to facilitate their transport downwards in the liquid carrier; to minimise bubble coalescence with the steam; and to help determine at what depth reaction conditions are reached.

Alternatively, or when a central lance would overmuch constrict the flow of fluid, the steam may be introduced by means of one or more hollow, split collars set around the drillhole casing at one of several, selected depths. Typically, these external collars would be welded onto the casing after accessing it via a second, shallow, access drillhole or mineshaft, drilled parallel, or possibly curved or angled to the first. The sideways excavation, drilling holes through the casing, collar placement and welding back might be done with remotely operated tools able to be lowered down the access drillhole. An insulated pipe would carry the superheated steam to the correct depth, where electrically-operated valves would open a nozzle to the required amount to heat the drillhole contents at the location to the required temperature. Potential downsides to this collar alternative may be that it would be somewhat more difficult to arrange for heat exchanges amongst different, concurrent processes occurring in concentric pipes, as there would need to be inserted crosswise pipes spanning the annular gap to the inner, downwards passage. Alternatively, the direction of flow could be reversed, though this might reduce heat exchange efficiency. A third alternative that overcomes both problems, is to insert a piping structure that moved an outer, downwards flow to an inner one and vice versa, once the collar had been passed on the way down. This may be termed a passage inversion exchanger or (PIE)—see later. It exchanges an inner flow for an outer one and vice versa.

The main factors determining the heating effect of steam on the carrier and its reactants are its temperature, pressure, and the degree to which its valves are opened. Maximum bulk temperatures in drillhole reactors may be constrained by the temperature at which the carrier (usually a heavy oil, wax, water, non-ionic fluid, or liquid metal such as gallium) degrades, oxidises, vaporises or turns into a supercritical fluid at a particular pressure. However, as much higher, highly-localised temperatures occur at the instant of bubble decavitation, it may promote some desired reactions even in the absence of the bulk temperature reaching the necessary level.

When cooling of an exothermic reaction is required, possibly on the upward leg, additional pipes containing cool fluid may be used to form a heat exchange or cooling system. However, it will usually be possible to arrange that the incoming reactants provide any required cooling effect—thereby improving overall process efficiency.

The construction, installation and maintenance of the inner pipings of a Winwick drillhole reactor require careful design. The design needs to address several problems. The first is that of suspending one or more concentric internal pipes up to five kilometers in length, some or many metersmeters above the sealed base of a drillhole. A second is that, despite the substantial velocity of the fluid in the pipes, settling or deposition of salts and oxides in the bottom of the reactor may well occur. A third is that the profiled pipe, or its profiling constriction(s), may occasionally need to be removed from the drillhole for cleaning, inspection, maintenance, relocation, alteration or replacement. A fourth is how to ensure the pipes remain centred within the drillhole. A fifth is that it may be advisable periodically to shift the locus along the pipe at which most deposition or corrosion takes place. And a sixth is how to minimise corrosion and embrittlement in SCW environments.

The first, third and fourth problems are addressed by having each pipe section fit into those above and below it and each section to be supported independently. To minimise cost and the number of joints, the length of each pipe section is chosen as the maximum that can readily be transported by road and erected vertically prior to lowering it into the drillhole. Some fifteen meters appears to be optimal or close to it.

Most WDR processes result in fluid pressures within adjacent pipes or annuli at a given depth being essentially equal. Thus, leakage through the pipe joints is not a problem. However, this is not the case for the WSS and WSS/WFTAS processes, as the upflowing product gases may be at considerably higher pressures than those of the downflowing and upflowing liquid slurries. To prevent leakages in this instance, these joints may need to be more strongly sealed. This may be effected by the placement of a ring of solder nestled at the butted end of the female coupling, at the base of the prongs. Such solders can be compounded to melt at a wide variety of temperatures. Once a new pipe section is resting on top of the previous one emplaced, local heat (provided by electrical induction or heat conduction delivered via a robotic tool) can be made to melt the solder that then fills the space between the male and female threads by capillary action to provide a strong seal, when combined with extra torsion to butt the two ends more closely together. The seal may be released by a similar heating process. Titanium powder may be added to the solder composition wherever conditions are sufficiently harsh as to require the extra protection from corrosion. This titanium and the tin and other solder metals will tend to oxidise to form a resistant coating at the exposed edges of the soldered seal.

The second problem is addressed two ways. First, the reactor is let cool to subcritical temperature. Then a double pipe, possibly with robotic attachments, is lowered down the inside pipe until their ends meet the bottom detritus. Then a high-pressure liquid is made to issue from one pipe and the swirling detritus resulting is sucked up the other pipe. The issuing liquid may contain successive chemical additives or abrasives that would help dissolve or abrade any adhering or coalesced deposits. A second way of addressing the problem is if the detritus has become difficult to remove economically by the previous method and its level is rising uncomfortably close to the bottom of the last, inner pipe section. In this case, an ultrasonically-visioned robot or tool under human control cuts up the unwanted pipe at an appropriate place. Bits of the pipe can either be removed or let fall to the bottom. If the robotic tool is light-visioned, then to control the cuts and handling, clear water, or a heavier, mineral brine, may be required to replace the murky contents. Any pipe portion that is cut and let fall has the effect of slightly shortening the drillhole reactor, but probably affects the SCWPO reaction very little. Typically, the drillhole reactor would be deep enough to allow this strategy to be repeated perhaps 50-150 times before other, more costly measures would be required to maintain production—such as drilling another hole.

The fifth problem can be addressed by one or more of the following steps: changing the pumping velocity; the biomass to oxidant concentration; the overpressure in one or more of the pipes; the additive-catalyst combination; or by means of changing the vertical location of the reaction. This last may be done by insertion of additional constriction; and/or by slightly changing the pressure at that point in the drillhole either by altering the overpressure or by changing the density of the fluid in the column with a different concentration or type of densifier material.

The sixth problem is addressed by finding materials, internal sheaths and/or coatings that are resistant to attack in sub and SCW environments and by finding cost-effective ways to apply them. Steel does not resist SCW oxidation or even dilute acid attack at high temperature well under these conditions. Corrosion-resistant metal alloys, such as those comprising blends of nickel, chromium, aluminium, iron, vanadium, molybdenum and manganese, tend to embrittle near 500° C., even those of normally corrosion resistant alloys such as Hastelloy C-276, and Inconel 625. They also tend to pit and craze under SCW conditions. Metals such as titanium, zirconium and yttrium perform much better, though they are more or less costly. Noble metals, such as iridium, that has been shown to have high resistance to SCWO conditions, are even more costly, though plating them on may be an acceptable solution in some circumstances. The oxides of aluminium and silicon do reasonably well when dense, though they perform best at sub-critical temperatures and in the absence of strong alkali. Some ceramics are very resistant, particularly the oxides of zirconium, yttrium, hafnium and titanium. However, most ceramics tend to be somewhat brittle, though are less so when in sintered form or grade-coated onto the respective metal.

Now, embrittlement is even more likely when thermal cycling occurs and when high concentrations of hydrogen are present (hydrogen embrittlement). However, it should be noted that embrittlement is not likely to be a serious problem with WDR, as the drillhole casing has countervailing pressure from the outside concrete, rock and fluids, and the inner, profiled pipe usually has countervailing pressure both inside and out—except high up in the pipe where SCW conditions do not apply and where the gas in the outer annulus may be at a much higher pressure (possibly 200-400 atm more) than are the liquids further inside. This difference may curiously require the upper, inner piping wall to be thicker and stronger than that lower down, where pressures, although higher, are more equal.

Steel piping may be protected at moderate cost in non-extreme, drillhole environments by being treated with activating titanium salts, then a combination of phosphoric acid, sodium nitrite and phosphate (iron, zinc or manganese) salts to form a resistant microcrystalline structure. For extra resistance and to reduce the phosphate coating's porosity, it may then be sealed, perhaps with a polymethylphenylsiloxane resin (say Kremnypolymer KO-08K) that in addition incorporates aluminium powder to form a heat-resistant varnish or enamel able to stand an operating temperature of over 600° C. At the SCW interface, the siloxane, aluminium (or better, titanium) powder and oxygen may react at the siloxane surface to form an impermeable mineral layer, rather like aluminium does in air or when anodised.

Alternatively, one or more cermets of aluminium, nickel, chromium, vanadium, zirconium, yttrium or titanium oxides may be used as coatings. Moderate SCW environments may call for either steel with multiple coatings built up from titanium (to ensure better bonding) grading into titania ($TiO_2$) or others of the above ceramics. The coatings might be applied via thermal or plasma spraying, diffusion or sol-gel processes, depending on the requirement. Harsh SCW environments require graded titania/titanium coatings on solid titanium (or on an alloy of titanium, vanadium and aluminium) pipe and fittings. The most cost-effective results come possibly from using combinations of the above at the drillhole locations for which they are most suited.

Drillhole Reactor Technology Prospects

There are potentially many uses for Winwick Drillhole Reactor (WDR) technology. For instance, it would find profitable use wherever industrial chemical reactions use catalysts, high pressures (10-1,000+atm) and temperatures up to the degradation point of heavy oil or wax, circa 1,000° C., or where large-scale, just sub- or supercritical fluid reactions are beneficial, such as in the generation from organics of valuable fuels, chemicals and energy. Such reactions comprise a large number of industrial, chemical engineering processes. Hence the technology may benefit many current industrial processes. In particular, supercritical fluid reactions and reactions utilising many different reactant gas mixtures and carrier combinations might be investigated quickly and economically using a drillhole reactor. In addition, technologies such as Virent's BioForming process for the production of biofuels from plant biomass via sugars and alcohols may be able to take advantage of WDR's more economical methods of obtaining moderate temperatures (150-300° C.) and pressures (10-90 atm) in a continuous, rather than a batch, process. WDR may also find use in 'cracking' biomass residues and hydrocarbons to form more valuable chemicals. The mechanism for this is the formation of free radicals as a result of decavitation. These lead to chain reactions that break and recombine organic molecules in many different ways. Using WDR, these reactions can be made to occur in aqueous solution—thereby avoiding expensive drying operations where biomass is the feedstock. Typically, the longer organic molecules are broken down by these processes into smaller, more valuable ones. The process can also form many, varied organic structures from a single organic input. Thus, transforming naphtha forms the basis of much of the chemicals and plastics industries. Hence, WDR may be used in a similar fashion to make abundant, but otherwise intransigent, biomass molecules, such as cellwall glycoproteins, hemicellulose, cellulose and lignin, into feedstock for the emerging biorefinery industry.

As a bonus, WDR technology could end up unifying, by means of a establishing a multifactorial matrix, many disparate chemical engineering processes. It could do this by providing both a common and an economical, high-pressure reaction vessel, at a useful scale, together with a means of economically experimenting with many reaction factors. As pressure-dependent reactions usually depend on a certain minimum pressure being reached before reasonably fast reaction occurs, a drillhole having a zone of much higher pressure usually would not deleteriously affect reactant conversion into product, whilst its results would cover the range. The likelihood of very high, instant decavitation temperatures might also mean that bulk temperature effects would be less controlling than in standard reactions. These factors mean that different-depth and width drillhole reactors could all contribute to filling in the matrix of possible valuable reactions, rather than being just isolated experiments.

Decavitation effects have potential to allow gas reactions to take place in bubbles of reactants, or where they have just decavitated, in oil carriers that are bulk-heated to well below normal reaction temperature. Decavitation produces very high, very short, and very localised temperatures to occur at decavitation sites. Due to the speed of catalytic reactions, particularly when assisted by the high Winwick pressures that are readily available, it is likely that temperatures well above that which are required for reaction would be produced at decavitation sites. Thus, the desired reactions might be found to proceed, even though the bulk temperature of the carrier oil never reached near to reaction, degradation or auto-ignition temperatures.

Likely, and possibly better for some purposes, alternative carrier candidates to water or the Residual Fuel Oil (RFO) by-product of algal lipid fractionation that have relatively high auto-ignition temperatures (compared to the 407° C. of RFO) and reasonable cost include: coal tar oil 580° C., benzene 560° C., naphtha 550° C., toluene 530° C. isobutane 462° C., cyclohexanone 420° C. or various hydrocarbon waxes. Amongst these, cyclohexanone or RFO are possibly the best for oxidative temperatures of 300-405° C., whereas coal tar oil or benzene may be best for higher oxidative temperatures. Cyclohexanone is not particularly cheap, is liquid at ambient temperatures, boils at 156° C., is not carcinogenic and is only moderately toxic. Coal tar oil is cheap, but can only be pumped when warm or hot. It is both carcinogenic and toxic. RFO is a cheap, thick, oily liquid or tarry semisolid that boils, at ambient pressure, in a range from 204-700° C. At higher pressure, the boiling range is increased. RFO is somewhat toxic and carcinogenic. However, unlike normal RFO derived from coal, RFO from algal lipids should not contain much sulphur and may be altogether more benign—plus it is available on-site. Therefore, it may be the best general, liquid hydrocarbon carrier of reactant gases to use in many, if not most, Winwick reactions. One of the exceptions to this is possibly the WFTAS reaction where one fraction or a mixture of product FT waxes may be an even better option. Such an arrangement would markedly reduce the cost of separating carrier from product, and catalyst from the rest. Product wax and catalyst would be continuously removed and replaced with (possibly regenerated) catalyst and part of the wax product after it had been partly or fully hydrocracked. However, as the FT waxes tend to be much less toxic than most alternatives described here, including RFO, it may be that the waxes may become the preferred carrier for most Winwick reactions.

Operators of Winwick drillhole reactors will tend to employ oxidative temperatures in the range 374-490° C. to ensure the partial oxidation of carbon and organics, whilst avoiding the wasteful further oxidation of ammonium and oxy-anions (such as nitrates) that can occur at temperatures over 500° C.

An alternative method of producing biofuels from biomass is supercritical water gasification, SCWG, of biomass. This employs reaction temperatures varying from 350-600° C. in the absence of additional oxidant, but, typically, may be performed with one or more catalysts. In this case, the temperature may be slightly below supercritical, whilst typically the pressure is above the supercritical point. This method may produce tars and carbon char as by-products, unless countered as indicated elsewhere in this paper.

The size, or more precisely the size range, distribution and concentration, of the reactant bubbles introduced into the carrier oil column, prior to its deep descent in the drillhole reactor, are important variables in most WDR processes. They can be controlled in a manner analogous to the sparging of microbubbles into the algal bioreactors. Providing two or more sizes of bubbles allows more complex, typically successive, reactions to occur that can produce a wider, or a more valuable, product range from a single drillhole pass. Each bubble size might even contain a different mix of gases for reaction. Small bubbles do not tend to coalesce in their passage through such drillhole reactors, particularly when gelators and additives may be employed to limit their relative movement and adhesion.

As large bubbles tend to coalesce easily and are often difficult to pump, it may be best to introduce relatively small bubbles into the downward-flowing carrier at a modest depth and pressure, by means of the collar attachment previously described, where the energy cost to inject a pressurised mix of gaseous reactants is still low and can be balanced against a desirable bubble size for pumping and to ensure that bubble decavitation takes place at optimal, designated depths.

This document relates how such different processes as: algal rupture; transesterification; biomass gasification; syngas synthesis; various F-T reactions, including the synthesis of methanol and alkanes; together with ammonia and nitric acid syntheses and similar high-pressure reactions might be placed in a multifactorial matrix using WDR. However, there are potentially many more, both known and as yet unknown reactions, that might be identified, unified, selected and made more economical by employing WDR technology.

Some of the many factors affecting reactions that might readily be explored under WDR standardisation could include: reactant concentrations; phases; different carriers and their effect on catalysis and product removal; catalyst mixes, forms, sizes, shapes and concentrations; densifiers; promoters; surfactants; solvents; temperature gradients and intensities; pressures; durations; decavitation; compression/decompression regimes; turbulence; sub- and supercritical fluids; bubble size; fluid velocity; additives; and catalytic adsorption, diffusion, desorption, conversion, reaction rate and separation. Typically, the easier to change variables would be changed early on and the optima determined from them be used in the more difficult changes of variables. Such an approach would not cover all combinations of variables, but should deliver valuable results in many cases. It has the major benefit of vastly reducing the number of experimental combinations, whilst detecting all but anomalous optima.

Why WDR could become an efficient means of finding better reaction conditions, quicker, is not only due to the ease and relatively low cost of testing new combinations, but because with WDR it is relatively easy in, most cases to use a research technique called acceleration-stat (A-stat). This is an experimental method that can be used as a fast and accurate tool to determine kinetic parameters to optimise conditions—in our case the optimal physicochemical reaction conditions. It was used to good effect in the Barbosa study. Basically, what it does is to change experimental conditions slowly enough so that new equilibria are closely approached, but rarely reached, whilst the results are periodically measured on-line, but without the need for separate or batch-type experiments. This allows optima to be plotted and determined far more quickly than otherwise, and with negligible error. It therefore allows far wider experimentation for a given cost. WDRs may therefore become useful tools for Winwick technology developers and extenders, and for the integration of chemical engineering processes in place of the current, almost cookbook, approaches.

Similarly, WDR might be used to re-optimise reasonably well-known chemical reactions falling within the WDR zone, as well as for discovering useful, new reactions. Such new reactions might even be suggested by observing the developing multifactorial matrix population of viable and optimised reactions. For instance, it might be a profitable way to search for new catalysts and catalytic forms and to trial them. Additional catalyst and promoter candidates might progressively be added to the carrier with jumps in product concentration reflecting a good, new catalyst or interaction amongst catalysts. Similarly, might other reaction conditions be progressively changed and the effects measured at any desired intervals, without batch-type interruption. It also means that given drillhole reaction conditions and reactor contents may often be progressively changed, without significant cleanout or downtime, until the required new reaction conditions and reactor contents are achieved. The sequence and nature of a set of A-stat experiments might even be left to programmed controls and artificial intelligence that determined the next experiment from the results of ones just run, whilst the sequence was still underway.

In WDRs where gaseous products are less in volume and/or temperature than are the reactants, then energy would need to be input to overcome the difference in fluid column weights between the up and down columns plus frictional losses. This may be done either by increasing pumping energy and/or by increasing the overhead pressure or by having the inlet column reaching significantly above ground level. For the converse case, pumping might not be required except perhaps to initiate the reaction.

Where foaming is a likely prospect with products of the reaction in their carrier, this may be addressed either by means of hydrocycloning, centrifuging, cooling the product and/or by having a sufficiently large receiving container in which the resulting foam may separate into phases, possibly assisted by known, pressure-reduction and other bubble-bursting and coalescence techniques. Gas-liquid cycloning may take place at pressure and in series to limit the amount of foaming that occurs at any one point.

Drillhole Reactor Uses in Winwick Biorefineries

Drillhole reactors may be used to produce syngas via partial oxidation using hydrothermal or supercritical water processes. Input biomass may include: the algal cell walls left over after lipid and selective protein and metabolite extraction from algae; biomass from methane; farm and forestry waste; from sewage, plastics, or virtually any other form of pure or mixed, but otherwise unadulterated, biomass, at almost any dilution. Insufficient or excess biomass concentration may readily be adjusted by the addition of the relevant constituent—possibly from a different source of biomass. Thus, pulp-mill liquid wastes might be adjusted to the desired biomass concentration by the addition of crop or forestry waste; unrecyclable, plastics/paper waste; and even coal or lignite (even of otherwise-unusable low grades) might be paired with used, cooling water from power plants. From the resulting syngas may be produced various F-T-fuels and chemicals, also using Winwick processes.

Processing steps using WDR for pressurisation and temperature control are likely to be far more economical and friendly to the environment than are traditional methods that rely on fossil fuel and high-pressure pumps to achieve elevated temperatures and/or pressures. In such ways methanol, ammonia and nitric acid may be produced by efficient, economical and sustainable drillhole reactors. Each of these chemicals, as well as syngas itself, can be used to produce very many downstream products.

There are other benefits to drillhole reactors. The up and down passages of the drillhole reactors can total up to several kilometersmeters in length. They can therefore act as highly efficient heat exchangers. Savings may be as much as 90% of process heat used, when a typical industry value for surface-mounted, liquid-liquid heat exchangers is 75%. This apparently modest difference translates into major savings in energy—ten-fold versus four-fold savings. Furthermore, the countervailing pressure of the surrounding rock also tends to ensure that the capital cost of pressure vessel containment is minimised and that pressure vessel wall failures do not occur. Safety is therefore improved. Moreover, as WDR can utilise 'dry wells', depleted ones, or non-functional HFR ones, much of the otherwise expensive drilling cost may often be avoided.

Processing microalgal cells to produce biofuels involves overcoming several physical and economic problems. These include the high costs involved in: rupturing the tiny, often tough and slippery, algal cell walls; heating; dewatering; chemically transforming the viscous, algal lipids into methyl esters; and separating, refining and recombining the various fractions into valuable transport fuels, other products and recyclable nutrients. Brute force methods have traditionally been used to address these problems. However, these are increasingly costly, unsustainable and typically involve damaging greenhouse gas and other emissions. The novel method proposed, bypasses the step of removing water from the algae by processing the algae in aqueous phase, thereby saving energy and facilitating oil, water, and solid phase separation. It also rationalises the number of separate processing steps, making use of low-carbon and economical drillhole processes.

For some algal species, particularly those low in lipids, it may actually be more profitable to bypass one or more of the nutrient-stressing and lipid/protein extraction stages and to pump the extracted algal froth directly (though possibly after heating and material additions) into a WSS or WSX drillhole reactor.

An HFR drillhole resource has two components in addition to the drillhole casing of thick steel (that often has an external, injected concrete cladding): pressure and heat. These components can separately be replicated away from a drilled, HFR or other mineral resource, but at typically greater financial and environmental cost. In the Winwick process, pressure and heat are used successively: to produce the desired transformations in the algal slurry (to rupture the algae); to transesterify the lipids; to separate (fractionate or condense) the individual oil fractions; and to produce syngas, methanol, ammonia, nitric acid, and various other F-T fuels and chemicals.

A geothermal drillhole often has three diameters, narrowing from the surface. When this occurs, the different diameters may be exploited to allow a number of different WDR processes to take place, concurrently or separately, in a single drillhole—albeit one with a number of pipes inserted to different depths to cater for the different processes. Otherwise, separate drillholes or pressure vessels may be used. For a three-diameter drillhole, either parallel or concentric pipes may be inserted inside the drillhole casing. One shallow pipe loop (or else a separate drillhole) might separate the up and down flows of the transesterification process, as this may require least pressure. The next deeper set of pipes might provide the algal cell rupture process. A third set might partially oxidise the biomass to syngas or gasify it in the absence of added oxidants to lighter hydrocarbons, tar and char. The upward leg of the syngas set might also be used to convert syngas to alkanes via a F-T process. A fourth might produce methanol. A fifth, possibly the deepest, might be used to produce ammonia. And a sixth to produce NOR. When two or more of these sets of pipes shared the same drillhole, there will frequently be opportunities for utilising heat exchanges amongst them to mutual advantage.

As the supercritical water, F-T and ammonia synthesis processes require the greatest pressures, these are the pipes requiring great depth. Of these, the WSS one involving supercritical water partial oxidation (SCWPO) of biomass may go least deep as it only requires pressure just above the supercritical pressure for water of around 220 atm (22.1 MPa). Depending on the average density of the fluid in the column, this pressure could occur at a drillhole depth of the order of 3 km, given the relatively low densities of the fluid portions of the column. Somewhat greater pressures are contra-indicated, as these favour the reverse equilibrium reaction, there being more moles of gas on the right hand side of the equation than on the left. However, most F-T processes, the Winwick variant of the Haber ammonia synthesis process, and many other reactions are typically favoured by very high pressure for the opposite reason. Hence, they will tend to use the deeper zones (3-5 km) of Winwick drillhole reactors. The entire length of drillhole reactors may be used for a wide variety of physico-chemical reactions. These may occur concurrently and often may be so arranged as to produce mutually beneficial exchanges of heating and cooling.

In a number of cases, a single drillhole may be able to accommodate multiple uses. Two examples of these are combining the WSS and WFTAS processes, and combining the WMS, WAS and possibly the WLE processes. Combining different processes in the one drillhole typically requires additional piping. In the former, an extra annular pipe is required and several, special assemblies. In the latter, a frictionally-supported, central coolant downpipe has one or more U-shaped pipes lowered circumferentially around it. These do not need to be strongly supported, as each U-tube can be filled with a fluid to make it of only slightly positive buoyancy when immersed in the upflowing coolant liquid or high-density 'mud' that surrounds all the pipes inside the casing. This means that any one of the U-tubes may be extracted independently, without disturbing the others. An additional benefit from this arrangement is that the changing buoyancy of a U-tube, as indicated by a stress or strain gauge, could be used to derive information regarding downhole reaction conditions, densities, products and temperatures. Should the buoyancy tend to vary too much from neutral, then the composition, velocity and/or temperature of one or other of the fluids might need to be adjusted to offset it to prevent damage to the system.

The central, downward-flowing coolant pipe does need supports. These are located periodically along it to carry its weight, as it cannot easily be made neutral in buoyancy. Each of these supports is in the form of three prongs on the female end of a pipe join that splay radially when a new, tapered male pipe end is screwed tightly into it. The prongs support the pipe frictionally by pressing against the drillhole casing. They also serve to separate the various other U-tubes when these are later lowered down the drillhole. Additional guidance and stability for these is provided by pulleys fixed to the base of the drillhole. Tension in the pulley cables offsets the slight, positive buoyancy of the U-tube. Vertical support for the U-tubes is provided by varying the density of the fluids contained within them and of that of the surrounding coolant liquid. To avoid possible implosion due to external pressure, emplaced U-tubes are never left evenly-partly empty of fluid of sufficient density or pressure to counter excessive external pressure. U-tubes are progressively inserted or removed from the drillhole by a process that combines adding or subtracting pipe lengths, with pulley action and fluid content changes. Pipe lengths comprising the U-tubes are typically screwed into one another progressively at the surface. Desired differential cooling at different drillhole depths may be achieved by opening directional, horizontal valves off the main coolant pipe by different amounts at different depths, and by changing the pumping rate or coolant temperature. Heated coolant is cooled in heat exchangers at the surface and recycled. The recovered heat from it can then be used in a variety of Winwick processes, depending on its temperature.

Winwick Cell Rupture (WCR)

For the first process, Winwick Cell Rupture, the gas-rich, aqueous algal slurry, from the froth-flotation harvesting process of the Winwick impeller/harvestor units, is pumped down a blank-ended drill-hole, typically via the annular passage between the drillhole casing and an inner pipe that carries the compressed, gaseous algal slurry upwards at such a velocity that explosive decompression ruptures the algal cell walls and inner vesicles.

Now, HFR resources are usually located a few kilometers below the surface. However, a much lesser depth (and hence lesser pressure) is adequate for the rupturing process. Nor must this drillhole be necessarily associated with a geothermal resource. It can be located anywhere, possibly having been drilled for some other, now obsolete, purpose. The increasing pressure on the slow, downward journey progressively provides an effect of dissolving most of the gas bubble contents into the algal media water and, by osmosis, into the algal cells and their inner vesicles (internal compartments containing separated contents, sometimes organised into structures).

A second effect of the increasing pressure in the drillhole is decavitation. As the increasing pressure compresses the gas bubbles ever smaller, they eventually implode as their last vestiges dissolve in the water. When this happens, tiny and highly-localised, but highly energetic shock waves and microjets occur, and very high, very localised, and very short-term temperatures result. The sudden appearance of bubbles (cavitation) may also have useful effects. The decavitation effects are often sufficient both to rupture nearby algal cell walls and can be employed to progress chemical reactions, even though the bulk temperature of the material may be much less than that normally required for the reactions to occur.

The inner, upward-flowing pipe may be profiled with constrictions placed within it such that there are created regions of relative local compression (chokes or choke points) and decompression points (widenings), as well as accompanying different fluid velocities and degrees of turbulent mixing. These may also serve to increase the number of decavitations and cavitations per unit volume. When gases are involved, compression and decompression also result in significant local, adiabatic (internally-generated due to gas compression) heating and equivalent cooling on decompression. To ensure rapid overall decompression on the upward journey, the downward outer annulus will normally have a substantially greater cross-section (and hence a much slower flow rate) than does the lesser cross-section of the inner pipe. However the difference is not made so large as to involve excessive wall-frictional losses in the narrower cross-section pipe. At the local decompression regions generated by the widening of the profile of the pipe, and due to the overall upwards decompression due to there being less weight of water above, gas tends to come out of solution explosively. When it comes out of solution rapidly within a vesicle or alga, at a rate that the alga cannot wholly offset by its normal means of gas transmission through the cellwall, the sudden increase in relative gas pressure inside tends to rupture the container (the vesicle or algal cell wall) with great efficiency and completeness, releasing its contents into the main, aqueous slurry. Thus, the algal lipids and other vesicle and cell contents are freed to take part in further transformational processes. Happily, as the rupturing force comes from expanding the entire contents of each alga or vesicle with gas, minimal damage is caused to their more fragile contents, such as the intricately-folded proteins. As heating is not required for rupture, and is indeed contra-indicated for high gas solubility, high, bulk temperatures are preferably to be avoided during the rupture process. Should these be likely in a drillhole combining several processes, then a separate, relatively shallow, drillhole may be used instead.

The incoming algal slurry may range in temperature from about 10-40° C., depending on the season, weather conditions, residence time in the conveying pipeline, and the time of day it is harvested. It will include some gelator content from the bioreactors, but may still tend to separate into different phases inside the transporting pipe. The gas will tend to be comprised of a roughly 90:10 oxygen:carbon dioxide mixture, though the ratio would tend slowly to decrease over time, due to respiration in the dark inside of the pipe by the algae.

As carbon dioxide dissolves 38.6 times more in water than does oxygen at ambient temperature (20° C.) and given partial pressure, should the volume of gas (produced in an alga of a given strain caused by the sudden release of pressure by fast upwards passage in a drillhole reactor from, say, thirty to one atmospheres of pressure) be insufficient to rupture the alga, then $CO_2$ might be added earlier to the slurry to provide the extra gas needed for effective lysis (rupture). However, this should be avoided if possible as it would decrease the value of both, nearly pure gases. A better way to avoid this somewhat costly step would be to increase the depth of the drillhole reactor, thereby increasing the amount of gas that osmosed into each alga. Simply adding more of the 90:10 gas mix (taken from previously lysed algal slurry) or using faster decompression might also be an even more cost-effective means of ensuring complete rupture. It is doubtful whether the short-term increase in acidity of algal contents caused by the carbonic acid produced by the compression would have any significantly adverse effect. However, this should be investigated. If found adverse, then air or a recyclable gas, such as hydrogen, nitrogen or argon, might be used to replace or supplement the 90:10 mixture, or ammonia might be added to neutralise the excess acidity.

There will be an optimum gas bubble proportion and bubble size (by individual bubble mass) distribution to ensure the complete and most efficient rupture of all algae of a certain strain and size range that are processed in a given drillhole reactor. Should the bubble population and size distribution from the harvesting process, after its piping to the processing facility, be outside the range for efficient rupture, then more bubbles of the right size and gaseous composition may be added just prior to drillhole processing.

A sample of a single strain of algae may contain quite a large size range of organisms, particularly when spores and juveniles are considered. The specific parameters can be determined by experiment. However, conditions sufficiently severe should be able to be established to ensure that all prospective strains and sizes over all likely temperatures and durations in a given reactor are successfully ruptured. The technique is also adaptable to extracting economically the valuable components of the cells of many other organisms and organic, cellular materials besides microalgae. It may even be useful in separating the cellulose fibres in woodchips and grasses for paper-making, for paper recycling, for covering removal (including seed husks and nut shells), and for similar separation and rupture purposes.

It is likely that some or all of any gas that separates in the pipe bringing the slurry to the drillhole reactor may need to be blended or sparged back into the slurry. Indeed additional gas may be required. The type and amount of gas that moves by osmosis into the liquid, and thence into the algae and vesicles will need to be sufficient that it cannot osmose out of them in the short period in which decompression occurs, such that it prevents each alga and vesicle from exploding. It should not be necessary to chill the slurry prior to the rupturing process to ensure that sufficient gas dissolves in the algae to cause rupture on its sudden release, whilst moving rapidly up the pipe into lower pressures. Depending on the toughness and gas permeability of the algal cell wall, this upwards velocity may need to be in excess of 40 km/hr from a drillhole reactor perhaps 300-500 m deep to ensure complete rupture. The downwards velocity of the gaseous slurry will need to be much slower than this, perhaps less than 5 km/hr, to ensure that sufficient gas osmoses into each alga and vesicle. Careful pipe profiling may be able to reduce these velocity differences somewhat, thereby causing less frictional losses in the overall upwards-flowing pipe cross-section.

The four main phases of rupturant (the product of the rupturing process) comprise: the solid components (chiefly the ruptured cell walls that are comprised of glycoproteins and polysaccharides); the aqueous phase (which may contain some fine, hydrophilic solids); the immiscible (non-mixing), oily lipid phase (which may contain some fine, lipophilic solids); and the gaseous phase. These can be coarsely separated either by means of letting stand (gravitational separation) or by centrifuging, using an inline, vortex centrifuge and near ambient pressure or by a machine similar to a milk separator, but one more complex to provide for the separation of solids and gases as well.

Even passing through a vortex centrifuge may not ensure that all the bubbles burst soon enough to result in an acceptable level of phase separation. Moreover, foam could cause other difficulties. Therefore, it may be necessary to apply other measures. These could include: inserting a powerful 'vacuum cleaner' nozzle to extract gas above the separating foam/liquid/solid slurry, thereby inducing the remaining bubbles to expand and burst; designing a succession of centrifuges to spin faster or for the fluid to travel in tighter, helically spiralled pipe further along; and/or by successively removing liquid/solid slurry from the gas/bubble component, thereby making room for more intensive treatment of the remaining foam. The liquid/solid slurry might itself then be passed through one or more separate vortex centrifuges to separate its two components. Rinsing the solids partway through this process, possibly between centrifuges to encourage the rinse water better to enter the flaccid, ruptured cells, with sprays of warm to hot water would be an efficient means of extracting most of the residual lipids and aqueous proteins and metabolites from the solids. The resulting lipid and aqueous fractions would then be separated using one or more other vortex centrifuges.

The centrifuging also serves to expel most of the residual cell contents from the ruptured cell sacs. It should be noted that it is far easier to separate, relatively dense, ruptured cell walls from water than it is to separate complete algae, having almost neutral buoyancy, from water—particularly when the deflated cell sacs can themselves remain moist. The WCR and vortex centrifuging technique also has the benefit of tending to separate the liquid lipids suitable for conversion into transport biofuels from those comprising the cell walls that may include fuel-undesirable phosphorus, nitrogen, sulphur, calcium and silicon. Lipids less desirable for biofuel production due to their degree of unsaturation or lack of branching also tend to reside mainly in the proteins and phospholipids of the cell wall and the semi-solid components of the thylakoid (photochemical-processing) system.

The main, non-cell-wall, lipid portion comprises algal triglycerides and triacylglycerides or TAGs. Other lipid fractions include glycerols, free fatty acids, carotenoids, lipophilic vitamins and chemical feedstocks useful for the production of bioplastics, surfactants, urethanes, epoxies and lubricants, some of all of which it may be desirable to extract at this or later stages.

As TAGS are somewhat viscous at ambient temperature, if sufficient temperature has not been reached by the rupturant, it may first be passed through a heat exchanger, using waste HFR or other heat energy, to bring its temperature up to a modest 60° C. This is sufficient to reduce the viscosity of the lipids significantly, if temporarily, making physical separation easier, less costly and more complete, whilst not usually being high enough to damage fragile co-products.

The released lipids are hydrophobic (water-repelling) and thus tend naturally to aggregate and to separate from the aqueous phase with only minimal subsequent de-watering effort being necessary. The solids, being typically denser than both water and free lipids will also tend to separate from the other fractions by gravity, the process being aided by the vortex centrifuging. The oxygen-rich gas is easily removed and used elsewhere.

As Winwick's rupturing, warming, drying, transesterification, fractionating, reaction initiation and bed-heating processes require heat, this can be obtained from the heat produced by the oxidation, WAS and F-T processes, or from heat from solar ponds, and heat that would be available from the HFR resource. Rarely should it be necessary to burn algal hydrocarbons (typically the least-valuable RFO or local methane) in algal-generated oxygen to produce high temperatures.

Winwick Lipid Esterification (WLE)

As the presence of water deleteriously affects the transesterification of lipids (it can cause undesirable saponification—soap sudsing), the lipid-rich component of the rupturant liquid is heated and any residual water is allowed to boil off as steam at atmospheric pressure when the lipid-rich mixture is heated to slightly over 100° C. The resulting steam itself is condensed and returned to the system, minus any light, organic components that might have been present in the condensate and which are subsequently extracted. After the steam has been removed from the lipids, they are pumped through a heat exchanger (maybe the same one but possibly using either narrower pipes for faster heat exchange or longer or ones with slower moving contents for longer residence time) to bring them to 107° C. and are thence transferred into a sealed reaction vessel or drillhole reactor where relatively shallow depths (~70 m) can produce 5 atm pressure.

Deeper drillhole reactors and possibly higher temperatures may be employed at little extra cost under Winwick conditions, should they be seen to improve the economics of the overall process. They do this when use is made of supercritical methanol which can be provided simply by heating the materials to around 240° C. and employing a much deeper drillhole reactor. Where process or HFR heat is not available, this heat may be produced by any other economical means. In warm to hot climates, most of this temperature elevation may be provided by using covered, black-lined, differentially-saline solar ponds. Otherwise, ordinary geothermal heat may be used, or waste heat from industry, or combustion. Because the triglycerides that make up most free algal lipids have boiling points well above these temperatures, they are typically not lost earlier on.

This supercritical process is fast, continuous, requires less water removal, and, importantly, avoids the use of expensive and contaminating catalysts. Moreover, if a helical, upward passage is used, the heavier glycerol can effectively be separated from the reaction by the centrifugal effect, thereby improving the yield of the reversible reaction.

Small bubbles of a non-reactive gas may also be added to the reactants by sparging, should their adiabatic effects (heating then cooling), decavitation and subsequent cavitation on the upward passage improve the FAME yield, energy use, speed of reaction, or reduce the quantity of less-desirable co-products. This additional element to the WLE process may have similarly beneficial effects to those of the ultrasound reactor and microwave methods of transesterification facilitation, but at much less cost.

The triglycerides in the lipid-rich liquid are thus transesterified in the reaction vessel or drillhole reactor to make them even less viscous and thus usable as transport fuels. This is done by mixing one or more of the many recognised catalysts (if required), together with six moles of methanol for every mole of triglyceride in the lipids to be transesterified and adding the mixture to the lipids. Although only three moles of methanol are required to react stoichiometrically (by fixed proportion) with one of triglyceride, the excess methanol is added so as to drive the equilibrium reaction to transform methanol and triglycerides into methyl esters (hence esterification) and glycerine. Due to the pressure applied, the methanol at these temperatures and pressures remains either liquid or in a supercritical state, so that it reacts in close contact with the lipids to produce fatty acid methyl esters (FAMES, which combined in different proportions constitute several different types of transport biofuel) and glycerine. With the possible use of decavitation or ultrasonics to hasten the reaction, and the right selection of vessels, pumping and (possibly, but probably not) catalysts, the whole process can be made a continuous one, rather than a batch one. Alternatively, and probably more cost-effectively for this purpose, the mixing, cavitation and decavitation produced when the reactants plus non-reactant gas microbubbles are pumped hot through a modestly deep, pressurised, profiled drillhole pipe as above, may be used to replace the function and high cost of contaminating catalysts and/or ultrasonic irradiation in transesterification, or else the reaction can just be left to take its time (several hours) at ambient conditions.

As some traditional, transesterification catalysts, such as sodium or potassium hydroxides and acids, including heteropolyacids, tend to cause the product FAMEs and glycerine to require extra processing before they become sufficiently pure to be valuable, other processes, such as the Saka-Dadan process that uses the lipase method, an ion-exchange resin catalyst, and treatment with subcritical water, followed by supercritical methanol have been successfully tried. Alternatively, methyl acetate ($CH_3COOCH_3$) can be used under supercritical conditions in place of methanol to produce FAMEs and valuable triacetin instead of glycerine. Alternatively again, dimethyl carbonate ($(CH_3O)_2CO$) may be used in place of methyl acetate. The economics of all three processes would be improved by the use of Winwick drillhole reactors. However, as cheap ingredients and economical processes are to be preferred, it may well be that simple transesterification with methanol and decavitation in a Winwick reactor is effective in the absence of finely-divided catalysts—due in part to the higher pressures readily available and in part to the effects of decavitation. Moreover, Winwick drillhole reactors can readily provide the conditions whereby the methanol becomes supercritical, thereby both facilitating and catalysing the transesterification reaction.

Should the presence of a solid catalyst and/or harsher conditions improve the yield and reaction speed, then the catalyst might be coated onto the long, inner pipe and/or the casing of a deeper drillhole reactor. Such solid catalysts might include recognised ones derived from titanium, such as $TiVO_4$, $HTiNbO_3$ or from some mixed metal oxides (MMO), possibly doped with metals such as iron (Fe) or gallium (Ga), or catalysts formed from the oxides of transition metals such as europium, $Eu_2O_3/Al_2O_3$. However, the plain, supercritical methanol reaction, in a drillhole, in the absence of any catalyst, may by itself be sufficient for a sufficiently fast reaction under Winwick conditions.

Excess reactant methanol drives the reaction forwards. In order to drive the reaction even further forwards, thereby increasing the yield, the lower part of the downward passage and the entirety of the upward passage of the drillhole reactor can be formed into helices. By this simple means, the heavier glycerine (density 1.261 g/cm3) may be partly separated from the lighter TAGs (av. 1.006 g/cm3), FAMEs (av. 0.886 g/cm3) and methanol (0.792 g/cm3). This is a form of density-based fractionation. Despite the undesirable tendency to separate the two reactants, the centrifugal separation could well cause the equilibrium reaction to move to the right—particularly as the undesirable tendency might be offset by baffles in the helices that continue to mix the inner, lighter three fractions, whilst leaving the heaviest one, that of the glycerine, relatively undisturbed. On exiting the drillhole reactor, each rough fraction may be captured and led off separately, probably to stronger vortex centrifuges or cyclones, for more effective separation.

As the oxygenated oils produced by the transesterification of algal lipids cannot sometimes be used as a direct replacement for fossil fuels; as the deoxygenation of oils via ketonic decarboxylation and hydrogenation reactions does provide such a replacement; and as the conditions for such reactions resemble WLE conditions, it may be possible to combine the three processes, successively, in a single drillhole reactor pass. Suggested catalysts are Pd/C for decarboxylation and $Pt/Al_2O_3$ for hydrogenation—though the material of the $TiO_2/Ti$ pipe might by itself suffice for one or more of the catalysts. The microbubbles of hydrogen (the element being generated by the WSS process and subsequent water shift reaction) would be produced and carried down the drillhole in a fashion similar to some other Winwick drillhole processes. The result would be a mix of 'green diesel' and other drop-in transport fuels.

Winwick Oil Fractionation (WOF)

When the transesterification reaction has occurred, the heavier glycerine may be drawn off from the bottom of the containing vessel, or vortex centrifuged off like the other components (they may all usually be separated in the one pass). The lighter lipid fractions may then be fractionally distilled (fractionation) using process, solar pond, solar concentrator, or HFR heat and then mixed in certain proportions to produce the various fuel products: methanol (the excess), petrol, jet turbine fuel, biodiesel and residual fuel oil (RFO). Now, HFR temperatures of 250° C. are not unknown. However, as only the C8:0 and C10:0 FAMES have lower boiling points than this at atmospheric pressure, the C12, 14 and 16 FAMES will require either partial-vacuum distillation, or else the application of higher temperatures from a different, hotter heat source.

The partial vacuum distillation route is probably the most economical one here, as it can use cheap, Winwick solar electricity to power it and cheap, HFR or solar heat to heat it. The bulk of the methanol and FAMES can be separated using atmospheric pressure distillation at less than maximum HFR temperatures. As most of the remaining FAMES can be separated using vacuum distillation at these temperatures, no extra high temperature heat source should be required. The smallest, least valuable, fraction is the RFO that is left behind undistilled, together with possibly some catalysts and other impurities. Unless catalyst recovery is economical, this RFO/catalyst mixture may be: used as the carrier in other Winwick processes; hydrocracked (thermochemically broken into smaller, more valuable hydrocarbons); sold as fuel oil; or become raw material to other conversion processes. It and any other biomass might perhaps also be treated with supercritical water, in the absence of oxygen in a Winwick variant reaction of hydrocracking, hydrothermal carbonisation, torrefaction, pyrolysis or gasification in a drillhole reactor to form saleable biochar, tar, volatiles (including methane) and syngas.

Biochar may be recovered either by subcritical water treatment (roughly the equivalent equivalent of low-temperature torrefaction) or by the precipitation of finely-divided carbon from supercritical water, on cooling. Note, that the subcritical route tends not to produce finely-divided biochar. The proportion of less-valuable tar may be minimised by the addition of reactant $CO_2$, which is thus an additional way of sequestering $CO_2$. The syngas may be converted, via WFTAS, into more valuable, liquid fuels, oils, or waxes. Tar may be used to make bitumen to form the sealed roads of the campus, biofarm, regional roads and airstrips; or it may be transformed by hydrocracking into other, more valuable products, or sold.

The catalysts from the transesterification process, if loose catalysts were required (unlikely), may be recovered from the RFO residue after fractionation. The separation may be facilitated by the earlier use of decavitational energy to produce free radicals and thence lighter hydrocarbons, by hydrocracking, gasification or pyrolysis. The catalysts may or may not be reusable as catalysts or otherwise be recyclable, depending on their nature and whether or not they have been neutralised, poisoned or otherwise affected. The methanol is recycled, transformed or sold.

Should high temperature distillation be desirable, the availability of gas/oil well methane and oxygen, or the development of solar concentrators for this and other purposes at some facilities, makes these obvious and reasonably economical sources of such heat energy.

Any heat recovered from these processes might be: fully utilised in the lower temperature processes of Winwick technology; used to generate power; or used in nearby agribusiness, factories, heat stores, industrial campuses and towns. Waste heat from the higher temperature processes is re-used in the lower temperature ones in cascade. The heat waste from the lowest temperature process may be employed to warm the bioreactors during cold or dark periods or for growing thermophilic strains of algae. Otherwise, it might be used in a Stirling engine to generate electric power, or sent to a solar or cooling pond.

The above methods of distillation may not be required if the syngas is produced by the combined WSSN/WFTAS process. This is so, because both processes are exothermic and it may well be that the alkanes are recovered at temperatures in excess of 400° C. Should this be the case, then the various fractions can be separated by fractional condensation, followed by heat recovery and re-use from each fraction.

Due to the availability of economical heat sources at the facility, the crude glycerine will usually be: distilled to pharmaceutical grade; fed to the algae; used as raw material to produce more fuel; or used elsewhere in the biorefinery or in associated agribusinesses. Should a separate pipeline for glycerine not be justifiable, then glycerine and other low-volume co-products may be able to be piped together in separately-identifiable, neutral-buoyancy, special containers carried by the pipe flow of one of the larger-volume liquid products. A separate, return pipeline would, however, be required, to take the return containers and other materials to the facility. This might usefully be one containing decarbonised or treated sewage (possibly employing drillhole technology to treat it before transportation) or industrial waste nutrients and water for the algal bioreactors. Sewage from the local campus and regional towns, farms and facilities might also be so used, thereby saving separate treatment costs and facilities.

At cool times, the waste heat resulting from the cascading of heat reuse and production in these processing steps, and/or other HFR heat, is used to improve algal insolation (exposure to sunlight) by convection and to warm the algae sufficiently to keep them at high activation and productivity. Cool times may also be a signal to introduce cool-climate algal inoculant into the bioreactors, and vice versa in warm or hot times.

Winwick Supercritical Extraction (WSX)

Sub- and supercritical extraction can be a scalable and cost-effective method of generating and separating different organic chemicals from biomass using WDRs. As the methods are both tunable to the desired extractants and to their subsequent separation by successive condensation, precipitation or other means, they can be put to good use when applied to such rich and varied sources of valuable organic chemicals as algae and other organic materials, such as foliage, food waste and macroalgae.

WSX may become the most cost and energy-efficient industrial method of separating organic molecules from any phase, or indeed of extracting these from any form of biomass. It applies sub or supercritical conditions to dissolve organic material. These conditions are progressively relaxed as the material ascends the drillhole reactor, thereby precipitating successive solid fractions. These are extracted by passing the material through a progressive, in-line WSX centrifuge system. Precipitating solid fractions, being generally of different density to the remaining fluid, are diverted into separate pipes along the helical way. Any fraction that happens to include more than one (rarely more than a low number) molecular species would usually be relatively easy to separate later by other, known means. Thus, might all the different molecular types be separated individually, and thereby increased in value, by what is effectively a single process—one made particularly economical and scalable due to its occurring in a Winwick drillhole reactor where sub and supercritical conditions can be achieved without the expenditure of substantial energy. The only avoidable downside of such sub/supercritical processing is that, except when using low-temperature supercritical fluids, the high temperatures sometimes involved could damage or denature some of the more fragile molecules, such as some proteins and vitamins.

Where the diseconomic effect of this would be large, then fluids of lower supercritical temperature than water (374° C.) should be considered. These include the fluids with supercritical temperatures of: ethanol 241° C., methanol 240° C., acetone 235° C., n-pentane 196° C., isopentene 187° C., neopentane 160° C., n-butane 152° C., isobutane 134° C., ammonia 132° C., DME 127° C., propane 97° C., ethane 32° C., carbon dioxide 31° C., and xenon 17° C. Combinations of these fluids, possibly with a gelator to keep them from coalescing, may be used to provide both the low-temperature solvent and a liquid to provide the gravitational pressure in the drillhole.

Such a method may be used as an alternative to separation of the lipid and solid fractions by other, more traditional, means. It can be used to separate different types of molecule from lipid, aqueous and slurried solid fractions. Typically, SFC, and hence WSX, may produce separated products of high purity.

Winwick drillhole reactor plant for both high and low temperature WSX is almost identical. Water, acetone, methanol and ethanol may be among the best supercritical fluids to use for relatively high temperature WSX separation. For low temperature separation, n-butane, DME, propane, ethane or $CO_2$ could be used. Butane may be the best general purpose, moderate supercritical temperature fluid to use for WSX, as it is cheap, relatively unreactive, has a critical temperature of 152° C., a critical pressure of 37 atm, and a moderate boiling point of −1° C. @1 atm, and 33° C. @3 atm pressure, though DME, isobutane, ammonia or $CO_2$ may be better in some instances. However, as DME, ammonia and $CO_2$ are available on-site at Winwick installations, one or more of these may well be preferable.

The material to be separated would be pumped down the central shaft of a drillhole reactor with the carrier/co-solvent/supercritical fluid. After the desired sub- or supercritical pressure has been reached by pumping compression and depth, and the biomass material dissolved, the fluid is directed to the outer, annular, upward passage. This is formed into a fairly tight helix by a titanium screw thread or stationary auger. The rapid passage of the fluid through the helix forms something akin to a continuous and progressive centrifuge that concentrates any (typically) heavier, precipitating material towards the outside. The next outer pipe wall is formed of interlocking lengths of thick-walled, titanium pipe. Smooth, narrow grooves, deepening upwards, run up the inside of each length. Each groove gathers and transports any heavier-than-carrier precipitate in a slurry. The pipe lengths are short enough to allow the grooves to angle outwards enough to maintain a reasonable slurry flow and to deter clogging. The whole pipe may itself be vibrated to improve the flow and break up any incipient blockages or bridging. At the end of each length, the grooves lead, by way of a collecting ring or collar, to one of many, narrow, titanium offtake pipes located in parallel around the outside of the grooved pipe. The grooves in several successive lengths may lead to the same one of these offtake pipes. Residual turbulence in the grooves and vibration of the assembly aids in keeping the grooves unblocked and their contents moving. Furthermore, as the process of nucleation from the supercritical state promotes the formation of very small, regularly sized particles over that of jagged or interlocking crystal growth, there is no great chance of the grooves blocking up.

The carrier fluid(s) is given an appropriate temperature and pressure at the surface to liquefy it, so that it provides substantially increasing pressure with depth. At the surface, or up to some considerable distance below, the (possibly pre-temperature-conditioned) material for separation into its various molecular types is mixed with the carrier fluid by injection.

It is a combination of changing pressure, density and temperature of the ascending sub/supercritical fluid that causes serial separations to occur. The components of the mix dissolve on the downward passage and the individual fractions precipitate out on the upward passage from the carrier fluids. Due to the decreasing amount of material in the helical passage as it ascends (due to bleed off), the helical passage would usually be made so that it narrows and possibly tightens as it ascends, thereby maintaining a strong, centrifugal effect.

Each of the collected offtake pipes carries a given precipitate fraction to the surface. There may be up to thirty or more of such offtake pipes. Hence, some thirty different fractions may be separated. This number may be increased to as many as is desired, provided that offtake pipes for them can be fitted into the annular space immediately inside the drillhole casing. Surface or subsurface pumping, possibly occurring as deep as where the offtakes are collected, and occasional backflushing or chemical flushing for some of the offtake pipes may be needed to improve the flow if the relevant fraction has clogging or depositional tendencies.

Where carriers to perform the sub/supercritical separation with low boiling points are used on their own (without higher boiling point ones and gelators), such as $CO_2$ or propane, the drillhole may need to be heavily insulated from the relatively warm, surrounding rock. When carriers such as these are to be used, in order to reduce energy usage, it may well be advisable to remove most of the water from the material for separation via nanofiltration, prior to the chilling operation. Indeed, it may even be worthwhile giving the material this pre-treatment for most or all carriers.

This SFC or WSX form of separation may be performed on each of three of the four separated WCR products: those of the lipid, aqueous and solid fractions (the gases are recycled). Amongst other benefits, the method could be used as an economical way to separate TAGs, alkanes and fatty acids from lipids that are less suitable for use as transport biofuels. It might also separate individual proteins economically and at low temperature, thereby possibly greatly improving their market value.

Substantial portions of algal nutrients are held in the solid fraction of the algal rupturant. These include some of the carbohydrate energy stores, the chloroplasts, internal structural elements and algal cell walls. The amino acid (glycoprotein)- and carbohydrate (polysaccharide)-rich algal cell walls and other solids may be treated to release valuable components such as polyunsaturated fatty acids (PUFAs), including Omega 3 ones. After extraction and separation of these and other valuable components, the remaining materials may be sent for anaerobic digestion or WSS, both of which release the material's nutrients to be recycled to the algae. It may also be possible for some of these materials to be fed directly to the algae as organic feed supplement, possibly after some further treatment to make them assimilable.

To enable inspection, maintenance, repair and replacement, the whole assembly of central pipe, grooved pipe and offtake pipes is immersed in a 'drilling mud' or fluid of appropriate density to offset the weight of the assembly and contents. As the assembly is floated and secured loosely inside the drillhole casing, it may thus be removed at will.

The WSX process begins after the mainly TAG lipids have been extracted from the WCR rupturant. However, more non-cellwall material should first be recovered from the ruptured cells by washing and settling. These processes remove most of the remaining free materials (lipid, solid and aqueous) from inside the ruptured cells. Vortex centrifuging can then be used to separate these materials, which may then be combined with their equivalent fractions, prior to further treatment. Similar treatment may be given to ruptured, cellular material from non-algal sources, such as foliage, bark, sewage and industrial waste.

The mixed lipids may then be separated into individual, molecular fractions either by supercritical fluid chromatography (SFC), WOF or other methods. Of these, SFC using a Winwick drillhole reactor is possibly the best option for the separation of the molecular components from each of the three fractions—lipid, aqueous and moist solid. The Winwick variant of SFC is WSX. It is different from SFC in that it does not require the movement of a solvent fluid through a close-packed column of solid substrate that differentially retards the movement of each molecular type. Instead, WSX uses the tunable dissolving power of sub- and supercritical fluids and a special type of sequential centrifugation to precipitate and separate the various molecular types.

The lipid phase will generally contain more lipid types than the TAGs that are readily transformed by WLE into transport fuels. Some of the other types, including lipid-soluble pigments, vitamins and omega oils, are particularly valuable. Now, the most cost-effective, industrial method of separating these may be by WSX using a solvent such as sub- or supercritical n-butane or DME. These fluids are relatively easy to use in WDRs and DME extracts both neutral and polar lipids. As both butane and DME are gases at standard temperature and pressure (STP), they are readily separated from the lipid fractions that they capture. When WSX is used on the recombined, lipid fraction, pure or minimally-mixed lipids are separated, as well as are some lipid-soluble but non-lipid components. It is likely that WSX will be a more cost-effective process than is WOF or other methods, but that awaits industrial-scale confirmation.

The recombined, aqueous phase from the WCR process contains a large portion of the nutrients, including proteins, hormones and vitamins. This phase may be treated to extract its more valuable components by WSX, by electrophoresis, adsorption or other standard methods. Once the molecular components have been separated, the more valuable ones can be marketed individually for their increased value on purification. If some of the residual, less-valuable ones are already in a form able to be ingested by an algal strain in use, then they may be sent directly back, together with the recycled water and minerals, either to some or all of the photobioreactors as a mixotrophic feed supplement; or as night-time heterotrophic fodder; or to fermenters where heterotrophic algae and/or bacteria use them to grow and reproduce. Each of these uses will tend to be more remunerative than sending the residual material for anaerobic digestion, as this wastes considerable chemical energy.

The aqueous mixture contains a high proportion of water-soluble molecules and finely-divided solids. The solids are separated from the main aqueous fraction by vortex centrifuging. They may then be combined with the main solids fraction or be separated by traditional means and marketed, whichever is most profitable. The remaining aqueous fraction is then concentrated by extracting most of its water, together with most of its mineral salts (which are much smaller in size than are virtually all of the organic components) by nanofiltration or large-pore, reverse osmosis. This mineral-rich water is returned to the algal bioreactors.

Some of the more valuable components in the aqueous phase (such as proteins, vitamins, and bioactive substances) can be damaged by high temperature, so most supercritical fluids are inadvisable to use here. There are some suitable fluids with boiling and critical points with acceptably low values. Of these, $CO_2$ is regarded as possibly the best. However, $CO_2$ is somewhat more costly to use in the WDR method than are many other supercritical fluids (as it requires the density of liquefied gases, liquids or supercritical fluids for it to work), so processing with $CO_2$ use should be restricted to where there are no better alternatives. One such alternative may be to mix two carriers as described above. DME, isobutane, propane, ethane, $CO_2$ and methane are all acceptable, alternative supercritical fluids with low critical temperatures, but unfortunately they also have low boiling points that are more difficult and/or costly to handle under WDR conditions—unless mixed as above. It is noted that liquid $CO_2$ is already in use to improve the extraction of oil from reservoirs, for geosequestration and for industrial SFC.

For processing the aqueous phase, an 85:15 combination of $CO_2$ and methanol co-solvent, added to the water-reduced, aqueous mixture may be close to an optimal sub- and supercritical fluid. The methanol component is useful as a co-solvent, able to dissolve some molecular types with which $CO_2$ on its own has difficulty. In this case, methanol is not brought to even near its supercritical point, whilst the $CO_2$ is.

After the addition of these solvents, the aqueous WCR mix is treated to WSX conditions of a temperature from 50-80° C. and a maximum pressure selected from within the range of 120-460 atm, but typically one in the vicinity of 250 atm for most types of input material and desired output chemicals. When sequentially condensed out by the WSX process, typical products may include: proteins, amino acids, flavonoids, vitamins, pigments, carotenoids, hormones, enzymes and polyphenols. Towards the end of the process, the $CO_2$ is allowed to warm or decompress just enough to boil off and is then chilled and recycled, whereas the method of extraction from each water/methanol fraction is determined by the nature of the valuable component and its future market use. Most fractions will tend to be either vacuum dried or extracted onto tailored adsorbants.

The recombined solids fraction of cellwalls and other solids may be treated similarly to the aqueous and lipid phase materials, that is to say by WSX. This will tend both to free and to separate the individual types of the molecular components of the cellwall material and other solids into their component phospholipids, glycoproteins, polysaccharides (sulphonated and otherwise), sporopollenin components, and minerals. By choosing the right treatment conditions, some of the polymeric materials may also be partially broken down into their respective monomers, typically sugars. As with the other phase materials, these components will tend to have more value when separated. Those that do not, may anyway have, through the treatment, become more digestible to algae or fermentable to alcohol than in their massive or polymerised forms, or at least have become more amenable to conversion into valuable products by other means.

Typically, the solids fraction is in the form of a sludge, comprising 93-98% water. This is heated with waste process or HFR heat to around 100° C. then pumped down the WSX drillhole reactor possibly with a gelator. At a depth where the pressure is sufficient to prevent volatilisation, DME and methanol are introduced to produce a mixture ranging from 3-7% and 5-13% concentration, respectively. Still further down, superheated steam is introduced to increase the temperature of the mix to around 135° C. (just above the critical temperature of DME). The combined action of the subcritical solvents tends to penetrate, open and dismember the solid matrices. Still further down the drillhole, a 90:10 mixture of $O_2$:$CO_2$ gas bubbles, sourced from the bioreactors, is finely bubbled into the gooey mixture. As conditions intensify further down the drillhole, progressively more of the molecules in the biomass are freed from their solid matrix, are depolymerised, or otherwise react with other chemicals present, and the products of this dissolve in the DME or water/methanol fractions, depending on their degree of hydrophobia. The hydrophobic substances tend to dissolve in the DME, the hydrophilic molecules in the water/methanol mix. Released minerals tend to dissolve in the aqueous fraction.

Yet further down the drillhole, heat exchange, adiabatic heating, decavitation, oxidation, hydrolysis and/or more introduced steam serve to release, break and dissolve further molecules from the solid feed. By the time that supercritical conditions for both DME (127° C. and 53 atm) and methanol (240° C. and 80 atm) have been attained, most, if not all, of the solids have been dissolved and most of the rest has at least been freed from its denser matrix.

At around this point, the material exits the central, downward WSX passage and enters the annular upward one. This is formed into a tight helix, so that a centrifugal separation forms in the passage by relative density. As pressure, density and temperature decrease up the passage, solids precipitate. Typically being heavier than their carrier fluids, these tend to migrate outwards. Still further upward, the condensing liquids and remaining gas similarly separate by density, the gas moving to the more central position.

According to the design of the WSX WDR, each discrete, centrifugal fraction is removed by its own, separate pipe and is conveyed to the surface. Along the way, the DME, methanol, and some of the water boil off from their various fractions and are recycled. Some of the product heat goes to warm the incoming material.

The various, aqueous fractions, each typically containing a single, pure, organic component or a limited mixture of organics, together with some minerals, have their more valuable components separated by known means for individual sale of the purified product. The balance, together with any remaining solid material, is recycled, either by way of the bioreactors, the fermenters, or the WSS process. However, released sugars and starches may instead be fermented on-site by yeast, or by algae or bacteria with yeast transgenes for their production, to produce ethanol or butanol.

Depending on the severity of the WSX conditions (they may even be made to approach the critical point of water, 374° C. and 221 atm), the largely separated products could include: carotenoids, chlorophyll and other pigments, phospholipids, glycoproteins, various sugars, erythrose and other carbohydrates, other organics, minerals, and unconverted biomass.

A WSX drillhole reactor may also be designed to include both sub- and supercritical water (including variants and mixes with other co-solvents) processes. In such cases, the lower part of the downward passage would include a helix and offtake system, but the offtake may instead or as well be taken from the inner part of the spinning fluid where the dissolving lipids would tend to concentrate in the minor, typically lighter, hydrophobic carrier. In the literature this is now termed subcritical water extraction (SCWE) or hydrothermal liquefaction. Further down the WDR, stronger sub- and then supercritical dissolution and hydrolysis would depolymerise and pull apart the more intransigent organic materials, such as some polysaccharides, glycoproteins, glycolipids and phospholipids, hemicellulose, cellulose and lignin, as well as freeing some of the nitrogenous and inorganic nutrients. Using methanol as the co-solvent has the additional effect of transesterifying some of the lipids, such as TAGs, into biofuels and glycerol. Although sodium carbonate has been used as a catalyst in the liquefaction of algal biomass, it is not expected that added catalysts will be required for WSX, as heat, pressure, decavitation and centrifugal separation are all available cheaply.

An alternative to treating the solid, algal fraction with WSX, and one that may be particularly attractive if more economical sources of nutrients can be made available to the algae (e.g. from WSX or WSS treated crop and forestry wastes, woody weeds, sewage, agribusiness, or by on-site ammonia production, or from industrial waste or rock leaching), the algal cell wall solids can readily be turned into high-protein, human food or stockfeed, including stockfeed for molluscs, worms, crustaceans such as brine shrimp, zooplankton (rotifers, copepods, etc.), tadpoles, fish larvae, fish, farmed birds and land animals. Some of these may even be farmed locally.

However, there are yet more alternatives. Of the various processes to process the residual WCR fractions, anaerobic digestion is not favoured as it degrades the chemical energy value of the biomass significantly and takes a relatively long time. Use as a combustion fuel or supplement to generate power in most cases is entirely too wasteful of a valuable, organic chemical resource. Use of the cellwall material for human, fish or animal nutrition or medication may well have the highest economic value; followed closely by those of: algal feed supplementation; use as heterotrophic feed in algal fermenters; or for supercritical water partial oxidation (SCWPO) to produce syngas, its downstream biofuels and chemicals, and recyclable, algal nutrients.

In a Winwick facility, the oxygen for the partial oxidation can be provided economically by algal photosynthesis, whereas economical pressure and process heat are available from the drillholes, solar ponds and HFR resource. Cooling can be provided from the other heat-absorbing Winwick processes. With appropriate catalysts, these sub- and supercritical water gasification (SCWG) and SCWPO processes, which are collectively termed hydrothermal oxidation (HTO) reactions, produce small-molecule hydrocarbons (and with SCWG some tar and char) using sub-critical or SCWG, or can produce syngas (comprising mainly $CO+H_2$) and free nutrients using SCWPO of the biomass. The latter reaction is the one termed here, the Winwick Syngas Synthesis (WSS).

Winwick Syngas Synthesis (WSS)

This WSS, or the biomass SCWG and SCWPO reactions are different from most other Winwick drillhole chemical reactions in that they do not use a heavy oil or wax to carry the bubbles of mixed, gaseous reactants down with it to regions of high pressure and temperature. Instead, the carrier is the water in which the slurry of empty algal cell walls, whole algae, and/or other organic material is carried, and of which a threshhold concentration of biomass is necessary to maintain the reaction. The slurry is introduced to the drillhole where it is combined with the ever-recycling, heavy titania or other densifier, possibly aluminium hydroxide and other additives and promoters previously noted. These additives are recovered from the by-product water for re-use, the titania by filtration, and the hydroxide by partial concentration, crystallisation, gravity separation (settling) and/or treatment with alcohol.

The biomass slurry may have water content ranging from 70-98% (excluding gases and being typically at the upper end of the range), depending on the degree of concentration it has undergone and what additions have been made to it. To it is added a large volume of small, blended or sparged bubbles of a gaseous mixture of 90:10 oxygen and carbon dioxide (excess $CO_2$ rarely matters adversely and may indeed participate usefully in the reaction) deriving mainly from the algal bioreactors to the desired stoichiometric proportions for the intended product. The oxygen content of the slurry at STP (standard temperature and pressure) required to partially oxidise the biomass in, say, a 5% biomass solids slurry to syngas is such that the slurry as it enters the drillhole may more resemble a dense foam than a typical liquid. However, after this foam is pumped down the drillhole a few hundred meters-meters and the bubbles compress, it acquires the properties more resemblant of a normal liquid. If it makes pumping easier early on, the additional gas may be added partway down the reactor.

Surface level, possibly separate, heating of biomass and gas by means of heat exchangers is made sufficient to start and then maintain the SCWG or SCWPO reactions, after allowance has been made for later supplementary heating: by the subterranean, superheated steam lance or collar; by heat exchange; by oxidation; by reformative reaction; by adiabatic, by decavitational, and/or by frictional heating—less any cooling effects and heat losses.

Catalysts are not usually necessary at the biomass concentrations used in WSS to ensure hydrolysis or partial oxidation, but water may be added to the slurry for pumpability or to ensure more complete, desired reactions. However, as Li reports in U.S. Pat. No. 5,565,616, additives such as NaOH, $Na_2B_4O_7$ and $Na_2CO_3$ (which may well act analogously to catalysts) may well be useful in varying the output product ratios in SCWPO to produce a better value mix. Li's tables provide the useful indication that, in the supercritical range, most salts and oxides tend to have lower solubility, the higher is the temperature and the lower the pressure. For the complete gasification of biomass, Sascha reports that in SCW conditions, ruthenium on a $TiO_2$ carrier ($Ru/TiO_2$) is able to gasify aqueous biomass concentrations from 1-17% by weight; whilst Xiaohong Hao et al report that a 5.0 wt. % ruthenium on activated carbon (Ru/C) catalyst produces hydrogen best under SCWG conditions. However, carbon substrate catalysts would be contra-indicated for a SCWPO process. Finely divided, heterogeneous catalysts such as $Ru/TiO_2$ may readily be carried in the WSS fluid slurry and/or be attached to the reactor walls. Sascha also reports that, once supercritical conditions have been achieved, additional pressure has no effect on the conversion to gas, or on product yields; however temperature, reaction time and concentration of feedstock do.

The reactants are pumped down a central pipe in the drillhole reactor, to return to the surface via one or more separate routes, typically one or more outer concentric pipes. Superheated steam may be injected into the reaction mixture a suitable way down the drillhole to ensure that the correct reaction temperature is reached even further down the drillhole, after allowing for the temperature increment caused by further heat exchanges and the compressing gases adiabatically heating up the slurry even more until they reach fast reaction temperature further down the drillhole. If necessary, cooling may be accomplished by injecting coolants (typically chilled water) on the upward journey or (better) via heat exchange processes with incoming reactants. Factors that ensure the desired reactions are: biomass and oxidant concentration, temperature, pumping velocity, catalysts, and the increasing pressure in the liquid on the downward journey. These ensure that the supercritical conditions and the duration of them are sufficient partially to oxidise the algal cell walls into principally $CO+H_2$ (that together comprise syngas) and possibly some, somewhat less-desirable $CO_2$ and $CH_4$. For SCWG, similar conditions ensure hydrolytic gasification of the biomass. In SCWPO, methane formation is favoured at sub-critical temperatures, whereas syngas is favoured at high temperatures and high dilution. Steam will also participate in the reaction, to a controllable degree, by means of the water-gas shift reaction to produce hydrogen:

$$CO+H_2O \rightarrow CO_2+H_2$$

Undesirable destruction of nutrient nitrates and ammonia formed from the oxidation of nitrogenous algal protein is minimised by the choice and concentration of oxidising and reducing agents and by the time and conditions provided for the various reactions to occur. After subsequent separation, the now freed nutrients and water are returned to the bioreactors, together with make-up nitrogenous nutrients processed from the cyanobacteria bioreactors, digestor or the WAS plant.

Supercritical conditions are also used in Winwick drillhole reactors to oxidise, or (with limited oxidant) to partially oxidise, all other hydrocarbons, carbohydrates, proteins and other organics held in the aqueous solution or slurry. These include the common organic compounds such as cellulose, lignocellulose, coal (especially brown coal or lignite), shale oil, tar sand, plastics, rubber, fibres, synthetic organics, sewage and/or hazardous organic waste. Due to the extraordinary dissolving power of supercritical water and the supercharged oxidative powers of oxidants under supercritical conditions, even material that is not finely divided, such as chunks of plastic waste (say from discarded consumer goods), or material that is otherwise intractable or hazardous, such as carcinogenic dioxins, infective agents and poisonous organics can all be turned into syngas or useful, easily recoverable, polymer monomers and light organics.

Beside algae, other productive sources of biomass for use in drillhole reactors include aquatic plants; sugarcane bagasse, sawdust, pine tree thinnings or offcuts, coppiced willows, poplars and eucalypts from high-rainfall areas; crop and forest wastes, eucalypts, miscanthus and switchgrass from modestly to well-watered areas; and native grasses, woody weeds, succulents, saltbush, scrub and mallee, eucalypt or acacia trees from marginal land. Of these, all but most algae have as principal components, hemicellulose, cellulose and lignin.

As cellulosic materials tend to pyrolyse in the range of 150°-325° C., tar and char may form temporarily. However, these will tend to oxidise to CO and $H_2$ further down the drillhole reactor under SCWPO, particularly if sufficient $CO_2$ is added to the initial gas mix. Thus, they and their like present little or no problem, provided the pipes are reasonably wide and where possibly (try to avoid this on economic grounds) a little excess oxidant may be used just prior to the active termination of supercritical conditions. It should be noted that using SCWG (without any additional oxidant) tends to produce more of the difficult to handle tar and char, as well as the more desirable light organics. However, it has recently been found (Castaldi et al, 2009) that the addition of carbon dioxide and steam will readily convert char, and presumably tar, into syngas under pyrolytic and hydrothermal conditions. Thus, the formation of undesirable tars and char, and/or their reconversion to more desirable products, may be controlled by the addition of the appropriate gas in both SCWPO and SCWG Winwick processes. The technique is applicable to the conversion of most forms of biomass, including coal and lignite, as well as to synthetic organic products, such as waste plastics.

The WSS process can also be used to process waste material from the bioreactor farm itself. Thus, polymeric material that can no longer be recycled into new capital equipment can be transformed into biofuel, chemicals or new polymers instead. Such might be the case for the PE and PET plastics forming the groundsheets and reflectors that have an aluminium component and thus are of doubtful utility in most new plant recycled from it.

Unlike most other types of SCWPO and SCWG reactor, the organic material fed into Winwick reactors fortunately does not need to be comminuted to fines. It can be as large and uneven as will flow down the wide, profiled drillhole without bridging. And a drillhole can be made almost any reasonable diameter wide. This flexibility both saves on comminution (chopping, chipping and grinding) costs and allows almost any mix of relatively pure (low in inorganic content), organic fuel or biomass to be used to produce syngas and thence biofuels and chemicals. Thus, seasonal changes in fuel, as well as multiple types of organic waste, may be used as feedstock. Furthermore, by careful selection of the amount of oxidant, reaction time, catalyst and conditions, the reaction may be stopped virtually at any desired point. For instance, if polymerised plastic or rubber waste were the feedstock, a SCWG reaction might be stopped just after depolymerisation, devulcanisation or deconstruction had occurred and before further degradation or oxidation of the monomer intermediate product happens. Thus, valuable intermediate chemicals might be retrieved, without incurring the cost of all the stages of forming them anew from syngas. This could provide significant economic advantages and be of environmental benefit—particularly where less or unadulterated source materials are available, such as from manufacturing industry wastes. Polysaccharides (polymerised sugars) may be treated similarly. However, where depolymerisation is desired, the material may need to be finely comminuted in order to limit the further reaction of desired intermediates.

Winwick technology can readily be used for the direct, partial oxidation of algal cell walls, which are composed mainly of carbohydrate and protein, or other, typically cellulosic, biomass using oxygen derived from algal photosynthesis to produce syngas and free nutrients. Using the Winwick drillhole method, the syngas in turn can be converted by supercritical and Fischer-Tropsch (F-T) processes into various biofuels or chemicals.

When algal cell wall or cellulosic biomass is used to produce sugars by the WSS method, partial oxidations with conditions of ever increasing severity may be advisable via a sequence of five, separate drillhole reactors. Each of the five would be targeted to depolymerise or deconstruct a different component. After each deconstruction process, the products would be run through hydroclones or vortex centrifuges, in order substantially to separate, firstly the liquid components from the solids, then the hydrophobic ones from the hydrophilic ones. Water would then be added to the slurry of solids, prior to the next drillhole process.

The first and mildest deconstructing WSS process might be targeted to depolymerise any starches and less-complex carbohydrates that may be present in feedstocks from sources such as: industrial wastes from flour mills, sugar mills, breweries, distilleries, feedlots, or starch-containing crop residues. The second might be targeted to free and/or partially deconstruct the phospholipids and glycolipids contained in algal cell walls or plant proteins, transforming them into free fatty acids (FFA), lipids and other components, such as choline, glycerol, amines, proteins and phosphate. The third might be targeted to depolymerise any hemicellulose content into its component sugars. The fourth might be targeted to do the same to any cellulose content. And the fifth, to do the same to any lignin and otherwise-resistant polymeric or tightly-bound material.

Feedstock for the processes after the first might include material from pulp and saw mills, comminuted (in this case, chipped up) crop and forestry wastes, sludge from sewage farms or agribusiness, other relatively-uncontaminated organic industrial waste, comminuted weed species and energy crops. Each successive WSS process would tend to open the remaining integral, solid material to more direct and stronger attack later on. For some feedstock materials, the WCR process might be used to open up the material to progressively harsher WSS attacks. Wood chips may benefit from such pre-treatment.

As WSS reactor facilities would tend to be sited at the industrial sites producing or handling their feedstock, nearby firms would tend to find it profitable to transport their own and/or other's biomass feedstock to the WSS facility. Thus, would new, local enterprise flourish; would less biomass be wasted or put to inferior use; would the volume of long distance transport be reduced; and would distributed WSS facilities spread across the land, even to some specially favoured, maritime locations.

As deconstruction, depolymerisation and gasification or partial oxidation under WSS supercritical water conditions are not entirely separable processes, some syngas and $CO_2$ might be expected to be produced at each stage, requiring their own separation by hydrocloning.

Together, the deconstruction processes might be expected to retain high values from the biomass input. Typically, the lipids and fatty acids would be channelled to the WSX or WOF processes; the sugars and glycerol to either the mixotrophic feedstock, to fermentation into ethanol, to stockfeed, or to other chemical transformation processes; the amines, choline and protein to their highest value use, possibly after further separation; and the phosphate and other minerals to the algal bioreactors as replacement nutrients.

Acids produced by supercritical water partial oxidation (SCWPO) may be neutralised by bases added beforehand to the reaction mix, or better, by the ammonia that is co-produced by SCWPO from nitrogenous protein, such as algal cell walls or by the WAS process. Wasteful ammonia destruction by oxidation into nitrate and then possibly into nitrogen can be minimised by keeping temperatures below 550° C.

As supercritical water reactions are harmful even to a thick, steel drillhole casing or profiled pipe, it will usually be necessary to coat, sheath, plasma spray or otherwise deposit on the pipes a protective layer or layers, at least in the zones of strongest likely attack. With the right feedstock material, supercritical conditions themselves may be made to provide part of the required non-reactive coatings, and refurbishments thereof, in-situ. Some oxy-anion salts (for instance some phosphates, chromates and aluminosilicates) and metal oxides (for instance yttria, titania and zirconia) may be sufficiently 'sticky' as to form additional protective coatings on passivated or rust-coated steel and on other protective coatings formed during construction or operation.

Although temperatures at any one point in the reactor will tend to remain constant, and thus not be subject to thermal stress during normal operation, the periodic salt/oxide-scale removal cycles, where the temperature at a point will change somewhat, may make it advisable for the protective layer to be refurbished after each cycle or so, leading to the sealing of any thermally-induced cracks or crazing in any protective ceramic coating. Thus, a special commissioning run of the drillhole reactor, and separate runs after each salt-flushing run, might be useful in refurbishing the overall corrosion protection system of the piping. Thus, dissolved phosphates and chromates, or their acids, might be flushed through the drillhole, thereby forming protective layers on the sides after they had reacted with the steel or when supercritical conditions had made them insoluble. Similarly, powdered metal slurries might be flushed down in catalysed and oxygenated water, later to form protective oxides on the sides. These oxides would tend to fill the slightly porous structure of the foregoing phosphate treatment. Such treatment might substantially reduce pipe protection costs, whilst extending pipe life.

Previous, gravity pressure vessel (drillhole) reactors suffered from two key problems. The first was clogging by somewhat intransigent organic material, caused by the premature decomposition and deposition of newly-polymerised biomass at sub-critical temperatures. The second is pipe and equipment corrosion by acids that occurs typically underneath any porous mineral depositions at temperatures between 300 and 374° C., where there is a transitional stage at which corrosion by dissociated acids is most intense. Above 374° C. (and presumably at supercritical pressures) it is reported that no further acidic corrosion takes place, because there is no acid dissociation.

Employing Winwick technology, both problems are addressed using different combinations of the following techniques or factors. First, Winwick drillhole reactors tend to be of greater diameter than are most other gravity pressure, pipe reactors, the inner pipe typically having an internal radius in excess of 170 mm and the outer annulus typically having a radius in excess of 240 mm—giving an annular gap of some 65 mm or more. Thus, to affect pipe resistance seriously, any deposition must be thick indeed (>7 mm). And the thicker the deposition, the more it is likely to break down under Winwick's high-velocity fluid (typically 5-50 km/hr), shearing conditions and often, large biomass particle sizes (up to 50 mm diameter in the case of woody waste or bagasse, somewhat less for lignite). Also, due to the deep depth of the reactor (typically 3-5 km), the reduction in heat exchange efficiency due to insulating salt, oxide or biomass deposition on the reactor walls is of relatively minor significance for anything less than thick layers. In addition, using an admixture of coarse biomass to the reactant mix may ensure that its scouring action early on limits the build-up of tar and char on the drillhole reactor components from premature oxidisation and polymerisation of the biomass.

Second, where finely divided biomass (non-scouring) is used, such as are ruptured algal cell walls, pulp mill waste or coarsely-filtered sewage or sludge, strong, near-neutral density, small spheres of some 2-6 mm diameter of inert, or useful additive, material may be introduced as part of the slurry to scour the reactor walls gently on a continuous basis. Though a bit heavy (density ~3 g/cm$^3$) small, free bauxite (principally $Al(OH)_3$) nodules might fit the bill economically.

The third technique results from the designed-in, partial choking of the Winwick reactor pipe that minimises the duration of the highly corrosive period. This intentional choking causes a sudden increase in temperature from adiabatic heating of the prevalent gas bubbles being compressed there. As this effect can be made to initiate the decavitation of a significant portion of the microbubbles, the instantaneous local heating to very high temperatures caused by this effect, combined with the sudden increase in pressure, will in its turn tend to initiate rapid partial oxidation of the biomass, which in turn will increase the bulk temperature still further, leading to a spike in the consumption rate of available oxidant and a sudden, step jump in temperature—thereby jumping through the dangerous period. Thus, it may be so arranged that corrosion-prone and auto-degradative temperatures are of too short a duration and are of too little zonal extent to cause undue clogging or deposition, or to do significant corrosive damage, particularly if the reactor metal is made of, or sheathed additionally, with titanium/titania in that narrow zone. Moreover, by the time the reactants reach the lesser-cross-sectional upwards passage, the biomass will have been dissolved and transformed into non-clogging syngas, SCW, salts and oxides (the dilute acids having been typically partly neutralised by the hydroxides), by the calibrated oxygen oxidant content and supercritical water conditions.

The temperature variation of the fluid moving through the drillhole reactor is controlled by several factors, most of which are subject to individual control during the process, through good maintenance, or in construction. The main, fine-control factors are: the temperature to which the various input fluids are brought by surface-based heat exchangers; the additional heat provided at a little distance below the surface due to the introduction of superheated steam; the contribution of adiabatic heating and cooling along the passages; the contribution from decavitational heating and its presumed inverse; bubble size range which influences the depth of later, depth-specific heating by decavitation; bubble size distribution and concentration; frictional heating contributed by the pumps, chokes and walls; heat exchange effects between reactants and products in different pipes; heat derived from partial combustion of the biomass; catalysts and additives (if any); phase change heating and cooling; and heat exchanges (principally losses) with the surrounding rock.

The principal means of finely controlling the reaction temperature in a given drillhole reactor are: the ability to vary separately the concentration of oxidant, additive/catalyst, and biomass; to vary the degree of pre-heating given to each material; bubble populations; outlet overhead pressures; and pumping velocity. With biomass of such even composition as single-strain, algal cell walls of given concentration and oxidant of known composition (90:10 $O_2:CO_2$), reaction temperature may be controlled quite closely—provided the necessary sensors, communication lines and automated program controls are installed and operating.

To initiate the oxidation reaction (ignition) in the drillhole reactor, it may be necessary to increase the concentrations of biomass, additive/catalyst and oxidant initially quite substantially, together with their initial temperatures. However, once ignition has occurred and the system has sufficiently warmed up, these may be progressively reduced to levels just sufficient to maintain the reaction. This technique is analogous to using a rich mixture to start an internal combustion engine, then making it lean for normal operation.

A positive aspect of WSS is that it will tend to use aqueous fluids of low biomass concentration, thereby leading to greatly diluted acids being produced. In addition, the consistency and finely-divided state of the algal feedstock, the relatively low concentration of oxidant applied, and the controllability of reaction time and conditions can be used to ensure that oxidation of nitrogenous material does not unnecessarily waste nitrogenous nutrients by conversion into nitrogen. Most such reaction can be stopped at the intermediate reaction product of ammonia, which can then be used to neutralise the acids, or of nitrate production. The resulting nutrient salts can be recycled to the bioreactors as make-up nutrients. Excess alkalinity does not appear likely to cause problems. Moreover, any formation of amine chelates (metal-amine/$NH_2$ complexes in this case) might be beneficial in a number of ways, for instance to form readily-available algal micronutrients and trace elements.

Diverse biomass feeds may be processed selectively and continuously under reasonably well-controlled conditions by WSS drillhole reactors. Feeds with low concentrations of salts are particularly suitable. However, as algae are frequently grown in solutions with high concentrations of minerals, particularly sodium chloride (NaCl) or calcium carbonate ($CaCO_3$), employing WSS to convert their residual material left after lipid extraction may require careful planning—particularly if no washing in fresh or distilled water is used.

Besides possible corrosion of untreated, drillhole or pipe reactor walls and embrittlement, the chief problem of previous SCW reactors has been clogging with polymerised material and the deposition of salts and oxides onto the reactor and pipe walls. As discussed previously, polymerised material and tars are unlikely-to cause significant problems for WDRs.

Most WSS units will simply output a fast stream of steamy water, syngas and titania, together with minor amounts of dissolved salts, oxides, acids and solid oxides, $CO_2$ and $CH_4$. Typically, these will reach the surface in a slurry, from which it is easy to separate the gases, liquids and solids. Some salts and oxides will plate out on the reactor walls, from which they are removed periodically by flushing.

In the less common instances where salt cannot so easily be managed, there are at least three solutions: removal of the salt prior to WSS; removal during WSS; and removal after WSS. Note, that another solution to the general deposition problem, a transpiring wall reactor, does not appear to be suitable or economically viable for WSS drillhole reactors.

Removal of the salt prior to WSS is feasible by washing and letting settle the heavy, empty cell walls in fresh water one or more times, as multiple, high-velocity centrifuging would be unnecessarily expensive and an uneconomical process for low-value biofuel production. This may be the simplest and best overall option. It is thought that the settled, heavy cell walls at the bottom of a deep settling tank would have sufficient fuel density (7-17% hydrocarbon) as to be capable of self-perpetuating, partial combustion in the WSS process, after initiation and when combined with heating from parallel Winwick process sources. This would save on fuel and the cost of other methods of concentration. The reasonably fresh water required for washing might come from the WSS process output itself, from reservoirs, from bores, and/or from the distilled water produced as a by-product by the Winwick bioreactors. A mildly, salty wash, using perhaps brackish bore water might be followed by one or more using distilled water for optimal effect.

Removal of syngas from liquid-borne salts and heavy oxides during WSS is feasible by means of passive (non-motorised) centrifuging or cycloning using a hydrocyclone or hydroclone. This is a liquid and solids separator that, with a slightly different design, can also be used to separate gas from liquid. Combining the designs, hydrocloning can even be used to separate all three phases in the one pass. Cyclonic separation may be used under supercritical conditions roughly to separate slurried solids from gases, liquids and supercritical fluids.

If washing the empty cell walls to remove salt is not used, depending on relative economics and technical ramifications, solids separation may be achieved by one of three or more paths in a drillhole reactor. Path A uses supercritical hydrocloning to separate salts and oxides in a supercritical slurry from the bulk of the supercritical fluid. This may or may not be followed by subcritical hydrocloning to separate gas from liquid. Path B uses subcritical cycloning to separate the bulk of the gas from the solid-liquid, briny slurry mix. Path C is Path B followed or accompanied by the separation of suspended solids from the brine.

Path A removes the great majority of salts and oxides on their own, but results in the technically difficult problems associated with bringing them to the surface. Path B leaves the (less-soluble or sticky) salts and oxides that have not plated out on the reactor walls in the briny, liquid slurry. Path C successively removes the gas from the less soluble oxides and from the liquid, but then has the technical problems associated with bringing the solids to the surface. Making no separation could result in difficult foaming problems. On balance, Path B appears to be the best choice.

The cyclone separator structure that is to effect the separation of syngas from liquid-solid slurry under Path B would need to be located at an appropriate depth in the drillhole, probably somewhat after the supercritical boundary had been passed for the second time (downwards then upwards) so that the majority steam content of the fluid had by then condensed to a highly-pressurised liquid. As the environment there is still one that is harsh on machinery, separation is best achieved using cycloning (which is akin to vortex centrifuging) rather than active centrifuging. Cycloning may be implemented by the insertion into a short length of the annular pipe space of a cyclonic structure made of corrosion-resistant titanium, possibly coated with titania. This would be designed to form passages that continued the upward fluid flow but that curl them helically to separate it centrifugally into its gas and liquid-solid slurry fractions by density. The lowest part of the structure divides the flow into several channels using vertical, radial dividing walls. Slightly further up, these channels or tubes are made to twist into increasingly numerous spirals per length of drillhole, around the central downpipe. The surface pumps driving the flow cause the heavier, slurry component to concentrate furthest from the central axis and the gases to concentrate nearest the axis. Each fraction from each helical pipe is captured by pipe content splitters, or other essentially-passive mechanisms in the structure, and then be combined with its like fraction from the other pipes.

As the cycloned gas is drawn off at an annular pipe inner to that of the liquid slurry, the previously mentioned PIE structure or assembly would be useful to bring the gas to the outermost annular pipe, where its low heat conductivity can be used to reduce heat loss to the surrounding rock. Such a structure can be provided by a tubing assembly inserted in the drillhole. It may be convenient if the assembly is incorporated in a pipe of the same length as a standard pipe section. The PIE consists of two annular pipes, each of which is divided radially into, say, a multiple of three tubes of equal number, three of which adjoin three thickened spacers. At a number of places along the assembly, a set three inner tubes lead into matching tubes opening into the thickened spacers. At the same time, three outer tubes lead into tubes formed in the inner, thickened spacers. At each place of transference, tubes not transferring move slightly circumferentially to accommodate the new arrangement. At the end of the assembly, the inner and outer tubes and their contents will have changed places radially.

Additional hydroclones and/or liquid traps may be provided further up the drillhole, should condensing steam or hydrocarbons at times provide too much liquid to be transported further upwards easily by the remaining syngas. As the dedicated, upward gas passage, when contained by controlled pressurisation from above, will tend to be at very high pressure, only somewhat less than those of its deep origin, this relatively higher pressure can be used to drive condensate into the slurry passage that is now at lower pressure due to its elevation in the gravity pressure well. The separating structure might in some way be said to resemble a steam trap.

The dedicated gas passage allows gases to move, relatively unencumbered by liquid, at controlled, possibly high velocity upwards. It also provides a level of gaseous insulation between the inner, high heat content (enthalpy), liquid contents of the drillhole and the surrounding rock—thereby helping to conserve the heat energy that warms the downward-flowing biomass slurry in the kilometers-long, heat exchange apparatus.

The slurry fraction is directed to an inner, annular pipe from whence it proceeds to the surface, probably as a three-phase mixture. Its velocity, which is controlled by the inlet pumps on the surface, although generally slower than that of the gas, is made sufficiently high as to prevent any solids or liquids from sinking before the slurry reaches the surface. It does not, however, necessarily prevent wall deposition. The slurry now also contains: water; partly dissolved salts and oxides, possibly some residual acids or alkali, and some gas.

Control of the pressure in the gas-receiving vessel on the surface and in the overlying gas of the vessel on the surface receiving the three-phase slurry are separately used to ensure that the gas and liquid separation underground is made as complete as is economically feasible. On reaching the surface, the less soluble oxides and salts from the slurry, including the titania and possibly some aluminium oxide/salt powders are let settle out, leaving above them a mixture of soluble salts in the possibly briny liquid, and some residual gases above that, to be separated by various known means.

Separating the gaseous fraction far down the gravity pressure (drillhole) reactor is a means of controlling the quantity or formation of foam that may otherwise be difficult to handle. It is also a means of providing insulation to the drillhole liquids and of maintaining the syngas at a usefully-high pressure and temperature.

In SCWPO of biomass in a Winwick drillhole reactor, the volume of product gases (mainly syngas and steam) reaching the surface is typically many times the volume of the input reactant gases. Therefore, bleeding off the bulk of them to a dedicated gas pipe, and thus reducing the density in the three phase column (which may be cooled to about 45° C. by the time it reaches the surface) should not cause the pumping cost to become uneconomic. Any chance of this may be prevented simply by separating less of the gas during hydrocloning. Indeed, once the reaction has commenced and the warm fluids have circulated to the surface and their heat exchange rates have stabilised in the drillhole, it may be possible to avoid pumping cost entirely, due to the 'inverted siphonic' effect of the process, where the heavier, input fluid column pushes up on the lighter, hotter, exiting one.

Removal of salts periodically, after some have been deposited on the drillhole reactor walls, is also feasible. This is so because the drillhole and pipe inserts can both be relatively wide in diameter and both are of great length—typically of the order of kilometersmeters. Thus, there is a large area on which deposits may form and rather less constraint over heating, cooling and agitation elements than is required in ordinary pipe reactors or other reaction vessels. Once salt deposits have reached an unacceptable thickness, the WSS operation may be transferred to a twinned, drillhole reactor and the first one may be de-salted and made ready again simply by passing distilled, fresh or brackish water through it at subcritical temperatures. The resulting brine might be returned to the bioreactors or used in solar ponds, after recovery of its more valuable nutrients by known means, including the use of hypersaline algal species. Less-soluble carbonate deposits may be removed by passing dilute acids through the drillhole reactor, possibly followed by either stronger acids or else alkaline, ammoniated water, without any of the flushes (after a sufficient volume to cool the pipe and immediate surrounds has been passed) being heated sufficiently to turn them supercritical. A source of the dilute acids might be that from the flue gas treatment system proposed later or from the WNAS process. This encrusted salt removal solution can also be applied to the option where the entire WSS product is brought to the surface before any separation is attempted.

Unlike most other biomass oxidation and partial oxidation processes, the WSS is designed to accept salt deposition on the reactor walls and to use this positively as a means of separating some of the salts from the bulk of the water and syngas. When the salts and readily soluble oxides are periodically flushed from the system, they are in fairly concentrated form, from which it is easy either selectively to precipitate or adsorb valuable minerals for extraction, or else to recycle the nutrients in their aqueous form directly back to the algal bioreactors.

Depending on input conditions and subsequent controls, WSS temperatures going down the drillhole reactor might vary as follows. The algal cellwall slurry or other biomass might arrive at 15-30° C. If required, surface heat exchangers using heat either from biorefinery processes, solar ponds, hot water from the drillhole reactor or HFR heat might be used to heat both the ingoing biomass and the oxygen to around 90° C. The bubble-filled slurry would be pumped down to around 70 m at which level the additional 90:10 oxygen (possibly itself heated) would be blended or sparged into the bubble-compressed slurry that would be at a pressure of around 5 atm. Heat from the rising, exiting fluids would continue to warm the slurry until at 300 m depth the temperature might have reached perhaps 110° C. From 300-2500 m, heat from heat exchange and adiabatic heating would help heat the slurry to a bulk temperature of nearly 150° C. During this stage, temperature would also increase due to adiabatic heating and decavitation. At around the supercritical boundary, somewhere between the depths of 2500 and 3000 m, one or more constrictions would initiate decavitation of the bubbles of pre-determined mass, thereby activating partial oxidation. This would step-jump the temperature to a new plateau of around 400-500° C. as the biomass rapidly consumed all the remaining oxygen and as the biomass' own oxygen content was reconfigured, both reactions producing mainly syngas. After the supercritical boundary had been passed, salts and oxides would come out of solution and a portion of them would plate out on the sides of the reactor. After the now supercritical fluid had moved into the upwards passage and reached subcritical conditions again, the gases present under such conditions would be cycloned off and the liquid would continue upwards to the containing vessel on or near the surface, losing most of its heat to the adjacent, downflowing biomass slurry in the inner pipe. After the hydrocloning separation processes, the separate gas and liquid/solid slurry fractions would pass through a piping mechanism that moved the gas to the outer passage and, at the same time, the slurry to an inner passage. The still-pressurised slurry might exit at perhaps 105° C., then pass through a settling tank or vortex centrifuge (to remove the less soluble salts and oxides), then the clarified liquid would transit to a surface-mounted heat exchanger to exit at perhaps 50° C. This exchanger would also require occasional desalting.

The WSS process may be beneficially integrated with the WFTAS process, or kept separate. Integration typically offers a number of benefits, but is more complex to arrange. Thus, making use of the high pressure and temperature of the syngas coming up the upward passage, one or more open-matrix, possibly sintered catalytic filters might be inserted into the passage at intervals, progressively to convert most of the syngas into alkanes and steam by a Fischer-Tropsch (F-T) reaction. Separate filter modules would be set in an annular frame in two layers. In cross section each module would resemble a filled hat with a thick brim. The modules would be set in two intermeshing layers, one with the hats right-side up, the other with them down. This arrangement reduces the tendency for gases to flow in the fine gap between modules, forcing them to move through the sintered, catalytic material. Each module would have protruding metal rings to aid in their handling. Securing rings would prevent modules lifting or tilting under gas pressure. These rings would also seal the radial ends of the modules from gas passage.

Each hat module could be reconditioned and replaced separately. Each, curved upper surface of the filter assembly frame would be given a low point from which any heavier alkanes that condensed or flowed there might be drawn off in a pipe, separated from the gases. The heavy alkanes would be pumped off by a mechanism similar to a water-pumping windmill's long and envalved pumping rod. The entrance to this pipe might require a mechanism similar to that of a steam trap to prevent gases from entering.

As the F-T reaction is exothermic, the additional heat would be transferred to the slurry (with some losses to the rock or to steam formation), and thence to the downflowing biomass slurry. However, due to the high velocity of the gas, these heat exchanges might not be large. On reaching the surface, the very hot, alkane-rich gases would be progressively condensed into their various fractions in a fractionation tower or similar device. The heat from this condensation might be used to generate most of that required for any required superheated steam for additional process heating, and the residual heat used to warm the incoming reaction materials. For accessibility, maintenance and control purposes, some catalytic filter reactors might best be located at or somewhat below the surface. However, either pressure reducing or controlling mechanisms, or additional filter reactors much lower down may well be required, in order to reduce the pressure difference between the otherwise very high pressure syngas and the down-flowing biomass in the inner, sectioned pipe that is at relatively low pressure near the surface. Unconverted syngas left over from the condensation process might either be returned to the WSS steam inlet or sent to the WFTAS, pre-WAS or other process.

With the right selection of catalysts and conditions, syngas may be made to produce: ammonia, i-$C_4$, mixed alcohols, waxes, olefins, gasoline, aldehydes; and, via conversion to methanol, also to produce ethanol, formaldehyde, MTBE, acetic acid, olefins, gasoline and DME. Many of these reactions may well be performed more economically than can present methods by replacing them with their Winwick drillhole reactor variants.

Should the diameter of the upper part of a geothermal or other drillhole, which is re-employed for WSS purposes, be unnecessarily wide, then its outer annulus might be used to turn any excess heat-exchanged energy into useful process steam.

Winwick DME Synthesis (WDS)

It has recently been reported by Kaoru Takeishi in Biofuels (2010) 1(1) journal (available at: http://www.future-science.com/doi/abs/10.4155/bfs.09.16?journalCode=bfs), that a single, multifunction, catalyst has been developed that converts syngas first to methanol and then to dimethyl ether (DME) in an economical, one-step process. Thus, it may be possible to combine this with the WMS process using the multifunction catalyst in a WDS drillhole reactor. This could share the same drillhole casing and cooling system with WMS and WAS reactors. Indeed, it may be possible to have any of the three processes run in any of the three drillhole reactors, thereby improving output flexibility greatly.

The Takeishi catalyst is a sol-gel one, made of Cu—Zn (19-25 wt %)/$Al_2O_3$. It works even when the feed is contaminated with oxygen. The reaction conditions used were: a $H_2$/CO ratio of 1.0, a 220-260° C. temperature range and 16 atm pressure. However, as the conversion rate appears to improve markedly when the pressure is higher, much higher, yet still economical, pressure would be used in the Winwick variant of the reaction conditions. Experimentation will be needed to determine what are the reactor conditions most favourable for the reaction to proceed optimally in a WDS reactor. The syngas and any non-deleterious, gaseous contaminants would be formed as bubbles in the catalyst-rich carrier oil or wax. The fluid would then be pumped through the drillhole reactor, being affected by the changing conditions there that cause virtually-complete (~97%) DME conversion. A series of relatively simple, phase separation processes would be used on the outputs to separate the DME from the other materials. Most of these would be recycled.

As DME is such a superb and flexible fuel; as it is compatible with the existing LPG distribution systems; and as Winwick process losses and costs would appear to be less for WDS than for the WFTAS process, and as the conversion rate is higher, it is thought that most Winwick facilities will eventually produce DME from biomass-derived syngas (derived from algal and other organic sources) as their dominant biofuel product. A gaseous product may have additional benefits regarding its distribution via pipeline, as surface irregularities and elevation differences may be less restricting than for a liquid.

Winwick Fischer-Tropsch Alkane Synthesis (WFTAS)

Syngas resulting from the WSS process may also be converted in a separate drillhole reactor into controllably-long alkanes that go to make petrol, diesel and jet fuel via a similar Fischer-Tropsch (F-T) process variant that utilises a Winwick drillhole reactor another way. This process is termed the Winwick Fischer-Tropsch Alkane Synthesis (WFTAS).

Fischer-Tropsch synthesis reactions can also utilise the products resulting from the partial combustion of wellhead methane and algal-produced oxygen that is synthesis gas or syngas, comprising hydrogen and carbon dioxide:

$$2CH_4 + O_2 \rightarrow 4H_2 + 2CO$$

Of the competing reactions in the Fischer-Tropsch process, important ones comprise the general set:

$$(2n+1)H_2 + nCO \rightarrow C_nH_{(2n+2)} + nH_2O$$

Such reactions are highly exothermic.

The low temperature Fischer-Tropsch (LTFT) reactions that produce the most valuable, long-chain alkanes occur from 200-280° C. in the presence of catalysts made typically from iron and/or cobalt and which often are deposited in thin films upon a non-reactive, high surface area base, such as some ceramics, zeolites or treated minerals may form. The high temperature (HTFT) process occurs from 300-350° C. and uses an iron catalyst. Both can be performed by Winwick F-T variants.

In these Winwick variants, the catalyst is typically incorporated in a gas-bubble-carrier liquid, rather than being loose or localised in a solid-matrix catalyst or slurry bed. Thus, in this Winwick variant, the catalysed reactions take place on solid, finely-divided, catalytic surfaces typically located within a few molecular distances of the bubble surface. The reaction occurs as each bubble is carried down and up the drillhole, the heavier, higher boiling point products dissolving into the, typically hydrocarbon, carrier for later release by fractionation. This dissolving action partially shields them from further carbon-chain addition reactions. Thus, the absorption of desirable, middle-boiling point alkane fractions into the carrier, before they become too long and heavy, may provide an additional means for ensuring that the production of the more valuable alkane fractions is favoured. By typically remaining as gases at these temperatures and pressures, the lighter fractions tend to remain inside the bubbles until they add sufficient $CH_2$ segments to become desirable-length alkanes. The carrier may however require selection or chemical treatment so that it is prevented, or at least hindered, from adding such segments.

F-T waxes are currently more valuable than fuels. Therefore, producing longer alkanes to form waxes may be an alternative for some WFTAS drillhole reactors. However, as the demand for waxes is unlikely ever to exceed that of 1% by weight of fuel, it may be considered to be out of the main game (except when used as the carrier), whilst still being able to add flexibility to the product range and to improve the profitability of the overall system. However, as the production of F-T waxes, followed by hydrocracking, tends to maximise transport fuel production, they may still form a central part of the fuel production process using Winwick processes.

Typically, LTFT reactions are carried out at pressures from 20-60 atm. Even higher pressures would be even more favourable, but are usually not cost effective. However, using Winwick technology these more favourable conditions are available economically from existing geothermal or other drillholes. As the F-T reactions are highly exothermic, it will be convenient for the drillhole used to also be the site for Winwick processes that require heat. Balancing the volumes used in each process can, possibly with some additional surface-based or near-surface thermal processes, be used to obtain the right temperature band for each process to occur in. Using Winwick variants of F-T processes, pressures of up to and exceeding 1000 atm may well be cheaper to achieve than ones a hundred times less (~10 atm) on the surface, thereby delivering superior economics of production.

Use of somewhat higher pressures also speeds up the formation time of the synthesis gas from possibly hours to minutes and may as well improve the yield considerably. Furthermore, combinations of higher pressure and reduced reaction time can be so chosen as to produce alkanes of the most valuable carbon-chain lengths, which are C12 to C20—those comprising diesel and jet fuel. Evidence for these claims may be derived from Latin American applied research conducted at the Universidade Federal do Ceara in Brazil reported in the reference of Farias, et al.

In Winwick's F-T process variation, the finely-divided iron, or iron on ceramic, catalyst is distributed in the carrier oil that is pumped down the central, profiled pipe and up inside the enclosing drillhole casing. The carrier oil or wax may vary in weight from relatively light diesel to heavy, residual fuel oil, coal tar oil, wax or passivated hydrocarbon. The chosen carrier oil carries the small, injected bubbles of stoichiometrically-mixed synthesis gas ($CO + H_2$), some of which hydrogen may have been produced by the water shift reaction. These bubbles are carried down and up the drillhole by the velocity of the circulating, pumped, carrier oil. The only pumping costs are those to offset pipe wall friction, turbulence and fluid density differentials. Energy is not required to compress gas. The reaction gases come into contact with the catalyst, typically at the bubble-carrier interface, their reactivity possibly being increased at the interface by the addition of an appropriate promoter or surfactant, as in froth flotation for mineral separation. As froth flotation is known to work particularly well in polar, aqueous solutions, an emulsion of oil and a high-boiling point polar solvent, or a chemically-shielded (passivated) hydrocarbon may possibly be used instead for some purposes as the carrier.

In the production of diesel by this means, the carrier oil would normally be wax, RFO or coal tar oil, but may itself be diesel (unless this has too low boiling and degradation points), thereby possibly simplifying the subsequent separation process. For the production of other products such as methanol, residual fuel oil or coal tar oil are similarly appropriate carriers. Although the carrier may itself contain long-chain alkanes, they may react less readily with CO and $H_2$ to lengthen their chains than do shorter alkanes, as they are both less mobile and possibly attach less readily to the catalytic surface. Nonetheless, the carrier may need to be replaced periodically, though it may also be regenerated or transformed into more valuable hydrocarbons via cracking. A short chain carrier may also be usefully transformed into one of somewhat longer chains and thus not require cracking or reforming.

By the above means, transport-fuel hydrocarbons produced by Winwick versions of F-T synthesis may be made considerably more profitably than those undertaken at traditionally lower pressures on the surface. In many circumstances, the improvement in economics will be sufficiently strong as to overcome the otherwise superior economics of piping natural gas to city consumers. The business case is likely to be even more compelling when "stranded gas" sites are considered.

The synthesis of methanol, diesel and other biofuels and chemicals under Winwick conditions is akin to other supercritical, fluid chemical reactions. Indeed, methanol can also be synthesised from syngas under supercritical conditions. One such synthesis uses n-hexane as an additional solvent, temperatures from 200-210° C., and pressure in excess of 80 atm. Using this method to produce methanol, or one analogous to it, the Winwick transesterification process can be freed of dependence upon a source of fossil methane or expensive, bought-in methanol.

Winwick Methanol Synthesis (WMS)

The optimal $CO:H_2$ ratio in syngas for the production of methanol, $CH_3OH$, is 1:2. Under certain conditions of temperature, pressure or supercritical water density, and catalyst, this ratio may be produced from biomass using a residence time of around 5 minutes (much less with higher pressure) and a concentration of 9% biomass or methane by weight. In Winwick operations, the syngas for conversion into methanol will usually be produced by a combination of the WSS process and the water shift reaction.

Due to the relative economics of transportation, methanol production may be particularly useful where methane is found in stranded deposits. Should methanol be chosen to be produced otherwise than from syngas, the methane and $CO_2$ from the digestor or methane from other sources (typically from local gas/oil wells, coal fields or refineries) can be reacted with the $O_2/CO_2$ mix from the bioreactors and steam to form methanol in a Winwick drillhole reactor. There may be additional benefits from thermally linking the various drillhole processes. The methanol-producing and similar F-T reactions are exothermic and will thus benefit from exchanging heat with heat-requiring, Winwick processes.

As methanol is typically produced by employing pressures of up to 1,000 atm and modest to high temperatures (80-800° C.), depending on the intermediates and catalysts used (typically a mixture of Cu, ZnO and $Al_2O_3$ at 250° C. and 50-100 atm for the ICI variant), it may also be produced, with very substantial economies, using geothermal or other drillholes, where the passive pressures can exceed 1000 atm and the temperatures can exceed 250° C. (or much more using superheated steam supplementation, followed by partial combustion, adiabatic and decavitational heating) at depths from 2,500-5,000 or more meters.

Furthermore, it may well be profitable to drill or establish drillhole reactors at remote, and/or offshore gas/oil wells in order to convert the methane and carbon dioxide extracted by the wells to methanol or DME that are more easily stored and transported. Using such a process would tend to eliminate GHG emissions from the wells. If the sea were deep enough there, it might even be possible to install a Winwick Methanol Synthesis facility there that required no drilling—simply by lowering buoyed pipes into the sea. Such systems might even be mounted on a mobile platform that would be able to move between oil/gas wells. Of course, the pipes would need to be well insulated to conserve heat and be designed for neutral buoyancy. An alternative to insulation would be to have one or more outer heat exchanging pipes and using the heat provided for other purposes. The same ocean-located processing system might also be applied with benefit to WCR, WLE, WSX, WDS, WSS, WFTAS, WAS and WNAS processes.

It should be noted that methanol powers high-performance racing cars and is likely to become an increasingly popular fuel to power fuel cells powering electric vehicles and portable devices. The particular advantages of methanol, ethanol, and even more so DME (dimethyl ether) derived from methanol is that they can use the existing supply chain and service station outlets with little or no modification. DME can also be sold in re-usable pressure packs or other gas containers and the alcohols in bottles or cans. Methanol can also be converted into petrol, plastics and important industrial chemicals—possibly again via cost-effective Winwick drillhole reactions.

Dimethyl ether (DME) can also probably be made directly from syngas using an economical Winwick variant of the Semelsberger process, using a bifunctional catalyst.

Parallel drillhole reactors in the one drillhole may be used for WMS, WDS and WAS purposes.

Winwick Ammonia Synthesis (WAS)

Using a Winwick variant of the Haber-Bosch process, it should also be possible to utilise the high pressures available in a drillhole reactor to produce ammonia ($NH_3$) and to use this directly in its aqueous $NH_4OH$ form, or its salts, to provide metabolically-available nitrogenous nutrient to the algae; or from the ammonia gas to produce other nitrogenous nutrients, such as ammonium nitrate ($NH_4NO_3$) or urea (($NH_2)_2CO$) for the algae, or for sale as pelletised or flaked fertiliser, or other chemical feedstocks.

The Haber process reacts nitrogen and hydrogen in the presence of a catalyst derived from the partial reduction of magnetite ($Fe_3O_4$) with hot hydrogen (osmium is a far better catalyst but is very expensive). A substantial proportion of heavy, magnetite catalyst in the Winwick carrier would serve a secondary purpose of increasing the carrier or 'drilling mud' density—a useful function in deep drillholes to help prevent crushed pipes and blowouts.

Before reaction with hot hydrogen, small quantities of calcium, potassium and aluminium oxides are added to the magnetite to improve subsequent catalytic performance. The resulting catalyst is highly porous and adsorbs onto its surface individual atoms from the molecular reactant gases that then can react to form ammonia after diffusion apart and radical formation of reactant molecules' atoms on the catalytic surface.

In the standard, exothermic Haber process the:

$$N_2(g) + 3H_2(g) \Leftrightarrow 2NH_3(g)$$

reaction occurs from 300-550° C. and at 150-250 atm. Under these conditions, a yield of 15% ammonia is achievable at each pass. However, as four molecules of reactant gases react to produce only two of ammonia gas in the equilibrium reaction, it will be seen that the forward reaction is favoured more strongly, the higher is the pressure. As the reaction does occur, but is slow at room temperature, fast reaction at much higher pressure may be feasible at temperatures from 20-280° C., thereby removing the need for one, more, or all of the expensive, between-pass cooling stages and multiple re-passages of the standard Haber process. Furthermore, with Winwick drillhole pressures of up to 1,000 atm being easily and economically achievable, it may be that a much higher, single-pass conversion rate is possible—possibly making just a single pass economically feasible.

The initial, validating field test might use drillhole conditions giving a maximum pressure of, say, 750 atm and a selected maximum temperature of ~200° C. The necessary heating is provided by the hot hydrogen from the WSS and water shift reactions, from heat exchange heating of the nitrogen at the surface using process or HFR heat sources, by heat exchange with the hot, upflowing WAS material, and from adiabatic and exothermic reaction heating down the WAS drillhole.

As there is a temperature trade-off required between rate of reaction and yield, the Winwick optimum can be selected. Under such conditions, virtually complete reaction (~98%) occurs within the time that the fast moving (15-50 km/hr) carrier liquid and contents transits one cycle within the drillhole reactor. However, as the forward reaction is also dependent upon the effectiveness of ammonia product removal, this removal may best be effected some distance down the upward passage, possibly by means of a hydroclone mechanism, similar to that described elsewhere in this document. As ammonia ($NH_3$) liquefies from the gas phase at around 70° C. at 40 atm and 30° C. at 12 atm, the depth at which one or more of these points is reached may be selected for the placement of hydroclones. These would remove the lighter, possibly cooled, ammonia liquid (~700 kg/m3) from the heavier and densified RFO carrier ('pure' RFO has density ~1,014 kg/m3)—thereby allowing the carrier fluid to be continuously re-used within the drillhole reactor, once it had been recharged with reactant gases.

As the Haber reaction is exothermic, the coolant water is likely to need to be pumped at a considerable velocity. Automatically controlled valves may be useful to direct cool water from the downwards coolant passage around the upper levels of the upwards WAS pipe to ensure ammonia liquefaction and removal. At intermediate levels, the upwards WAS pipe might even temporarily be split into a few or several smaller pipes, so as to improve heat transfer.

The feasibility of the desired catalytic reaction still occurring when the catalyst is carried in heavy oil, wax or other liquid carrier and is exposed principally to the reactant gases at bubble surfaces will only be proven by experimentation. However, the mass transfer characteristics of supercritical reactions make success likely. If it indeed becomes proven, then the Winwick variant might well replace the standard Haber process—with profitable economic and beneficial environmental ramifications. Besides, at high enough pressures, the reaction may take place sufficiently fast even without catalyst or promoter, or else with a gaseous or liquid catalyst, or with catalyst coated onto the inside of the drillhole reactor.

One or more WAS reactors might also be adapted to produce urea (($NH_2$)$_2$CO) efficiently in the same pass, taking advantage of the generated temperatures and pressures, by means of adding $CO_2$ gas, partway down the reactor. However, this might require a different separation technology to be used, and possibly by the addition of a different catalyst. Contrary to ammonia, urea is denser (1.32 gm/cm3) than the carrier wax (F-T wax has density ~0.8 gm/cm3) or oil, but still might be separated by hydrocloning, provided it did not dissolve in the carrier. Most algae are able to use urea as a nutrient in place of ammonia. Indeed, there may be some advantages in using urea as the, or one of the, nitrogenous nutrients, as: it is not so alkaline; is not a pungent gas at ambient conditions; and does not contribute to possibly excessive $CO_2$ partial pressure; yet it also dissolves easily in water.

At Winwick sites, the hydrogen to produce the ammonia or urea is readily generated from methane or algal cell walls reacted supercritically with water and oxygen. It can also be retrieved from syngas using membrane filtration techniques to separate the hydrogen from the carbon monoxide (CO). And the CO left over may then be reacted with water to produce even more hydrogen via the water-gas shift reaction.

There are several challenges regarding transport logistics to be met to create the new industry. Flue gas from coal-fired power plants has the approximate composition of: $N_2$ 72%; $O_2$ 13%; $H_2O$ 8%; $CO_2$ 5%; CO 1%; and $SO_x/NO_x$ 1% (source: EngSoft). Cement works and gas/oil fired power plants typically produce higher proportions of $CO_2$. Given the volume of flue gas produced daily by each nation and the large number and variety of sources, in many circumstances it may well be worthwhile developing a separate utility service or pipeline grid cum temporary storage and in-line processing system for flue gas. Unlike the $CO_2$ pipelines, this system would not need to extend to the possibly very remote bioreactor farms, as there would be no economic advantage in transporting its 70-80% nitrogen content there, when air with 78% nitrogen is available on-site. Instead, the flue gas pipeline would only need to extend far enough: to have the necessary storage capacity; to cool the flue gas to temperatures at which most of its water content could condense out, taking with it the acidic gases ($NO_x/SO_x$), fly ash and soot; and to cool it to a temperature at which the $CO_2$ could be extracted cost-effectively from it.

Now, many producers, such as power plants, produce hot, flue gas around the clock and in large volume. However, although algae can only use $CO_2$ during daylight hours, the volume of gas needing to be stored may be reduced by more than 95% by cooling and by the separation of the valuable dilute acids, minerals and $CO_2$. The residual $N_2$ and CO may be passed through a catalytic filter to oxidise the CO to less-harmful $CO_2$, and the resultant mix vented. After possible processing to remove valuable (and possibly harmful) heavy metals, the dilute acids and nutrients may then either be used locally or transported by pipeline to the biorefinery. The $CO_2$ is pumped into the $CO_2$ pipeline for transportation to the bioreactor farms.

The pipeline grid system for flue gas is designed to take in high temperature flue gas from regional, stationary, major sources, as the cost of cooling it and removing acids from it would not be economical when done at each source. Now, cooling by natural conductance of the flue gas heat to the pipe walls and thence to the surrounding earth and atmosphere over tens or hundreds of kilometers does not appear to be particularly problematical. Moreover, near power stations, additional electricity (usable for pumping the flue gas) might be generated by the use of Stirling engines or of half-buried, J-shaped, air-cooling towers mounting turbine generators acting as heat exchangers along the pipeline. The cooling would tend to condense the water vapour that would then absorb the acidic flue gases to form an aqueous liquid. The result being that a combination of more or less dilute acids, with principal components of nitrous, nitric, phosphoric, sulphurous, sulphuric and hydrochloric acids, plus possibly various alkaline fly ash constituents, would tend to collect in the bottom of the pipe. These materials would need to be collected at low points along the pipeline for reclamation, piping and processing into useful products. Should that processing utilise the addition of limestone to neutralise any excess acidity and/or precipitate valuable minerals and fertilisers, then the $CO_2$ so released could be returned to the $CO_2$ pipeline for biosequestration.

Alternatively, the hot flue gas might undergo Norwegian company, $RCO_2$'s Catalytic $CO_2$ Recycle (CCR) process to cool the flue gas to below 300° C., whilst generating methane from the reaction between the $CO_2$ and water, then use Winwick's flue gas pipe system to cool it further and extract the residual 40+% of the $CO_2$.

Cooled and semi-purified flue gas might be exposed to zeolite imidazolate frameworks (ZIFs) that would adsorb most of its $CO_2$. As water can destroy some types of zeolitic structure and hydrogen sulphide ($H_2S$) be irreversibly be adsorbed on them, these compounds may need to be removed before the $CO_2$ is. Alternatively, activated charcoal or molecular sieves may be used to extract the $CO_2$. Where pressure changes are used, instead of temperature-based ones, to extract the $CO_2$, the process is termed Pressure Swing Adsorption (PSA). The two methods are often used in tandem. ZIF assemblies with a full load of $CO_2$ would be sealed off and gently heated to drive off their $CO_2$, thereby regenerating the ZIFs adsorptive power for re-use and re-exposure to the flue gas. The resulting $CO_2$ would then also be pumped to an adjacent or nearby $CO_2$ pipeline for biosequestration.

Nitrogen for the ammonia synthesis might be obtained on-site at the biorefinery via molecular filtration, using the cheap, local PV power to effect the separation; the oxygen component being added to that from the algae for sale (typically by pipeline) or local use.

Whilst WAS facilities are useful when located beside algal bioreactor farms for the nitrogenous nutrients they provide, and because syngas from the WSS process can provide the hydrogen feedstock they need, they may also have potential located near to other biomass sources, such as crop and forestry wastes, sewer mains, solid waste processing facilities, natural gas or lignite deposits. These resources can equally use WSS technology to produce syngas, and thence hydrogen, in a clean and cost-effective way. They would also often be closer: to industries using ammonia gas as their primary feedstock; and to ports and markets for the products of these industries. Major users of ammonia include the fertiliser/agribusiness, explosives and the chemical industries.

For the WAS, and possibly also the WMS, DME and urea-producing drillhole reactions, it may also be possible to use much shallower drillholes with a much heavier, carrier fluid, such as the low-melting point alloy, galinstan. This is made of a eutectic mixture of gallium, indium and tin metals, with a typical composition of 68.5% Ga, 21.5% In and 10% Sn. Galinstan is of low toxicity and low reactivity. It has a melting point of −19° C., a boiling point of >1,300° C. and a density of 6.44 g/cm3 at 20° C. Its main obstacle for more general use is its cost (~$600/kg) and its tendency to dissolve other metals. However, this last is unlikely to be a problem when used in a drillhole reactor made of titanium coated with titania. Due to the greater density difference between reactant gases and alloy carrier, the alloy might need to be pumped at a faster velocity than a lighter carrier, and the reactant gases introduced under higher pressure, perhaps somewhat further down the drillhole reactor.

In the WAS process, the ammonia produced tends to dissolve in the galinstan, yet has little tendency to react with it to produce gallium nitride (GaN) because the temperature reached in the drillhole reactor is kept below the reaction temperature (>700° C.)—unless of course the intention is to produce valuable, co-product GaN semiconductor microcrystals for extraction. However, to produce pure GaN sponge as a co-product, it may be necessary to substitute pure gallium, which melts at 30° C., for the galinstan alloy carrier. Such a co-product would probably best be made by extracting a portion of the ammonia-saturated metal from the drillhole and heating it to reaction temperature (~1,100° C.) in a separate operation. Subsequent to the WAS reaction, most of the ammonia product portion that is dissolved in the alloy may be released from the alloy by the application of a partial vacuum. Alternatively, the alloy or pure metal might still do its job whilst saturated with ammonia.

Winwick Nitric Acid Synthesis (WNAS)

In the Ostwald process, ammonia is first burnt with oxygen at 900° C. at 4-10 atm in the presence of a 90:10 Pt/Rh catalyst to produce nitric oxide (NO). In the presence of water in an absorption apparatus, a second stage oxidises the NO to $NO_2$ that then reacts with the water to form nitric acid ($HNO_3$) and more NO, which is recycled.

Now, it has been estimated that temperatures in decavitating bubbles reach as high as 5,000° C. Thus, a Winwick variant of the first stage of the Ostwald process, using a wax, residual fuel oil, or metallic galinstan carrier, that also carries powdered or dissolved Pt/Rh catalyst, in a drillhole reactor, should be able, when aided by decavitation effects, to convert a mixture of ammonia and oxygen gas in bubble form, into NO and water by the strongly exothermic reaction:

$$4NH_3 + 5O_2 \rightarrow 4NO + 6H_2O \quad (\Delta = -950 \text{ kJ/mol})$$

Provided that the highly-localised and short-lived decavitation temperatures were still sufficient to progress the reaction, the carrier might be maintained at a low, bulk temperature. The Winwick variant saves the cost of pressurising the reactant gases and retains the excess heat produced in a recycling liquid, thereby making its energy more re-usable. The higher reaction pressure may also discourage a countervailing reaction that might otherwise reduce yield, which is:

$$4NH_3 + 6NO \rightarrow 5N_2 + 6H_2O$$

Winwick reactors may fairly readily, and at negligible operating cost, attain pressures up to 1,000 atm.

It is even conceivable that the bulk temperature of the system might be maintained at <100° C., thereby allowing the instantaneous steam product to condense, whereby the higher operating pressure of the Winwick variant might have the effect of favouring the forward reaction, due to nine moles of reactant gas producing only four moles of product gas, rather than ten.

Stage two of the traditional, Ostwald process involves two reaction steps, on neither of which Winwick is likely to improve. The first is typically carried out in an oxidation chamber at 50° C., the second at ordinary temperatures in a large absorption column packed with quartz and involving countercurrent flows of water and gases:

$$2NO\,(g) + O_2\,(g) \rightarrow 2NO_2\,(g) \quad (\Delta - 114 \text{ kJ/mol})$$

and $$2NO_2\,(g) + H_2O\,(l) + \tfrac{1}{2}O_2 \rightarrow 2HNO_3\,(aq)$$

The last reaction can involve greater complexity than is depicted and may produce NO. This is simply recycled to the previous step.

Sodium nitrate ($NaNO_3$) salt, that is useful to store concentrated solar power (CSP) heat energy in molten form, or be used as fertiliser, may readily be produced from nitric acid, simply by reacting it with soda ash ($Na_2CO_3$), produced from table salt and limestone by the Solvay process, and using solar or geothermal energy to evaporate off the (reclaimable) water. The pure $CO_2$ by-product of the reaction may then be fed to the algal bioreactors. In fact, should a large and economical source of $CO_2$ not be available near otherwise-desirable locations for biofarms, then it may be produced regionally by calcining limestone with concentrated solar heat, provided there is a source of limestone within economical piping distance of either the NO or $NO_2$ gases or the liquid nitric acid. Ammonium nitrate ($NH_4NO_3$) for use by the algae as a crop fertiliser, or in explosives, may also be produced using the products of the WAS and WNAS processes, together with solar or geothermal evaporation. Both salts may best be transported long distances in the aqueous solution in which they are produced, or a concentrated version of the same, by pipeline. The same pipeline might be used to transport different aqueous products at different times, thereby saving both capital cost and increasing pipeline utilisation. The one pipeline might even be designed to transport products in different directions at different times, possibly separated only by a flushing operation with water.

Conclusion

This document outlines how a new, clean, efficient, scalable, sustainable and profitable fuel, food, chemical and power industry might be created. It is based on the biorefinery concept and employs key elements from the algal, photovoltaic, geothermal and chemical engineering industries. The technology it propounds provides transition paths to a low-carbon future and benefits for many other industries, including those involved with fossil fuel extraction, petroleum refining, forestry, agribusiness, chemical, plastics, sewage treatment, water reclamation, pipeline, pharmaceutical, waste management, carbon sequestration and power generation.

References

Barbosa, M. J. G. V. (2003) Microalgal photobioreactors: Scale-up and optimisation Ph.D. Thesis, Wageningen University, Wageningen, The Netherlands. library.wur.nl/wda/dissertations/dis3423.pdf Farias, Silva, Cartaxo, Fernandes and Sales (2007). Effect of operating conditions on Fischer-Tropsch liquid products. Latin American Applied Research, 37 (4), www.scielo.org.ar/pdf/laar/v37n4/v37n4a09.pdf

The invention claimed is:

1. A method of performing processing operations on a flowable feed material in a drillhole reactor, the flowable feed material being composed of a carrier liquid, reactants to be subjected to and to take part in the processing operations, and gas bubbles of predetermined sizes and/or contents that are entrained in or formed in the carrier liquid and which perform functionally in the processing operations, said reactants comprise organic cellular material having cells from which valuable substances are to be recovered, the method comprising the steps of:

flowing the feed material which comprises a slurry of the cellular material, the flowable carrier liquid and gases including the gas bubbles from a ground surface level down a confined path or drill hole which descends underground by a substantial vertical distance to a working depth so that the pressure experienced by the feed material at that working depth is substantially greater than the ground surface level whereby the cellular material is exposed to substantially increased pressure and osmotic gas transfer from the bubbles to the carrier liquid and thence into the cells of the cellular material and into their inner vesicles but without active pressurization;

providing working conditions for the flowing feed material at the working depth to utilise the relatively high pressure in performing the processing operations on the cellular material and so produce a flowable output material, the working conditions including conditions to produce rapidly changing pressures by means of depth change, choking and decompression, including decompression and the formation of pressurised gas within the cells that cannot osmose out sufficiently quickly to avoid cell and vesicle rupture as a result of rapid ascent of the flowing feed material, that induces lysis of the cellular material and thereby produces reaction products which are included in the flowable output material; and returning to the ground surface level an output slurry of lysed cellular material and substances released by the lysis for processing and separation of released valuable substances.

2. A method as claimed in claim 1 wherein said gas bubbles being of sizes chosen to decavitate at predetermined pressures which are reached or exceeded in the feed material at various working depths.

3. A method as claimed in claim 2 in which the gas bubbles collapse violently or implode upon decavitation producing energetic microjets of liquid which promote the lysis of the cellular material.

4. A method as claimed in claim 1 wherein the cellular material comprises microalgae or diatoms or other microorganisms.

5. A method as claimed in claim 1 wherein the step of providing conditions to induce lysis comprises flowing the slurry in a closed and profiled passage or loop, typically formed by a profiled pipe within an outer pipe, with a series of expansion and compression zones where the gas-bubble-containing slurry of microorganisms or other cellular material undergoes abrupt pressure changes thereby inducing lysis of the microorganisms via ruptures of cells and vesicles caused by explosive decompression and creation, release or expansion of gas bubbles, and by the microjets and the intense, localised heating resulting from decavitation of the gas bubbles.

6. A method as claimed in claim 5 wherein the passage has multiple restrictions inducing rapid pressure increases in the slurry and promoting decavitation of gas bubbles, the restrictions being arranged in series so that the slurry passes through the restrictions sequentially, each of the restrictions being followed in the flow path in the passage by an abrupt increase in cross-sectional area of the passage to thereby define the respective expansion zone of relatively lower pressure causing the explosive decompression.

7. A method as claimed in claim 6 wherein the downward passage or bore descends underground by at least 100 meters to produce a relatively slow-moving material during which the cellular material is exposed to said substantially increased pressure and osmotic gas transfer and osmosis stages and to allow subsequent rapid upward passage de-pressurisation sufficient for the lysis process.

8. A method as claimed in claim 1 wherein the output slurry comprising the carrier liquid, gases and the lysed cellular material resulting from the reaction at the working depth includes lipids released upon lysis of the cellular material, the method including the further steps of separating or at least concentrating the lipids and each other component separately by gravitational or centrifugal separation, and reacting the lipids in a transesterification reaction with excess methanol conducted under controlled temperature and pressure conditions at a predetermined level in a drillhole reactor where elevated pressures and decavitation are experienced sufficient to facilitate the transesterification reaction.

9. A method as claimed in claim 1 wherein the processing operations include chemical reactions induced to occur within the flowable feed material, the chemical reactions being initiated, caused, accelerated, or enhanced as a result of changes in pressure and temperature to which the feed material is subjected in descending from the initial level to the working level or experienced at the working level including adiabatic compression of the gas bubbles, decavitation and the consequent promotion of the chemical reactions, and wherein surfaces of the confined path for the feed material provide locations of catalytic surfaces promoting the chemical reactions.

10. A method as claimed in claim 1 wherein the processing operations include chemical reactions induced to occur within the flowable feed material, the chemical reactions being initiated, caused, accelerated, or enhanced as a result of changes in pressure and temperature to which the feed material is subjected in descending from the initial level to the working level or experienced at the working level including adiabatic compression of the gas bubbles, decavitation and the consequent promotion of the chemical reactions, and wherein the path comprises a passage or bore which descends underground by at least 100 meters, and preferably by some thousands of meters, so that the pressure in the fluid at that depth is of the order of 1,000 atmospheres, and wherein the feed material comprises a heated mixture of reactant fluids (typically heated via heat exchangers located on the ground surface level or by the underground introduction of superheated steam or other fluid into the feed material in the passage) which are entrained typically as said bubbles in a fast moving, catalyst bearing high boiling point carrier liquid such as residual fuel oil, and at the working depth in the passage or bore there is generated methanol from stoichiometric volumes of methane, steam, oxygen and carbon dioxide.

11. A method as claimed in claim 10 wherein the methane is sourced from anaerobic digestion of algal cell walls from the processing of microorganisms, or from waste organic material, or from hydrocarbon deposits, and wherein the oxygen is sourced from photosynthesis by microorganisms.

12. A method as claimed in claim 1 wherein the processing operations include chemical reactions induced to occur within the flowable feed material, the chemical reactions being initiated, caused, accelerated, or enhanced as a result of changes in pressure and temperature to which the feed material is subjected in descending from the initial level to the working level or experienced at the working level including adiabatic compression of the gas bubbles, decavitation and the consequent promotion of the chemical reactions, and wherein the chemical reaction comprises synthesis of a syngas comprising a mixture of carbon monoxide (CO) and hydrogen ($H_2$), the feed material comprising said bubbles composed of a mix of oxygen and carbon dioxide and steam in an aqueous carrier liquid forming a slurry of carbon based, organic substances and wherein the slurry at least upon reaching the working level achieves either sub or supercritical water conditions.

13. A method as claimed in claim 12 where the carbon-based substances includes one or more of: microorganisms, algae or algal cell wall material, crop and forestry wastes, lignocellulose products, sewage, plastics and rubber, wastewater, or wastes from agribusiness, pulp mills, or other carbon based products from industrial sources and waste recycling.

14. A method as claimed in claim 12 wherein the carbon based reactants include the cell walls of micro-organisms and other cellular materials which have undergone lysis so as to release lipids and proteins which have been recovered and removed therefrom.

15. A method as claimed in claim 1 wherein the processing operations include chemical reactions induced to occur within the flowable feed material, the chemical reactions being initiated, caused, accelerated, or enhanced as a result of changes in pressure and temperature to which the feed material is subjected in descending from the initial level to the working level or experienced at the working level including adiabatic compression of the gas bubbles, decavitation and the consequent promotion of the chemical reactions, and wherein the chemical reaction comprises a Haber ammonia synthesis and wherein the feed material includes said gas bubbles composed of mixed nitrogen and hydrogen gases in stoichiometric proportions, and suitable catalyst substances, promoters and densifiers added to the reactants or carrier liquid to promote the Haber process.

16. A method as claimed in claim 1 wherein the processing operations include chemical reactions induced to occur within the flowable feed material, the chemical reactions being initiated, caused, accelerated, or enhanced as a result of changes in pressure and temperature to which the feed material is subjected in descending from the initial level to the working level or experienced at the working level including adiabatic compression of the gas bubbles, decavitation and the consequent promotion of the chemical reactions, and wherein the chemical reaction comprises a Fischer-Tropsch alkane synthesis and wherein the feed material includes said gas bubbles composed of syngas comprising a mixture of carbon monoxide (CO) and hydrogen ($H_2$) and wherein suitable catalytic substances and promoters are either added to the reactants or to the liquid carrier or are located in a separate assembly to promote the Fischer-Tropsch process.

17. A method as claimed in claim 16 wherein the reactants comprise syngas produced by a chemical reaction in which the feed material comprising said bubbles is composed of a mix of oxygen and carbon dioxide and steam in an aqueous carrier liquid forming a slurry of carbon based, organic substances and wherein the slurry at least upon reaching the working level achieves either sub or supercritical water conditions, and wherein the production of syngas is carried out at a first working depth, and wherein the Fischer-Tropsch synthesis is carried out at a second working depth to which the products from the syngas synthesis are flowed.

18. A method as claimed in claim 15 wherein the reactants and catalysts are entrained in the said carrier liquid and the small gas bubbles therein provide large surface areas exposed to the catalyst-bearing carrier liquid at, or near which, the chemical processes progress.

19. A method as claimed in claim 1 wherein the processing operations include chemical reactions induced to occur within the flowable feed material, the chemical reactions being initiated, caused, accelerated, or enhanced as a result of changes in pressure and temperature to which the feed material is subjected in descending from the initial level to the working level or experienced at the working level including adiabatic compression of the gas bubbles, decavitation and the consequent promotion of the chemical reactions, and wherein the carrier liquid is composed of at least one of said reactants and includes lipids, and wherein the chemical reaction comprises a transesterification reaction with excess methanol conducted under controlled temperature and pressure conditions at a predetermined level in a drillhole reactor where elevated pressures and decavitation are experienced sufficient to facilitate the transesterification reaction.

20. A method as claimed in claim 1 wherein the steps of the method are at least partially performed underground in a deep drillhole so that the elevated pressures experienced by the flowable feed material comprising carrier liquid, reactants and gas bubbles result from the ambient pressure experienced in substantial depths of liquid, the depth of the confined path or drill hole being at least 100 meters and typically being in the range of from 1,000 to several thousand meters.

21. A method as claimed in claim 20 wherein heat for promoting the processing operations carried out at depth is in part derived from elevated temperatures of the ground in which the deep drill hole is provided or from heat derived from it in surface-mounted, geothermal heat exchangers.

* * * * *